United States Patent
Castelhano et al.

(10) Patent No.: US 7,645,754 B2
(45) Date of Patent: Jan. 12, 2010

(54) PYRROLOPYRIMIDINE $A_{2B}$ SELECTIVE ANTAGONIST COMPOUNDS, THEIR SYNTHESIS AND USE

(75) Inventors: Arlindo Castelhano, New City, NY (US); Bryan McKibben, Hopewell Junction, NY (US); Arno Steinig, East Northport, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 155 days.

(21) Appl. No.: 10/536,119

(22) Filed: Jun. 19, 2007

(65) Prior Publication Data

US 2008/0261943 A1 Oct. 23, 2008

Related U.S. Application Data

(63) Continuation of application No. 10/326,005, filed on Dec. 20, 2002, now abandoned.

(60) Provisional application No. 60/343,443, filed on Dec. 20, 2001.

(51) Int. Cl.
C07D 487/04 (2006.01)
A61K 31/519 (2006.01)
A61P 11/06 (2006.01)

(52) U.S. Cl. .................. 514/234.2; 544/117; 544/280; 544/391; 544/398; 544/403; 514/265.1; 546/215; 546/217; 546/212; 546/221; 546/216; 546/227; 546/230; 546/232

(58) Field of Classification Search ................. 544/117, 544/280; 514/234.2, 265.1
See application file for complete search history.

(56) References Cited

U.S. PATENT DOCUMENTS 3,037,980 A 6/1962 Hitchings et al.

(Continued)

FOREIGN PATENT DOCUMENTS

EP 322 242 A2 6/1989

(Continued)

OTHER PUBLICATIONS

West, J. Org. Chem 26, 3809 (1961).*

(Continued)

*Primary Examiner*—Mark L Berch
(74) *Attorney, Agent, or Firm*—John P. White; Cooper & Dunham LLP

(57) ABSTRACT

The subject invention provides compounds having the structure:

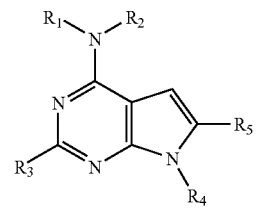

wherein,
$R_1$ is a substituted or unsubstituted alkyl, wherein the substituent is hydroxyl, dihydroxy, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$;

$R_2$ is hydrogen or a substituted or unsubstituted alkyl, wherein the substituent is hydroxyl, dihydroxy, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$, or $R_1$, $R_2$ and N together form a substituted piperazine, substituted azetidine ring, or a pyrrolidine ring substituted with —(CH$_2$)$_2$OH or —CH$_2$C(=O)OH;

$R_3$ is a substituted or unsubstituted phenyl or a 5-6 membered heteroaryl ring, wherein the substituent is halogen, hydroxyl, cyano, (C$_1$-C$_{15}$)alkyl, (C$_1$-C$_{15}$)alkoxy, or —NR$_a$R$_b$;

$R_4$ is hydrogen or substituted or unsubstituted (C$_1$-C$_{15}$) alkyl;

$R_5$ is —(CH$_2$)$_m$OR$_6$, —CHNOR$_7$, —C(=O)NR$_8$R$_9$, —(CH$_2$)$_m$C(=O)OR$_{10}$, —(CH$_2$)$_k$C(=O)NR$_{11}$R$_{12}$; wherein $R^6$ is a substituted or unsubstituted (C$_1$-C$_{30}$) alkyl, (C$_3$-C$_{10}$)cycloalkyl, or an aryl, heteroaryl or 4-8 membered heterocyclic ring;

$R_7$ is hydrogen, or a substituted or unsubstituted (C$_1$-C$_{30}$)alkyl, (C$_1$-C$_{30}$)alkylaryl;

$R_8$ and $R_9$ are each independently hydrogen, or a substituted or unsubstituted (C$_1$-C$_{30}$)alkyl, (C$_1$-C$_{30}$) alkylaryl, (C$_1$-C$_{30}$)alkylamino, (C$_1$-C$_{30}$)alkoxy, or a saturated or unsaturated, monocyclic or bicyclic, carbocyclic or heterocyclic ring, or $R_8$, N, and $R_9$ together form a substituted or unsubstituted 4-8 membered heterocyclic ring;

$R_{10}$ is hydrogen or a substituted or unsubstituted (C$_1$-C$_{30}$)alkyl, (C$_3$-C$_{10}$)cycloalkyl, or an aryl, heteroaryl or heterocyclic ring;

$R_{11}$, N and $R_{12}$ together form a 4-8 membered heterocyclic ring;

$R_a$ and $R_b$ are each independently hydrogen or alkyl;
m is 0, 1, 2 or 3; and
k is 1, 2 or 3,
or a specific enantiomer thereof, or a specific tautomer thereof, or a pharmaceutically acceptable salt thereof, and a method for treating a disease associated with the $A_{2b}$ adenosine receptor in a subject in need of such treatment comprising administering to the subject a therapeutically effective amount of the compounds of the invention.

10 Claims, No Drawings

U.S. PATENT DOCUMENTS

| | | | |
|---|---|---|---|
| 3,910,913 A | 10/1975 | Kim et al. | |
| 5,409,930 A | 4/1995 | Spada et al. | |
| 5,516,894 A | 5/1996 | Reppert | |
| 5,580,870 A | 12/1996 | Barker et al. | |
| 5,639,913 A | 6/1997 | Lidor et al. | |
| 5,681,941 A | 10/1997 | Cook et al. | |
| 5,710,158 A | 1/1998 | Myers et al. | |
| 5,714,493 A | 2/1998 | Myers et al. | |
| 5,721,237 A | 2/1998 | Myers et al. | |
| 5,747,498 A | 5/1998 | Schnur et al. | |
| 5,780,450 A | 7/1998 | Shade | |
| 5,834,609 A | 11/1998 | Horne et al. | |
| 5,877,218 A | 3/1999 | Herzig et al. | |
| 5,877,221 A | 3/1999 | Cohen et al. | |
| 5,880,159 A | 3/1999 | Herzig et al. | |
| 5,914,349 A | 6/1999 | Cohen et al. | |
| 5,962,458 A | 10/1999 | Lohmann et al. | |
| 5,994,408 A | 11/1999 | Cohen et al. | |
| 6,103,899 A | 8/2000 | Horne et al. | |
| 6,117,878 A | 9/2000 | Linden | |
| 6,664,252 B2 | 12/2003 | Castelhano et al. | |
| 6,673,802 B2* | 1/2004 | Castelhano et al. | 514/263.2 |
| 6,680,322 B2* | 1/2004 | Castelhano et al. | 514/252.02 |
| 6,680,324 B2* | 1/2004 | Castelhano et al. | 514/265.1 |
| 6,686,366 B1* | 2/2004 | Castelhano et al. | 514/264.1 |
| 6,800,633 B2 | 10/2004 | Castelhano et al. | |
| 6,878,716 B1* | 4/2005 | Castelhano et al. | 514/265.1 |
| 6,916,804 B2 | 7/2005 | Castelhano et al. | |
| 7,160,890 B2 | 1/2007 | Castelhano et al. | |
| 7,429,574 B2 | 9/2008 | Castelhano et al. | |
| 7,504,407 B2 | 3/2009 | Castelhano et al. | |
| 2002/0028782 A1 | 3/2002 | Castelhano et al. | |
| 2002/0058667 A1 | 5/2002 | Castelhano et al. | |
| 2002/0094974 A1 | 7/2002 | Castelhano et al. | |
| 2003/0036545 A1 | 2/2003 | Castelhaneo et al. | |
| 2003/0045536 A1 | 3/2003 | Castelhano et al. | |
| 2003/0073708 A1 | 4/2003 | Castelhano et al. | |
| 2003/0139427 A1* | 7/2003 | Castelhano et al. | 514/261.1 |
| 2003/0229067 A1 | 12/2003 | Castelhano et al. | |
| 2004/0082598 A1* | 4/2004 | Castelhano et al. | 514/265.1 |
| 2004/0082599 A1* | 4/2004 | Castelhano et al. | 514/265.1 |
| 2005/0090513 A1* | 4/2005 | Castelhano et al. | 514/265.1 |
| 2005/0119258 A1* | 6/2005 | Wilson et al. | 514/227.8 |
| 2005/0119271 A1 | 6/2005 | Castelhano et al. | |
| 2005/0288503 A1* | 12/2005 | Adams et al. | 544/276 |
| 2008/0070936 A1 | 3/2008 | Castelhano et al. | |
| 2009/0082369 A1 | 3/2009 | Castelhano et al. | |
| 2009/0192177 A1 | 7/2009 | Castelhano et al. | |

FOREIGN PATENT DOCUMENTS

| | | |
|---|---|---|
| EP | 514 540 A1 | 11/1992 |
| EP | 682 027 A1 | 11/1995 |
| EP | 729 758 A2 | 9/1996 |
| EP | 773 023 A1 | 5/1997 |
| GB | 915303 | 1/1963 |
| GB | DE 31 45 287 A1 | 5/1993 |
| IN | 157280 | 2/1986 |
| WO | WO 93/20078 | 10/1993 |
| WO | WO 94/13676 | 6/1994 |
| WO | WO 94/17090 | 8/1994 |
| WO | 94/24136 | 10/1994 |
| WO | WO 95/11681 | 5/1995 |
| WO | 95/19774 | 7/1995 |
| WO | WO 95/18617 | 7/1995 |
| WO | WO 95/20597 | 8/1995 |
| WO | WO 96/19478 | 6/1996 |
| WO | WO 97/02266 | 1/1997 |
| WO | 97/05138 | 2/1997 |
| WO | 97/33879 | 9/1997 |
| WO | WO 98/07726 | 2/1998 |
| WO | 98/08382 | 3/1998 |
| WO | 98/22465 | 5/1998 |
| WO | WO 98/29397 | 7/1998 |
| WO | WO 98/57651 | 12/1998 |
| WO | 99/06053 | 2/1999 |
| WO | 99/33815 | 7/1999 |
| WO | WO 99/42093 | 8/1999 |
| WO | WO 99/62518 | 12/1999 |
| WO | WO 01/39777 | 6/2001 |
| WO | WO 0139777 A1 * | 6/2001 |
| WO | WO 02/057267 | 7/2002 |
| WO | PCT/US02/38055 | 11/2002 |

OTHER PUBLICATIONS

Polosa, Eur. Respir Journal 20, 488-496 (2002).*

Blazynski, C., "Discrete Distributions of Adenosine Receptors in Mammalian Retina" J. Neurochem. (1990) 54(2): 648-655.

Braas, K.M. et al., "Endogenous adenosine and adenosine receptors localized to ganglion cells of the retina" Proc. Natnl. Acad. Sci. (1987) 84: 3906-3910.

Christofi, F.L. et al., "Differential Gene Expression of Adenosine A1, A2a, A2b, and A3 Receptors in the Human Enteric Nervous System" J. Comp. Neurol. (2001) 439(1): 46-64.

Corset, V. et al., "Netrin-1-mediated axon outgrowth and cAMP production requires interaction with adenosine A2b receptor" Nature (2000) 407(6805): 747-7500.

Dubey, R.K. et al., "A2B Receptors Mediate the Antimitogenic Effects of Adenosine in Cardiac Fibroblasts" Hypertension (2001) 37: 716-721.

Faivre, K. et al., "Suppression of Cellular Invasion by Activated G-Protein Subunits Gαo, Gαi1, and Gαi3 and Sequestration of Gβγ" Mol. Pharmacol. (2001) 60: 363-372.

Feoktistov, I. and Biaggioni, I., "Adenosine A2B Receptors" Pharmacol. Rev. (1997) 49(4): 381-402.

Feoktistov, I. et al., "Differential Expression of Adenosine Receptors in Human Endothelial Cells" Circulation Research (2002) 90: 531-538.

Feoktistov, I. et al., "Adenosine A2B receptors: a novel therapeutic target in asthma?" (1998) TiPS 19:148-153.

Gao, Z. et al., "A2B Adenosine and P2Y2 Receptors Stimulate Mitogen-activated Protein Kinase in Human Embryonic Kidney-293 Cells" J. Bio. Chem. (1999) 274(9): 5972-5980.

Grant, M.B. et al., "Proliferation, Migration, and ERK Activation in . . . through A2B Adenosine Receptor Stimulation" Invest. Opthalmol. Vis. Sci. (2001) 42(9): 2068-2073.

Haynes, J. Jr. et al., "5-(N-ethylcarboxamido)adenosine desensitizes the A2b-adenosine receptor in lung circulation" Am. J. Physiol. (1999) 276(6):H1877-H1883.

Linden, J. et al., "The Structure and Function of A1 and A2B Adenosine Receptors" Life Sciences (1998) 62(17-18): 1519-1524.

Mirabet, M. et al., "Expression of A2B adenosine receptors in human lymphocytes: their role in T cell activation" J. Cell. Sci. (1999) 112(4): 491-502.

Muller, C.E. and Stein, B., "Adenosine Receptor Antagonists: Structures and Potential Therapeutic Applications" Current Pharm. Design (1996) 2:501-530.

Muller, C.E., "A1 Adenosine receptor antagonists" Exp. Opin. Ther. Patents (1997) 7(5):419-440.

Nyce, J.W. and Metzger, J.W., "DNA antisense therapy for asthma in an animal model" Nature (1997) 385: 721-725.

Ralevic, V. and Burnstock, G., "Receptors for Purines and Pyrimidines" Pharmacol. Rev. (1998) 50(3): 413-492.

Regnauld, K. et al. "G-protein αolf subunit promotes cellular invasion, survival, and neuroendocrine differentiation in . . . epithelial cells" Oncogene (2002) 21(25): 4020-4031.

Strohmeier, G.R. et al., "The A2b Adenosine Receptor Mediates cAMP Responses to Adenosine Receptor Agonists in Human Intestinal Epithelia" J. Bio. Chem. (1995) 270: 2387-2394.

Williams, E.F. et al., "Nucleoside transport sites in a cultured human retinal cell line established by SV-40 T antigen gene" Current Eye Research (1994) 13: 109-118.

Woods, C.L. and Blazynski, C., "Characterization of Adenosine A1-receptor Binding Sites in Bovine Retinal Membranes" Exp. Eye Research (1991) 53: 325-331.

Seela, F., and Lupke, U., Mannich-Reaktion am 2-Amino-3,7-dihydropyrrolo [2,3-d] pyrimidin-4-on, dem Chromophor des Ribonucleosids "Q" (1977) Chem. Ber. 110: 1462-1469.

Nagarathnam, D. et al., "Design and Synthesis of Novel α1a . . . Antagonists for the Treatment of Benign Prostatic Hyperplasia" J. Med. Chem. (1998) 41(26): 5320-5333.

Klumpp, D.A. et al., "Synthesis of Aryl-Substituted Piperidines by Superacid Activation of Piperidones" J. Org. Chem. (1999) 64(18): 6702-6705.

Herndon, J.L. et al., "Ketanserin Analogs: Structure-Affinity Relationships for 5-HT2 and 5-HT1C Serotonin Receptor binding" J. Med. Chem. (1992) 35(26): 4903-4910.

Kiritsy, J.A. et al., "Synthesis and . . . of Some Antibacterial 3-Formylrifamycin SV N-(4-Substituted phenyl) piperazinoacethydrazones" J. Med. Chem. (1978) 21(12): 1301-1307.

Japanese Patent Application No. JP 09-291089, (English abstract only) published May 11, 1999.

Bundy, G.L. et al. "Synthesis of Novel 2,4-Diaminopyrrolo-[2,3-d]pyrimidines with Antioxidant, Neuroprotective, and Antiasthma Activity" J. Med. Chem. (1995) 38: 4161-4163.

Iwamura, H. et al. "Quantitative Aspects of the Receptor Binding of Cytokinin Agonists and Antagonists" J. Med. Chem., (1983) 26: 838-844.

Jorgensen, A. et al. "Synthesis of 7H-Pyrrolo[2,3-d]pyrimidin-4-amines" Liebigs, Ann. Chem., (1985) pp. 142-148.

Kiichiro, K. et al. "Synthesis of pyrazinecarboxylic acid derivs.—(II) derivs. of 3-aminopyrazinecarboxylic acid" Yakugaku Zasshi (1961) 81: 1650-1653 (Abstract only).

Muller, C. E. et al. (1990) "7-Deaza-2-phenyladenines: Structure-Activity Relationships of Potent A1 Selective Adenosine Receptor Antagonists" J Med. Chem., (1990) 33: 2822-28.

Muller, C.E. et al. "Chiral Pyrrolo[2,3-d]pyrimidine and Pyrimido[4,5-b]indole Derivatives: Structure-Activity Relationships of . . . Antagonists" J Med Chem (1996) 39: 2482-2491.

Venugopalan, B. et al. "Synthesis of 6,7-Dimethoxypyrimido[4,5-b]-indoles as Potential Antihypertensive Agents" J. Heterocyclic Chem., (1998) 25: 1633-1639.

West, R. A. et al. "2-Alkyl(aryl)-and 2,7-Dimethyl-4-substituted Aminopyrrolo[2,3-d]pyrimidines" J. Org. Chem., (1961) 26: 3809-3812.

Mautner, H.G., "Potential Deoxyribonucleic Acid Cross-linking Agents. 8,8'-Bispurines", J. Org. Chem. (1961) 26(6):1914-1917.

Kaiser, S.M. and R.J. Quinn, Drug Discovery Today (1999) 4(12): 542-551.

Barrett, R.J., Proc. West. Pharmacol. Soc. (1996) 39: 61-66.

Marx, D. et al., Drug News Perspec. (2001) 14(2): 89-100.

U.S. Appl. No. 09/454,074, filed Dec. 02, 1999, Castelhano et al.

U.S. Appl. No. 09/454,075, filed Dec. 02, 1999, Castelhano et al.

Campbell, R.M. et al., "Selective A1-Adenosine Receptor Antagonists Identified Using Yeast . . . Cerevisiae Functional Assays" Bioorg. & Med. Chem. Lett. (1999) 9(16): 2413-2418.

Zhao, Z. et al., "Bioactivation of 6,7-Dimethyl-2,4-di-1-pyrrolidinyl-7H-pyrrolo[2,3-d] pyrimidine (U-89843) to Reactive Intermediates . . . Genotoxicity" Chem Res Toxicol, (1996).

Dhainaut, A. et al., "New Purines and Purine Analogs as Modulators of Multidrug Resistance" J. Med. Chem. (1996) 39: 4099-4108.

Advisory Action in connection with U.S. Appl. No. 10/326,005, issued Apr. 11, 2006.

Office Action in connection with U.S. Appl. No. 10/326,005, issued Sep. 19, 2005).

Office Action in connection with U.S. Appl. No. 10/326,005, issued Jan. 27, 2005.

Office Action in connection with U.S. Appl. No. 10/326,005, issued Jan. 10, 2005.

Advisory Action in connection with U.S. Appl. No. 10/326,005, issued Nov. 10, 2004.

Office Action in connection with U.S. Appl. No. 10/326,005, issued Jun. 25, 2004.

Office Action in connection with U.S. Appl. No. 10/326,005, issued Feb. 4, 2004.

* cited by examiner

PYRROLOPYRIMIDINE $A_{2b}$ SELECTIVE ANTAGONIST COMPOUNDS, THEIR SYNTHESIS AND USE

This application is a continuation of U.S. Ser. No. 10/326,005, filed Dec. 20, 2002 now abandoned, which claims the benefit of U.S. Provisional Application No. 60/343,443, filed Dec. 20, 2001, the contents of all of which are hereby incorporated by reference into this application.

Throughout this application, various publications are referenced by full citations. The disclosures of these publications in their entireties are hereby incorporated by reference into this application in order to more fully describe the state of the art as known to those skilled therein as of the date of the invention described and claimed herein.

BACKGROUND OF THE INVENTION

Adenosine is an ubiquitous modulator of numerous physiological activities, particularly within the cardiovascular and nervous systems. The effects of adenosine appear to be mediated by specific cell surface receptor proteins. Adenosine modulates diverse physiological functions including induction of sedation, vasodilation, suppression of cardiac rate and contractility, inhibition of platelet aggregability, stimulation of gluconeogenesis and inhibition of lipolysis. In addition to its effects on adenylate cyclase, adenosine has been shown to open potassium channels, reduce flux through calcium channels, and inhibit or stimulate phosphoinositide turnover through receptor-mediated mechanisms (See for example, C. E. Muller and B. Stein "Adenosine Receptor Antagonists: Structures and Potential Therapeutic Applications," *Current Pharmaceutical Design*, 2:501 (1996) and C. E. Muller "$A_1$-Adenosine Receptor Antagonists," *Exp. Opin. Ther. Patents* 7(5):419 (1997)).

Adenosine receptors belong to the superfamily of purine receptors which are currently subdivided into $P_1$ (adenosine) and $P_2$ (ATP, ADP, and other nucleotides) receptors. Four receptor subtypes for the nucleoside adenosine have been cloned so far from various species including humans. Two receptor subtypes ($A_1$ and $A_{2a}$) exhibit affinity for adenosine in the nanomolar range while two other known subtypes $A_{2b}$ and $A_3$ are low-affinity receptors, with affinity for adenosine in the low-micromolar range. $A_1$ and $A_3$ adenosine receptor activation can lead to an inhibition of adenylate cyclase activity, while $A_{2a}$ and $A_{2b}$ activation causes a stimulation of adenylate cyclase.

A few $A_1$ antagonists have been developed for the treatment of cognitive disease, renal failure, and cardiac arrhythmias. It has been suggested that $A_{2a}$ antagonists may be beneficial for patients suffering from Morbus Parkinson (Parkinson's disease). Particularly in view of the potential for local delivery, adenosine receptor antagonists may be valuable for treatment of allergic inflammation and asthma. Available information (for example, Nyce & Metzger "DNA antisense Therapy for Asthma in an Animal Model" *Nature* (1997) 385: 721-5) indicates that in this pathophysiologic context, $A_1$ antagonists may block contraction of smooth muscle underlying respiratory epithelia, while $A_{2b}$ or $A_3$ receptor antagonists may block mast cell degranulation, mitigating the release of histamine and other inflammatory mediators. $A_{2b}$ receptors have been discovered throughout the gastrointestinal tract, especially in the colon and the intestinal epithelia. It has been suggested that $A_{2b}$ receptors mediate cAMP response (Strohmeier et al., *J. Bio. Chem.* (1995) 270:2387-94).

$A_{2b}$ receptors have also been implicated in wide variety of physiological activities, thereby suggesting that treatment of associated disorders can be effected by blocking the $A_{2b}$ receptor. For example, $A_{2b}$ receptor sites play a role in the degranulation of mast cells and hence in the treatment of asthma, myocardial reperfusion injury, allergic reactions including but not limited to rhinitis, poison ivy induced responses, urticaria, scleroderm arthritis, other autoimmune diseases and inflammatory bowel diseases (Gao, Z. et al., *J. Biol. Chem.* (1999), 274(9):5972-5980, Linden, J. et al., *Life Sciences* (1998), 62(17-18):1519-1524 and U.S. Pat. No. 6,117,878, issued Sep. 12, 2000). $A_{2b}$ receptors have also been shown to: inhibit the growth of cardiac fibroblasts, thereby suggesting that they may prevent cardiac remodeling associated with hypertension, myocardial infarction and myocardial reperfusion after ischemia (Dubey, R. K. et al., *Hypertension* (2001), 37:716-721), mediate the role of adenosine in lymphocyte activation (Mirabet, M. et al., *J. Cell. Sci.* (11999), 112(4):491-502), regulate vasodilation and growth (Ralevic, V. and Burnstock, G., *Pharmacol. Rev.* (1998), 50(3):413-492, Corset, V. et al., *Nature* (2000), 407 (6805):747-750, and Haynes, J. Jr. et al., *Am. J. Physiol.* (1999), 276(6):H1877-83), participate in neural reflexes in the human gut (Christofi, F. L. et al., *J. Comp. Neurol.* (2001), 439(1):46-64), and regulate retinal angiogenesis—thereby suggesting the use of $A_{2b}$ antagonists in treating diseases associated with aberrant neovascularization such as diabetic retinopathy and retinopathy of prematurity (Grant, M. B. et al., *Invest. Opthalmol. Vis. Sci.* (2001), 42(9):2068-2073). They are also involved in the modulation of intestinal tone and secretion and neurotransmission and neurosecretion (Feoktistov, I. and Biaggioni, I., *Pharmacol. Rev.* (1997), 49(4):381-402).

$A_{2b}$ receptors are also coupled to Gs/Gq signaling which has been shown to be involved in cellular transformations such as cellular invasion (Faivre, K. et al., *Molecular Pharmacology* (2001), 60:363-372 and Regnauld, K. et al., *Oncogene* (2002), 21 (25):4020-4031), thereby suggesting that treatment of cancer can be effected with $A_{2b}$ antagonists.

Adenosine receptors have also been shown to exist on the retinas of various mammalian species including bovine, porcine, monkey, rat, guinea pig, mouse, rabbit and human (See, Blazynski et al., *Discrete Distributions of Adenosine Receptors in Mammalian Retina, Journal of Neurochemistry*, volume 54, pages 648-655 (1990); Woods et al., *Characterization of Adenosine $A_1$-Receptor Binding Sites in Bovine Retinal Membranes, Experimental Eye Research*, volume 53, pages 325-331 (1991); and Braas et al., *Endogenous adenosine and adenosine receptors localized to ganglion cells of the retina, Proceedings of the National Academy of Science*, volume 84, pages 3906-3910 (1987)). Recently, Williams reported the observation of adenosine transport sites in a cultured human retinal cell line (Williams et al., *Nucleoside Transport Sites in a Cultured Human Retinal Cell Line Established By SV-40 T Antigen Gene, Current Eye Research*, volume 13, pages 109-118 (1994)).

Compounds which regulate the uptake of adenosine have previously been suggested as potential therapeutic agents for the treatment of retinal and optic nerve head damage. In U.S. Pat. No. 5,780,450 to Shade, Shade discusses the use of adenosine uptake inhibitors for treating eye disorders. Shade does not disclose the use of specific $A_3$ receptor inhibitors. The entire contents of U.S. Pat. No. 5,780,450 are hereby incorporated herein by reference.

Compounds specific to the adenosine $A_1$, $A_{2a}$ and $A_3$ receptors and their uses thereof have been previously disclosed in PCT International Publication Nos. WO 99/62518 and WO 01/39777 A1. The entire contents of PCT International Publication Nos. WO 99/62518 and WO 01/39777 A1 are hereby incorporated herein by reference.

Additional adenosine receptor antagonists are needed as pharmacological tools and are of considerable interest as drugs for the above-referenced disease states and/or conditions.

SUMMARY OF THE INVENTION

The subject invention provides compounds having the structure:

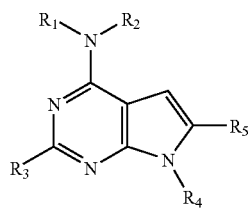

wherein, $R_1$ is a substituted or unsubstituted alkyl, wherein the substituent is hydroxyl, dihydroxy, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$;

$R_2$ is hydrogen or a substituted or unsubstituted alkyl, wherein the substituent is hydroxyl, dihydroxy, carboxyl, —C(=O)NR$_a$R$_b$, NR$_a$R$_b$, —NR$_a$C(=O)NR$_a$R$_b$, NR$_a$C(=O)OR$_a$, OC(=O)NR$_a$R$_b$, or —NHC(=O) R$_a$, or $R_1$, $R_2$ and N together form a substituted piperazine, substituted azetidine ring, or a pyrrolidine ring substituted with —(CH$_2$)$_2$OH or —CH$_2$C(=O)OH;

$R_3$ is a substituted or unsubstituted phenyl or a 5-6 membered heteroaryl ring, wherein the substituent is halogen, hydroxyl, cyano, (C$_1$-C$_{15}$)alkyl, (C$_1$-C$_{15}$)alkoxy, or —NR$_a$R$_b$;

$R_4$ is hydrogen or substituted or unsubstituted (C$_1$-C$_{15}$) alkyl;

$R_5$ is —(CH$_2$)$_m$OR$_6$, —CHNOR$_7$, —C(=O)NR$_8$R$_9$, —(CH$_2$)$_m$C(=O)OR$_{10}$, —(CH$_2$)$_k$C(=O)NR$_{11}$R$_{12}$;

wherein $R_6$ is a substituted or unsubstituted (C$_1$-C$_{30}$) alkyl, (C$_3$-C$_{10}$)cycloalkyl, or an aryl, heteroaryl or 4-8 membered heterocyclic ring;

$R_7$ is hydrogen, or a substituted or unsubstituted (C$_1$-C$_{30}$)alkyl, (C$_1$-C$_{30}$)alkylaryl;

$R_8$ and $R_9$ are each independently hydrogen, or a substituted or unsubstituted (C$_1$-C$_{30}$)alkyl, (C$_1$-C$_{30}$)alkylaryl, (C$_1$-C$_{30}$)alkylamino, (C$_1$-C$_{30}$)alkoxy, or a saturated or unsaturated, monocyclic or bicyclic, carbocyclic or heterocyclic ring, or $R_8$, N, and $R_9$ together form a substituted or unsubstituted 4-8 membered heterocyclic ring;

$R_{10}$ is hydrogen or a substituted or unsubstituted (C$_1$-C$_{30}$)alkyl, (C$_3$-C$_{10}$)cycloalkyl, or an aryl, heteroaryl or heterocyclic ring;

$R_{11}$, N and $R_{12}$ together form a 4-8 membered heterocyclic ring;

$R_a$ and $R_b$ are each independently hydrogen or alkyl;

m is 0, 1, 2 or 3; and k is 1, 2 or 3, or a specific enantiomer thereof, or a specific tautomer thereof, or a pharmaceutically acceptable salt thereof.

The subject invention also provides compounds having the structure:

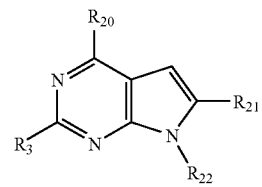

wherein $R_3$ is a substituted or unsubstituted 4-10 membered aryl, heteroaryl or heterocyclic ring;

$R_{20}$ is halogen or —NH(CHR$_{20}$')$_n$NHC(=O)CH$_3$, where $R_{20}$' is H, OH, alkyl, hydroxyalkyl, cycloalkyl, heteroalkyl, or amino;

$R_{21}$ is H or —C(=O)OH;

$R_{22}$ is H or SO$_2$Ph; and n is 2, 3, 4 or 5;

wherein when $R_{20}$ is —NH(CHR$_{20}$')$_n$NHC(=O)CH$_3$, $R_{21}$ is —C(=O)OH.

The subject invention also provides a method for treating a disease associated with the A$_{2b}$ adenosine receptor in a subject in need of such treatment comprising administering to the subject a therapeutically effective amount of the compounds of Structure I so as to thereby treat the disease associated with the A$_{2b}$ adenosine receptor in the subject, wherein the disease associated with the A$_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

DETAILED DESCRIPTION

The subject invention provides compounds having the structure:

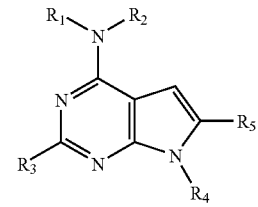

wherein, $R_1$ is a substituted or unsubstituted alkyl, wherein the substituent is hydroxyl, dihydroxy, carboxyl, —C(=O)NR$_a$R$_b$, —NR$_a$R$_b$, —NR$_a$C(=O)NR$_a$R$_b$, —NR$_a$C(=O)O R$_a$, —OC(=O)NR$_a$R$_b$, or —NHC(=O) R$_a$;

R₂ is hydrogen or a substituted or unsubstituted alkyl, wherein the substituent is hydroxyl, dihydroxy, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$, or R₁, R₂ and N together form a substituted piperazine, substituted azetidine ring, or a pyrrolidine ring substituted with —(CH₂)₂OH or —CH₂C(=O)OH;

R₃ is a substituted or unsubstituted phenyl or a 5-6 membered heteroaryl ring, wherein the substituent is halogen, hydroxyl, cyano, (C₁-C₁₅)alkyl, (C₁-C₁₅)alkoxy, or —NR$_a$R$_b$;

R₄ is hydrogen or substituted or unsubstituted (C₁-C₁₅) alkyl;

R₅ is —(CH₂)$_m$OR₆, —CHNOR₇, —C(=O)NR₈R₉, —(CH₂)$_m$C(=O)OR₁₀, —(CH₂)$_k$C(=O)NR₁₁R₁₂;

wherein R₆ is a substituted or unsubstituted (C₁-C₃₀) alkyl,
(C₃-C₁₀)cycloalkyl, or an aryl, heteroaryl or 4-8 membered heterocyclic ring;

R₇ is hydrogen, or a substituted or unsubstituted (C₁-C₃₀)alkyl, (C₁-C₃₀)alkylaryl;

R₈ and R₉ are each independently hydrogen, or a substituted or unsubstituted (C₁-C₃₀)alkyl, (C₁-C₃₀) alkylaryl, (C₁-C₃₀)alkylamino, (C₁-C₃₀)alkoxy, or a saturated or unsaturated, monocyclic or bicyclic, carbocyclic or heterocyclic ring, or R₈, N, and R₉ together form a substituted or unsubstituted 4-8 membered heterocyclic ring;

R₁₀ is hydrogen or a substituted or unsubstituted (C₁-C₃₀)alkyl,
(C₃-C₁₀)cycloalkyl, or an aryl, heteroaryl or heterocyclic ring;

R₁₁, N and R₁₂ together form a 4-8 membered heterocyclic ring;

R$_a$ and R$_b$ are each independently hydrogen or alkyl;
is 0, 1, 2 or 3; and
k is 1, 2 or 3, or a specific enantiomer thereof, or a specific tautomer thereof, or a pharmaceutically acceptable salt thereof.

In a further embodiment of the above compounds, wherein any heterocyclic or heteroaryl ring, if present, is a piperazine, piperidine, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydro-1H-isoquinoline, dihydro-2H-pyridine, 1,3,4,9-tetrahydro-β-carboline, 2,8-diazaspiro[4.5]decane, 2,5-diazabicyclo[2.2.1]heptane, or [1,4]diazepane ring, dihydroisoquinoline, indole, isoindole, triazaspiro[4.5]decane, morpholine, furan or an isothiazole ring In a further embodiment of Structure I, the compounds have the structure:

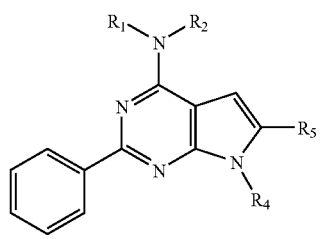

wherein,

R₁ is hydrogen or methyl;

R₂ is —(CH₂)₂NHC(=O)CH₃, —(CH₂)₂OH, —(CH₂)₂ NHC(=O)NHCH₃, —CH₂CH(CH₃)OH, —CH(CH₂OH)CH₂CH(CH₃)₂, —CH(CH₂OH)₂, —CH(CH₃)CH₂OH, —CH(CH₂OH)CH(CH₃)₂, —(CH₂)₃ OH, —(CH₂)₂NH₂, —(CH₂)₂NHC(=O)N(CH₃)₂, —(CH₂)₂C(=O)NH₂, —CH₂C(=O)NH₂, —CH₃, —CH₂CH(OH)CH₂OH, —CH₂C(=O)(NC₅H₈[OCH₃])(C₆H₄Cl) or

R₁, R₂ and N together form a pyrrolidine ring substituted with —(CH₂)₂OH or —CH₂C(=O)OH, a piperazine ring substituted with —C(=O)CH₃, or an azetidine ring substituted with —OH or CH₂OH;

R₄ is hydrogen, or methyl; and

R₅ is —CH₂O(C₆H₅), —CH₂O(C₆H₄Cl), —CH₂O(C₆H₄Br), —CH₂O(C₆H₄F), —CHNOCH₂(C₆H₅), —CH₂O(C₆H₄[OCH₃]), —CH₂O(C₆H₄[CH₃]), —CHNOC(CH₃)₃, —CH₂O(C₅H₄N), —CH₂(NC₅H₄[O]), —CH₂O(C₆H₄[NH₂]), —CH₂O(C₅H₉N)SO₂(C₆H₅), —CH₂O(C₅H₉N)SO₂CH₂(C₆H₅), —CH₂O(C₆H₄[NHC(=O)CH₃]), —CH₂O(C₅H₉N)(CH₂)$_p$(C₆H₅), —CH₂O(C₅H₉N)(CH₂)$_p$(C₆H₄Br), —CH₂O(C₅H₉N)(CH₂)$_p$(C₆H₄Cl), —CH₂O(C₅H₉N)(CH₂)$_p$(C₆H₄[OCH₃]), —CH₂O(C₅H₉N)(CH₂)$_p$(C₆H₃Cl), —CH₂O(C₅H₉N)(CH₂)$_p$(C₆H₄[CF₃]), —CH₂O(CH₂)₂CH(OH)(C₆H₅), —CH₂NOCH₂(C₆H₅), —CH₂NOC(CH₃)₃, —C(=O)(NC₄H₈O), —C(=O)(NC₄H₈N)CH₂CHCH(C₆H₅), —C(=O)(NC₄H₈N)(CH₂)$_p$(C₆H₅), —C(=O)(NC₄H₈N)(CH₂)₂O(C₆H₄Cl), —C(=O)(NC₅H₈[CN])(C₆H₅), —C(=O)(NC₄H₈N)CH₂C₂(C₆H₅), —C(=O)(NC₄(CH₃)₂N)(CH₂)$_p$(C₆H₅), —C(=O)(NC₅H₉)CH(OH)(C₆H₄F), —C(=O)(NC₄(CH₃)₂NH), —C(=O)(NC₅H₈[CH₃])(C₆H₅), —C(=O)(NC₄H₈N)(C₅H₃N[CF₃]), —C(=O)(NC₅H₈[OCH₃])(C₆H₄[C₆H₄Cl]), —C(=O)(NC₅H₈[OCH₃])(C₆H₄Cl), —C(=O)(NC₅H₈[OH])(C₆H₄Cl), —C(=O)(NC₅H₈[OH])(C₆H₄[C₆H₄Cl]), —C(=O)(NC₅H₈[OCH₃])(C₆H₄F), —C(=O)NH(C₅H₉N)(CH₂)$_p$(C₆H₅), —C(=O)(NC₅H₉)(CH₂)$_p$(C₆H₅), —C(O)(NC₅H₉)(NC₄H₈), —C(=O)(NC₄H₈N)(CH₂)$_p$(C₆H₁₁), —C(=O)(NC₄H₈N)(CH₂)$_p$CH(CH₃)₂, —C(=O)(NC₅H₉[NC₅H₁₀]), —C(=O)(NC₄H₈N)(C₅H₉), —C(O)(NC₅H₉)NH₂, —C(=O)(NC₅H₈[C(=O)CH₃])(C₆H₅), —C(=O)(NC₅H₇)C₂(C₆H₅), —C(=O)(NC₅H₉)(C(CH₃)₃, —C(=O)(NC₄H₈N)CH₂C₂(C₆H₄[CN]), —C(=O)(NC₅H₈[C(=O)OCH₃])(C₆H₅), —C(=O)(NC₅H₈[C(=O)O(CH₂)$_p$CH₃])(C₆H₅), —C(=O)(NC₅H₈[C(=O)NH₂])(C₆H₅), —C(=O)(NC₅H₈[C(=O)NHCH₃])(C₆H₅), —C(=O)(NC₅H₈[NHC(=O)CH₃])(C₆H₅), —C(=O)(NC₅H₈[C(=O)N(CH₃)₂])(C₆H₅), —C(=O)(NC₅H₈[C(=O)NHCH₂(C₆H₅)])(C₆H₅), —C(=O)(NC₅H₈[C(=O)NH(CH₂)$_p$CH₃])(C₆H₅), —C(=O)(NC₅H₈[C(=O)N{(CH₂)$_p$CH₃}₂])(C₆H₅), —C(=O)(NC₅H₈[C(=O)(NC₃H₆)])(C₆H₅), —C(=O)(NC₅H₈[C(=O)OC(CH₃)₃])(C₆H₅), —C(=O)(NC₅H₈[C(=O)NH₂])(NHCH₂CH₃), —C(=O)(NC₅H₈[OCH₃])(C₆H₄[OCH₃]), —C(=O)(NC₅H₈[C(=O)NH₂])(NC₄H₈), —C(=O)(NC₅H₇)(C₆H₄[OCH₃]), —C(=O)

(NC$_5$H$_8$[NH$_2$])(C$_6$H$_5$), —C(=O)(NC$_5$H$_8$[C(=O)H])(C$_6$H$_5$), —C(=O)(NC$_5$H$_8$[OCH$_3$])(CH$_2$)$_p$(C$_6$H$_5$), —C(=O)(NC$_5$H$_8$[OCH$_3$])(C$_6$H$_4$[CH$_3$]), —C(=O)(NC$_5$H$_8$[(CH$_2$)$_p$OCH$_3$])(C$_6$H$_5$), —C(=O)NH(C$_4$H$_7$N)(CH$_2$)$_p$(C$_6$H$_5$), —C(=O)(NC$_4$H$_8$N)(CH$_2$)$_p$(C$_6$H$_4$Cl), —C(=O)(NC$_4$H$_8$N)(CH$_2$)$_p$(C$_6$H$_4$[OCH$_3$]), —C(=O)NH(CH$_2$)$_p$(C$_6$H$_4$[C$_2$HSN$_2$]), —C(=O)(NC$_4$H$_8$N)C(=O)(CH$_2$)$_p$(C$_6$H$_4$Cl), —C(=O)(NC$_5$H$_9$)(C$_3$N$_2$H$_2$)(C$_6$H$_4$Cl), —C(=O)(NC$_4$H$_8$N)CH$_2$C(=O)N(CH$_3$)(C$_6$H$_5$), —C(=O)(NC$_4$H$_8$N)C(=O)O(CH$_2$)$_p$(C$_6$H$_5$), —C(=O)(NC$_5$H$_8$[C$_2$H$_3$N$_2$O])(C$_6$H$_5$), —C(=O)(NC5H$_9$)N(CH$_3$)(CH$_2$)$_p$(C$_6$H$_5$), —C(=O)(NC$_5$H$_9$)NH(CH$_2$)$_p$(C$_6$H$_5$), —C(=O)(NC$_5$H$_9$)NH(CH$_2$)$_p$(C$_6$H$_4$Cl), —C(=O)(NC$_5$H$_9$)NH(CH$_2$)$_p$(C$_3$N$_2$H$_3$), —C(=O)(NC$_5$H$_9$)NH(CH$_2$)$_p$(C$_5$H$_4$N), —C(=O)(NC$_5$H$_9$)NH(CH$_2$)$_p$(C$_6$H$_5$), —C(=O)(NC$_5$H9)N(CH$_3$)(CH$_2$)$_p$(C$_6$H$_5$), —C(=O)(NC$_5$H$_9$)NHCH(CH$_3$)(C$_6$H$_5$), —(CH$_2$)$_p$C(=O)(NC$_4$H$_8$N)(CH$_2$)$_p$(C$_6$H$_5$), —C(=O)NH(CH$_2$)$_p$(C$_6$H$_5$), —C(=O)NHCH[(CH$_2$)$_p$OH]$_2$—C(=O)NH(CH$_2$)$_p$(OH)(C$_6$H$_{10}$), —C(=O)NH(CH$_2$)$_p$(C$_6$H$_4$ {O[C$_6$H$_5$]}), —C(=O)(NC$_4$H$_7$)(CH$_2$)$_p$NH(C$_6$H$_5$), —C(=O)(NC$_4$H$_8$N)(CH$_2$)$_p$(C$_6$H$_4$)CF$_3$, —C(=O)(NC$_4$H$_8$N)(CH$_2$)$_p$(C$_6$H$_4$F), —C(=O)(NC$_4$H$_8$N)(CH$_2$)$_p$(C$_7$O$_2$H$_5$), —C(=O)(NC$_4$H$_8$N)(CH$_2$)$_p$(C$_6$H$_4$)CH$_3$, —C(=O)(NC$_4$H$_8$N)(CH$_2$)$_p$(C$_6$H$_4$Br), —C(=O)(NC$_4$H$_8$N)(CH$_2$)$_p$(C$_6$H$_3$Cl$_2$), —C(=O)(NC$_5$H oN)(CH$_2$)$_p$(C$_6$H$_5$), —C(=O)(NC$_4$H$_8$)(C$_6$H$_4$)NHC(=O)CH$_3$, —C(=O)(NC$_4$H$_8$N)(C$_6$H$_4$[CN]), —C(=O)(NC$_4$H$_8$N)(C$_6$H$_4$[N(CH$_3$)C(=O)CH$_3$]), —C(=O)(NC$_4$H$_8$N)(C$_6$H$_3$[(CH$_3$)$_2$]), —C(=O)(NC$_4$HgN)(C$_6$H$_4$Cl), —C(=O)(NC$_4$H$_8$N)(C$_6$H$_3$[(OCH$_3$)$_2$]), —C(=O)(NC$_4$H$_8$N)(C$_6$H$_3$Cl[(OCH$_3$)]), —C(=O)(NC$_5$H$_9$N)(CH$_2$)$_p$O(C$_6$H$_4$Cl), —C(=O)(NC$_5$H$_8$N)(CH$_2$)$_p$(C$_6$H$_5$), —C(=O)(NC$_5$H$_9$)(CH$_2$)PO(C$_6$H$_5$), —C(=O)(NC$_5$H$_9$)(CH$_2$)$_p$O(C$_6$H$_4$[CN]), —C(=O)(NC$_4$H$_8$N)(C$_6$H$_4$[NO$_2$]), —C(=O)(NC$_4$H$_8$N)(C$_6$H$_4$[C(=O)OCH$_3$]), —C(=O)(NC$_4$H$_8$N)(C$_6$H$_4$[CH$_3$]), —C(=O)(NC$_5$H$_9$)(CH$_2$)$_p$O(C$_6$H$_3$Cl$_2$), —C(=O)(NC$_5$H$_9$)(CH$_2$)$_p$O(C6H3[CN]), —C(=O) (NC$_5$H$_9$[CN])(C$_6$H$_4$Cl), —C(=O)(NC$_5$H$_8$N)(C$_6$H$_4$[C(=O)NH$_2$]), —C(=O)(NC$_5$H$_8$[CN])(C$_6$H$_4$[OCH$_3$]), —C(=O)(NC$_5$H$_8$[CN])(C$_6$H$_4$Cl), —C(=O)(NC$_5$H$_8$[C(=O)(NC$_4$H$_8$)])(C$_6$H$_5$), —C(=O)(NC$_5$H$_8$[C(=O)(NC$_5$H$_{10}$)])(C$_6$H$_5$), —C(=O)(NCsH$_8$[C(=O)(NC$_4$H$_8$O)])(C$_6$H$_5$), —C(=O)(NC$_5$H$_8$[C(=O)NHC(CH$_3$)$_3$])(C$_6$H$_5$), —C(=O)(NC$_5$H$_8$[C(=O)(NC$_3$H$_6$)])(C$_6$H$_5$), —C(=O)(NC$_5$H$_8$[CH(CH$_3$)$_2$])(C$_6$H$_5$), —C(=O)(NC$_4$H$_8$N)CH$_2$C$_2$(C$_4$H$_3$S), —C(=O)(NC$_5$H$_8$[C(=O)OCH$_2$(C$_4$H$_7$)])(C$_6$H$_5$), —C(=O)(NC$_5$H$_8$ [OCH$_3$])(C$_6$H$_4$Cl), —C(=O)(NC$_5$H$_8$[OCH$_3$])(C$_6$H$_4$[CF$_3$]), —C(=O)(NC$_5$H$_8$[OCH$_3$])(C(CH$_3$)$_2$), —C(=O)(NC$_4$H$_8$N)(CH$_2$)$_p$(C$_6$H$_4$[CN]), —C(=O)(NC$_5$H$_8$)(C$_6$H$_5$)$_2$—CH$_2$—O—(CH$_2$)$_p$N(CH$_3$)CH$_2$CHCH(C$_6$H$_5$), or —CH$_2$—O—(CH$_2$)$_p$NH(CH$_2$)$_3$(C$_6$H$_5$);

wherein p is 0, 1, 2, 3 or 4, or a specific enantiomer thereof, or a specific tautomer thereof, or a pharmaceutically acceptable salt thereof.

In a further-embodiment, the subject invention provides compounds having the structure:

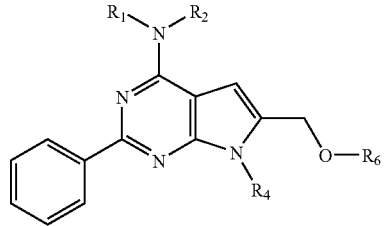

wherein, $R_1$, $R_2$ and N together form a substituted azetidine or piperazine ring;

$R_4$ is H; and $R_6$ is a substituted or unsubstituted aryl or heteroaryl ring.

In one embodiment, $R_1$, $R_2$ and N together form a substituted azetidine ring.

In another embodiment, $R_1$, $R_2$ and N together form a substituted piperazine ring.

In another embodiment of Structure I, the subject invention provides compounds having the structure:

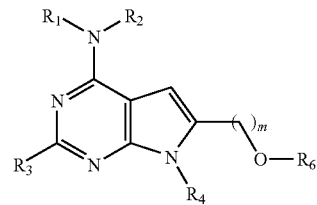

wherein, $R_6$ is a substituted or unsubstituted aryl or heteroaryl ring; and m is 0, 1, 2 or 3.

In one embodiment, $R_4$ is H.

In another embodiment, $R_3$ is substituted or unsubstituted phenyl.

In a further embodiment, $R_1$ is —(CH$_2$)$_2$NHC(=O)CH$_3$;

$R_2$ is hydrogen or methyl;

$R_4$ is hydrogen or methyl; and $R_6$ is substituted or unsubstituted phenyl or pyridine.

In a further embodiment, $R_2$ is H.

In a further embodiment, $R_6$ is substituted phenyl.

In another embodiment, the compound is selected from the group consisting of:

N-{2-[6-(4-Fluorophenoxymethyl)-2-phenyl-7H-pyrrolo[2,3-d]pyrimidin-4-ylamino]-ethyl}-acetamide;

N-{2-[6-(4-Methoxyphenoxymethyl)-2-phenyl-7H-pyrrolo[2,3-d]pyrimidin-4-ylamino]-ethyl}-acetamide;

N-[2-(2-Phenyl-6-m-tolyloxymethyl-7H-pyrrolo[2,3-d]pyrimidin-4-ylamino)-ethyl]-acetamide;

N-{2-[6-(3-Bromophenoxymethyl)-2-phenyl-7H-pyrrolo[2,3-d]pyrimidin-4-ylamino]-ethyl}-acetamide;

3-[4-(2-Acetylaminoethylamino)-2-phenyl-7H-pyrrolo[2,3-d]pyrimidin-6-ylmethoxy]-benzoic acid methyl ester;

N-{2-[6-(4-Chlorophenoxymethyl)-2-phenyl-7H-pyrrolo[2,3-d]pyrimidin-4-ylamino]-ethyl}-acetamide; and N-{2-[6-(3-Methoxyphenoxymethyl)-2-phenyl-7H-pyrrolo[2,3-d]pyrimidin-4-ylamino]-ethyl}-acetamide.

In a further embodiment of Structure I, the subject invention provides compounds having the structure:

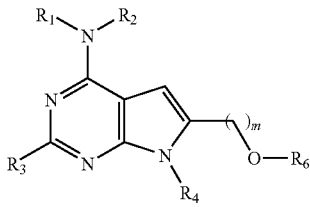

wherein,
$R_6$ is a substituted or unsubstituted ($C_1$-$C_{30}$)alkyl or ($C_3$-$C_{10}$)cycloalkyl;
m is 0, 1, 2 or 3.

In one embodiment, $R_4$ is H;
In another embodiment, $R_3$ is substituted or unsubstituted phenyl; in a further embodiment,
$R_1$ is —$(CH_2)_2$NHC(=O)$CH_3$;
$R_2$ is hydrogen or methyl;
$R_4$ is hydrogen or methyl; and
$R_6$ is substituted or unsubstituted cyclopentyl.

In a further embodiment, $R_2$ is H.

In another embodiment, the compound is N-(2-(6-{2-[Methyl-(3-phenylallyl)amino]ethoxymethyl}-2-phenyl-7H-pyrrolo[2,3-d]pyrimidin-4-ylamino}ethyl]acetamide.

In a further embodiment of Structure I, the subject invention provides compounds having the structure:

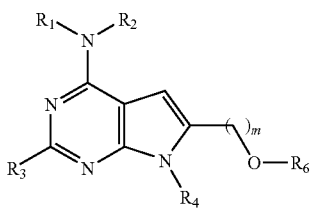

wherein,
$R_6$ is a substituted or unsubstituted 4-8 membered heterocyclic ring; and
m is 0, 1, 2 or 3.

In one embodiment, $R_4$ is H.
In a further embodiment, $R_3$ is substituted or unsubstituted phenyl;
In a further embodiment,
$R_1$ is —$(CH_2)_2$NHC(=O)$CH_3$;
$R_2$ is hydrogen or methyl;
$R_4$ is hydrogen or methyl; and
$R_6$ is substituted or unsubstituted piperidine.

In a further embodiment, $R_2$ is H.

In another embodiment, the compound is selected from the group consisting of:
N-(2-{6-[1-(Benzenesulfonyl)piperidin-4-yloxymethyl]-2-phenyl-7H-pyrrolo[2,3-d]pyrimidin-4-ylamino}ethyl)acetamide;
N-{2-[6-(1-Phenethylpiperidin-4-yloxymethyl)-2-phenyl-7H-pyrrolo[2,3-d]-pyrimidin-4-ylamino]ethyl}acetamide;
N-[2-{6-[1-(3-Phenylpropyl)piperidin-4-yloxymethyl]-2-phenyl-7H-pyrrolo[2,3-d]pyrimidin-4-ylamino}ethyl]acetamide;
N-(2-{6-[1-(4-Bromobenzyl)piperidin-4-yloxymethyl]-2-phenyl-7H-pyrrolo[2,3-d]pyrimidin-4-ylamino}ethyl)acetamide;
N-[2-(6-{1-[2-(2-Chlorophenyl)ethyl]piperidin-4-yloxymethyl}-2-phenyl-7H-pyrrolo[2,3-d]pyrimidin-4-ylamino)ethyl]acetamide;
N-[2-(6-{1-[2-(3-Chlorophenyl)ethyl]piperidin-4-yloxymethyl}-2-phenyl-7H-pyrrolo[2,3-d]pyrimidin-4-ylamino)ethyl]acetamide;
N-(2-{6-[1-(3-Chlorobenzyl)piperidin-4-yloxymethyl]-2-phenyl-7H-pyrrolo[2,3-d]pyrimidin-4-ylamino}ethyl)acetamide;
N-[2-(6-{1-[2-(4-Chlorophenyl)ethyl]piperidin-4-yloxymethyl}-2-phenyl-7H-pyrrolo[2,3-d]pyrimidin-4-ylamino)ethyl]acetamide;
N-[2-(6-{1-[2-(2-Methoxyphenyl)ethyl]piperidin-4-yloxymethyl}-2-phenyl-7H-pyrrolo[2,3-d]pyrimidin-4-ylamino)ethyl]acetamide;
N-[2-(6-{1-[2-(3-Methoxyphenyl)ethyl]piperidin-4-yloxymethyl}-2-phenyl-7H-pyrrolo[2,3-d]pyrimidin-4-ylamino)ethyl]acetamide;
N-[2-(6-{1-[2-(4-Methoxyphenyl)ethyl]piperidin-4-yloxymethyl}-2-phenyl-7H-pyrrolo[2,3-d]pyrimidin-4-ylamino)ethyl]acetamide;
N-[2-(6-{1-[2-(4-Fluorophenyl)ethyl]piperidin-4-yloxymethyl}-2-phenyl-7H-pyrrolo[2,3-d]pyrimidin-4-ylamino)ethyl]acetamide;
N-[2-(6-{1-[2-(2-Chloro-4-fluorophenyl)ethyl]piperidin-4-yloxymethyl}-2-phenyl-7H-pyrrolo[2,3-d]pyrimidin-4-ylamino)ethyl]acetamide;
N-[2-(6-{1-[2-(2-Chloro-6-fluorophenyl)ethyl]piperidin-4-yloxymethyl}-2-phenyl-7H-pyrrolo[2,3-d]pyrimidin-4-ylamino)ethyl]acetamide;
N-[2-(6-{1-[2-(2-Trifluoromethylphenyl)ethyl]piperidin-4-yloxymethyl}-2-phenyl-7H-pyrrolo[2,3-d]pyrimidin-4-ylamino)ethyl]acetamide; and
N-[2-(6-{1-[2-(2-Bromophenyl)ethyl]piperidin-4-yloxymethyl}-2-phenyl-7H-pyrrolo[2,3-d]pyrimidin-4-ylamino)ethyl]acetamide.

In a further embodiment of Structure I, the subject invention provides compounds having the structure:

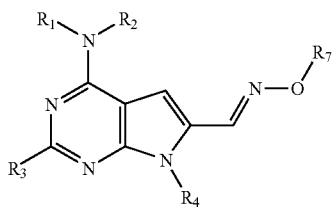

wherein,
$R_7$ is hydrogen, or a substituted or unsubstituted ($C_1$-$C_{30}$) alkyl, ($C_1$-$C_{30}$)alkylaryl.

In one embodiment, $R_3$ is substituted or unsubstituted phenyl.

In a further embodiment, $R_4$ is hydrogen.

In a further embodiment of Structure I, the subject invention provides compounds having the structure:

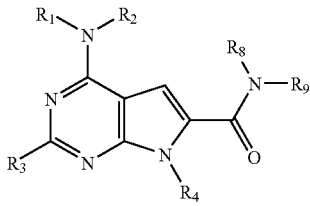

wherein, $R_8$; N, and $R_9$ together form a substituted or unsubstituted 4-8 membered heterocyclic ring.

In one embodiment, $R_8NR_9$ together form a substituted or unsubstituted azetidine, pyrrolidine, piperazine, piperidine, morpholine, azocane, dihydro-1H-isoquinoline, 1,2,3,6-tetrahydropyridine, dihydro-2H-pyridine, 1,3,4,9-tetrahydro-β-carboline, 1,3,8-triazaspiro[4.5]decane, 2,8-diazaspiro[4.5]decane, 2,5-diazabicyclo[2.2.1]heptane, 1,4-dioxa-8-azaspiro[4.5]decane, or [1.4]diazepane ring.

In a further embodiment, $R_8NR_9$ together form a substituted or unsubstituted azetidine, pyrrolidine, piperazine, piperidine or [1.4]diazepane ring.

In another embodiment, the ring formed by $R_8NR_9$ is substituted with one or more aryl, heteroaryl, $(C_1-C_{30})$alkylaryl, $(C_1-C_{30})$alkylheteroaryl, $(C_1-C_{30})$alkenylaryl, $(C_1-C_{30})$alkenylheteroaryl, $(C_1-C_{30})$alkynylaryl, or $(C_1-C_{30})$alkynylheteroaryl moiety, which itself can be substituted.

In another embodiment, $R_3$ is a substituted or unsubstituted phenyl.

In a further embodiment, $R_1$ is $-(CH_2)_2NHC(=O)CH_3$;

$R_2$ is hydrogen or methyl; and $R_4$ is hydrogen or methyl.

In another embodiment, the compound is selected from the group consisting of:

N-(2-{2-Phenyl-6-[4-(3-phenylallyl)-piperazine-1-carbonyl]-7H-pyrrolo[2,3-d]pyrimidin-4-ylamino}-ethyl)-acetamide;

N-{2-[6-(4-Hydroxy-4-isopropylpiperidine-1-carbonyl)-2-phenyl-7H-pyrrolo[2,3-d]pyrimidin-4-ylamino]-ethyl}-acetamide;

N-(2-{2-Phenyl-6-[4-(3-phenylpropyl)-piperazine-1-carbonyl]-7H-pyrrolo[2,3-d]pyrimidin-4-ylamino}-ethyl)-acetamide;

N-{2-[6-(4-Phenethylpiperazine-1-carbonyl)-2-phenyl-7H-pyrrolo[2,3-d]pyrimidin-4-ylamino]-ethyl}-acetamide;

2-{2-Phenyl-6-[4-(3-phenylpropyl)-piperazine-1-carbonyl]-7H-pyrrolo[2,3-d]pyrimidin-4-ylamino}-acetamide;

N-[2-(6-{4-[2-(4-Chlorophenoxy)-ethyl]-piperazine-1-carbonyl}-2-phenyl-7H-pyrrolo[2,3-d]pyrimidin-4-ylamino)-ethyl]-acetamide;

N-{2-[6-(4-Cyano-4-phenylpiperidine-1-carbonyl)-2-phenyl-7H-pyrrolo[2,3-d]pyrimidin-4-ylamino]-ethyl}-acetamide;

N-(2-{2-Phenyl-6-[4-(3-phenylprop-2-ynyl)-piperazine-1-carbonyl]-7H-pyrrolo[2,3-d]pyrimidin-4-ylamino}-ethyl)-acetamide;

N-(2-{6-[cis-3,5-Dimethyl-4-(3-phenylpropyl)-piperazine-1-carbonyl]-2-phenyl-7H-pyrrolo[2,3-d]pyrimidin-4-ylamino}-ethyl)-acetamide;

N-{2-[6-(4,4-Diphenylpiperidine-1-carbonyl)-2-phenyl-7H-pyrrolo[2,3-d]pyrimidin-4-ylamino]-ethyl}-acetamide;

N-{2-[6-(3,3-Diphenylpiperidine-1-carbonyl)-2-phenyl-7H-pyrrolo[2,3-d]pyrimidin-4-ylamino]-ethyl}-acetamide;

N-{2-[6-(4-Methoxy-4-phenylpiperidine-1-carbonyl)-2-phenyl-7H-pyrrolo[2,3-d]pyrimidin-4-ylamino]-ethyl}-acetamide;

N-(2-{6-[trans-2,5-Dimethyl-4-(3-phenylpropyl)-piperazine-1-carbonyl]-2-phenyl-7H-pyrrolo[2,3-d]pyrimidin-4-ylamino}-ethyl)-acetamide;

N-{2-[6-(trans-2,5-Dimethylpiperazine-1-carbonyl)-2-phenyl-7H-pyrrolo[2,3-d]pyrimidin-4-ylamino]-ethyl}-acetamide;

N-{2-[6-(4-Benzyl-cis-3,5-dimethylpiperazine-1-carbonyl)-2-phenyl-7H-pyrrolo[2,3-d]pyrimidin-4-ylamino]-ethyl}-acetamide;

N-{2-[6-(cis-3,5-Dimethyl-4-phenethylpiperazine-1-carbonyl)-2-phenyl-7H-pyrrolo[2,3-d]pyrimidin-4-ylamino]-ethyl}-acetamide;

N-{2-[6-(3-Methyl-3-phenylpiperidine-1-carbonyl)-2-phenyl-7H-pyrrolo[2,3-d]-pyrimidin-4-ylamino]-ethyl}-acetamide;

N-(2-{2-Phenyl-6-[4-(5-trifluoromethylpyridin-2-yl)-piperazine-1-carbonyl]-7H-pyrrolo[2,3-d]pyrimidin-4-ylamino}-ethyl)-acetamide;

N-(2-{6-[4-(2'-Chlorobiphenyl-2-yl)-4-methoxypiperidine-1-carbonyl]-2-phenyl-7H-pyrrolo[2,3-d]pyrimidin-4-ylamino}-ethyl)-acetamide;

N-(2-{6-[4-(2-Chlorophenyl)-4-methoxypiperidine-1-carbonyl]-2-phenyl-7H-pyrrolo[2,3-d]pyrimidin-4-ylamino}-ethyl)-acetamide;

N-(2-{6-[4-(2-Chlorophenyl)-4-hydroxypiperidine-1-carbonyl]-2-phenyl-7H-pyrrolo[2,3-d]pyrimidin-4-ylamino}-ethyl)-acetamide;

N-(2-{6-[4-(2'-Chlorobiphenyl-2-yl)-4-hydroxypiperidine-1-carbonyl]-2-phenyl-7H-pyrrolo[2,3-d]pyrimidin-4-yl amino}-ethyl)-acetamide;

N-(2-{6-[4-(4-Fluorophenyl)-4-methoxypiperidine-1-carbonyl]-2-phenyl-7H-pyrrolo[2,3-d]pyrimidin-4-ylamino}-ethyl)-acetamide;

N-(2-{2-Phenyl-6-[4-(4-phenylbutyl)-piperazine-1-carbonyl]-7H-pyrrolo[2,3-d]pyrimidin-4-ylamino}-ethyl)-acetamide;

N-(2-{2-Phenyl-6-[4-(3-phenylpropyl)-piperidine-1-carbonyl]-7H-pyrrolo[2,3-d]pyrimidin-4-ylamino}-ethyl)-acetamide;

N-{2-[2-Phenyl-6-(4-pyrrolidin-1-yl-piperidine-1-carbonyl)-7H-pyrrolo[2,3-d]pyrimidin-4-ylamino]-ethyl}-acetamide;

N-(2-{6-[4-(3-Cyclohexylpropyl)-piperazine-1-carbonyl]-2-phenyl-7H-pyrrolo[2,3-d]pyrimidin-4-ylamino}-ethyl)-acetamide;

N-(2-{6-[4-(4-Methylpentyl)-piperazine-1-carbonyl]-2-phenyl-7H-pyrrolo[2,3-d]pyrimidin-4-ylamino}-ethyl)-acetamide;

N-{2-[6-([1,4']Bipiperidinyl-1'-carbonyl)-2-phenyl-7H-pyrrolo[2,3-d]pyrimidin-4-ylamino]-ethyl}-acetamide;

N-{2-[6-(4-Cyclopentylpiperazine-1-carbonyl)-2-phenyl-7H-pyrrolo[2,3-d]-pyrimidin-4-ylamino]-ethyl}-acetamide;

N-{2-[6-(4-Aminopiperidine-1-carbonyl)-2-phenyl-7H-pyrrolo[2,3-d]pyrimidin-4-ylamino]-ethyl}-acetamide;

N-{2-[6-(4-Acetyl-4-phenylpiperidine-1-carbonyl)-2-phenyl-7H-pyrrolo[2,3-d]pyrimidin-4-ylamino]-ethyl}-acetamide;

N-(2-{6-[4-(2-Cyclohexylethyl)-piperazine-1-carbonyl]-2-phenyl-7H-pyrrolo[2,3-d]pyrimidin-4-ylamino}-ethyl)-acetamide;

N-{2-[2-Phenyl-6-(4-phenylethynyl-3,6-dihydro-2H-pyridine-1-carbonyl)-7H-pyrrolo[2,3-d]pyrimidin-4-ylamino]-ethyl}-acetamide;

N-{2-[6-(4-tert-Butylpiperidine-1-carbonyl)-2-phenyl-7H-pyrrolo[2,3-d]pyrimidin-4-ylamino]-ethyl}-acetamide;

N-{2-[6-(4-Phenethylpiperidine-1-carbonyl)-2-phenyl-7H-pyrrolo[2,3-d]pyrimidin-4-ylamino]-ethyl}-acetamide;

N-[2-(6-{4-[3-(2-Cyanophenyl)-prop-2-ynyl]-piperazine-1-carbonyl}-2-phenyl-7H-pyrrolo[2,3-d]pyrimidin-4-ylamino)-ethyl]-acetamide;

N-[2-(6-{4-[3-(3-Cyanophenyl)-prop-2-ynyl]-piperazine-1-carbonyl}-2-phenyl-7H-pyrrolo[2,3-d]pyrimidin-4-ylamino)-ethyl]-acetamide;

N-[2-(6-{4-[3-(4-Cyanophenyl)-prop-2-ynyl]-piperazine-1-carbonyl}-2-phenyl-7H-pyrrolo[2,3-d]pyrimidin-4-ylamino)-ethyl]-acetamide;

1-[4-(2-Acetylaminoethylamino)-2-phenyl-7H-pyrrolo[2,3-d]pyrimidine-6-carbonyl]-4-phenylpiperidine-4-carboxylic acid methyl ester;

N-(2-{6-[4-(1-Hydroxyethyl)-4-phenylpiperidine-1-carbonyl]-2-phenyl-7H-pyrrolo[2,3-d]pyrimidin-4-ylamino}-ethyl)-acetamide;

N-[2-(6-{4-[3-(4-Cyanophenyl)-propyl]-piperazine-1-carbonyl}-2-phenyl-7H-pyrrolo[2,3-d]pyrimidin-4-ylamino)-ethyl]-acetamide;

1-[4-(2-Acetylaminoethylamino)-2-phenyl-7H-pyrrolo[2,3-d]pyrimidine-6-carbonyl]-4-phenylpiperidine-4-carboxylic acid ethyl ester;

1-[4-(2-Acetylaminoethylamino)-2-phenyl-7H-pyrrolo[2,3-d]pyrimidine-6-carbonyl]-4-phenylpiperidine-4-carboxylic acid amide;

1-[4-(2-Acetylaminoethylamino)-2-phenyl-7H-pyrrolo[2,3-d]pyrimidine-6-carbonyl]-4-phenylpiperidine-4-carboxylic acid methylamide;

1-[4-(2-Acetylaminoethylamino)-2-phenyl-7H-pyrrolo[2,3-d]pyrimidine-6-carbonyl]-4-phenylpiperidine-4-carboxylic acid dimethylamide;

1-[4-(2-Acetylaminoethylamino)-2-phenyl-7H-pyrrolo[2,3-d]pyrimidine-6-carbonyl]-4-phenylpiperidine-4-carboxylic acid benzylamide;

1-[4-(2-Acetylaminoethylamino)-2-phenyl-7H-pyrrolo[2,3-d]pyrimidine-6-carbonyl]-4-phenylpiperidine-4-carboxylic acid ethylamide;

1-[4-(2-Acetylaminoethylamino)-2-phenyl-7H-pyrrolo[2,3-d]pyrimidine-6-carbonyl]-4-phenylpiperidine-4-carboxylic acid diethylamide;

N-(2-{6-[4-(Azetidine-1-carbonyl)-4-phenylpiperidine-1-carbonyl]-2-phenyl-7H-pyrrolo[2,3-d]pyrimidin-4-ylamino}-ethyl)-acetamide;

N-(2-{2-Phenyl-6-[4-phenyl-4-(pyrrolidine-1-carbonyl)-piperidine-1-carbonyl]-7H-pyrrolo[2,3-d]pyrimidin-4-ylamino}-ethyl)-acetamide;

N-(2-{2-Phenyl-6-[4-phenyl-4-(piperidine-1-carbonyl)-piperidine-1-carbonyl]-7H-pyrrolo[2,3-d]pyrimidin-4-ylamino}-ethyl)-acetamide;

N-(2-{6-[4-(Morpholine-4-carbonyl)-4-phenylpiperidine-1-carbonyl]-2-phenyl-7H-pyrrolo[2,3-d]pyrimidin-4-ylamino}-ethyl)-acetamide;

1-[4-(2-Acetylaminoethylamino)-2-phenyl-7H-pyrrolo[2,3-d]pyrimidine-6-carbonyl]-4-phenylpiperidine-4-carboxylic acid tert-butylamide;

N-{2-[6-(4-Isopropyl-4-phenylpiperidine-1-carbonyl)-2-phenyl-7H-pyrrolo[2,3-d]pyrimidin-4-ylamino]-ethyl}-acetamide;

N-(2-{2-Phenyl-6-[4-(3-thiophen-2-yl-prop-2-ynyl)-piperazine-1-carbonyl]-7H-pyrrolo[2,3-d]pyrimidin-4-ylamino}-ethyl)-acetamide;

1-[4-(2-Acetylaminoethylamino)-2-phenyl-7H-pyrrolo[2,3-d]pyrimidine-6-carbonyl]-4-phenylpiperidine-4-carboxylic acid cyclobutylmethyl ester;

N-(2-{6-[4-(4-Chlorophenyl)-4-methoxypiperidine-1-carbonyl]-2-phenyl-7H-pyrrolo[2,3-d]pyrimidin-4-ylamino}-ethyl)-acetamide;

N-(2-{6-[4-Methoxy-4-(3-trifluoromethylphenyl)-piperidine-1-carbonyl]-2-phenyl-7H-pyrrolo[2,3-d]pyrimidin-4-ylamino}-ethyl)-acetamide;

N-{2-[6-(4-Isopropyl-4-methoxypiperidine-1-carbonyl)-2-phenyl-7H-pyrrolo[2,3-d]pyrimidin-4-ylamino]-ethyl}-acetamide;

N-{2-[6-(4-Acetylamino-4-phenylpiperidine-1-carbonyl)-2-phenyl-7H-pyrrolo[2,3-d]pyrimidin-4-ylamino]-ethyl}-acetamide;

1-[4-(2-Acetylaminoethylamino)-2-phenyl-7H-pyrrolo[2,3-d]pyrimidine-6-carbonyl]-4-phenylpiperidine-4-carboxylic acid isopropyl ester;

1-[4-(2-Acetylaminoethylamino)-2-phenyl-7H-pyrrolo[2,3-d]pyrimidine-6-carbonyl]-4-ethylaminopiperidine-4-carboxylic acid amide;

N-(2-{6-[4-Methoxy-4-(3-methoxyphenyl)-piperidine-1-carbonyl]-2-phenyl-7H-pyrrolo[2,3-d]pyrimidin-4-ylamino}-ethyl)-acetamide;

1-[4-(2-Acetylaminoethylamino)-2-phenyl-7H-pyrrolo[2,3-d]pyrimidine-6-carbonyl]-4-pyrrolidin-1-ylpiperidine-4-carboxylic acid amide;

N-(2-{6-[4-(2-Methoxyphenyl)-3,6-dihydro-2H-pyridine-1-carbonyl]-2-phenyl-7H-pyrrolo[2,3-d]pyrimidin-4-ylamino}-ethyl)-acetamide;

N-{2-[6-(4-Amino-4-phenylpiperidine-1-carbonyl)-2-phenyl-7H-pyrrolo[2,3-d]pyrimidin-4-ylamino]-ethyl}-acetamide;

N-{2-[6-(4-Formyl-4-phenylpiperidine-1-carbonyl)-2-phenyl-7H-pyrrolo[2,3-d]pyrimidin-4-ylamino]-ethyl}-acetamide;

N-{2-[6-(4-Benzyl-4-methoxypiperidine-1-carbonyl)-2-phenyl-7H-pyrrolo[2,3-d]pyrimidin-4-ylamino]-ethyl}-acetamide;

N-{2-[6-(4-Methoxy-4-o-tolylpiperidine-1-carbonyl)-2-phenyl-7H-pyrrolo[2,3-d]pyrimidin-4-ylamino]-ethyl}-acetamide;

N-{2-[6-(4-Methoxymethyl-4-phenylpiperidine-1-carbonyl)-2-phenyl-7H-pyrrolo[2,3-d]pyrimidin-4-ylamino]-ethyl}-acetamide;

N-[2-(6-{4-[3-(2-Chlorophenyl)-propyl]-piperazine-1-carbonyl}-2-phenyl-7H-pyrrolo[2,3-d]pyrimidin-4-ylamino)-ethyl]-acetamide;

N-[2-(6-{4-[3-(3-Chlorophenyl)-propyl]-piperazine-1-carbonyl}-2-phenyl-7H-pyrrolo[2,3-d]pyrimidin-4-ylamino)-ethyl]-acetamide;

N-[2-(6-{4-[3-(4-Chlorophenyl)-propyl]-piperazine-1-carbonyl}-2-phenyl-7H-pyrrolo[2,3-d]pyrimidin-4-ylamino)-ethyl]-acetamide;

N-[2-(6-{4-[3-(2-Methoxyphenyl)-propyl]-piperazine-1-carbonyl}-2-phenyl-7H-pyrrolo[2,3-d]pyrimidin-4-ylamino)-ethyl]-acetamide;

N-[2-(6-{4-[3-(3-Methoxyphenyl)-propyl]-piperazine-1-carbonyl}-2-phenyl-7H-pyrrolo[2,3-d]pyrimidin-4-ylamino)-ethyl]-acetamide;

N-[2-(6-{4-[3-(4-Methoxyphenyl)-propyl]-piperazine-1-carbonyl}-2-phenyl-7H-pyrrolo[2,3-d]pyrimidin-4-ylamino)-ethyl]-acetamide;

N-[2-(6-{4-[3-(4-Chlorophenyl)-propionyl]-piperazine-1-carbonyl}-2-phenyl-7H-pyrrolo[2,3-d]pyrimidin-4-ylamino)-ethyl]-acetamide;

N-[2-(6-{4-[3-(3-Chlorophenyl)-propionyl]-piperazine-1-carbonyl}-2-phenyl-7H-pyrrolo[2,3-d]pyrimidin-4-ylamino)-ethyl]-acetamide;

N-[2-(6-{4-[3-(2-Chlorophenyl)-propionyl]-piperazine-1-carbonyl}-2-phenyl-7H-pyrrolo[2,3-d]pyrimidin-4-ylamino)-ethyl]-acetamide;

N-[2-(6-{4-[5-(4-Chlorophenyl)-2H-pyrazol-3-yl]-piperidine-1-carbonyl}-2-phenyl-7H-pyrrolo[2,3-d]pyrimidin-4-ylamino)-ethyl]-acetamide;

2-{4-[4-(2-Acetylaminoethylamino)-2-phenyl-7H-pyrrolo[2,3-d]pyrimidine-6-carbonyl]-piperazin-1-yl}-N-methyl-N-phenylacetamide;

4-[4-(2-Acetylaminoethylamino)-2-phenyl-7H-pyrrolo[2,3-d]pyrimidine-6-carbonyl]-piperazine-1-carboxylic acid benzyl ester;

N-{2-[6-(4-Oxo-1-phenyl-1,3,8-triazaspiro[4.5]decane-8-carbonyl)-2-phenyl-7H-pyrrolo[2,3-d]pyrimidin-4-ylamino]-ethyl}-acetamide;

N-(2-{6-[4-(Methylphenethylamino)-piperidine-1-carbonyl]-2-phenyl-7H-pyrrolo[2,3-d]pyrimidin-4-ylamino}-ethyl)-acetamide;

N-{2-[6-(4-Phenethylaminopiperidine-1-carbonyl)-2-phenyl-7H-pyrrolo[2,3-d]pyrimidin-4-ylamino]-ethyl}-acetamide;

N-[2-(6-{4-[2-(4-Chlorophenyl)-ethylamino]-piperidine-1-carbonyl}-2-phenyl-7H-pyrrolo[2,3-d]pyrimidin-4-ylamino)-ethyl]-acetamide;

N-[2-(6-{4-[2-(3H-Imidazol-4-yl)-ethylamino]-piperidine-1-carbonyl}-2-phenyl-7H-pyrrolo[2,3-d]pyrimidin-4-ylamino)-ethyl]-acetamide;

N-(2-{2-Phenyl-6-[4-(2-pyridin-4-ylethylamino)-piperidine-1-carbonyl]-7H-pyrrolo[2,3-d]pyrimidin-4-ylamino}-ethyl)-acetamide;

N-(2-{2-Phenyl-6-[4-(2-pyridin-2-ylethylamino)-piperidine-1-carbonyl]-7H-pyrrolo[2,3-d]pyrimidin-4-ylamino}-ethyl)-acetamide;

N-{2-[6-(4-Benzylaminopiperidine-1-carbonyl)-2-phenyl-7H-pyrrolo[2,3-d]-pyrimidin-4-ylamino]-ethyl}-acetamide;

N-(2-{6-[4-(Benzylmethylamino)-piperidine-1-carbonyl]-2-phenyl-7H-pyrrolo[2,3-d]pyrimidin-4-ylamino}-ethyl)-acetamide;

N-{2-[2-Phenyl-6-{4-[(pyridin-4-ylmethyl)-amino]-piperidine-1-carbonyl}-7H-pyrrolo[2,3-d]pyrimidin-4-ylamino)-ethyl}-acetamide;

N-(2-{2-Phenyl-6-[4-(2-pyridin-3-ylethylamino)-piperidine-1-carbonyl]-7H-pyrrolo[2,3-d]pyrimidin-4-ylamino}-ethyl)-acetamide;

N-{2-[2-Phenyl-6-((S)-2-phenylaminomethylpyrrolidine-1-carbonyl)-7H-pyrrolo[2,3-d]pyrimidin-4-ylamino]-ethyl}-acetamide;

N-[2-(2-Phenyl-6-{4-[3-(4-trifluoromethylphenyl)-propyl]-piperazine-1-carbonyl}-7H-pyrrolo[2,3-d]pyrimidin-4-ylamino)-ethyl]-acetamide;

N-[2-(6-{4-[3-(4-Fluorophenyl)-propyl]-piperazine-1-carbonyl}-2-phenyl-7H-pyrrolo[2,3-d]pyrimidin-4-ylamino)-ethyl]-acetamide;

N-(2-{6-[4-(3-Benzo[1,3]dioxol-5-yl-propyl)-piperazine-1-carbonyl]-2-phenyl-7H-pyrrolo[2,3-d]pyrimidin-4-ylamino}-ethyl)-acetamide;

N-(2-{2-Phenyl-6-[4-(3-p-tolylpropyl)-piperazine-1-carbonyl]-7H-pyrrolo[2,3-d]pyrimidin-4-ylamino}-ethyl)-acetamide;

N-[2-(6-{4-[3-(4-Bromophenyl)-propyl]-piperazine-1-carbonyl}-2-phenyl-7H-pyrrolo[2,3-d]pyrimidin-4-ylamino)-ethyl]-acetamide;

N-[2-(6-{4-[3-(3,4-Dichlorophenyl)-propyl]-piperazine-1-carbonyl}-2-phenyl-7H-pyrrolo[2,3-d]pyrimidin-4-ylamino)-ethyl]-acetamide;

N-[2-(6-{4-[3-(2,4-Dichlorophenyl)-propyl]-piperazine-1-carbonyl}-2-phenyl-7H-pyrrolo[2,3-d]pyrimidin-4-ylamino)-ethyl]-acetamide;

N-{2-[6-(4-Benzyl-[1,4]diazepane-1-carbonyl)-2-phenyl-7H-pyrrolo[2,3-d]pyrimidin-4-ylamino]-ethyl}-acetamide;

N-{2-[6-(4-Phenethyl-[1,4]diazepane-1-carbonyl)-2-phenyl-7H-pyrrolo[2,3-d]pyrimidin-4-ylamino]-ethyl}-acetamide;

N-(2-{2-Phenyl-6-[4-(3-phenylpropyl)-[1,4]diazepane-1-carbonyl]-7H-pyrrolo[2,3-d]pyrimidin-4-ylamino}-ethyl)-acetamide;

N-(2-{6-[4-(4-Acetylaminophenyl)-piperazine-1-carbonyl]-2-phenyl-7H-pyrrolo[2,3-d]pyrimidin-4-ylamino}-ethyl)-acetamide;

N-(2-{6-[4-(2-Cyanophenyl)-piperazine-1-carbonyl]-2-phenyl-7H-pyrrolo[2,3-d]pyrimidin-4-ylamino}-ethyl)-acetamide;

N-[2-(6-{4-[4-(Acetylmethylamino)-phenyl]-piperazine-1-carbonyl}-2-phenyl-7H-pyrrolo[2,3-d]pyrimidin-4-ylamino)-ethyl]-acetamide;

N-(2-{6-[4-(2,6-Dimethylphenyl)-piperazine-1-carbonyl]-2-phenyl-7H-pyrrolo[2,3-d]pyrimidin-4-ylamino}-ethyl)-acetamide;

N-(2-{6-[4-(2-Chlorophenyl)-piperazine-1-carbonyl]-2-phenyl-7H-pyrrolo[2,3-d]pyrimidin-4-ylamino}-ethyl)-acetamide;

N-(2-{6-[4-(2,4-Dimethoxyphenyl)-piperazine-1-carbonyl]-2-phenyl-7H-pyrrolo[2,3-d]pyrimidin-4-ylamino}-ethyl)-acetamide;

N-(2-{6-[4-(5-Chloro-2-methoxyphenyl)-piperazine-1-carbonyl]-2-phenyl-7H-pyrrolo[2,3-d]pyrimidin-4-ylamino}-ethyl)-acetamide;

N-(2-{6-[4-(4-Chlorophenoxymethyl)-piperidine-1-carbonyl]-2-phenyl-7H-pyrrolo[2,3-d]pyrimidin-4-ylamino}-ethyl)-acetamide;

N-{2-[6-(5-Benzyl-2,5-diazabicyclo[2.2.1]heptane-2-carbonyl)-2-phenyl-7H-pyrrolo[2,3-d]pyrimidin-4-ylamino]-ethyl}-acetamide;

N-{2-[6-(4-Phenoxymethylpiperidine-1-carbonyl)-2-phenyl-7H-pyrrolo[2,3-d]pyrimidin-4-ylamino]-ethyl}-acetamide;

N-(2-{6-[4-(4-Cyanophenoxymethyl)-piperidine-1-carbonyl]-2-phenyl-7H-pyrrolo[2,3-d]pyrimidin-4-ylamino}-ethyl)-acetamide;

N-(2-{6-[4-(3-Cyanophenoxymethyl)-piperidine-1-carbonyl]-2-phenyl-7H-pyrrolo[2,3-d]pyrimidin-4-ylamino}-ethyl)-acetamide;

N-(2-{6-[4-(2-Nitrophenyl)-piperazine-1-carbonyl]-2-phenyl-7H-pyrrolo[2,3-d]pyrimidin-4-ylamino}-ethyl)-acetamide;

2-{4-[4-(2-Acetylaminoethylamino)-2-phenyl-7H-pyrrolo[2,3-d]pyrimidine-6-carbonyl]-piperazin-1-yl}-benzoic acid methyl ester;

N-{2-[2-Phenyl-6-(4-o-tolylpiperazine-1-carbonyl)-7H-pyrrolo[2,3-d]pyrimidin-4-ylamino]-ethyl}-acetamide;

N-(2-{6-[4-(3,4-Dichlorophenoxymethyl)-piperidine-1-carbonyl]-2-phenyl-7H-pyrrolo[2,3-d]pyrimidin-4-ylamino}-ethyl)-acetamide;

N-(2-{6-[4-(2-Cyanophenoxymethyl)-piperidine-1-carbonyl]-2-phenyl-7H-pyrrolo[2,3-d]pyrimidin-4-ylamino}-ethyl)-acetamide;

N-(2-{6-[4-(2-Chlorophenyl)-4-cyanopiperidine-1-carbonyl]-2-phenyl-7H-pyrrolo[2,3-d]pyrimidin-4-ylamino}-ethyl)-acetamide;

2-{4-[4-(2-Acetylaminoethylamino)-2-phenyl-7H-pyrrolo[2,3-d]pyrimidine-6-carbonyl]-piperazin-1-yl}-benzamide;

N-(2-{6-[4-Cyano-4-(2-methoxyphenyl)-piperidine-1-carbonyl]-2-phenyl-7H-pyrrolo[2,3-d]pyrimidin-4-ylamino}-ethyl)-acetamide;

N-(2-{6-[4-(3-Chlorophenyl)-4-cyanopiperidine-1-carbonyl]-2-phenyl-7H-pyrrolo[2,3-d]pyrimidin-4-ylamino}-ethyl)-acetamide;

N-(2-{6-[4-Cyano-4-(3-methoxyphenyl)-piperidine-1-carbonyl]-2-phenyl-7H-pyrrolo[2,3-d]pyrimidin-4-ylamino}-ethyl)-acetamide; and N-(2-{6-[4-Cyano-4-(4-methoxyphenyl)-piperidine-1-carbonyl]-2-phenyl-7H-pyrrolo[2,3-d]pyrimidin-4-ylamino}-ethyl)-acetamide.

In another embodiment of Structure I, the subject invention provides compounds having

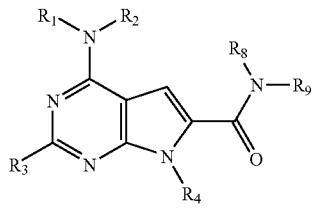

wherein, $R_8$ and $R_9$ are each independently hydrogen, or a substituted or unsubstituted $(C_1-C_{30})$alkyl, $(C_1-C_{30})$alkylaryl, $(C_1-C_{30})$alkylamino, $(C_1-C_{30})$alkoxy, or a saturated or unsaturated, monocyclic or bicyclic, carbocyclic or heterocyclic ring.

In one embodiment, $R_8$ or $R_9$ is a $(C_1-C_{30})$alkyl substituted with one or more hydroxy, dihydroxy or amino moiety.

In another embodiment, $R_8$ or $R_9$ is a substituted or unsubstituted pyrrolidine, piperidine, bicycle[2.2.1]heptane, 2-oxoazepan, indane, or cyclopropylbenzene ring.

In another embodiment, the compound is selected from the group consisting of:

4-(2-Acetylaminoethylamino)-2-phenyl-7H-pyrrolo[2,3-d]pyrimidine-6-carboxylic acid (3-phenoxyphenyl)-amide;

4-(2-Acetylaminoethylamino)-2-phenyl-7H-pyrrolo[2,3-d]pyrimidine-6-carboxylic acid (1-benzylpiperidin-4-yl)-amide;

4-(2-Acetylaminoethylamino)-2-phenyl-7H-pyrrolo[2,3-d]pyrimidine-6-carboxylic acid (1-benzylpyrrolidin-3-yl)-amide;

4-(2-Acetylaminoethylamino)-2-phenyl-7H-pyrrolo[2,3-d]pyrimidine-6-carboxylic acid 4-[1,2,3]thiadiazol-4-yl-benzamide;

4-(2-Acetylaminoethylamino)-2-phenyl-7H-pyrrolo[2,3-d]pyrimidine-6-carboxylic acid benzylamide;

4-(2-Acetylaminoethylamino)-2-phenyl-7H-pyrrolo[2,3-d]pyrimidine-6-carboxylic acid (2-hydroxy-1-hydroxymethylethyl)-amide;

4-(2-Acetylaminoethylamino)-2-phenyl-7H-pyrrolo[2,3-d]pyrimidine-6-carboxylic acid (1-hydroxycyclohexylmethyl)-amide; and 4-(2-Acetylaminoethylamino)-2-phenyl-7H-pyrrolo[2,3-d]pyrimidine-6-carboxylic acid [2-(4-phenoxyphenyl)-ethyl]-amide.

In another embodiment of Structure I, the subject invention provides compounds having the structure:

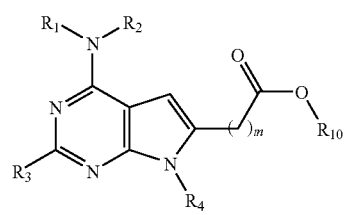

wherein, $R_{10}$ is hydrogen or a substituted or unsubstituted $(C_1-C_{30})$alkyl, $(C_3-C_{10})$cycloalkyl, or an aryl, heteroaryl or heterocyclic ring.

In one embodiment, $R_{10}$ is a substituted or unsubstituted piperidine ring.

In another embodiment, $R_3$ is a substituted or unsubstituted phenyl.

In a further embodiment, $R_4$ is hydrogen.

In a further embodiment, $R_1$ is $-(CH_2)_2NHC(=O)CH_3$;

In a further embodiment, $R_2$ is hydrogen.

In a further embodiment, the compound has the structure:

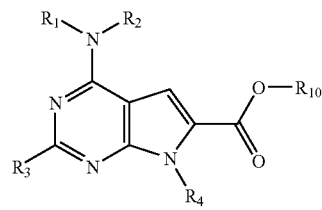

In a further embodiment of Structure I, the subject invention provides compounds having the structure:

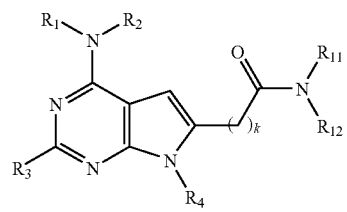

wherein, $R_{11}NR_{12}$ together form a substituted or unsubstituted 4-8 membered heterocyclic ring; and k is 1, 2 or 3.

In one embodiment, $R_{11}NR_{12}$ together form a substituted or unsubstituted azetidine, pyrrolidine, piperazine, piperidine, morpholine, azocane, dihydro-1H-isoquinoline, 1,2,3,6-tetrahydropyridine, dihydro-2H-pyridine, 1,3,4,9-tetrahydro-β-carboline, 1,3,8-triazaspiro[4.5]decane, 2,8-diazaspiro[4.5]decane, 2,5-diazabicyclo[2.2.1]heptane, 1,4-dioxa-8-azaspiro[4.5]decane, or [1.4]diazepane ring.

In a further embodiment, $R_{11}NR_{12}$ together form a substituted or unsubstituted azetidine, pyrrolidine, piperazine, piperidine or [1.4]diazepane ring.

In another embodiment, the ring formed by $R_{11}NR_{12}$ is substituted with one or more aryl, heteroaryl, $(C_1-C_{30})$alkylaryl, $(C_1-C_{30})$alkylheteroaryl, $(C_1-C_{30})$alkenylaryl, $(C_1-C_{30})$alkenylheteroaryl, $(C_1-C_{30})$alkynylaryl, or $(C_1-C_{30})$alkynylheteroaryl moieties, which itself can be substituted.

In another embodiment, $R_3$ is a substituted or unsubstituted phenyl.

In a further embodiment, $R_4$ is hydrogen.

In a further embodiment, $R_1$ is $—(CH_2)_2NHC(=O)CH_3$.

In another embodiment, the compound is N-(2-{6-[3-(4-Benzylpiperazin-1-yl)-3-oxopropyl]-2-phenyl-7H-pyrrolo[2,3-d]pyrimidin-4-ylamino}-ethyl)-acetamide.

5. In a further embodiment of Structure I, the subject invention provides compounds having the structure:

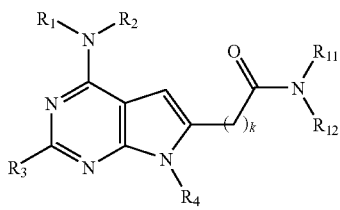

wherein,
$R_{11}NR_{12}$ together form a substituted or unsubstituted 4-8 membered heterocyclic ring; and
k is 1, 2 or 3.

In one embodiment, $R_{11}NR_{12}$ together form a substituted or unsubstituted azetidine, pyrrolidine, piperazine, piperidine, morpholine, azocane, dihydro-1H-isoquinoline, 1,2,3,6-tetrahydropyridine, dihydro-2H-pyridine, 1,3,4,9-tetrahydro-β-carboline, 1,3,8-triazaspiro[4.5]decane, 2,8-diazaspiro[4.5]decane, 2,5-diazabicyclo[2.2.1]heptane, 1,4-dioxa-8-azaspiro[4.5]decane, or [1.4]diazepane ring.

In a further embodiment, $R_{11}NR_{12}$ together form a substituted or unsubstituted azetidine, pyrrolidine, piperazine, piperidine or [1.4]diazepane ring.

In another embodiment, the ring formed by $R_{11}NR_{12}$ is substituted with one or more aryl, heteroaryl, $(C_1-C_{30})$alkylaryl, $(C_1-C_{30})$alkylheteroaryl, $(C_1-C_{30})$alkenylaryl, $(C_1-C_{30})$alkenylheteroaryl, $(C_1-C_{30})$alkynyl aryl, or $(C_1-C_{30})$alkynylheteroaryl moiety.

In another embodiment, $R_3$ is a substituted or unsubstituted phenyl.

In a further embodiment, $R_4$ is hydrogen.

In a further embodiment, $R_1$ is $—(CH_2)_2NHC(=O)CH_3$.

The subject invention also provides compounds having the structure:

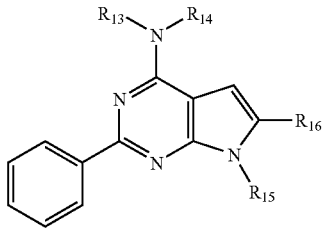

wherein,
$R_{13}$ and $R_{14}$ are each independently a hydrogen atom or a substituted or unsubstituted alkyl or alkylaryl moiety;
or $R_{13}NR_{14}$ together form a substituted or unsubstituted 4 membered heterocyclic ring, a substituted or unsubstituted 5 membered ring, or a substituted or unsubstituted piperazine, wherein the five-membered ring is substituted with
$—CH_2C(=O)OH$;
$R_{15}$ is hydrogen or a substituted or unsubstituted alkyl; and
$R_{16}$ is $—CH_2NR_{17}$, $—CH_2OR_{17}$, $—CH_2CH_2C(=O)OR_{17}$, $CH_2CH_2C(=O)NR_{18}R_{19}$, $—C(=O)NR_{18}R_{19}$, or $—C(=O)OR_{17}$, wherein $R_{17}$, $R_{18}$ and $R_{19}$ are each independently a hydrogen atom, a substituted or unsubstituted alkyl, aryl or alkylaryl moiety, or $R_{14}NR_{15}$ together form a substituted or unsubstituted 4 to 8 membered heterocyclic ring.

In one embodiment, any alkyl is a straight chain $(C_1-C_{30})$alkyl or a branched chain $(C_3-C_{30})$alkyl.

In a further embodiment, any heterocyclic ring, if present, is a substituted or unsubstituted morpholine, pyrrolidine, piperazine, piperidine, azocane, dihydro-1H-isoquinoline, dihydro-2H-pyridine, 1,3,4,9-tetrahydro-β-carboline, 1,3,8-triazaspiro[4.5]decane, 2,8-diazaspiro[4.5]decane, 2,5-diazabicyclo[2.2.1]heptane, or [1,4]diazepane ring.

The subject invention also provides compounds having the structure:

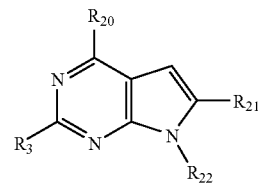

wherein
$R_3$ is a substituted or unsubstituted 4-10 membered aryl, heteroaryl or heterocyclic ring;
$R_{20}$ is halogen or $—NH(CHR_{20}')_nNHC(=O)CH_3$, where $R_{20}'$ is H, OH, alkyl, hydroxyalkyl, cycloalkyl, heteroalkyl, or amino;
$R_{21}$ is H or $—C(=O)OH$;
$R_{22}$ is H or $SO_2Ph$; and
n is 2, 3, 4 or 5;
wherein when $R_{20}$ is $—NH(CHR_{20}')_nNHC(=O)CH_3$, $R_{21}$ is $—C(=O)OH$.

In one embodiment, $R_3$ is substituted or unsubstituted phenyl.

In a further embodiment, $R_{20}$ is Cl.

In a further embodiment, $R_{22}$ is $SO_2Ph$.

In a further embodiment, $R_{21}$ is H.

In a further embodiment, $R_{21}$ is —C(=O)OH.

In another embodiment, $R_{20}$ is —NH(CH$_2$)$_n$NHC(=O)CH$_3$ and $R_{21}$ is —C(=O)OH.

In a further embodiment, $R_{22}$ is H.

In a further embodiment, $R_{22}$ is $SO_2Ph$.

The subject invention also provides a method for treating a disease associated with the $A_{2b}$ adenosine receptor in a subject in need of such treatment comprising administering to the subject a therapeutically effective amount of the compounds of Structure I so as to thereby treat the disease associated with the $A_{2b}$ adenosine receptor in the subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

In one embodiment, the disease associated with the $A_{2b}$ adenosine receptor is diabetes.

In another embodiment, the disease associated with the $A_{2b}$ adenosine receptor is asthma.

In another embodiment, the disease associated with the $A_{2b}$ adenosine receptor is associated with mast cell degranulation.

In another embodiment, the disease associated with the $A_{2b}$ adenosine receptor is a proliferating tumor.

The subject invention also provides a method for treating a disease associated with the $A_{2b}$ adenosine receptor in a subject in need of such treatment comprising administering to the subject a therapeutically effective amount of the compound of Structure II so as to thereby treat the disease associated with the $A_{2b}$ adenosine receptor in the subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

The subject invention also provides a pharmaceutical composition comprising a compound of the invention and a pharmaceutically acceptable carrier.

In one embodiment, the pharmaceutical composition is formulated for oral, topical, parenteral or nasal administration.

The subject invention also provides a process for the manufacture of a pharmaceutical composition comprising admixing a compound of the invention with a pharmaceutically acceptable carrier.

The subject invention also provides an article of manufacture comprising
  packaging material;
  the above pharmaceutical composition; and
  instructions for use of the pharmaceutical composition in the treatment of a disease associated with the $A_{2b}$ adenosine receptor.

The subject invention also provides a process of manufacturing a compound having the structure:

wherein,
  $R_8$ and $R_9$ are each independently hydrogen, or a substituted or unsubstituted ($C_1$-$C_{30}$)alkyl, ($C_1$-$C_{30}$)alkylaryl, ($C_1$-$C_{30}$)alkylamino, ($C_1$-$C_{30}$)alkoxy, or a saturated or unsaturated, monocyclic or bicyclic, carbocyclic or heterocyclic ring, or
  $R_8$, N, and $R_9$ together form a substituted or unsubstituted 4-8 membered heterocyclic ring, comprising:

(a) reacting with PhSO$_2$Cl and a reducing agent in the presence of solvent to produce:

(b) reacting the product of step (a) with $CO_2$ in the presence of lithium diisopropylamide (LDA) and a solvent to produce:

(c) reacting the product of step (b) with

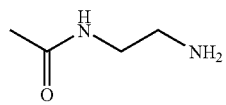

in the presence solvent to produce:

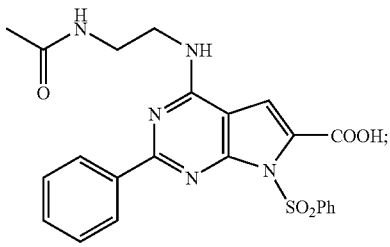

(d) reacting the product of step (c) with a hydroxide base and a coupling agent in solution to produce:

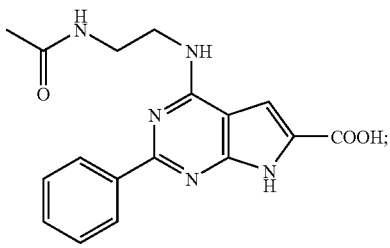

and (e) reacting the product of step (d) with $HNR_7R_8$ in the presence of a base to produce the compound.

In one embodiment of the above process, the reducing agent in step (a) is NaH and the solvent is dimethylfotrmamide (DMF).

In another embodiment, the solvent in step (b) is tetrahydrofuran (THF).

In another embodiment, the solvent in step (c) is dimethyl sulfoxide (DMSO).

In another embodiment, the hydroxide base in step (d) is sodium hydroxide.

In another embodiment, the base in step (e) is triethylamine, the coupling agent is O-(benzotriazol-1-yl)-N,N,N', N'-tetramethyluronium tetrafluoroborate (TBTU), benzotriazol-1-yl-oxytripyrrolidinophosphonium hexafluorophosphate, or 1-ethyl-3-(3-dimethylaminopropyl)-carbodiimide (EDC) and N-Hydroxybenzotriazole, and the solvent is DMF.

In another embodiment, the order of the steps is (a), (b), (c), (e), then (d).

The subject invention also provides a compound produced by the above process.

The subject invention also provides the use of a compound of the invention for manufacturing a medicament useful for treating a disease associated with the $A_{2b}$ adenosine receptor in a subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor, or is associated with mast cell degranulation, vasodilation, hypertension, hypersensitivity or the release of allergic mediators.

In one embodiment of the above use, the disease associated with the $A_{2b}$ adenosine receptor is diabetes.

In another embodiment, the disease associated with the $A_{2b}$ adenosine receptor is asthma.

In another embodiment, the disease associated with the $A_{2b}$ adenosine receptor is associated with mast cell degranulation.

In another embodiment, the disease associated with the $A_{2b}$ adenosine receptor is a proliferating tumor.

The subject invention also provides any of the above compounds, wherein any substituent, if present, is selected from halogen, hydroxyl, carbonyl, straight chain ($C_1$-$C_{30}$)alkyl, branched chain ($C_3$-$C_{30}$)alkyl, ($C_3$-$C_{10}$)cycloalkyl, straight chain ($C_1$-$C_{30}$)alkylcarbonyloxy, branched chain ($C_3$-$C_{30}$) alkylcarbonyloxy, arylcarbonyloxy, straight chain ($C_1$-$C_{30}$) alkoxycarbonyloxy, branched chain ($C_3$-$C_{30}$)alkoxycarbonyloxy, aryloxycarbonyloxy, carboxylate, straight chain ($C_1$-$C_{30}$)alkylcarbonyl, branched chain ($C_3$-$C_{30}$)alkylcarbonyl, arylcarbonyl, straight chain ($C_1$-$C_{30}$)alkoxycarbonyl, branched chain ($C_3$-$C_{30}$)alkoxycarbonyl, aminocarbonyl, straight chain ($C_1$-$C_{30}$)alkylthiocarbonyl, branched chain ($C_3$-$C_{30}$)alkylthiocarbonyl, straight chain ($C_1$-$C_{30}$)alkylsulfonyl, branched chain ($C_3$-$C_{30}$)alkylsulfonyl, straight chain ($C_1$-$C_{30}$)alkoxyl, branched chain ($C_1$-$C_{30}$)alkoxyl, phosphate, phosphonato, cyano, amino, straight chain ($C_1$-$C_{30}$) alkylamino, branched chain ($C_3$-$C_{30}$)alkylamino, straight chain ($C_1$-$C_{30}$)dialkylamino, branched chain ($C_3$-$C_{30}$)dialkylamino, arylamino, diarylamino, straight chain ($C_1$-$C_{30}$)alkylarylamino, branched chain ($C_3$-$C_{30}$)alkylarylamino, acylamino, straight chain ($C_1$-$C_{30}$)alkylcarbonylamino, branched chain ($C_3$-$C_{30}$)alkylcarbonylamino, arylcarbonylamino, carbamoyl, ureido, amidino, imino, sulfhydryl, straight chain ($C_1$-$C_{30}$)alkylthio, branched chain ($C_3$-$C_{30}$) alkylthio, arylthio, thiocarboxylate, sulfates, sulfonato, sulfamoyl, sulfonamido, sulfonyl, benzenesulfonyl, nitro, trifluoromethyl, azido, 6-methoxy-2,2-dimethyltetrahydrofuro [3,4-d][1,3]dioxole, 3,4-dihydroxy-5-methoxytetrahydrofuran, 4-10 membered heterocyclyl, straight chain ($C_1$-$C_{30}$)alkylaryl, branched chain ($C_3$-$C_{30}$) alkylaryl, straight chain ($C_1$-$C_{30}$)alkylheteroaryl, branched chain ($C_3$-$C_{30}$)alkylheteroaryl, ($C_1$-$C_{30}$)alkenylaryl, ($C_1$-$C_{30}$)alkenylheteroaryl, ($C_1$-$C_{30}$)alkynylaryl, ($C_1$-$C_{30}$)alkynylheteroaryl or an aromatic or 5-6 membered heteroaromatic moiety, which substituent may be further substituted by any of the above.

The subject invention also includes the specific compounds that are included by each of the above structures. The specific compounds are described in the examples.

The number of carbons when represented as "($C_1$-$C_{30}$)" or "($C_3$-$C_{30}$)" is intended to mean any incremental whole number between 1 and 3 and 30, e.g. 1, 2, 3, 4, 5 . . . or 30.

The present invention is based on compounds which selectively bind to adenosine $A_{2b}$ receptor, thereby treating a disease associated with $A_{2b}$ adenosine receptor in a subject by administering to the subject a therapeutically effective amount of such compounds. The diseases to be treated are associated with, for example, asthma, mast cell degranulation, myocardial reperfusion injury, allergic reactions including but not limited to rhinitis, poison ivy induced responses, urticaria, scleroderm arthritis, autoimmune diseases, inflammatory bowel diseases, hypertension, myocardial infarction, myocardial reperfusion after ischemia, lymphocyte activation, vasodilation, growth, neural reflexes in the human gut, retinal angiogenesis, abberant neovascularization such as diabetic retinopathy and retinopathy of prematurity, modulation of intestinal tone and secretion and neurotransmission and neurosecretion.

$A_{2b}$ receptors have also been implicated in hypersensitivity, hay fever, serum sickness, allergic vasculitis, atopic dermatitis, dermatitis, eczema, idiopathic pulmonary fibrosis, eosinophilic chlorecystitis, chronic airway inflammation, hypereosinophilic syndromes, eosinophilic gastroenteritis, edema, eosinophilic myocardial disease, episodic angioedema with eosinophilia, ulcerative colitis, allergic granulomatosis, carcinomatosis, eosinophilic granuloma, familial histiocytosis, tumor, cardiac hypoxia, cerebral ischemia, diuresis, renal failure, neurological disorder, mental disorder, cognitive disorder, myocardial ischemia, bronchoconstriction, Crohn's disease, Grave's disease, diabetes, multiple sclerosis, anaemia, psoriasis, fertility disorders, lupus erthyematosus, brain arteriole diameter, the release of allergic mediators, scleroderma, stroke, global ischemia, central nervous system disorder, cardiovascular disorder, renal disorder, inflammatory disorder, gastrointestinal disorder, eye disorder, allergic disorder, respiratory disorder, or immunological disorder.

The invention further pertains to methods for treating $A_{2b}$ associated disorders in a mammal by administering to the mammal a therapeutically effective amount of the compounds of the present invention, such that treatment of the disorder in the mammal occurs.

The invention further pertains to methods for treating $A_{2b}$ associated disorders in a mammal by administering to the mammal a therapeutically effective amount of the compounds of the present invention, such that treatment of the disorder in the mammal occurs.

The present invention also pertains to packaged pharmaceutical compositions for treating $A_{2b}$ associated disorders. The packaged pharmaceutical composition includes a container holding a therapeutically effective amount of at least one of the compounds of the present invention and instructions for using the said compounds for treating an $A_{2b}$ associated disease.

The compounds of this invention may advantageously be selective $A_{2b}$ receptor antagonists.

In a particularly-preferred embodiment, the compound is a water soluble prodrug that is capable of being metabolized in vivo to an active drug by, for example, esterase catalyzed hydrolysis.

In yet another embodiment, the invention features a method for inhibiting the activity of an adenosine receptor (e.g., $A_{2b}$) in a cell, by contacting the cell with a compound of the present invention (e.g., preferably, an adenosine receptor antagonist).

The invention also features a pharmaceutical composition comprising a compound of the present invention. Preferably, the pharmaceutical preparation is an ophthalmic formulation (e.g., an periocular, retrobulbar or intraocular injection formulation, a systemic formulation, or a surgical irrigating solution).

The present invention pertains to methods for treating an $A_{2b}$ associated disorder in a mammal. The methods include administration of a therapeutically effective amount of the compounds of the invention, described infra, to the mammal, such that treatment of the $A_{2b}$ associated disorder in the mammal occurs.

The language "treatment of an $A_{2b}$ associated disorder" refers to treatment which includes a significant diminishment of at least one symptom or effect of the disorder achieved with a compound of the invention. Typically such disorders are associated with an increase of adenosine within a host such that the host often experiences physiological symptoms which include, but are not limited to, urticaria, scleroderm arthritis, allergic rhinitis, asthma, inflammatory bowel diseases, hypertension, diabetic retinopathy and retinopathy of prematurity. (See for example, C. E. Muller and B. Stein "Adenosine Receptor Antagonists: Structures and Potential Therapeutic Applications," *Current Pharmaceutical Design*, 2:501 (1996) and C. E. Muller "$A_1$-Adenosine Receptor Antagonists," *Exp. Opin. Ther. Patents* 7(5):419 (1997) and I. Feoktistove, R. Polosa, S. T. Holgate and I. Biaggioni "Adenosine $A_{2B}$ receptors: a novel therapeutic target in asthma?" TiPS19; 148 (1998)). The effects often associated with such symptoms include, but are not limited to, fever, shortness of breath, nausea, diarrhea, weakness, headache, and even death. In one embodiment, the disorder includes those disease states which are mediated by stimulation of adenosine receptors, e.g., $A_1$, $A_{2a}$, $A_{2b}$, $A_3$, etc., such that calcium concentrations in cells and/or activation of PLC (phospholipase C) is modulated. In a preferred embodiment, the disorder is associated with adenosine receptor(s), e.g., the compound of the invention acts as an antagonist. Examples of suitable responsive states which can be treated by the compounds of the invention, e.g., adenosine receptor subtypes which mediate biological effects, include central nervous system (CNS) effects, cardiovascular effects, renal effects, respiratory effects, immunological effects, gastrointestinal effects and metabolic effects. The relative amount of adenosine in a subject can be associated with the effects listed below; that is increased levels of adenosine can trigger an effect, e.g., an undesired physiological response, e.g., an asthmatic attack.

Immunological effects include mast cell degranulation ($A_{2b}$). Therapeutic applications of antagonists include allergic and non allergic inflammation, e.g., release of histamine and other inflammatory mediators.

Gastrointestinal effects include colonic, intestinal and diarrheal disease, e.g., diarrheal disease associated with intestinal inflammation ($A_{2b}$).

The term "disease state" is intended to include those conditions caused by or associated with unwanted levels of adenosine, adenylyl cyclase activity, increased physiological activity associated with aberrant stimulation of adenosine receptors and/or an increase in cAMP. In one embodiment, the disease state is, for example, asthma, chronic obstructive pulmonary disease, allergic rhinitis, bronchitis, renal disorders, gastrointestinal disorders, or eye disorders. Additional examples include chronic bronchitis and cystic fibrosis. Suitable examples of inflammatory diseases include non-lymphocytic leukemia, myocardial ischaemia, angina, infarction, cerebrovascular ischemia, intermittent claudication, critical limb ischernia, venous hypertension, varicose veins, venous ulceration and arteriosclerosis. Impaired reperfusion states include, for example, any post-surgical trauma, such as reconstructive surgery, thrombolysis or angioplasty.

This invention also provides a combination therapy for glaucoma, comprising one of the compounds of the invention, and a prostagladin agonist, beta-2 agonist, or a muscarinic antagonist.

The language "treating an $A_{2b}$ associated disorder" or "treating an $A_{2b}$ associated disease" is intended to include changes in a disease state or condition, as described above, such that physiological symptoms in a mammal can be significantly diminished or minimized. The language also includes control, prevention or inhibition of physiological symptoms or effects associated with an aberrant amount of adenosine. In one preferred embodiment, the control of the disease state or condition is such that the disease state or condition is eradicated. In another preferred embodiment, the control is selective such that aberrant levels of adenosine receptor activity are controlled while other physiologic systems and parameters are unaffected.

The language "therapeutically effective amount" of the compounds of the invention, described infra, refers to that amount of a therapeutic compound necessary or sufficient to perform its intended function within a mammal, e.g., treat an $A_{2b}$ associated disorder, or a disease state in a mammal. An effective amount of the therapeutic compound can vary according to factors such as the amount of the causative agent already present in the mammal, the age, sex, and weight of the mammal, and the ability of the therapeutic compounds of the present invention to affect the $A_{2b}$ associated disorder in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

A therapeutically effective amount preferably diminishes at least one symptom or effect associated with the $A_{2b}$ associated disorder being treated by at least about 20%, (more preferably by at least about 40%, even more preferably by at least about 60%, and still more preferably by at least about 80%) relative to untreated subjects. Assays can be designed by one skilled in the art to measure the diminishment of such symptoms and/or effects. Any art recognized assay capable of measuring such parameters are intended to be included as part of this invention. For example, if asthma is the state being treated, then the volume of air expended from the lungs of a subject can be measured before and after treatment for measurement of increase in the volume using an art recognized technique. Likewise, if inflammation is the state being treated, then the area which is inflamed can be measured before and after treatment for measurement of diminishment in the area inflamed using an art recognized technique.

The term "cell" includes both prokaryotic and eukaryotic cells.

The term "animal" includes any organism with adenosine receptors. Examples of animals include yeast, mammals, reptiles, and birds. It also includes transgenic animals.

The term "mammal" is art recognized and is intended to include an animal, more preferably a warm-blooded animal, most preferably cattle, sheep, pigs, horses, dogs, cats, rats, mice, and humans. Mammals susceptible to $A_{2b}$ associated disorders responsive state, inflammation, emphysema, asthma, central nervous system conditions, or acute respiratory distress syndrome, for example, are included as part of this invention.

In another aspect, the present invention pertains to methods for modulating an adenosine receptor(s) in a mammal by administering to the mammal a therapeutically effective amount of the compounds of the invention, such that modulation of the adenosine receptor in the mammal occurs. Suitable adenosine receptors include the families of $A_1$, $A_2$, or $A_3$. In a preferred embodiment, the compound is an adenosine receptor antagonist.

The language "modulating an adenosine receptor" is intended to include those instances where a compound interacts with an adenosine receptor(s), causing increased, decreased or abnormal physiological activity associated with an adenosine receptor or subsequent cascade effects resulting from the modulation of the adenosine receptor. Physiological activities associated with adenosine receptors include induction of sedation, vasodilation, suppression of cardiac rate and contractility, inhibition of platelet aggregbility, stimulation of gluconeogenesis, inhibition of lipolysis, opening of potassium channels, reducing flux of calcium channels, etc.

The terms "modulate", "modulating" and "modulation" are intended to include preventing, eradicating, or inhibiting the resulting increase of undesired physiological activity associated with abnormal stimulation of an adenosine receptor, e.g., in the context of the therapeutic methods of the invention. In another embodiment, the term modulate includes antagonistic effects, e.g., diminishment of the activity or production of mediators of allergy and allergic inflammation which results from the overstimulation of adenosine receptor(s). For example, the therapeutic deazapurines of the invention can interact with an adenosine receptor to inhibit, for example, adenylate cyclase activity.

The language "condition characterized by aberrant adenosine receptor activity" is intended to include those diseases, disorders or conditions which are associated with aberrant stimulation of an adenosine receptor, in that the stimulation of the receptor causes a biochemical and or physiological chain of events that is directly or indirectly associated with the disease, disorder or condition. This stimulation of an adenosine receptor does not have to be the sole causative agent of the disease, disorder or condition but merely be responsible for causing some of the symptoms typically associated with the disease, disorder, or condition being treated. The aberrant stimulation of the receptor can be the sole factor or at least one other agent can be involved in the state being treated. Examples of conditions include those disease states listed supra, and those symptoms manifested by the presence of increased adenosine receptor activity.

The language "treating or treatment of a condition characterized by aberrant adenosine receptor activity" is intended to include the alleviation of or diminishment of at least one symptom typically associated with the condition. The treatment also includes alleviation or diminishment of more than one symptom. Preferably, the treatment cures, e.g., substantially eliminates, the symptoms associated with the condition.

The invention further pertains to a method for inhibiting the activity of an adenosine receptor (e.g., an $A_{2b}$ adenosine receptor) in a cell by contacting the cell with a compound of the invention. Preferably, the compound is an antagonist of the receptor.

In another embodiment, the invention relates to a pharmaceutical composition containing a compound of the invention and a pharmaceutically acceptable carrier.

The invention also pertains to a method for treating an $A_{2b}$ associated disease in an animal, by administering to a mammal a therapeutically effective amount of a compound of the invention, such that treatment of the $A_{2b}$ associated disorder occurs.

Advantageously, the disease state may be a disorder mediated by adenosine. Examples of preferred disease states include: central nervous system disorders, cardiovascular disorders, renal disorders, inflammatory disorders, allergic disorders, gastrointestinal disorders, eye disorders, and respiratory disorders.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 4-10 carbon atoms in their ring structure, and more preferably have 5, 6 or 7 carbons in the ring structure.

The term "substituted alkyls" refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulthydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively. For example, the invention contemplates cyano and propargyl groups.

Unless the number of carbons is otherwise specified, "lower alkyl" as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "heterocycle" or "heterocyclic system" as used herein is intended to mean a stable 5, 6 or 7-membered monocyclic or 7, 8, 9, 10 or 11-membered bicyclic heterocyclic ring which is saturated or partially unsaturated.

The terms "carbocyclic" or "heterocyclic" further include spiro compounds, which denote a bicyclic compound in which the two rings have one atom in common and the atom may be carbon or a heteroatom.

The term "amino acids" includes naturally and unnaturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. Amino acid analogs include amino acids with lengthened or shortened side chains or variant side chains with appropriate functional groups. Amino acids also include D and L stereoisomers of an amino acid when the structure of the amino acid admits of stereoisomeric forms. The term "dipeptide" includes two or more amino acids linked together. Preferably, dipeptides are two amino acids linked via a peptide linkage. Particularly preferred dipeptides include, for example, alanine-alanine and glycine-alanine.

It will be noted that the structure of some of the compounds of this invention includes asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The invention further pertains to pharmaceutical compositions for treating $A_{2b}$ associated disorders in a mammal. The pharmaceutical composition includes a therapeutically effective amount of a compound of the invention and a pharmaceutically acceptable carrier. It is to be understood, that all of the compounds described below are included for therapeutic treatment. It is to be further understood that the compounds of the invention can be used alone or in combination with other compounds of the invention or in combination with additional therapeutic compounds, such as antibiotics, antiinflammatories, or anticancer agents, for example.

The term "antibiotic" is art recognized and is intended to include those substances produced by growing microorganisms and synthetic derivatives thereof, which eliminate or inhibit growth of pathogens and are selectively toxic to the pathogen while producing minimal or no deleterious effects upon the infected host subject. Suitable examples of antibiotics include, but are not limited to, the principle classes of aminoglycosides, cephalosporins, chloramphenicols, fuscidic acids, macrolides, penicillins, polymixins, tetracyclines and streptomycins.

The term "antiinflammatory" is art recognized and is intended to include those agents which act on body mechanisms, without directly antagonizing the causative agent of the inflammation such as glucocorticoids, aspirin, ibuprofen, NSAIDS, etc.

The term "anticancer agent" is art recognized and is intended to include those agents which diminish, eradicate, or prevent growth of cancer cells without, preferably, adversely affecting other physiological functions. Representative examples include cisplatin and cyclophosphamide.

The term "cancer" as used herein is intended to mean a cellular malignancy whose unique trait—loss of normal controls—results in unregulated growth, lack of differentiation, and ability to invade local tissues and metastasize. The presence of a cellular malignancy is often indicated by the presence of a tumor. Local tissue invasion can result from local tumor pressure on normal tissues that can lead to inflammation, or the tumor may elaborate substances that lead to enzymatic destruction.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g. Berge et al. (1977) "Pharmaceutical Salts", *J. Pharm. Sci.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.)

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chapter 8). Such prodrugs can be used to alter the biodistribution (e.g., to allow compounds which would not typically enter the reactive site of the protease) or the pharmacokinetics of the therapeutic compound. For example, a carboxylic acid group, can be esterified, e.g., with a methyl group or an ethyl group to yield an ester. When the ester is administered to a subject, the ester is cleaved, enzymatically or non-enzymatically, reductively or hydrolytically, to reveal the anionic group. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular reactive sites, as described below for carrier moieties.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, acetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert dilutents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Preferably, the pharmaceutical preparation is an ophthalmic formulation (e.g., an periocular, retrobulbar or intraocular injection formulation, a systemic formulation, or a surgical irrigating solution).

The ophthalmic formulations of the present invention may include one or more of the compounds of the invention and a pharmaceutically acceptable vehicle. Various types of vehicles may be used. The vehicles will generally be aqueous in nature. Aqueous solutions are generally preferred, based on case of formulation, as well as a patient's ability to easily administer such compositions by means of instilling one to two drops of the solutions in the affected eyes. However, the deazapurines of the present invention may also be readily incorporated into other types of compositions, such as suspensions, viscous or semi-viscous gels or other types of solid or semi-solid compositions. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquatemium-1, or other agents known to those skilled in the art. Such preservatives are typically employed at a level of from 0.001 to 1.0% weight/volume ("% w/v").

When the compounds of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth. W. B. Sanders Co., Philadelphia, Pa., U.S.A., pages 85-87 (1990).

As indicated above, use of the compounds of the present invention to prevent or reduce damage to retinal and optic nerve head tissues at the cellular level is a particularly important aspect of one embodiment of the invention. Ophthalmic conditions which may be treated include, but are not limited to, retinopathies and damage associated with injuries to ophthalmic tissues, such as ischemia reperfusion injuries. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 200 mg per kilogram of body weight per day, more preferably from about 0.01 to about 150 mg per kg per day, and still more preferably from about 0.2 to about 140 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present invention also pertains to packaged pharmaceutical compositions for treating $A_{2b}$ associated disorders in a mammal. The packaged pharmaceutical compositions include a container holding a therapeutically effective amount of at least one compound of the invention, as described below, and instructions for using the compound for treating the $A_{2b}$ associated disorder in the mammal.

The compounds of the invention may comprise water-soluble prodrugs which are described in WO 99/33815, International Application No. PCT/US98/04595, filed Mar. 9, 1998 and published Jul. 8, 1999. The entire content of WO 99/33815 is expressly incorporated herein by reference. The water-soluble prodrugs are metabolized in vivo to an active drug, e.g., by esterase catalyzed hydrolysis.

In another aspect, the invention features a method for treating damage to the eye of an animal (e.g., a human) by administering to the animal an effective amount of the compounds of the present invention. Preferably, the compound is an antagonist of $A_{2b}$ adenosine receptors in cells of the animal. The damage is to the retina or the optic nerve head and may be acute or chronic. The damage may be the result of, for example, glaucoma, edema, ischemia, hypoxia or trauma.

The invention further pertains to a method for inhibiting the activity of an adenosine receptor (e.g., an $A_{2b}$ adenosine receptor) in a cell by contacting the cell with a compound of the invention. Preferably, the compound is an antagonist of the receptor.

In another embodiment, the invention relates to a pharmaceutical composition containing a compound of the invention and a pharmaceutically acceptable carrier.

The invention also pertains to a method for treating an $A_{2b}$ associated disease state in an animal, by administering to a mammal a therapeutically effective amount of a compound of the invention, such that treatment of disorder in the animal occurs. Advantageously, the disease state may be a disorder mediated by adenosine. Examples of preferred disease states include: central nervous system disorders, cardiovascular disorders, renal disorders, inflammatory disorders, allergic disorders, gastrointestinal disorders, eye disorders, and respiratory disorders.

The invention further pertains to pharmaceutical compositions for treating an $A_{2b}$ associated disease state in a mammal, e.g., respiratory disorders (e.g., asthma, bronchitis, chronic obstructive pulmonary disorder, and allergic rhinitis), renal disorders, gastrointestinal disorders, and eye disorders. The pharmaceutical composition includes a therapeutically effective amount of a compound of the invention, described below, and a pharmaceutically acceptable carrier. It is to be understood, that all of the compounds described below are included for therapeutic treatment. It is to be further understood that the compounds of the invention can be used alone or in combination with other compounds of the invention or in combination with additional therapeutic compounds, such as antibiotics, antiinflammatories, or anticancer agents, for example.

As indicated above, use of the compounds of the invention to prevent or reduce damage to retinal and optic nerve head tissues at the cellular level is a particularly important aspect of one embodiment of the invention. Ophthalmic conditions which may be treated include, but are not limited to, retinopathies, macular degeneration, ocular ischemia, glaucoma, and damage associated with injuries to ophthalmic tissues, such as ischemia reperfusion injuries, photochemical injuries, and injuries associated with ocular surgery, particularly injuries to the retina or optic nerve head by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

The features and other details of the invention will now be more particularly described and pointed out in the claims. It is to be understood that the particular embodiments of the invention are shown by way of illustration and not as limitations of the invention. The principal features of this invention can be employed in various embodiments without departing from the scope of the invention.

This invention will be better understood from the Experimental Details which follow. However, one skilled in the art will readily appreciate that the specific methods and results discussed are merely illustrative of the invention as described more fully in the claims which follow thereafter.

Experimental Details

General Information

LC/MS analysis was performed using a Gilson 215 autosampler and Gilson 819 autoinjector, attached to a Hewlett Packard HP110.

Mass spectra were obtained on a Micromass Platform II mass spectrometer, using positive electrospray ionization.

LC analysis was undertaken at 254 nm using a UV detector. Samples were eluted on a Phenomenex Luna C18(2) (5 microns, 4.6×150 mm) column using either a linear gradient of 15-99% solvent A in solvent B over 10 minutes (method A, non-polar) or 5-100% solvent A in solvent B over 15 minutes (method B, polar). The solvent A was 100% acetonitrile, solvent B was 0.01% formic acid, which was observed to have no noticeable effect on sample retention time, in water.

IR spectra were recorded on a Perkin-Elmer Spectrum 1000 FT-IR spectrometer as thin films using diffuse reflectance.

$^1$H NMR and $^{13}$C NMR spectra were recorded with Varian instruments (400 MHz or 200 MHz for $^1$H, 100.6 MHz or 50.3 MHz for $^{13}$C) at ambient temperature with TMS or the residual solvent peak as internal standards. The line positions or multiplets are given in ppm (δ) and the coupling constants (J) are given as absolute values in Hertz, while the signal multiplicities are abbreviated as follows: s (singlet), d (doublet), t (triplet), q (quartet), quint (quintet), m (multiplet), $m_c$ (centered multiplet), br (broadened). All melting points were determined with a Mel-Temp II apparatus and are uncorrected. Elemental analyses were carried out at Atlantic Microlab, Inc., Norcross, Ga. Commercially available anhydrous solvents and HPLC-grade solvents were used without further purification.

EXAMPLE 1

Synthesis of Non-commercial 3,3- and 4,4-Disubstituted Piperidines 29

The syntheses of several 4,4-disubstituted piperidines 29 are shown in scheme 1. Boc-protected alcohols Boc-29 were prepared from commercially available aminoalcohols 29.6-29.8, 29.10, and 29.18 by reaction with di-tert-butyl dicarbonate or from N-Boc-4-pyridone (Boc-29.155) by addition of Grignard or organolithium reagents. Methylation with methyl iodide and KHMDS yielded the corresponding methyl ethers. Deprotection with HCl/MeOH gave the methyl ether amine hydrochlorides, and/or, in some cases, the corresponding 1,2,3,6-tetrahydropyridines. Alkylation of the nitriles 35 with the protected nitrogen mustard 34 followed by Boc removal with HCl in dioxane gave amines 29.237 and 29.240-29.244.

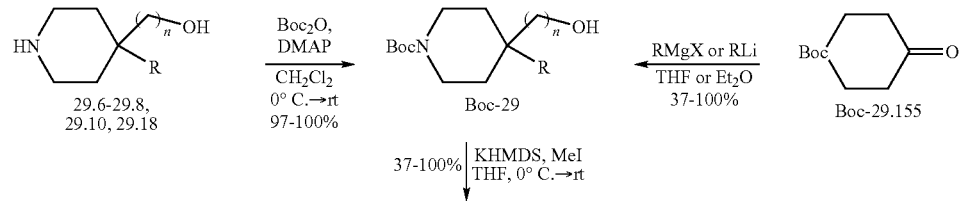

Scheme 1. Synthesis of non-commercial 4,4-disubstituted piperidines 29.

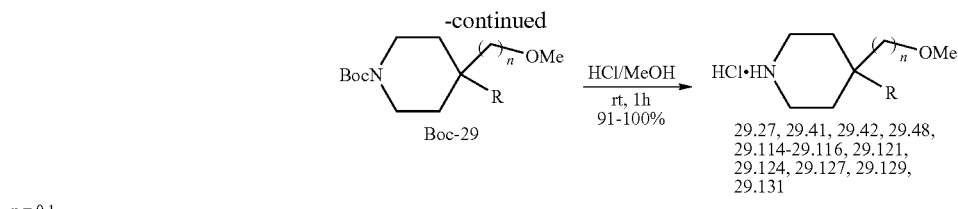

n = 0,1
R = iPr, cHex, Bn, 2-thienyl,
Ph, 2-ClPh, 4-ClPh, 2-FPh,
4-FPh, 2-BrPh, 3-CF₃Ph,
2-MeOPh, 3-MeOPh,
2-MePh, 2'-Cl-biphenyl,
5-Me-pyridin-2-yl

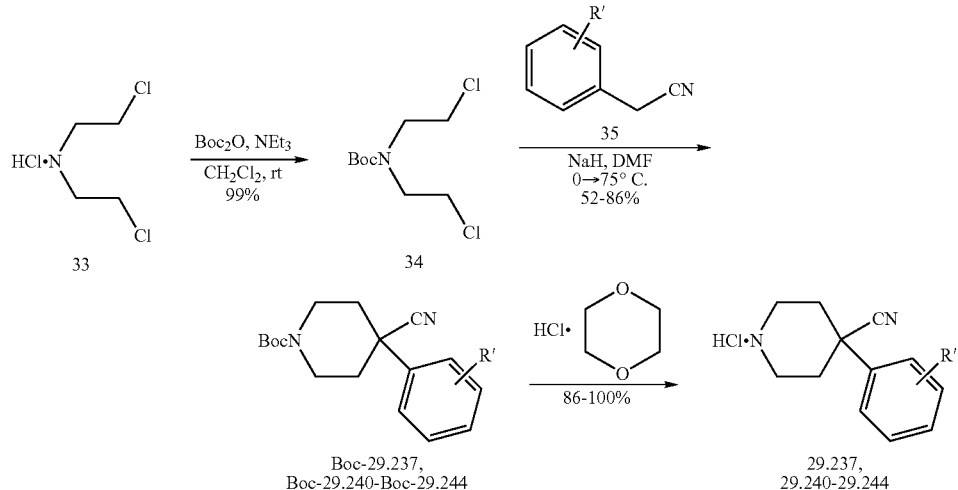

In addition, standard reactions with 4-acetyl-4-phenylpiperidine 29.76 (reduction and addition of methyllithium) gave piperidines 29.93 and 29.102, respectively. 4-Alkyl-4-phenylpiperidines 29.108, 29.110, and 29.128 and 3,3-diphenylpiperidine (29.26) were synthesized by Friedel-Crafts reactions using aluminium trichloride (see J. Med. Chem. 1998, 41, 5320-5333) or triflic acid (see J. Org. Chem. 1999, 64, 6702-6705), respectively. Esters 29.92, 29.95, and 29.118 were prepared from the acid 29.85 using the alcohol as solvent and $H_2SO_4$ as acid catalyst.

4-(2-Chlorophenyl)-4-hydroxypiperidine-1-carboxylic acid tert-butyl ester (Boc-29.43), method A (I-Li exchange)

To a solution of 2-chloroiodobenzene (122 µL, 0.999 mmol) in THF (10 mL), cooled by dry ice/acetone, was added nBuLi (2.5M in hexanes, 0.5 mL, 1.25 mmol). After 30 min, a solution of N-Boc-4-piperidone (Boc-29.155) (225 mg, 1.13 mmol) in THF (1 mL) was added. After 1.5 h the cooling bath was removed, and after another 1.5 h the reaction was quenched by adding sat. $NaHCO_3$ solution and water. The mixture was extracted with EtOAc (4×15 mL), the combined organic layers were washed with 2N NaOH, water, and brine, dried over $MgSO_4$, filtered and concentrated. This material was dissolved in MeOH (5 mL), $NaBH_4$ (19 mg, 0.5 mmol) was added, and the solution was stirred at ambient temperature for 1 h. The solvent was evaporated, water was added, and the solution was extracted with EtOAc (4×15 mL). The combined organic layers were washed with water and brine, dried over $MgSO_4$, filtered and concentrated. The crude material was chromatographed on silica gel, giving 180 mg of a mixture of Boc-29.43 (49%) and Boc-29.47 (7%). Boc-29.47: MS (ES): m/z 388.0/390.0 (20/7) [MH⁺]. ¹H NMR ($CDCl_3$, 200 MHz): most peaks overlap with those of the 2-chlorophenyl compound, δ=1.45 (s, 9H), 6.96-7.03 (m, 1H). $t_R$ (non-polar)=11.0 min.

Method B (I-Mg exchange): To a solution of 2-chloroiodobenzene (145 µL, 1.19 mmol) in THF (3 mL), cooled to −20 to −15° C., was added iPrMgCl (2M in THF, 0.6 mL, 1.2 mmol). After 30 min, a solution of N-Boc-4-piperidone (Boc-29.155) (203 mg, 1.02 mmol) in THF (2 mL) was added, and the reaction mixture was stirred overnight, warming up to ambient temperature. Sat. $NH_4Cl$ solution and water were added, and the solution was extracted with EtOAc (3×15 mL). The combined organic layers were washed with brine, dried over $MgSO_4$, filtered and concentrated. This material was dissolved in MeOH (10 mL), $NaBH_4$ (38 mg, 1 mmol) was added, and the solution was stirred at ambient temperature for 1.5 h. The solvent was evaporated, water was added, and the solution was extracted with EtOAc (3×15 mL). The combined organic layers were washed with water and brine, dried over $MgSO_4$, filtered and concentrated. The crude material was chromatographed on silica gel, giving 168 mg (0.540 mmol, 53%) of Boc-29.43. Trituration of the slowly solidifying oil with hexanes yielded 158 mg (0.507 mmol, 50%) of analytically pure compound as colorless crystals, mp 126-127° C. MS (ES): m/z 312.0/314.0 (10/3) [MH⁺]. ¹H NMR ($CDCl_3$, 200 MHz): δ=1.48 (s, 9H), 1.98 brd, J=14.0 Hz, 2H), 2.24 (brdt, J=4.8, 12.8 Hz, 2H), 2.82 (s, 1H), 3.16 (brt, J=12.8 Hz, 2H), 4.04 (brd, J=10.8 Hz, 2H), 7.15-7.29 (m, 2H), 7.31-7.41 (m, 1H), 7.50-7.56 (m, 1H). $t_R$ (non-polar)=9.9 min.

$C_{16}H_{22}ClNO_3$ (311.81): calcd. C, 61.63; H, 7.11; N, 4:49; Cl, 11.37. Found C, 61.75; H, 7.14; N, 4.42; Cl, 11.50.

4-Hydroxy-4-o-tolylpiperidine-1-carboxylic acid tert-butyl ester

N-Boc-4-piperidone (Boc-29.155) (200 mg, 11.0 mmol) was dissolved in 5 ml of anhydrous ethyl ether, cooled in dry ice/acetone bath. 2-Tolylmagnesium bromide (550 µl, 2M in ethyl ether, 1.1 mmol) was added dropwise over 5 min. White precipitate was formed. After 5 h, remove the dry ice/acetone bath and rise to room temperature gradually. After 2 h, cooled in ice bath, 8 ml of saturated $NH_4Cl$ and 2 ml of $H_2O$ were added. The organic phase was separated and aqueous phase was extracted with 4×10 ml of $Et_2O$. Combined with organic phase and washed with 8 ml of $H_2O$ and 10 ml of brine, dried over $MgSO_4$. Concentrated and dried to obtain 361 mg of colorless oil. Separated by silica gel to obtain 4f (229.7 mg, 79% yield) as colorless oil. $^1H$ NMR ($CDCl_3$, 200 MHz) δ 1.47 (s, 9H), 1.93 (m, 4H), 2.60 (s, 3H), 3.27 (t, 2H, J=13.0 Hz), 3.96 (d, 2H, J=12.2 Hz), 7.15 (m, 3H), 7.35 (m, 1H).

4-Methoxy-4-thiophen-2-ylpiperidine-1-carboxylic acid tert-butyl ester

To a solution of N-Boc-4-piperidone (Boc-29.155) (201 mg, 1.01 mmol) in THF (5 mL), cooled by dry ice/acetone, was added 2-thienyllithium (1M in THF, 1.5 mL, 1.5 mmol). After 50 min, the cooling bath was removed; after additional 1 h, methyl iodide (125 µL, 2.01 mmol) was added, and the solution was stirred at ambient temperature overnight. The solvent was evaporated, water was added, and the mixture was extracted with EtOAc (4×15 mL). The combined organic layers were washed with water and brine, dried over $MgSO_4$, filtered and concentrated. The crude material (acc. to $^1H$ NMR mixture of methyl ether and the alcohol in a 1:2 ratio) was methylated according to the general procedure, yielding 300 mg (1.01 mmol, 100% yield) of the title compound as yellow oil. $^1H$ NMR ($CDCl_3$, 200 MHz): δ=1.46 (s, 9H), 1.93 (brdt, J=4.3, 12.6 Hz, 2H), 2.00 (brd, J=12.8 Hz, 2H), 3.05 (s, 3H), 3.16 (brt, J=11.0 Hz, 2H), 3.84 (brd, J=12.2 Hz, 2H), 6.93-7.00 (m, 2H), 7.25-7.31 (m, 1H).

4-Cyclohexyl-4-hydroxypiperidine-1-carboxylic acid tert-butyl ester

Prepared according to the procedure for Boc-29.43. White solid, 37% yield of analytically pure material, mp. 87-89° C. $C_{16}H_{29}NO_3$ (283.41): calcd. C, 67.81; H, 10.31; N, 4.94. Found C, 67.89; H, 10.31; N, 4.94.

4-(2-Fluorophenyl)-4-hydroxypiperidine-1-carboxylic acid tert-butyl ester

Prepared according to method A of preparation of Boc-29.43. White solid, 61% yield of analytically pure material, mp. 109-110° C. $C_{16}H_{22}FNO_3$ (295.36): calcd. C, 65.07; H, 7.51; N, 4.74. Found C, 64.79; H, 7.45; N, 4.70.

4-(2-Bromophenyl)-4-hydroxypiperidine-1-carboxylic acid tert-butyl ester

Prepared according to method B of preparation of Boc-29.43. MS (ES): m/z 356/358 [MH+].

4'-Hydroxy-3-methyl-3',4',5',6'-tetrahydro-2'H-[2,4']bipyridinyl-1'-carboxylic acid tert-butyl ester Prepared according to method B of preparation of Boc-29.43. $^1H$ NMR ($CDCl_3$, 200 MHz): δ=1.50 (s, 9H), 2.22-2.40 (m, 4H), 2.50 (s, 3H), 3.33 (brt, J=12.8 Hz, 2H), 4.10 (brd, J=10.8 Hz, 2H), 7.17 (dd, J=4.7, 7.7 Hz, 1H), 7.50 (dd, J=1.2, 7.7 Hz, 1H), 8.37 (dd, J=1.2, 4.8 Hz, 1H).

General Procedure for the Boc-protection of aminoalcohols: To a solution of the aminoalcohol (1.99 mmol) in $CH_2Cl_2$ (20 ml) are added $Boc_2O$ (440 mg, 2.02 mmol) and DMAP (5 mg, 0.04 mmol). After stirring at ambient temperature for 18 h, the reaction mixture is concentrated and dried to obtain the Boc-protected aminoalcohol, which is typically used directly in the next step or purified by chromatography.

4-Hydroxy-4-phenylpiperidine-1-carboxylic acid tert-butyl ester (Boc-29.7)

Prepared according to general procedure, 100% yield. White solid, mp. 120-121° C. $^1H$ NMR ($CDCl_3$, 200 MHz): δ=1.48 (s, 9H), 1.65-1.80 (m, 2H), 2.00 (brdt, J=4.7, 13.0 Hz, 2H), 3.24 (brt, J=11.7 Hz, 2H), 4.02 (brd, J=11.7 Hz, 2H), 7.21-7.41 (m, 3H), 7.44-7.52 (m, 2H).

4-(4-Fluorophenyl)-4-hydroxypiperidine-1-carboxylic acid tert-butyl ester (Boc-29.18)

Prepared according to general procedure, 86% yield. $^1H$ NMR ($CDCl_3$, 200 MHz): δ=1.48 (s, 9H), 1.65-1.80 (m, 2H), 1.97 (brdt, J=4.8, 12.4 Hz, 2H), 3.23 (brt, J=12.8 Hz, 2H), 4.03 (brd, J=12.8 Hz, 2H), 6.99-7.10 (m, 2H), 7.40-7.50 (m, 2H).

General Procedure for the methylation of alcohols: To a solution of the alcohol (0.55 mmol) in dry THF (5 mL), cooled by ice/water, is added KHMDS (0.5M solution in toluene, 1.6 mL, 0.80 mmol). After 30 min, methyl iodide (50 µL, 0.80 mmol) is added.

A white precipitate appears almost immediately. The cooling bath is then removed, and the reaction mixture is stirred at ambient temperature. As judged by TLC, the reaction is usually complete after 1 h; if the starting alcohol is still present, additional KHMDS and methyl iodide are added to drive the reaction to completion. For workup, sat. $NaHCO_3$ sol. and water are added, the mixture is extracted with $CH_2Cl_2$ (4×15 mL). The combined organic layers are washed with brine, dried over $MgSO_4$, filtered and concentrated. The crude material can typically be used directly in the next step or is purified by chromatography.

4-(2-Chlorophenyl)-4-methoxypiperidine-1-carboxylic acid tert-butyl ester (Boc-29.42) and 4-(2'-chlorobiphenyl-2-yl)-4-methoxypiperidine-1-carboxylic acid tert-butyl ester (Boc-29.46)

Synthesized from the mixture of Boc-29.43 and Boc-29.47 according to the general procedure in 95% yield. Boc-29.42: $^1H$ NMR ($CDCl_3$, 200 MHz): δ=1.47 (s, 9H), 1.92 (m_c, 2H), 2.38 (brd, J=13.8 Hz, 2H), 3.02 (s, 3H), 3.20 (brt, J=12.6 Hz, 2H), 3.99 (brd, J=10.2 Hz, 2H), 7.15-7.43 (m, 4H). Boc-2946: $^1H$ NMR ($CDCl_3$, 200 MHz): most peaks overlap with those of the 2-chlorophenyl compound. δ=1.41 (s, 9H), 3.01 (s, 3H), 6.96-7.03 (m, 1H), 7.60-7.65 (m, 1H).

4-Methoxy-4-phenylpiperidine-1-carboxylic acid tert-butyl ester (Boc-29.27)

Synthesized according to the general procedure in 100% yield. IR (film): ν=3059 cm$^{-1}$, 2974, 2933, 2874, 1693, 1446, 1422, 1365, 1281, 1246, 1214, 1169, 1130, 1070, 1024, 893, 864, 761, 700. $^1$H NMR (CDCl$_3$, 200 MHz): δ=1.47 (s, 9H), 1.85 (brdt, J=2.2, 12.0 Hz, 2H), 2.03 (brd, J=12.6 Hz, 2H), 2.98 (s, 3H), 3.18 (brt, J=12.3 Hz, 2H), 3.97 (brd, J=11.0 Hz, 2H), 7.26-7.40 (m, 5H).

4-(4-Fluorophenyl)-4-methoxypiperidine-1-carboxylic acid tert-butyl ester (Boc-29.48)

Synthesized according to the general procedure in 70% yield. $^1$H NMR (CDCl$_3$, 200 MHz): δ=1.47 (s, 9H), 1.81 (brdt, J=3.6, 13.2 Hz, 2H), 2.00 (brd, J=12.2 Hz, 2H), 2.96 (s, 3H), 3.16 (brt, J=11.9 Hz, 2H), 3.97 (brd, J=10.2 Hz, 2H), 7.00-7.10 (m, 2H), 7.30-7.40 (m, 2H).

General Procedure for the removal of Boc groups: Acetyl chloride (1.5 mL, 21 mmol) is added dropwise into dry methanol (8 mL) at ambient temperature. After 10 min, this solution is added to a solution of the Boc-protected amine (0.9 mmol), and the reaction is stirred at ambient temperature. Upon complete consumption of starting material as judged by TLC, the solvents are evaporated. The residue (amine hydrochloride) is used directly for the amide formation.

4-(2-Chlorophenyl)-4-methoxypiperidine hydrochloride (29.42) and 4-(2'-Chloro-biphenyl-2-yl)-4-methoxypiperidine hydrochloride (29.46)

General procedure was followed using the material derived from the mixture of Boc-29.42 and Boc-29.46. Pale yellow foam, 100% yield. 29.42: MS (ES): m/z 226.0/228.0 (22/8) [MH$^+$], 194.0/196.0 (100/35) [MH$^+$-MeOH]. $^1$H NMR (CDCl$_3$, 200 MHz): δ=2.2-2.5 (brs, 2H), 2.5-2.7 (brs, 2H), 2.99 (s, 3H), 3.42 (brs, 4H), 7.25-7.45 (m, 4H). t$_R$ (non-polar)= 3.8 min. 29.46: MS (ES): m/z 302.0/304.0 (4/1) [MH$^+$], 270.0/272.0 (100/35) [MH$^+$-MeOH]. No distinct peaks in the $^1$H NMR. t$_R$ (non-polar)=4.7 min.

4-(2-Chlorophenyl)-piperidin-4-ol (29.43) and 4-(2'-chlorobiphenyl-2-yl)-piperidin-4-ol (29.47)

A solution of the mixture of amines Boc-29.43 and Boc-29.47 (34 mg, 0.11 mmol) and H$_2$SO$_4$ (20 mg, 0.20 mmol) in methanol (3 mL) was stirred at ambient temperature for 3.5 days. Sat. NaHCO$_3$ was added, and the mixture was extracted with CH$_2$Cl$_2$ (5×10 mL). The combined organic layers were dried over MgSO$_4$, filtered and concentrated to yield 12 mg (0.057 mmol, 52%) of 29.43, containing ≈15% of the chlorobiphenyl piperidine 29.47. 29.43: $^1$H NMR (CDCl$_3$, 200 MHz): δ=1.90-2.10 (brm, 2H), 2.28 (brdt, J=4.4, 13.6 Hz, 2H), 2.8-3.1 (brm, 2H), 3.1-3.3 (brm, 2H), 7.15-7.45 (m, 3H), 7.55-7.61 (m, 2H). Only distinguishable peak of 29.47: $^1$H NMR (CDCl$_3$, 200 MHz): δ=6.98-7.16 (m, 1H).

4-Methoxy-4-phenylpiperidine hydrochloride (29.27)

General procedure was followed, beige solid, 97% yield. $^1$H NMR (CDCl$_3$, 200 MHz): δ=2.19 (brd, J=14.2 Hz, 2H), 2.24-2.44 (brm, 2H), 2.98 (s, 3H), 3.40 (brs, 4H), 7.27-7.44 (m, 5H), 9.6 (brs, 2H).

4-(4-Fluorophenyl)-4-methoxypiperidine hydrochloride (29.48)

General procedure was followed, beige solid, 99% yield. $^1$H NMR (CDCl$_3$, 200 MHz): δ=2.10-2.25 (brm, 2H), 2.25-2.45 (brm, 2H), 2.96 (s, 3H), 3.39 (brs, 4H), 7.00-7.15 (m, 2H), 7.25-7.38 (m, 2H), 9.6 (brs, 2H).

Following the general procedures for Boc-protection, methylation, and deprotection, the following 7 piperidines were prepared.

4-(4-Chlorophenyl)-4-methoxypiperidine hydrochloride salt (29.114)

44% yield. $^1$H NMR (CDCl$_3$, 200 MHz): δ=2.21 (brs, 4H), 2.97 (s, 3H), 3.36 (brs, 4H), 7.35 (m, 4H).

4-Methoxy-4-(3-trifluoromethylphenyl)-piperidine hydrochloride salt (29.115)

49% yield. $^1$H NMR (CDCl$_3$, 200 MHz): δ=1.99 (brs, 4H), 2.99 (s, 3H), 3.20 (brs, 2H), 3.99 (brs, 2H), 7.55 (m, 4H).

4-Isopropyl-4-methoxypiperidine hydrochloride salt (29.116)

18% yield. $^1$H NMR (CDCl$_3$, 200 MHz): δ=0.85 (d, 6H, J=6.6 Hz), 1.54 (brs, 4H), 1.94 (m, 1H), 2.96 (brs, 2H), 3.20 (s, 3H), 3.87 (brs, 2H).

4-Methoxy-4-(3-methoxyphenyl)-piperidine hydrochloride salt (29.121)

42% yield. $^1$H NMR (CD$_3$OD, 200 MHz): δ=2.25 (m, 4H), 2.99 (s, 3H), 3.31 (m, 4H), 3.80 (s, 3H), 6.96 (m, 3H), 7.32 (t, 1H, J=7.6 Hz).

4-Benzyl-4-methoxypiperidine hydrochloride salt (29.129)

49% yield. $^1$H NMR (CD$_3$OD, 200 MHz): δ=1.89 (m, 4H), 2.86 (s, 2H), 3.14 (brs, 4H), 3.34 (brs, 2H), 3.37 (s, 3H), 7.22 (m, 5H).

4-Methoxy-4-o-tolylpiperidine hydrochloride salt (29.130):

38% yield. $^1$H NMR (CD$_3$OD, 200 MHz): δ=2.12 (m, 2H), 2.48 (brs, 2H), 2.53 (s, 3H), 2.97 (s, 3H), 3.33 (brs, 4H), 7.20 (brs, 4H).

4-Methoxymethyl-4-phenylpiperidine hydrochloride salt (29.131)

64% yield. $^1$H NMR (CD$_3$OD, 200 MHz): δ=2.20 (m, 2H), 2.48 (d, 2H, J=15.0 Hz), 2.93 (t, 2H, J=11.4 Hz), 3.24 (s, 3H), 3.31 (m, 4H), 7.28-7.43 (m, 5H).

4-Methoxy-4-(2-methoxyphenyl)-piperidine (29.124)

Boc-29.70 was dissolved in 30 ml anhydrous MeOH and then 10 drops of conc. H$_2$SO$_4$ was added. The whole mixture was reflux under N$_2$ overnight. After heating, triethylamine was added till pH=7-8. Concentrated and then dissolved in 6 ml saturated NaHCO$_3$, extracted with 5×12 ml EtOAc, washed with 2×10 ml brine and dried over MgSO$_4$. Filtered and concentrated to obtain 5.1 mg (10%) of beige oil. This oil was used for further reaction without purification.

Bis-(2-chloroethyl)-carbamic acid tert-butyl ester (34)

To a suspension of 33 (10.05 g, 56.3 mmol) and Boc$_2$O (13.6 g, 62.3 mmol) in CH$_2$Cl$_2$ (70 mL), cooled by ice/water, was added triethylamine (9.5 mL, 68.2 mmol). After 45 min, the cooling bath was removed, and the reaction mixture was stirred at ambient temperature overnight. Water (50 mL) was added, and the mixture was extracted with ether:hexanes 1:1 (3×100 mL). The combined organic layers were washed with water (2×) and brine, dried over MgSO$_4$ and concentrated to give a pale yellow liquid, which was a 1:1 mixture of 34 and Boc$_2$O. The reaction was therefore repeated with this material twice, first with 5.89 g (33.0 mmol) of 33 and 4.8 mL of NEt$_3$ (34 mmol) and then with 2.5 g (14 mmol) of 33 and 2.3 mL of NEt$_3$ (17 mmol). This gave 14.887 g (61.5 mmol, 99%) of the known amine 34 as pale yellow liquid, pure by $^1$H NMR and TLC. $^1$H NMR (CDCl$_3$, 200 MHz): δ=1.47 (s, 9H), 3.55-3.70 (brm, 8H).

4-(2-Chlorophenyl)-4-cyanopiperidine-1-carboxylic acid tert-butyl ester (Boc-29.237)

To a suspension of NaH (60% oil suspension, 7.37 g, 184.4 mmol) in DMF (110 mL), cooled by ice/water, was added a solution of the nitrile 35.237 (9.782 g, 64.52 mmol) in DMF (20 mL) over 20 min. Hydrogen evolved, and the reaction mixture turned yellow. After 30 min, a solution of the chloroamine 34 (14.88 g, 61.45 mmol) in DMF (15 mL) was added. After 15 min the cooling bath was removed, and the reaction mixture was heated to 75° C. (bath temperature) for 5.5 h. TLC indicated the complete consumption of both starting materials. The DMF was evaporated. Upon addition of water and ether (200 mL each) a solid separated, which was filtered off, washed thoroughly with ether and EtOAc, and dried, yielding 8.018 g (24.99 mmol, 41%) of Boc-29.237. The layers of the combined filtrate and washings were separated, and the aqueous layer was extracted with more ether (2×150 mL). The combined organic layers were washed with 5% HOAc, water, 1N NaOH, water, and brine and dried over MgSO$_4$. This solution was filtered through a pad of silica gel. Upon concentration a solid precipitated, which was filtered off, washed with ether and hexanes and dried, yielding 6.138 g (19.13 mmol, 31%) of Boc-29.237. The mother liquor was concentrated and the residue purified by column chromatography on silica gel, yielding 2.885 g (8.99 mmol, 15%) of Boc-29.237. The total yield was 17.04 g (53.12 mmol, 86%), mp 165-166° C. $^1$H NMR (CDCl$_3$, 200 MHz): δ=1.48 (s, 9H), 2.00 (brdt, J=4.2, 13.0 Hz, 2H), 2.43-2.53 (m, 2H), 3.28 (brt, J=12.8 Hz, 2H), 4.28 (brd, J=13.2 Hz, 2H), 7.28-7.50 (m, 4H). C$_{17}$H$_{21}$ClN$_2$O$_2$ (320.82): calcd. C, 63.65; H, 6.60; Cl, 11.05; N, 8.73. Found C, 63.82; H, 6.61; Cl, 10.90; N, 8.72.

4-(2-Chlorophenyl)-piperidine-4-carbonitrile hydrochloride (29.237)

A solution of HCl in dioxane (4M, 200 mL, 800 mmol) was added to the Boc-protected amine Boc-29.237 (18.4 g, 57.4 mmol). After 1.5 h the solvent was evaporated and the residue dried in vacuo, giving 14.8 g (57.4 mmol, 100%) of 29.237, colorless solid, mp 241-243° C. (decomp.). MS (ES) 221 [MH$^+$], t$_R$ (method B)=8.15 min. $^1$H NMR (CDCl$_3$, 200. MHz): δ=2.5-2.8 (brm, 4H), 3.43.6 (brm, 2H), 3.63.8 (brm, 2H), 7.33-7.39 (m, 3H), 7.48-7.53 (m, 1H), 10.01 (brs, 2H). C$_{12}$H$_{14}$Cl$_2$N$_2$ (257.16): calcd. C, 56.05; H, 5.49; Cl, 27.57; N, 10.89. Found C, 55.67; H, 5.48; Cl, 27.86; N, 10.61.

The following compounds were prepared in a similar manner:

4-Cyano-4-(2-methoxyphenyl)-piperidine-1-carboxylic acid tert-butyl ester (Boc-26.240)

MS (ES) 217.0 [MH$^+$-Boc], t$_R$ (method A)=9.9 min.

4-(3-Chlorophenyl)-4-cyanopiperidine-1-carboxylic acid tert-butyl ester (Boc-26.241)

MS (ES) 221.0 [MH$^+$-Boc].

4-Cyano-4-(3-methoxyphenyl)-piperidine-1-carboxylic acid tert-butyl ester (Boc-26.242)

MS (ES) 217.0 [MH$^+$. Boc].

4-(4-Chlorophenyl)-4-cyanopiperidine-1-carboxylic acid tert-butyl ester (Boc-26.243)

MS (ES) 221.0 [MH$^+$-Boc], t$_R$ (method A)=10.7 min.

4-Cyano-4-(4-methoxyphenyl)-piperidine-1-carboxylic acid tert-butyl ester (Boc-26.244)

$^1$H NMR (CDCl$_3$, 200 MHz): δ=1.48 (s, 9H), 1.90 (brdt, J=4.3, 12.8 Hz, 2H), 2.02-2.14 (m, 2H), 3.19 (brt, J=12.4 Hz, 2H), 3.81 (s, 3H), 4.28 (brd, J=13.6 Hz, 2H), 6.93 and 7.38 (AA'BB', 4H).

4-(2-Methoxyphenyl)-piperidine-4-carbonitrile hydrochloride (29.240)

MS (ES) 217.07 [MH$^+$], t$_R$ (method B)=7.70 min.

4-(3-Chlorophenyl)-piperidine-4-carbonitrile hydrochloride (29.241)

MS (ES) 220.98 [MH$^+$], t$_R$ (method B)=8.57 min.

4-(3-Methoxyphenyl)-piperidine-4-carbonitrile hydrochloride (29.242)

MS (ES) 217.02 [MH$^+$], t$_R$ (method B)=7.28 min.

4-(4-Chlorophenyl)-piperidine-4-carbonitrile hydrochloride (29.243)

MS (ES) 220.96 [MH$^+$], t$_R$ (method B)=8.83 min.

4-(4-Methoxyphenyl)-piperidine-4-carbonitrile hydrochloride (29.244)

MS (ES) 217.02 [MH$^+$], t$_R$ (method B)=7.43 min.

General Procedure for Friedel-Crafts Reaction: 4-Isopropylpiperidin-4-ol 29.4 (62.4 mg, 0.436 mmol) and AlCl$_3$ (178 mg, 3 eq.) was suspended in benzene (15 ml), refluxed under argon for 24 h. the reaction mixture was poured into 20 ml of ice-water, extracted with 5×10 ml of EtOAc, washed with 2×15 ml of brine, dried over MgSO$_4$. After solvent removed and purified by TLC, brownish oil 29.110 (25.3 mg, 29%) was obtained. 29.128 and Bn-29.108 were prepared by the same method.

1-Benzyl-4-methyl-4-phenylpiperidine (Bn-29.108)

$^1$H NMR (CDCl$_3$, 200 MHz) δ 1.20 (m, 3H), 1.78 (m, 2H), 2.13 (m, 2H), 2.45 (m, 4H), 3.45 (s, 2H), 7.13-7.32 (m, 10H).

4-Ethyl-4-phenylpiperidine (29.128)

$^1$H NMR (CDCl$_3$, 200 MHz) δ 0.56 (t, 3H, J=7.3 Hz), 1.58 (m, 2H), 1.87 (m, 2H), 2.19 (m, 2H), 3.03 (brs, 2H), 3.56 (brs, 2H), 7.10-7.37 (m, 5H).

4-Isopropyl-4-phenylpiperidine (29.110)

$^1$H NMR (CDCl$_3$, 200 MHz) δ 1.12-1.20 (m, 2H), 1.27 (d, 6H), 1.41-1.63 (m, 3H), 2.28 (brs, 1H), 2.50 (t, 2H, J=11.2 Hz), 3.09 (d, 2H, J=12.2 Hz), 4.49 (s, 2H), 7.14-7.31 (m, 5H).

4-Phenylpiperidine-4-carboxylic acid methyl ester (29.92)

After 29.85 (113 mg, 0.3 mmol) and methanol (50 ml) were combined together, 2 drops of concentrated H$_2$SO$_4$ were added and the solution was heated to reflux. After 14 h, the solvent was removed and 2N NaOH was added till pH=13-14. Extracted with 3×10 ml of CH$_2$Cl$_2$, washed with 2×10 ml of brine, dried over MgSO$_4$. After solvent was removed, white solid 29.92 (20 mg, 31% yield) was obtained. $^1$HNMR (CD$_3$OD, 200 MHz): δ=1.92 (m, 2H), 2.52 (m, 2H), 2.78 (m, 2H), 3.02 (m, 2H), 3.65 (s, 3H), 7.20-7.42 (m, 5H). 29.95 and 29.118 were prepared by the same method, using ethanol and isopropanol, respectively, as solvents in place of methanol.

4-Phenylpiperidine-4-carboxylic acid ethyl ester (29.95)

25% yield. $^1$H NMR (CD$_3$OD, 200 MHz): δ=1.16 (t, 3H, J=7 Hz), 1.91 (m, 2H), 2.52 (m, 2H), 2.80 (m, 2H), 3.03 (m, 2H), 4.11 (q, 2H, J=11.5 Hz), 7.20-7.41 (m, 5H).

4-Phenylpiperidine-4-carboxylic acid isopropyl ester (29.118)

12% yield. $^1$H NMR (CDCl$_3$, 200 MHz): δ=1.17 (d, 6H, J=3.1 Hz), 2.23 (brs, 2H), 2.64 (brs, 2H), 3.01 (brs, 2H), 3.39 (brs, 2H), 5.03 (m, 1H), 7.27-7.34 (m, 5H).

EXAMPLE 2

Preparation of Non-commercial 3- and 4-monosubstituted Piperidines 29

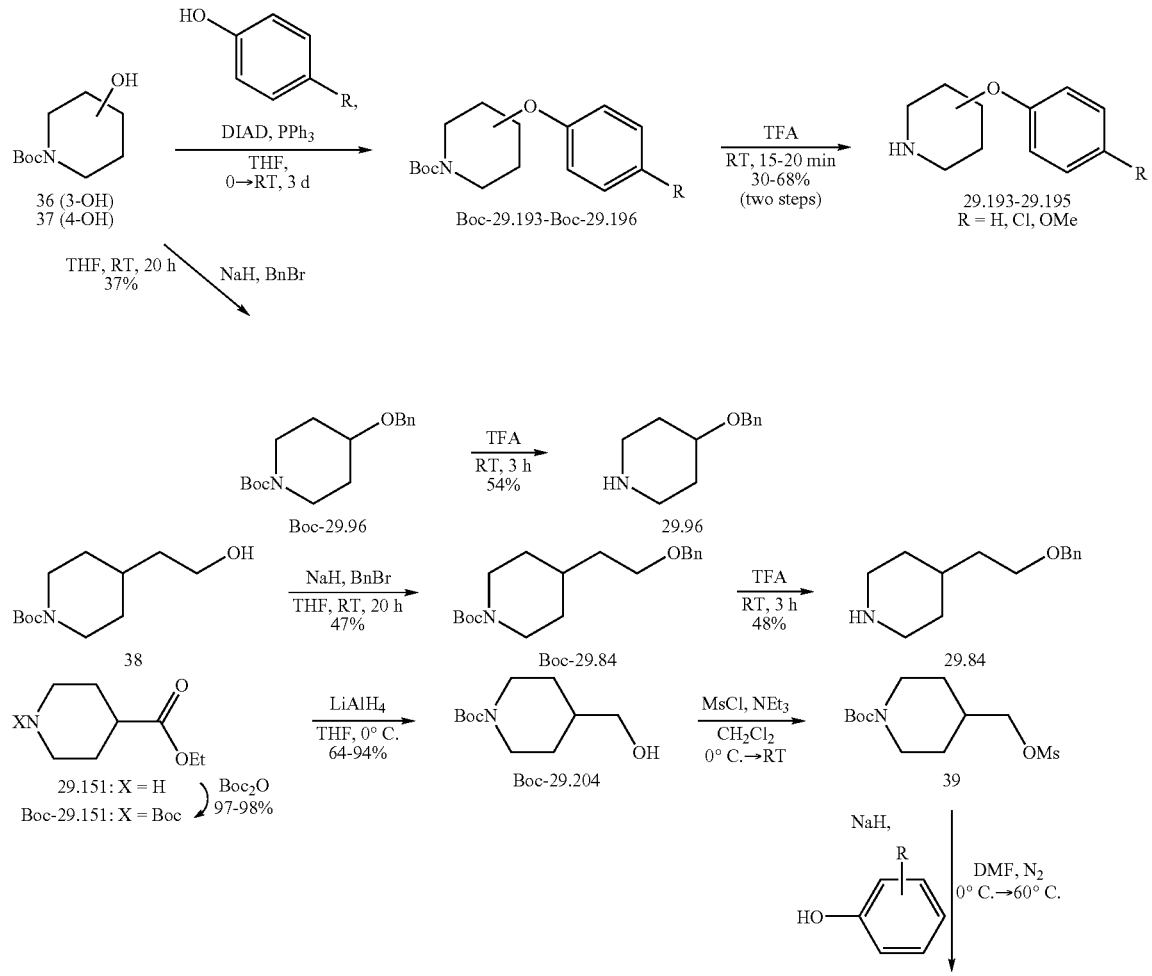

Scheme 2. Preparation of non-commercial 3- and 4-monosubstituted piperidines 29.

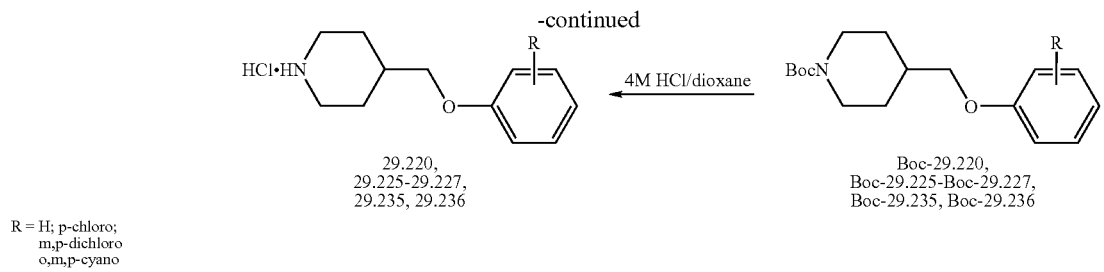

R = H; p-chloro;
m,p-dichloro
o,m,p-cyano

4-(4-Chlorophenoxy)-piperidine-1-carboxylic acid tert-butyl ester (Boc-29.194)

A solution of DIAD (11.4 mL; 55.0 mmol) in THF (15 mL) was added dropwise over 35 min to an ice-cold solution of 4-hydroxypiperidine-1-carboxylic acid tert-butyl ester (10.06 g; 50.0 mmol), 4-chlorophenol (5.1 mL; 50.4 mmol) and triphenylphosphine (14.44 g; 55.1 mmol) in THF (40 mL). After 2.9 days at room temperature the solvent was removed on a rotary evaporator leaving a viscous liquid; hexanes was added then evaporated leaving a solid. Ether (25 mL), followed by hexanes (100 mL), was added and the solid was filtered and washed with hexanes. The filtrate was concentrated on a rotary evaporator leaving a golden, viscous liquid (19.6 g). The crude product was used as is. ESIMS 311.9/313.8 (25/10) [MH$^+$], 296.9/298.8 (100/34) [MH$^+$—C$_4$H$_9$+CH$_3$CN], 255.9/257.8 (94/32) [MH$^+$—C$_4$H$_9$], 212.0/214.0 (13/5) [MH$^+$—C$_4$H$_9$—CO$_2$].

4-(4-Chlorophenoxy)-piperidinium chloride (29.194)

Trifluoroacetic acid (40 mL) was added to crude carbamate Boc-29.194 (18.6 g; 59.7 mmol) cooled in an ice-water bath. After 1 min the reaction was stirred at rt for 15 min, then concentrated on a rotary evaporator. Ether (200 mL) was added and this washed with 3 M NaOH (3×50 mL) and water (50 mL). The product was extracted into 1 M HCl (3×50 mL) and the aq phase was basified with 3 M NaOH (60 mL). The free base was extracted into DCM (1×50 mL then 2×25 mL), dried (MgSO$_4$), filtered and concentrated to an oil. The hydrochloride salt was precipitated from a methanolic (6 mL) solution of the free base by the dropwise addition of HCl in ether (200 mL of HCl-saturated ether plus 150 mL of ether). The salt was collected by filtration and washed with ether (100 mL) giving an off-white solid (7.97 g; 68% from 4-hydroxypiperidine-1-carboxylic acid tert-butyl ester). ESIMS (free base) 212.0/213.9 (100/35) [MH$^+$].

29.193 and 29.19529.196 were prepared in the same way.

General Procedure for benzyl ether formation: A solution of 4-(2-hydroxyethyl)-piperidine-1-carboxylic acid tert-butyl ester (114.7 mg, 0.5 mmol) in THF (2 ml) was added into NaH (13.2 mg, 1.1 eq.) and THF (2 ml) suspension at rt and under N$_2$. After 30 min a solution of benzyl bromide (65.4 μl, 1.1 eq.) in THF (2 ml) was added. After 20 h, solvent was removed and poured into 10 ml of H$_2$O, extracted with 3×10 ml of EtOAc, washed with 10 ml of H$_2$O and 10 ml of brine, dried over MgSO$_4$. After solvent removed and purified by silica gel, Boc-29.84 was obtained (75.5 mg, 47% yield). Into Boc-29.84, TFA (1 ml) was added and stirred for 3 h. Excess TFA was removed and neutralized by 2N NaOH till pH=13, dissolved in 8 ml of H$_2$O, extracted with 5×8 ml of EtOAc, washed with 10 ml of brine, dried over MgSO$_4$. Remove solvent to obtain 29.84 (24.6 mg, 48% yield).

29.96 was prepared by the same route.

4-(2-Benzyloxyethyl)-piperidine-1-carboxylic acid tert-butyl ester (Boc-29.84)

$^1$H NMR (CDCl$_3$, 200 MHz) δ 1.13 (m, 2H), 1.45 (s, 9H), 1.59 (m, 5H), 2.67 (t, 2H, J=12.1 Hz), 3.50 (t, 2H, J=6 Hz), 4.09 (d, 2H, J=12.8 Hz), 4.49 (s, 2H), 7.26-7.35 (m, 5H).

4-(2-Benzyloxyethyl)-piperidine (29.84)

$^1$H NMR (CDCl$_3$, 200 MHz) δ 1.15 (m, 2H), 1.58 (m, 5H), 2.60 (brs, 2H), 3.04 (brs, 2H), 3.51 (t, 2H, J=5.6 Hz), 4.49 (s, 2H), 7.26-7.34 (m, 5H).

4-Benzyloxypiperidine-1-carboxylic acid tert-butyl ester (Boc-29.96)

37% yield. $^1$H NMR (CDCl$_3$, 200 MHz) δ 1.45 (s, 9H), 1.90 (m, 2H), 1.84 (m, 2H), 3.10 (m, 2H), 3.56 (m, 1H), 3.77 (m, 1H), 4.55 (s, 2H), 7.25-7.35 (m, 5H).

4-Benzyloxypiperidine (29.96)

54% yield. $^1$H NMR (CDCl$_3$, 200 MHz) δ 1.42 (brs, 2H), 1.88 (brs, 2H), 2.56 (brs, 2H), 3.03 (brs, 2H), 3.41 (m, 1H), 4.55 (s, 2H), 7.25-7.35 (m, 5H).

General Procedure for aryloxymethylpiperidines (*J. Med. Chem*, 1997, 40, 50-59)

Piperidine-1,4-dicarboxylic acid 1-tert-butyl ester 4-ethyl ester (Boc-29.151)

1 equiv. of ethyl isonipecotate was dissolved in ethyl acetate (anhydrous) and cooled to 0° C. in an ice-bath. Then 1 equiv. of Boc anhydride was dissolved in ethyl acetate and added dropwise to the stirring reaction mixture and allowed to slowly reach room-temp and stirred overnight. Reaction mixture was poured into water then washed with 1 portion of water, 0.1M HCl, sat'd sodium bicarb., and brine. This was dried with sodium sulfate, filtered and concentrated which resulted in a clear/colorless oil.

4-Hydroxymethylpiperidine-1-carboxylic acid tert-butyl ester (Boc-29.204)

1 equiv. of Boc-29.151 was dissolved in THF (anhydrous) and taken down to 0° C. in an ice-bath then 0.7 equiv. of LiAlH$_4$ (1 M in THF) was added dropwise to this stirring solution and was stirred for 2 hours at 0° C. Reaction mixture was then quenched at 0° C. with water and 2M sodium hydroxide and filtered through a fritted funnel and solid was washed with ethyl acetate. The filtrate was washed with water, brine, and dried with sodium sulfate, filtered and concentrated.

4-Methanesulfonyloxymethylpiperidine-1-carboxylic acid tert-butyl ester (39)

1 equiv. of Boc-29.204 was dissolved in DCM (anhydrous) and 1.2 equiv of TEA was also added to the reaction mixture and taken down to 0° C. in an ice-bath. 1.1 equiv. of methansulfonyl chloride was added to reaction mixture and slowly allowed to reach room temp. The reaction mixture was partitioned between chloroform and water and aqueous was washed 3 times with chloroform. Chloroform washes were combined dried with sodium sulfate, filtered, and concentrated resulting in a light brown/yellow oil which turned to a light tan solid upon standing in refrigerator.

4-Aryloxymethylpiperidine-1-carboxylic acid tert-butyl ester 1.1 equiv. of appropriate phenol was dissolved in DMF (anhydrous) and taken down to 0° C. in a ice-bath then 1.0 equiv of NaH was added and allowed to stir at 0° C. for 1 hour while slowly reaching room-temp. The mesylate 39 was dissolved in a minimum of DMF (anhydrous) and dropwise added to the reaction mixture and heated to 60° C. in an oil-bath overnight. The reaction mixture was concentrated via reduced pressure then partitioned between ether and 0.5M sodium hydroxide. The etherate was washed with 2 more portions of 0.5M sodium hydroxide, 1 portion water, and 1 portion of brine dried with sodium sulfate, filtered and concentrated resulting in an off-white to white solid.

4-Aryloxymethylpiperidines 1 equiv of Boc-protected aryloxymethylpiperidine was dissolved in 25-30 mL of 4M HCl in dioxane and stirred for 2 hours at room temp. reactions were complete by this time. Then reaction mixtures were concentrated and dried via reduced pressure.

4-Phenoxymethyl-piperidine-1-carboxylic acid tert-butyl ester MS (ES)

4-(4-Chlorophenoxymethyl)-piperidine-1-carboxylic acid tert-butyl ester MS (ES) no ionization [MH$^+$], t$_R$ (method A)=12.1 min.

4-(4-Cyanophenoxymethyl)-piperidine-1-carboxylic acid tert-butyl ester MS (ES) no ionization [MH$^+$] t$_R$ (method A)=10.7 min.

4-(3,4-Dichlorophenoxymethyl)-piperidine-1-carboxylic acid tert-butyl ester MS (ES) no ionization [MH$^+$], t$_R$ (method A)=12.7 min.

4-(3-Cyanophenoxymethyl)-piperidine-1-carboxylic acid tert-butyl ester MS (ES) no ionization [MH$^+$], t$_R$ (method A)=10.9 min.

4-(2-Cyanophenoxymethyl)-piperidine-1-carboxylic acid tert-butyl ester MS (ES) 316.89 [MH$^+$], t$_R$ (method A)=10.1 min.

4-Phenoxymethylpiperidine; hydrochloride MS (ES) 191.93 [MH$^+$], t$_R$ (method A)=3.6 min.

4-(4-Chlorophenoxymethyl)-piperidine; hydrochloride no ms data 4-(3,4-Dichlorophenoxymethyl)-piperidine; hydrochloride MS (ES) 259.80 [MH$^+$], t$_R$ (method A)=4.6 min.

4-(Piperidin-4-ylmethoxy)-benzonitrile; hydrochloride MS (ES) 216.93 [MH$^+$], t$_R$ (method A)=3.2 min.

3-(Piperidin-4-ylmethoxy)-benzonitrile; hydrochloride MS (ES) 216.94 [MH$^+$], t$_R$ (method A)=3.5 min.

2-(Piperidin-4-ylmethoxy)-benzonitrile; hydrochloride MS (ES) 217.0 [MH$^+$], t$_R$ (method A)=8.3 min.

Phenyl ethers were synthesized from N-Boc-hydroxypiperidines 36 and 37 and the phenols by Mitsunobu reaction, and from N-Boc-4-hydroxymethylpiperidine (Boc-29.204) via mesylate formation and displacement with phenolates. Benzyl ethers were prepared by alkylation with benzyl bromide. Benzyl piperidines 29.28, 29.29, 29.81, and 29.82 were prepared from the corresponding ketone by reduction with TFA/Et$_3$SiH (J. Med. Chem. 1992, 35, 4903-4910).

EXAMPLE 3

Preparation of Non-commercial Piperazines and Homopiperazines 29

Scheme 3: Preparation of non-commercial piperazines and homopiperazines 29

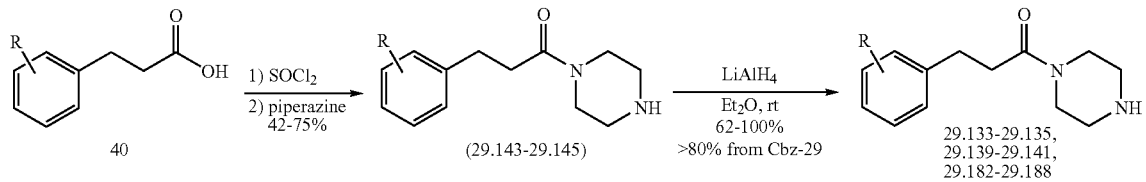

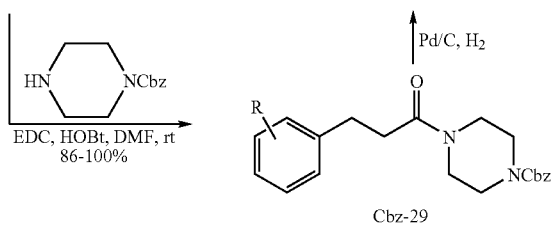

R = F, Cl, Br, CF$_3$,
2,4-diCl, 3,4-diCl,
OMe, 3,4-OCH$_2$O, Me

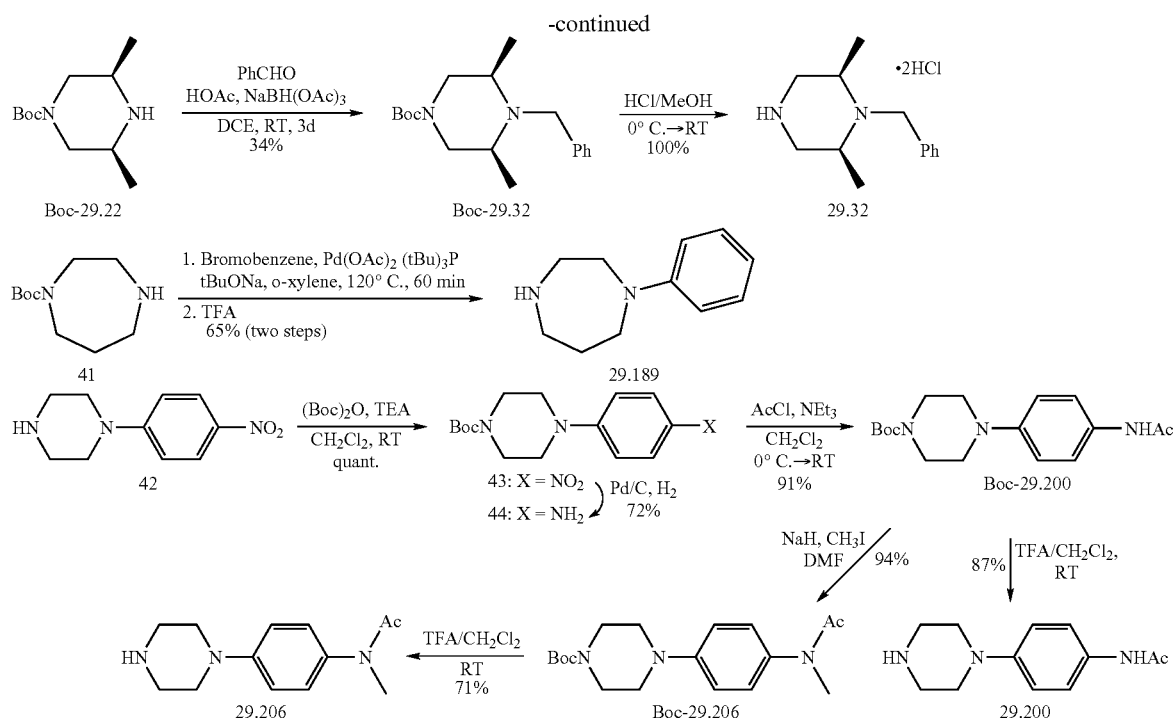

Substituted (phenylpropyl)piperazines were prepared starting from the commercially available aylpropionic acids 40, either by formation of the acid chloride using thionyl chloride, reaction with piperazine and reduction of the amide thus formed with LiAlH$_4$ to the amine 29, or EDC coupling of the acid with monoprotected piperazine followed by deprotection and reduction to the amine 29. The latter sequence was also used for the preparation of phenylpropylhomopiperazine (29.192). Further alkylarylpiperazines were prepared from the mono-Boc-protected derivatives by reductive amination with the appropriate aldehyde using NaBH(OAc)$_3$ as reducing agent followed by deprotection HCl/MeOH, or by reductive amination with 26.22 and 2631. Homopiperazine 29.189 was prepared from 41 by Buchwald-Hartwig coupling. The piperazinyl acetamides 29.200 and 29.206 were prepared in 4 or 5 steps, respectively, from the nitrophenyl-piperazine 42.

In addition, 1-(2-methanesulfinylphenyl)-piperazine (29.238) was prepared from the thiomethyl compound 29.228 by oxidation with sodium periodate. SNAr of methyl 2-bromobenzoate with piperazine gave the 2-piperazinyl benzoic ester 29.232. Its reaction with ammonia yielded the 2-piperazinylbenzamide 29.239. Alkylation of piperazine with propargyl bromide, (3-bromoprop-1-ynyl)-benzene, and the mesylate of 4-phenyl-1-butanol gave 1-prop-2-ynylpiperazine (29.83), 1-(3-phenylprop-2-ynyl)-piperazine (29.21), and 1-(4-phenylbutyl)-piperazine (29.56), respectively.

General Procedure for the Reductive Amination of Boc-protected Piperazines and Homopiperazine with Aldehydes 4-(3-Chlorobenzyl)-piperazine-1-carboxylic acid tert-butyl ester (20.24)

To a solution of piperazine-1-carboxylic acid tert-butyl ester (4.00 g, 21.5 mmol) in dry dichloroethane (70 mL) are added 3-chlorobenzaldehyde (2.49 mL, 3.08 g, 21.9 mmol), HOAc (2.58 mL, 2.71 g, 45.1 mmol) and NaBH(OAc)$_3$ (5.46 g, 25.8 mmol) at ambient temperature. After stirring at ambient temperature for 3d, 2N NaOH (40 mL) is added, the layers are separated, and the aqueous layer is extracted with CH$_2$Cl$_2$ (4×50 mL). The combined organic extracts are washed with water (3×50 mL) and brine (80 mL) and dried over MgSO$_4$. The crude material is purified by chromatography on silica gel, eluting with hexane:EtOAc mixtures, yielding 5.83 g (18.8 mmol, 87%) of the title compound as yellow oil. MS (ES): m/z 311.0/313.0 (50/18) [MH$^+$]. t$_R$ (method A)=5.0 min.

4-Benzyl-cis-3,5-dimethylpiperazine-1-carboxylic acid tert-butyl ester (20.16)

The procedure for the corresponding 3-chlorobenzyl piperazine was used. The title compound was obtained as yellow oil (34% yield) after chromatography on silica gel. $^1$H NMR (200 MHz, CDCl$_3$) δ 7.40-7.18 (m, 5H), 3.90-3.80 (m, 2H), 3.81 (s, 2H), 2.72-2.50 (m, 4H), 1.45 (s, 9H), 1.04 (d, J=6.0 Hz, 6H).

1-Benzyl-cis-2,6-dimethylpiperazine dihydrochloride (29.32)

Following the general procedure for Boc removal with HCl, the title compound was obtained from 4-benzyl-cis-3,5-dimethylpiperazine-1-carboxylic acid tert-butyl ester as beige solid (quant.). MS (ES, free base): m/z 205.1 (100) [MH$^+$]. t$_R$ (method B, free base)=5.8 min.

1-Prop-2-ynylpiperazine (29.83)

Propargyl bromide (1.19 g, 10 mmol) and piperazine (8.61 g, 100 mmol) were dissolved in THF (90 ml). Stir under N$_2$ and reflux for 4 h. Remove solvent and dissolve in 40 ml of H$_2$O. Extracted with 4×40 ml of EtOAc, washed with 2×15 ml of brine, dried over MgSO$_4$. After solvent was removed, brownish solid 29.83 (285 mg, 23% yield) was obtained. $^1$H NMR (CDCl$_3$, 200 MHz): δ=2.28 (t, 1H, J=2.4 Hz), 2.56 (m, 4H), 2.92 (m, 4H), 3.30 (d, 2H, J=2.6 Hz).

1-(3-Phenylprop-2-ynyl)-piperazine (29.21)

To a solution of piperazine (862 mg, 10.0 mmol) in THF (16 mL) is added (3-bromoprop-1-ynyl)-benzene (245 mg, 1.26 mmol), and the reaction mixture is stirred overnight. THF is evaporated, water/Na$_2$CO$_3$ is added, the mixture is extracted with Et$_2$O (6×10 mL), the combined extracts are washed with water, brine, dried over MgSO$_4$, filtered, and concentrated. The residue is purified by chromatography (silica gel, MeOH/CH$_2$Cl$_2$), yielding 179 mg (0.892 mmol, 71%) of the target compound. $^1$H NMR (CDCl$_3$, 200 MHz): δ=1.97 (s, 1H), 2.63 (m, 4H), 2.97 (m, 4H), 3.51 (s, 2H), 7.25-7.35 (m, 3H), 7.40-7.48 (m, 2H).

1-[3-(4-Chlorophenyl)-allyl]-piperazine (29.135)

$^1$H NMR (CDCl$_3$, 200 MHz): δ=1.60 (brs, 1H), 1.79 (tt, J=7.6, 7.6 Hz, 2H), 2.28-2.50 (m, 6H), 2.60 (t, J=7.8 Hz, 2H), 2.85-2.94 (m, 4H), 7.08-7.15 (m, 2H), 7.20-7.27 (m, 2H).

2-piperazin-1-yl-benzoic acid methyl ester (29.232)

(see *J. Med. Chem.*, 1978, 21(12), 1301-1306): 10 equiv of piperazine, 1 equiv of bromide starting material 10, and potassium carbonate were dissolved in 1,4 dioxane and refluxed overnight then stirred at room-temp for another day then reaction was worked up. The reaction mixture was concentrated and partitioned between 2M NaOH and chloroform. The aqueous fraction was washed 3 time with chloroform and organic fractions were combined dried with sodium sulfate, filtered, and concentrated which resulted in 8 g of a white solid which contained large amounts of the piperazine starting material. Therefore, material was washed again with water and neutralized with 1M HCl and concentrated. This mixture was triturated with chloroform/methanol and filtered through a fritted funnel. The filtrate was once again washed with water and aqueous was extracted 4 times with chloroform. Chloroform fractions were combined dried with sodium sulfate, filtered and concentrated with resulted in a yellow oil (14% yield) and was used as crude for subsequent reaction. MS (ES) 221 [MH$^+$], $t_R$ (method A)=3.56 min.

2-piperazin-1-yl-benzamide (29.239)

1 equiv of 29.232 was dissolved in MeOH (anhydrous) and cooled to 0° C. in a ice-bath in Parr bomb then ammonia gas was bubbled into mixture until saturated. This mixture was then heated to 50° C. in an oil-bath overnight. Material was concentrated and purified by silica column using 20% MeOH in CHCl$_3$ as eluent which resulted in an off-white solid (20% yield) and recovered starting material. MS (ES) 206 [MH$^+$], $t_R$ (method B)=4.14 min.

1-(2-Methanesulfinylphenyl)-piperazine (29.238)

1 equiv of 29.228 was dissolved in acetonitrile/water and taken down to 0° C. in an ice-bath. Then 1.5 equiv. of sodium periodate was added in one portion to the first mixture and allowed stir at room temp. overnight. Reaction mixture was partitioned between chloroform and water and neutralized with sat'd sodium bicarbonate and aqueous was washed with six portions of chloroform. Chloroform washes were combined dried with sodium sulfate, filtered and concentrated which resulted in a yellow solid, was used as crude for the next step. MS (ES) 225 [MH$^+$], $t_R$ (method A)=2.07 min.

4-(4-Nitrophenyl)-piperazine-1-carboxylic acid tert-butyl ester (43)

1 equiv of piperazine 42 was dissolved in DCM (anhydrous) followed by 1.5 equiv. of TEA and taken down to 0° C. in an ice-bath and then 1.25 equiv. of Boc anhydride was added to the reaction mixture and allowed to stir for one hour. The reaction mixture was washed with one portion of water, one portion of sat'd sodium bicarbonate, dried with sodium sulfate filtered and concentrated and resulted in a yellow solid. MS (ES) 307.9 [MH$^+$].

4-(4-Aminophenyl)-piperazine-1-carboxylic acid tert-butyl ester (44)

1 equiv of 43 dissolved in methanol (anhydrous) and 10% of 10% Pd/C was added under a hydrogen atmosphere and allowed to stir overnight at room-temp. Reaction was filtered through a pad of celite and concentrated to give a blue/purple oil. The oil was brought up in DCM acidified using 1 M HCl and organic wash was removed. The aqueous was neutralized with sat'd sodium bicarbonate and washed 3 times with DCM, dried with sodium sulfate, filtered and concentrated and resulted in a pale red oil, 72% yield. MS (ES) 277.8 [MH$^+$].

4-(4-Acetylaminophenyl)-piperazine-1-carboxylic acid tert-butyl ester (Boc-29.200)

1 equiv. of 15 was dissolved in DCM (anhydrous) and 1.5 equiv of TEA was added to reaction mixture and taken down to 0° C. in an ice-bath. To this mixture was added 1.1 equiv of acetyl chloride and was allowed to reach room-temp and stopped after 1 hour. The solvent was removed by reduced pressure and was partitioned between DCM and water. The aqueous was washed 3 times with DCM and all organic washes were combined and dried with sodium sulfate, filtered and concentrated which resulted in a light brown/tan solid (91%). MS (ES) 320.3 [MH$^+$]

4-[4-(Acetylmethylamino)-phenyl]-piperazine-1-carboxylic acid tert-butyl ester (Boc-29.206)

1 equiv of Boc-29.200 was dissolved in DMF (anhydrous) and taken to 0° C. in an ice-bath. Then 1.5 equiv of NaH was added to the reaction mixture and was continued being stirred at 0° C. for ½ hour. Then 1.2 equiv of methyl iodide was added to reaction mixture and was stirred for an additional hour. The reaction was quenched with water then aqueous was washed three times with ethyl acetate. Organic fractions were combined dried with sodium sulfate, filtered and concentrated and resulted in a light brown/tan solid (94% yield). MS (ES) 334.2 [MH+].

N-Methyl-N-(4-piperazin-1-ylphenyl)-acetamide (29.206)

1 equiv of Boc-29.206 was dissolved in a 25% TFA in DCM solution and stirred at room temp. under a nitrogen atmosphere and was allowed to stir for 1 hour. Solvent was removed and crude mixture was partitioned between DCM and sat'd sodium bicarbonate and aqueous was washed 3 times with DCM. The organic washes were combined dried with sodium sulfate, filtered and concentrated. The aqueous was concentrated and triturated with DMC/MeOH. The organic was combined with the previous organic washes and resulted in a pale yellow solid (71% yield). MS (ES) 234.2 [MH+]

N-(4-piperazin-1-ylphenyl)-acetamide (29.200)

Following the procedure for 29.206, 29.200 was prepared from Boc-29.200 in 87% yield, pale yellow solid. MS (ES) 220.1 [MH+].

EXAMPLE 4

Synthesis of Intermediate 7

The key intermediate for pyrrolo[2,3-d]pyrimidines with phenoxymethylene, alkoxymethylene or oxime ether moieties at C-6 is the bromide 7, which is prepared in 6 steps from methyl cyanoacetate and chloroacetone (scheme 4). The monoalkylation product 2 is protected as 1,3-dioxolane, then the pyrimidine ring is formed by reaction with a benzamidine. Cyclization of the pyrrole ring occurs on reaction with aqueous HCl, and refluxing with POCl3 yields the chloride 5. Boc-protection of the pyrrole followed by radical bromination with NBS gives the bromide 7.

Scheme 4. Synthesis of the bromide 7.

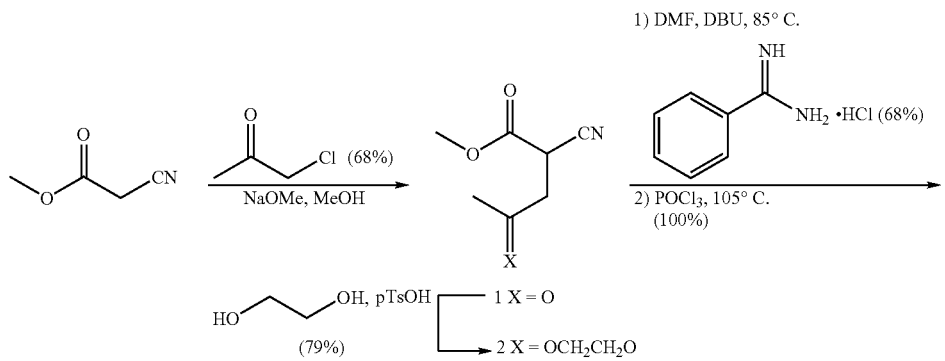

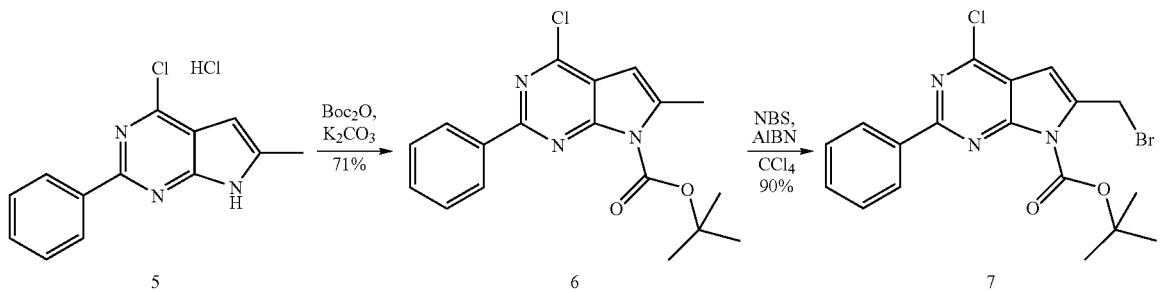

2-Cyano-4-oxopentanoic acid methyl ester (1)

To an ice-cooled (0° C.) solution of ethyl cyanoacetate (6.58 g, 58.1 mmol) in MeOH (20 mL) was slowly added a solution of NaOMe (25% w/v; 58.1 mmol). After 10 min, chloroacetone (5 mL; 62.8 mmol) was slowly added. After 4 h, the solvent was removed. The brown oil was diluted the EtOAc (100 mL) and washed with $H_2O$ (100 mL). The organic fraction was dried, filtered, and concentrated to a brown oil (7.79 g; 79%). The oil was a mixture of methyl/ethyl ester products (9/1), and was used without further purification. $^1$H NMR (200 MHz, $CDCl_3$): δ 1.26 (t, J=7.1 Hz), 2.44 (s, 3H), 3.02 (dd, 1H, J=15.0, 7.0 Hz), 3.42 (dd, 1H, J=15.0, 7.1 Hz), 3.62 (s, 3H), 3.91 (dd, 1H, J=7.2, 7.0 Hz), 4.24 (q, J=7.2 Hz).

2-Cyano-3-(2-methyl-[1,3]-dioxolan-2-yl)-propionic acid methyl ester (2)

The procedure of Seela and Lüpke was used.[1] Thus, protection of the ketone (1) (5.0 g, 32.2 mmol) with ethylene glycol (4 mL, 64.4 mmol) in the presence of TsOH (100 mg) afforded 2 as an oil (5.2 g, 81.0%) after flash chromatography ($SiO_2$; 3/7 EtOAc/Hex, $R_f$ 0.35). Still contains ~5% ethyl ester: $^1$H NMR (200 MHz, $CDCl_3$): δ 1.26 (t, J=7.1 Hz), 1.35 (s, 3H), 2.32 (dd, 1H, J=15.0, 7.0 Hz), 2.48 (dd, 1H, J=15.0, 7.1 Hz), 3.62 (dd, 11H, J=7.2, 7.0 Hz), 3.79 (s, 3H), 3.98 (s, 4H), 4.24 (q, J=7.2 Hz); MS (ES) 200.1 ($M^+$+1).

6-Amino-5-(2-methyl-[1,3]-dioxolan-2-ylmethyl)-2-phenylpyrimidin-4-ol (3)

A solution of acetal (2) (1 g, 5.02 mmol), benzamidine (786 mg, 5.02 mmol), and DBU (1.5 mL, 10.04 mmol) in dry DMF (15 mL) was heated to 85° C. for 15 h. The mixture was diluted with $CHCl_3$ (30 mL) and washed with 0.5 N NaOH (10 mL) and $H_2O$ (20 mL). The organic fraction was dried, filtered and concentrated to a brown oil. Flash chromatography ($SiO_2$; 1/9 EtOAc/$CH_2Cl_2$, $R_f$ 0.35) was attempted, but material crystallized on the column. The silica gel was washed with MeOH. Fractions containing the product (3) were concentrated and used without further purification (783 mg, 54.3%):

$^1$H NMR (200 MHz, $CDCl_3$): δ 1.38 (s, 3H), 3.60-3.15 (m, 2H), 3.98 (s, 4H), 5.24 (brs, 2H), 7.45 (m, 3H), 8.24 (m, 2H); MS (ES) 288.1 ($M^+$+1).

6-Methyl-2-phenyl-7H-pyrrolo[2,3-d]pyrimidin-4-ol hydrochloride (4)

A solution of acetal 3 (700 mg, 2.44 mmol) in 1 N HCl (40 mL) was stirred for 2 h at RT. The resulting slurry was filtered yielding the HCl salt 4 as a tan solid (498 mg, 78.0%):

$^1$H NMR (200 MHz, DMSO-$d_6$): δ 2.25 (s, 3H), 6.17 (s, 1H), 7.45 (m, 3H), 8.05 (m, 2H), 11.78 (s, 1H); MS (ES) 226.1 ($M^+$+1).

4-Chloro-6-methyl-2-phenyl-7H-pyrrolo[2,3-d]pyrimidine hydrochloride (5)

A heterogeneous mixture of 4 (4.0 g, 17.76 mmol) and phosphorus oxychloride (125 mL) was heated to reflux. After 14 h the homogeneous solution was cooled to room temperature and concentrated in vacuo yielding a black oil. Water was added to the oil and the mixture was warmed. The resulting solid was filtered, washed with water and dried at room temperature to yield 4.22 g of a brown solid (97%). $^1$H NMR (200 MHz, DMSO-$d_6$): δ 2.43 (s, 3H), 6.31 (s, 1H), 7.49 (m, 3H), 8.34 (m, 2H).

4-Chloro-6-methyl-2-phenylpyrrolo[2,3-d]pyrimidine-7-carboxylic acid tert-butyl ester (6)

Di-tert-butyl dicarbonate (5.37 g, 24.6 mmol) and dimethylaminopyridine (1.13 g, 9.2 mmol) were added to a solution containing (5) (1.50 g, 6.15 mmol) and pyridine (30 mL). After 20 h the reaction was concentrated and the residue was partitioned between $CH_2Cl_2$ and water. The $CH_2Cl_2$ layer was separated, dried over $MgSO_4$, filtered and concentrated to yield a black solid. Flash chromatography ($SiO_2$; 1/9 EtOAc/Hexanes, $R_f$ 0.40) yielded 1.70 g of a white solid (80%). mp=175-177° C.; $^1$H NMR (200 MHz, $CDCl_3$): δ 1.76 (s, 9H), 2.66 (s, 3H), 6.39 (s, 1H), 7.45 (m, 3H), 8.50 (m, 2H); MS (ES): 344.1 ($M^+$+1).

6-Bromomethyl-4-chloro-2-phenylpyrrolo[2,3-d]pyrimidine-7-carboxylic acid tert-butyl ester (7)

N-Bromosuccinimide (508 mg, 2.86 mmol) and AIBN (112 mg, 0.68 mmol) were added to a solution containing 6 (935 mg, 2.71 mmol) and $CCl_4$ (50 mL). The solution was heated to reflux. After 2 h the reaction was cooled to room temperature and concentrated in vacuo to yield a white solid. Flash chromatography ($SiO_2$; 1/1 $CH_2Cl_2$/Hexanes, $R_f$ 0.30) yielded 960 mg of a white solid (84%). mp=155-157° C.; $^1$H NMR (200 MHz, $CDCl_3$): δ 1.79 (s, 9H), 4.93 (s, 2H), 6.76 (s, 1H), 7.48 (m, 3H), 8.52 (m, 2H); MS (ES): 423.9 ($M^+$+1).

EXAMPLE 5

C-6 Phenoxymethylene Derivatives

The benzylic bromide in 7 is easily displaced with phenoxides to give 8. Upon heating with amines in DMSO, the chloride at C-4 is displaced and the Boc group is removed, yielding the $A_{2B}$ antagonists 9.1-9.51 (scheme 5).

Scheme 5. Preparation of C-6 phenoxymethylene derivatives 9.1-9.51.

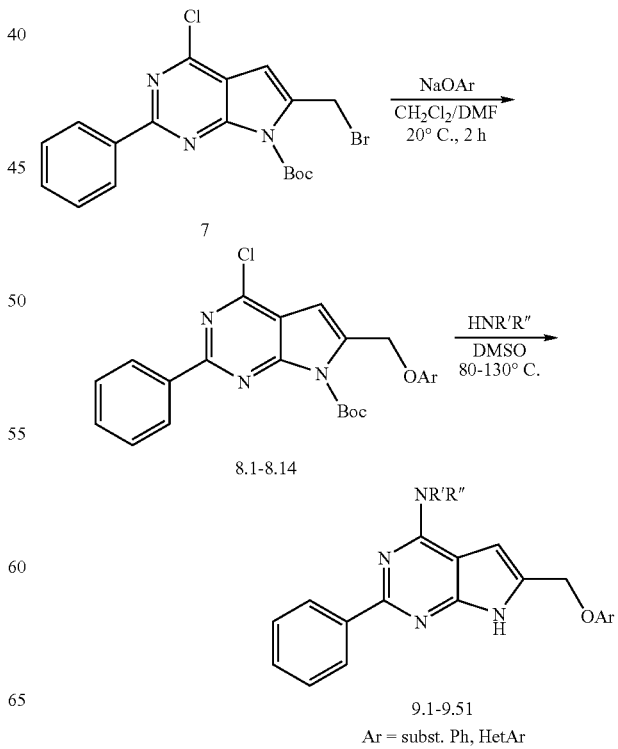

Ar = subst. Ph, HetAr

TABLE 1

A$_{2B}$ antagonists 9.1-9.51.

| Comp. # | Structure | MW |
|---|---|---|
| 9.1 | 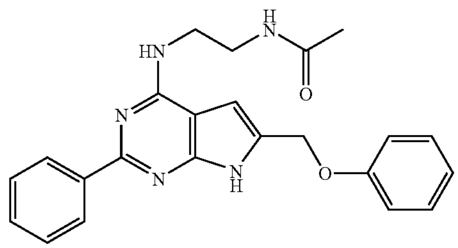 | 401.47 |
| 9.2 | 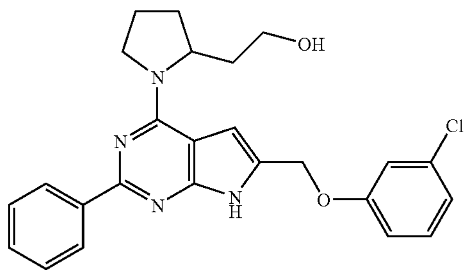 | 448.96 |
| 9.3 | 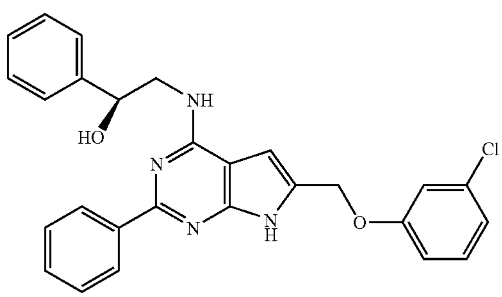 | 470.96 |
| 9.4 | 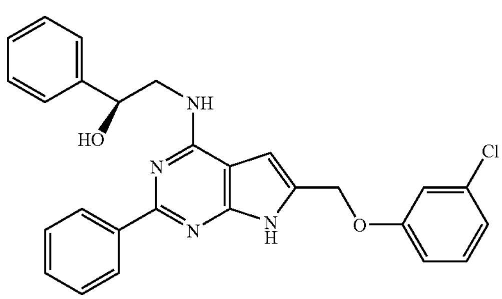 | 470.96 |

TABLE 1-continued

A$_{2B}$ antagonists 9.1-9.51.

| Comp. # | Structure | MW |
|---|---|---|
| 9.5 | 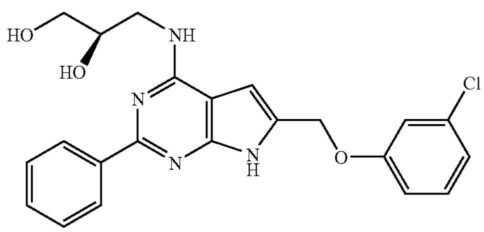 | 424.89 |
| 9.6 | 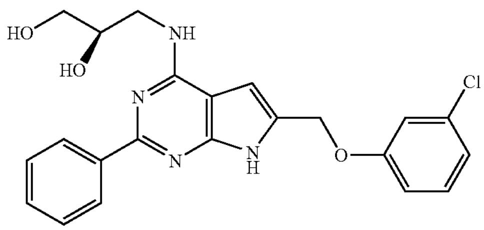 | 424.89 |
| 9.7 | 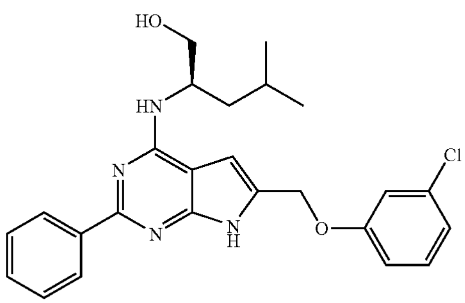 | 450.97 |
| 9.8 | 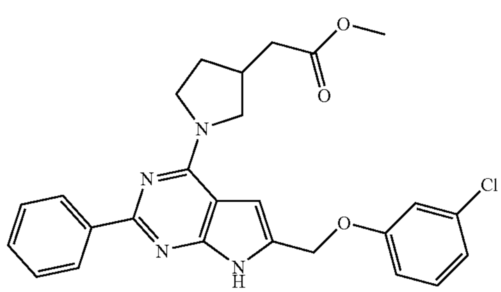 | 476.97 |
| 9.9 | 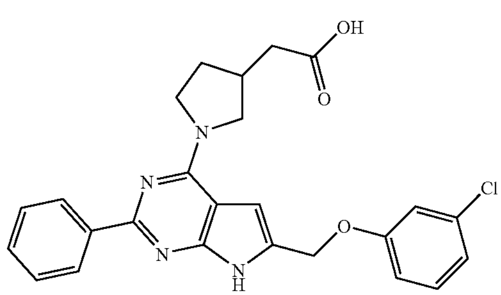 | 462.94 |

TABLE 1-continued

A_{2B} antagonists 9.1-9.51.

| Comp. # | Structure | MW |
|---|---|---|
| 9.10 | 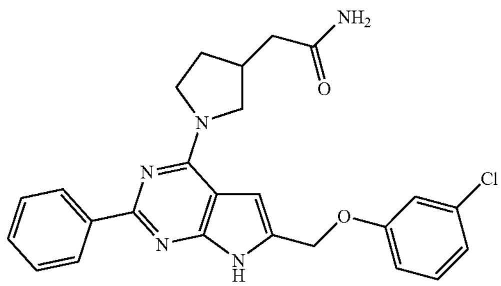 | 461.96 |
| 9.11 | 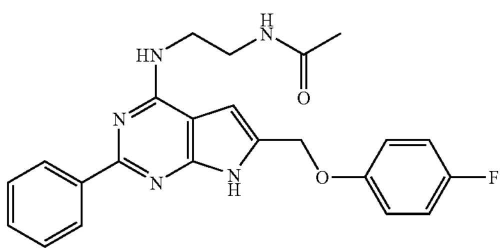 | 419.46 |
| 9.12 | 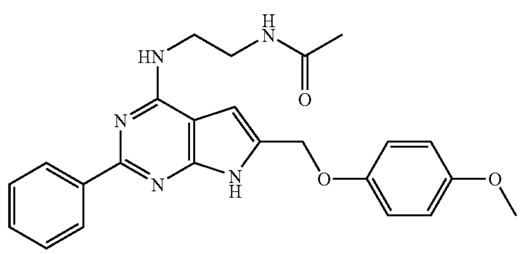 | 431.50 |
| 9.13 | 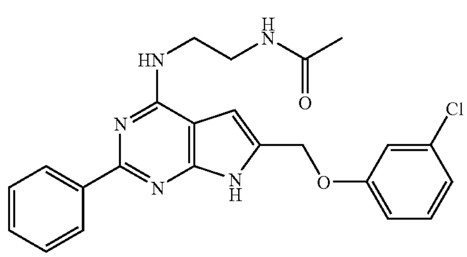 | 435.92 |
| 9.14 | 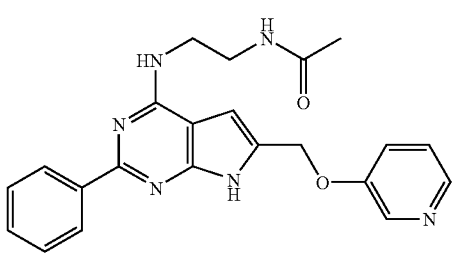 | 402.46 |

TABLE 1-continued

A$_{2B}$ antagonists 9.1-9.51.

| Comp. # | Structure | MW |
|---------|-----------|-----|
| 9.15 | 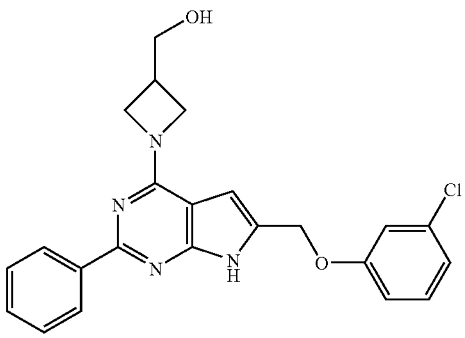 | 420.90 |
| 9.16 | 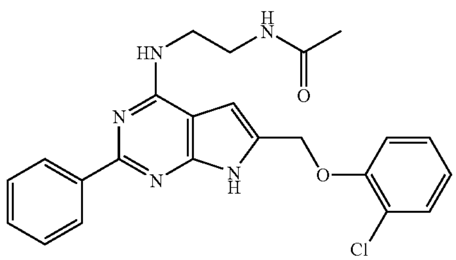 | 435.92 |
| 9.17 | 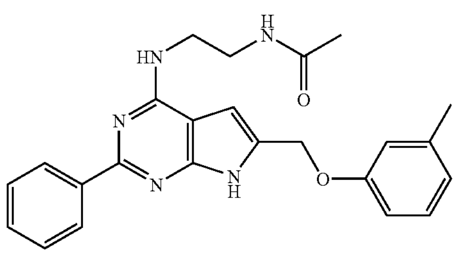 | 415.50 |
| 9.18 | 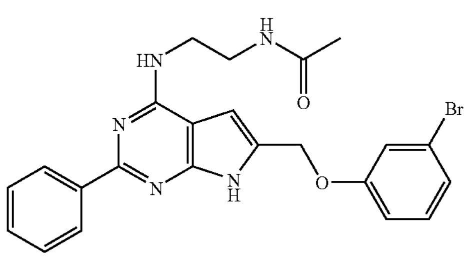 | 480.37 |
| 9.19 | 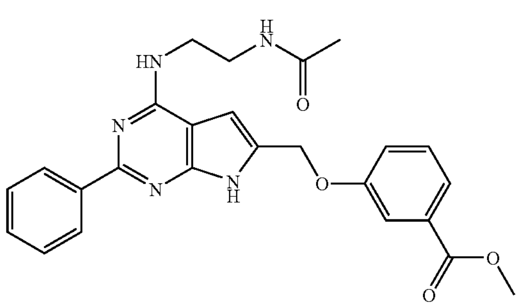 | 459.51 |

TABLE 1-continued
A$_{2B}$ antagonists 9.1-9.51.
| Comp. # | Structure | MW |
|---|---|---|
| 9.20 | 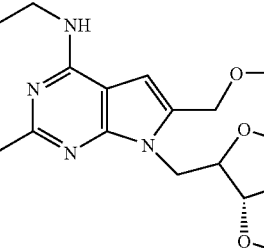 | 522.01 |
| 9.21 | 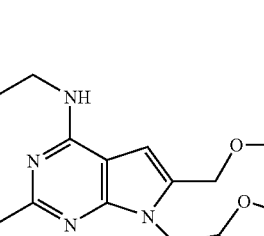 | 622.13 |
| 9.22 | 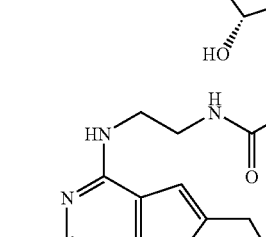 | 582.06 |
| 9.23 | 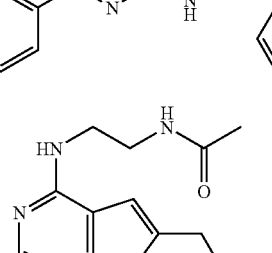 | 402.46 |
| 9.24 | 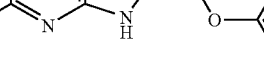 | 435.92 |

TABLE 1-continued

A$_{2B}$ antagonists 9.1-9.51.

| Comp. # | Structure | MW |
|---|---|---|
| 9.25 | 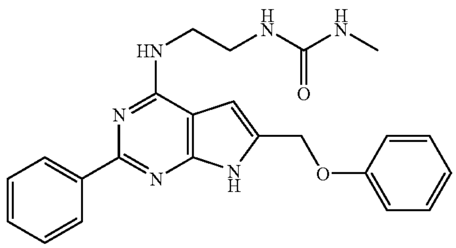 | 416.49 |
| 9.26 | 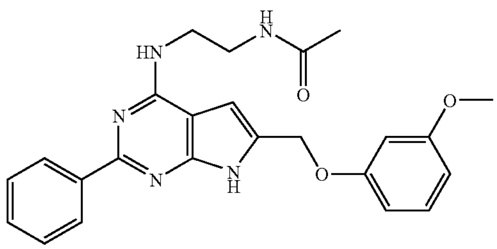 | 431.50 |
| 9.27 | 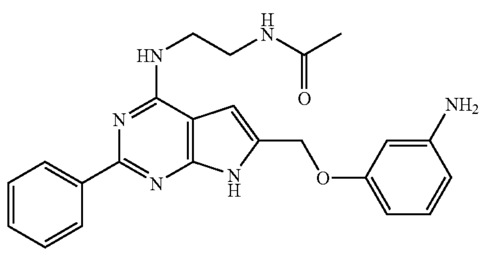 | 416.49 |
| 9.28 | 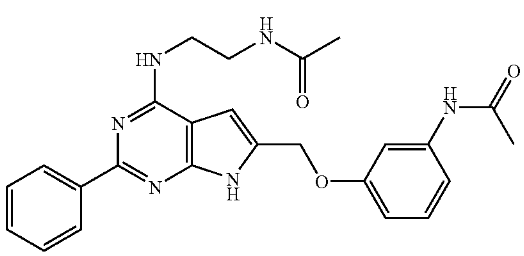 | 458.52 |
| 9.29 | 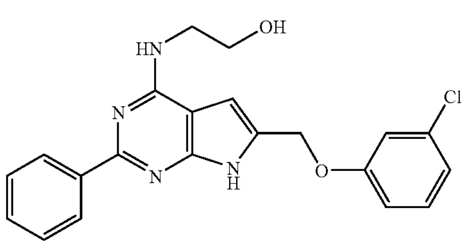 | 394.86 |

TABLE 1-continued

A$_{2B}$ antagonists 9.1-9.51.

| Comp. # | Structure | MW |
|---|---|---|
| 9.30 | 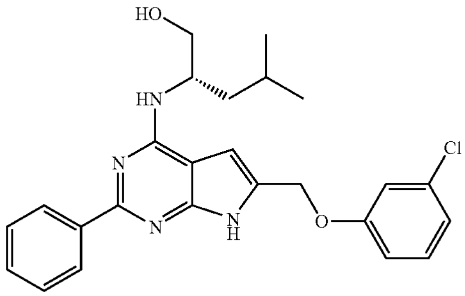 | 450.97 |
| 9.31 | 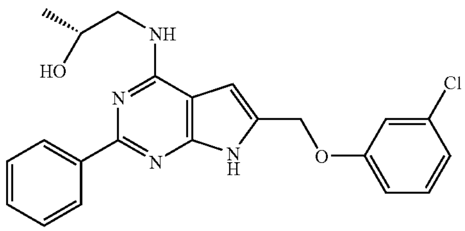 | 408.89 |
| 9.32 | 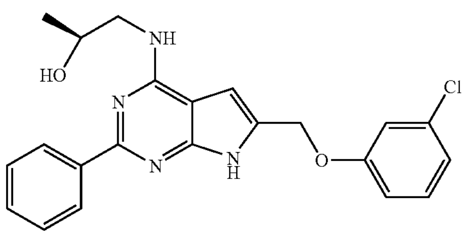 | 408.89 |
| 9.33 | 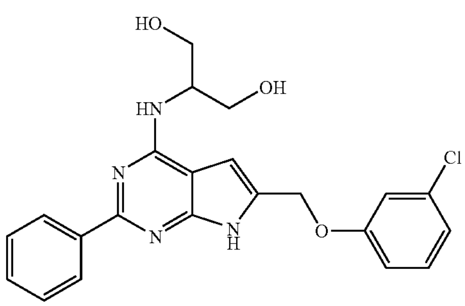 | 424.89 |
| 9.34 | 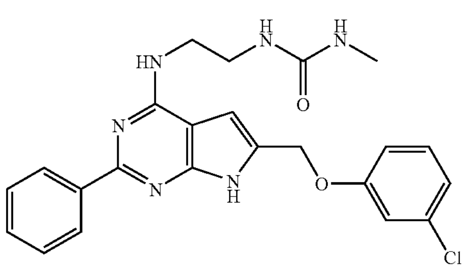 | 450.93 |

TABLE 1-continued

A_{2B} antagonists 9.1-9.51.

| Comp. # | Structure | MW |
|---|---|---|
| 9.35 | 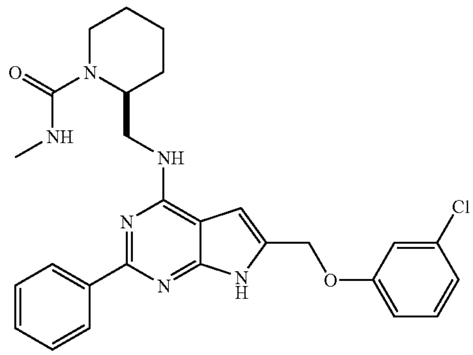 | 505.02 |
| 9.36 | 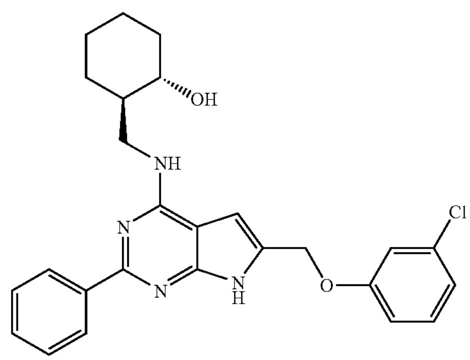 | 462.98 |
| 9.37 | 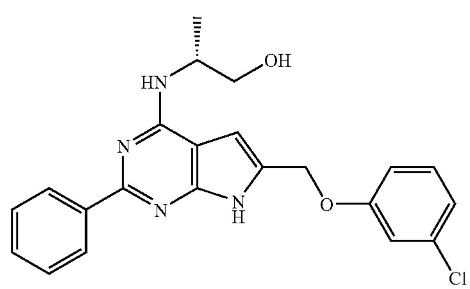 | 408.89 |
| 9.38 | 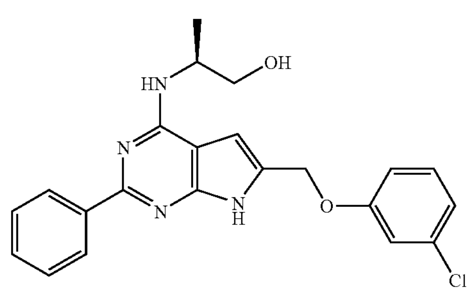 | 408.89 |
| 9.39 | 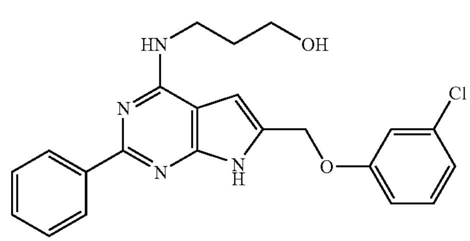 | 408.89 |

TABLE 1-continued

A$_{2B}$ antagonists 9.1-9.51.

| Comp. # | Structure | MW |
|---------|-----------|-----|
| 9.40 | 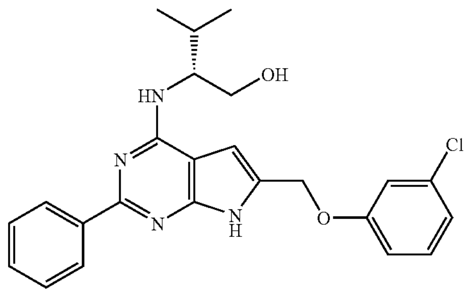 | 436.95 |
| 9.41 | 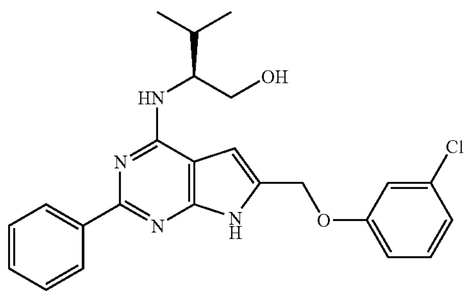 | 436.95 |
| 9.42 | 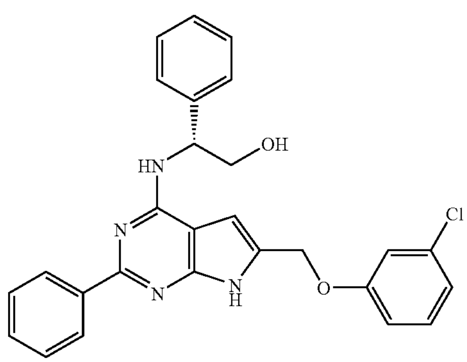 | 470.96 |
| 9.43 | 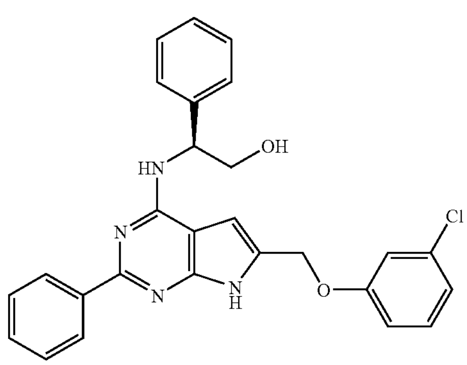 | 470.96 |

TABLE 1-continued
A$_{2B}$ antagonists 9.1-9.51.
| Comp. # | Structure | MW |
|---|---|---|
| 9.44 | 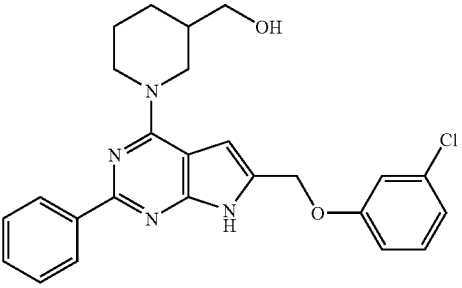 | 448.96 |
| 9.45 | 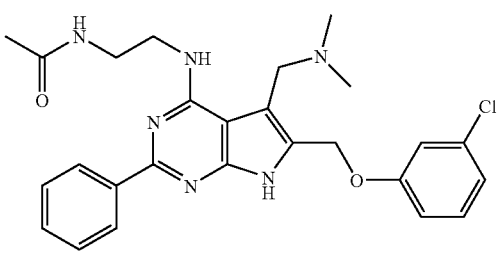 | 493.01 |
| 9.46 | 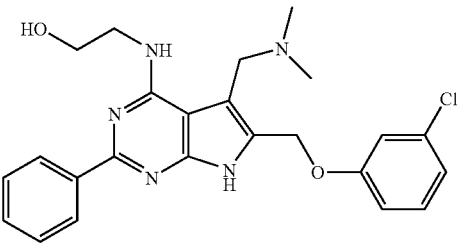 | 451.96 |
| 9.47 | 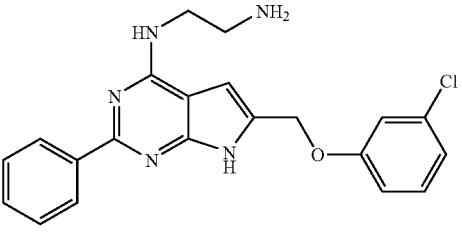 | 393.88 |
| 9.48 | 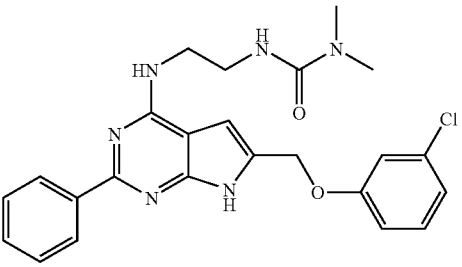 | 464.96 |

TABLE 1-continued

A$_{2B}$ antagonists 9.1-9.51.

| Comp. # | Structure | MW |
|---|---|---|
| 9.49 | 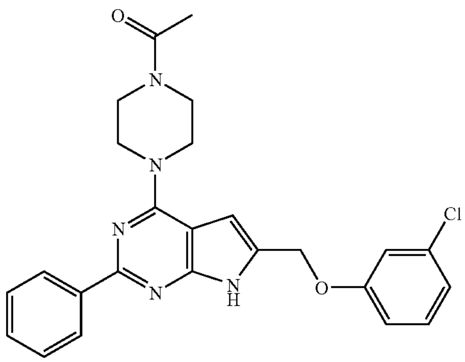 | 461.96 |
| 9.50 | 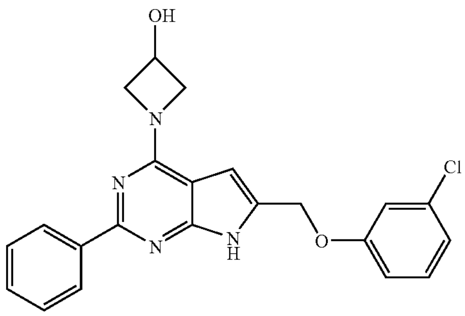 | 406.88 |
| 9.51 | 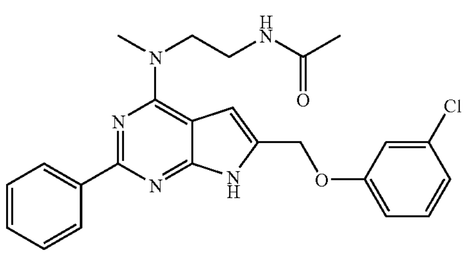 | 449.94 |

General Procedure for Bromide Displacement with Phenols:

4-Chloro-6-phenoxymethyl-2-phenyl-pyrrolo[2,3-d]pyrimidine-7-carboxylic acid tert-butyl ester (8.1)

Sodium phenoxide trihydrate (173 mg, 1.02 mmol) was added in one portion to a solution of bromide (7) (410 mg, 0.97 mmol) dissolved in CH$_2$Cl$_2$ (5 mL) and DMF (10 mL). After 2 h the reaction solution was partitioned between CH$_2$Cl$_2$ and water. The water layer was extracted with CH$_2$Cl$_2$. The combined CH$_2$Cl$_2$ layers were washed with water, dried over MgSO$_4$, filtered and concentrated to yield a yellow solid. Flash chromatography (SiO$_2$; 1/6 EtOAc/Hexanes, R$_f$ 0.30) yielded 210 mg of a white solid (50%). $^1$H NMR (200 MHz, CDCl$_3$): δ 1.76 (s, 9H), 5.45 (s, 2H), 6.83 (s, 1H), 7.03 (m, 3H), 7.34 (m, 2H), 7.48 (m, 3H), 8.53 (m, 2H); MS (ES): 436.2 (M$^+$+1).

General Procedure for C-4 Chloride Displacement with Amines:

N-[2-(6-Phenoxymethyl-2-phenyl-7H-pyrrolo[2,3-d]pyrimidin-4-ylamino)-ethyl]-acetamide (9.1)

A solution containing (8.1) (85 mg, 0.20 mmol), N-acetylethylene-diamine (201 mg, 1.95 mmol) and DMSO (3 mL) was heated to 100° C. After 1 h the temperature was raised to 130° C. After 3 h the reaction was cooled to room temperature and partitioned between EtOAc and water. The water layer was extracted with EtOAc (2×). The combined EtOAc layers are washed with water, dried over MgSO$_4$, filtered and concentrated. Flash chromatography (SiO$_2$; 1/10 EtOH/CHCl$_3$, R$_f$ 0.25) yielded 73 mg (93%) of a white foamy solid, mp. 196-197° C. $^1$H NMR (200 MHz, DMSO-d$_6$): δ 1.79 (s, 3H), 3.36 (m, 2H), 3.61 (m, 2H), 5.12 (s, 2H), 6.59 (s, 1H), 6.89-7.09 (m, 3H), 7.20-7.50 (m, 5H), 7.57 (brt, 1H), 8.03 (brt, 1H), 8.39 (m, 2H), 11.81 (br s, 1H); MS (ES): 402.6 (MH$^+$). t$_R$ (method A)=3.6 min.

The following compounds 9.2-9.51 were prepared in the same manner:

2-{1-[6-(3-Chlorophenoxymethyl)-2-phenyl-7H-pyrrolo[2,3-d]pyrimidin-4-yl]-pyrrolidin-2-yl}-ethanol (9.2)

MS (ES): 449.0 (M$^+$+1).

3-(S)-[6-(3-Chlorophenoxymethyl)-2-phenyl-7H-pyrrolo[2,3-d]pyrimidin-4-ylamino]-1-phenylethanol (9.3)

$^1$H-NMR (200 MHz, CDCl$_3$) δ 8.27 (m, 2H), 7.35 (m, 8H), 7.06 (m, 1H), 6.87 (m, 1H), 6.51 (m, 2H), 6.23 (s, 1H), 5.67 (m, 1H), 5.06 (m, 1H), 4.52 (s, 2H), 4.20-4.00 (m, 1H), 3.90-3.60 (m, 1H). MS (ES): 471.0 (M$^+$+1).

2-(R)-[6-(3-Chlorophenoxymethyl)-2-phenyl-7H-pyrrolo[2,3-d]pyrimidin-4-ylamino]-1-phenylethanol (9.4)

$^1$H-NMR (200 MHz, CDCl$_3$): δ 8.27 (m, 2H), 7.32 (m, 8H), 7.06 (m, 1H), 6.88 (m, 1H), 6.54 (m, 2H), 6.23 (s, 1H), 5.66 (m, 1H), 5.07 (m, 1H), 4.56 (s, 2H), 4.20-4.00 (m, 1H), 3.90-3.70 (m, 1H). MS (ES): 471.0 (M$^+$+1).

3-(S)-[6-(3-Chlorophenoxymethyl)-2-phenyl-7H-pyrrolo[2,3-d]pyrimidin-4-ylamino]-propane-1,2-diol (9.5)

$^1$H-NMR (200 MHz, CD$_3$OD): δ 8.27 (m, 2H), 7.39 (m, 3H), 7.22 (dd, 1H, J=8.2 Hz), 7.02 (m, 1H), 6.96-6.86 (m, 2H), 6.57 (s, 1H), 5.09 (s, 2H), 3.99-3.86 (m, 1H), 3.86-3.64 (m, 2H), 3.56 (d, 2H, J=5.2 Hz). MS (ES): 425.0 (M$^+$+1).

3-(R)-[6-(3-Chlorophenoxymethyl)-2-phenyl-7H-pyrrolo[2,3-d]pyrimidin-4-ylamino]-propane-1,2-diol (9.6)

$^1$H-NMR (200 MHz, CD$_3$OD): δ 8.26 (m, 2H), 7.39 (m, 3H), 7.22 (dd, 1H, J=8.2 Hz), 7.02 (m, 1H), 6.96-6.86 (m, 2H), 6.57 (s, 1H), 5.09 (s, 2H), 4.00-3.86 (m, 1H), 3.86-3.65 (m, 2H), 3.56 (d, 2H, J=5.3 Hz). MS (ES): 425.0 (M$^+$+1).

2-(R)-[6-(3-Chlorophenoxymethyl)-2-phenyl-7H-pyrrolo[2,3-d]pyrimidin-4-ylamino]-4-methylpentan-1-ol (9.7)

$^1$H-NMR (200 MHz, CDCl$_3$): δ 8.27 (m, 2H), 7.38 (m, 3H), 7.10 (m, 1H), 6.90 (m, 1H), 6.54 (m, 2H), 6.37 (s, 1H), 5.30-5.10 (m, 1H), 4.71-4.45 (m, 2H), 4.00-3.85 (m, 1H), 3.80-3.65 (m, 1H), 1.89-1.65 (m, 1H), 1.65-1.50 (m, 1H), 1.01 (d, 3H, J=6.6 Hz), 0.97 (d, 3H, J=6.6 Hz). MS (ES): 451.0 (M$^+$+1).

{1-[6-(3-Chlorophenoxymethyl)-2-phenyl-7H-pyrrolo[2,3-d]pyrimidin-4-yl]-pyrrolidin-3-yl}-acetic acid methyl ester (9.8)

$^1$H-NMR (200 MHz, CD$_3$OD): δ 8.32 (m, 2H), 7.39 (m, 3H), 7.23 (dd, 1H, J=8.1 Hz), 7.02 (m, 1H), 6.92 (m, 2H), 6.58 (s, 1H), 5.06 (s, 2H), 4.10 (m, 1H), 3.93 (m, 1H), 3.72 (m, 1H), 3.69 (s, 3H), 3.38 (m, 1H), 2.64 (m, 1H), 2.49 (br d, 2H, J=6.2 Hz), 2.18 (m, 1H), 1.65 (m, 1H). MS (ES): 477.1 (M$^+$+1).

{1-[6-(3-Chlorophenoxymethyl)-2-phenyl-7H-pyrrolo[2,3-d]pyrimidin-4-yl]-pyrrolidin-3-yl}-acetic acid (9.9)

$^1$H-NMR (200 MHz, CD$_3$OD): δ 8.32 (m, 2H), 7.40 (m, 3H), 7.25 (dd, 1H, J=8.2 Hz), 7.07 (m, 1H), 6.95 (m, 2H), 6.69 (s, 1H), 5.14 (s, 2H), 4.25-4.15 (m, 1H), 4.12-3.99 (m, 1H), 3.92-3.78 (m, 1H), 3.38 (m, 1H), 2.64 (m, 1H), 2.49 (m, 2H), 2.18 (m, 1H), 1.65 (m, 1H). MS (ES): 463.0 (M$^+$+1).

2-{1-[6-(3-Chlorophenoxymethyl)-2-phenyl-7H-pyrrolo[2,3-d]pyrimidin-4-yl]-pyrrolidin-3-yl}-acetamide (9.10)

$^1$H-NMR (200 MHz, CD$_3$OD): δ 8.35 (m, 2H), 7.39 (m, 3H), 7.25 (dd, 1H, J=8.0 Hz), 7.06 (m, 1H), 6.96 (m, 2H), 6.69 (s, 1H), 5.14 (s, 2H), 4.14 (dd, 1H, J=10.6 & 7.0 Hz), 4.02 (m, 1H), 3.83 (m, 1H), 3.53 (m, 1H), 2.72 (m, 1H), 2.42 (d, 2H, J=7.4 Hz), 2.26 (m, 1H), 1.69 (m, 1H). MS (ES): 462.2 (M$^+$+1).

N-{2-[6-(4-Fluorophenoxymethyl)-2-phenyl-7H-pyrrolo[2,3-d]pyrimidin-4-ylamino]-ethyl}-acetamide (9.11)

MS (ES) 420 (M$^+$+H); t$_R$ (method A)=6.8 min.

N-{2-[6-(4-Methoxyphenoxymethyl)-2-phenyl-7H-pyrrolo[2,3-d]pyrimidin-4-ylamino]-ethyl}-acetamide (9.12)

MS (ES) 432 (M$^+$); t$_R$ (method A)=6.4 min.

N-{2-[6-(3-Chlorophenoxymethyl)-2-phenyl-7H-pyrrolo[2,3-d]pyrimidin-4-ylamino]-ethyl}-acetamide (9.13)

MS (ES) 436 (M$^+$); t$_R$ (method A)=7.7 min.

N-{2-[2-Phenyl-6-(pyridin-3-yloxymethyl)-7H-pyrrolo[2,3-d]pyrimidin-4-ylamino]ethyl}-acetamide (9.14)

MS (ES) 403 (M$^+$+H); t$_R$ (method A)=3.8 min.

{1-[6-(3-Chlorophenoxymethyl)-2-phenyl-7H-pyrrolo[2,3-d]pyrimidin-4-yl]-azetidin-3-yl}-methanol (9.15)

MS (ES) 421 (M$^+$); t$_R$ (method A)=9.5 min.

N-{2-[6-(2-Chlorophenoxymethyl)-2-phenyl-7H-pyrrolo[2,3-d]pyrimidin-4-ylamino]-ethyl}-acetamide (9.16)

MS (ES) 436 (M$^+$); t$_R$ (method A)=8.6 min.

N-[2-(2-Phenyl-6-m-tolyloxymethyl-7H-pyrrolo[2,3-d]pyrimidin-4-ylamino)-ethyl]-acetamide (9.17)

MS (ES) 416 (M⁺); $t_R$ (method A)=8.6 min.

N-{2-[6-(3-Bromophenoxymethyl)-2-phenyl-7H-pyrrolo[2,3-d]pyrimidin-4-ylamino]-ethyl}-acetamide (9.18)

MS (ES) 480/482 (91/100) [MH⁺]; $t_R$ (method B)=6.0 min.

3-[4-(2-Acetylaminoethylamino)-2-phenyl-7H-pyrrolo[2,3-d]pyrimidin-6-ylmethoxy]-benzoic acid methyl ester (9.19)

yellow solid, mp. 80-85° C. (decomp.); MS (ES) 459.9 [MH⁺]; $t_R$ (method A)=6.8 min.

[4-(2-Acetylaminoethylamino)-6-(3-chlorophenoxymethyl)-2-phenylpyrrolo[2,3-d]-pyrimidin-7-yl]-acetic acid ethyl ester (9.20)

MS (ES) 522 (M⁺); $t_R$ (method A)=10.6 min.

N-{2-[6-(3-Chlorophenoxymethyl)-7-(6-methoxy-2,2-dimethyltetrahydrofuro[3,4-d][1,3]dioxol-4-ylmethyl)-2-phenyl-7H-pyrrolo[2,3-d]pyrimidin-4-ylamino]-ethyl}-acetamide (9.21)

MS (ES) 622 (M⁺); $t_R$ (method A)=11.3 min.

N-{2-[6-(3-Chlorophenoxymethyl)-7-(3,4-dihydroxy-5-methoxytetrahydrofuran-2-ylmethyl)-2-phenyl-7H-pyrrolo[2,3-d]pyrimidin-4-ylamino]-ethyl}-acetamide (9.22)

MS (ES) 582 (M⁺); $t_R$ (method A)=8.0 min.

N-{2-[6-(2-Oxo-2H-pyridin-1-ylmethyl)-2-phenyl-7H-pyrrolo[2,3-d]pyrimidin-4-ylamino]-ethyl}-acetamide (9.23)

¹H NMR (200 MHz, DMSO-d₆): δ 1.78 (s, 3H), 3.32 (m, 2H), 3.59 (m, 2H), 5.14 (s, 2H), 6.27 (dd, 1H, J=6.6, 6.6 Hz), 6.34 (s, 1H), 6.43 (d, 1H, J=8.8 Hz), 7.44 (m, 5H), 7.76 (d, 1H, J=6.9 Hz), 8.00 (brt, 1H), 8.38 (m, 2H); MS (ES): 403.1 (M⁺+1).

N-{2-[6-(4-Chlorophenoxymethyl)-2-phenyl-7H-pyrrolo[2,3-d]pyrimidin-4-ylamino]-ethyl}-acetamide (9.24)

¹H NMR (200 MHz, DMSO-d₆): δ 1.79 (s, 3H), 3.56 (m, 2H), 3.61 (m, 2H), 5.13 (s, 2H), 6.60 (s, 1H), 7.05 (d, 2H, J=9.2 Hz), 7.34 (d, 2H, J=9.2 Hz), 7.60 (m, 3H), 7.57 (brt, 1H), 8.03 (brt, 1H), 8.40 (m, 2H); MS (ES): 436.1 [MH⁺].

1-Methyl-3-[2-(6-phenoxymethyl-2-phenyl-7H-pyrrolo[2,3-d]pyrimidinylamino)-ethyl]-urea (9.25)

¹H NMR (200 MHz, CD₃OD): δ 2.64 (s, 3H), 3.51 (t, 2H, J=6.0 Hz), 3.82 (t, 2H, J=6.0 Hz), 5.19 (s, 2H), 6.60 (s, 1H), 6.97 (dd, 1H, J=7.4 Hz), 7.06 (d, 2H, J=7.8 Hz), 7.32 (m, 2H), 7.44 (m, 3H), 8.39 (m, 2H); MS (ES): 416.9 (M⁺+1) $t_R$ (method A)=6.1 min.

N-{2-[6-(3-Methoxyphenoxymethyl)-2-phenyl-7H-pyrrolo[2,3-d]pyrimidin-4-ylamino]-ethyl}-acetamide (9.26)

¹H NMR (200 MHz, CDCl₃): δ 1.75 (s, 3H), 3.56 (m, 2H), 3.75 (s, 3H), 3.87 (m, 2H), 4.88 (s, 2H), 5.80 (brs, 1H), 6.35 (d, 3H, J=6.2 Hz), 6.50 (d, 1H, J=6.6 Hz), 7.10 (d, 1H, J=7.2 Hz), 7.40 (m, 3H), 8.36 (m, 2H) 10.47 (brs, 1H); MS (ES): 432.0 (M⁺+1).

N-{2-[6-(3-Aminophenoxymethyl)-2-phenyl-7H-pyrrolo[2,3-d]pyrimidin-4-ylamino]-ethyl}-acetamide (9.27)

¹H NMR (200 MHz, CDCl₃): δ 1.78 (s, 3H), 3.57 (m, 2H), 3.75 (s, 3H), 3.88 (m, 2H), 5.02 (s, 2H), 5.90 (brs, 1H), 6.20-6.60 (m, 4H), 7.04 (m, 2H), 7.44 (m, 3H), 8.38 (m, 2H) 9.45 (brs, 1H).

N-{2-[6-(3-Acetylaminophenoxymethyl)-2-phenyl-7H-pyrrolo[2,3-d]pyrimidin-4-ylamino]-ethyl}-acetamide (9.28)

¹H NMR (200 MHz, CD₃OD): δ 1.83 (s, 3H), 2.10 (s, 3H), 3.50 (t, 2H, J=6.0 Hz), 3.80 (t, 2H, J=6.2 Hz), 5.14 (s, 2H), 6.55 (s, 1H), 6.76 (m, 1H), 7.02 (d, 1H, J=8.4 Hz), 7.20 (dd, 1H, J=8.0, 8.0 Hz), 7.40 (m, 3H), 8.37 (m, 2H).

2-[6-(3-Chlorophenoxymethyl)-2-phenyl-7H-pyrrolo[2,3-d]pyrimidin-4-ylamino]-ethanol (9.29)

¹H NMR (200 MHz, CD₃OD): δ 3.15 (t, 2H, J=5.8 Hz), 3.55 (t, 2H, J=5.4 Hz), 5.17 (s, 2H), 6.59 (s, 1H), 7.00 (m, 2H), 7.08 (s, 1H), 7.26 (dd, 1H, J=8.4, 8.4 Hz) 7.42 (m, 3H), 8.34 (m, 2H); MS (ES): 395.0 (M⁺+1); $t_R$ (method A)=8.4 min.

(2S)-2-[6-(3-Chlorophenoxymethyl)-2-phenyl-7H-pyrrolo[2,3-d]pyrimidin-4-ylamino]-4-methylpentan-1-ol (9.30)

MS (ES): 451.0 (M⁺+1); $t_R$ (method A)=10.5 min.

(2R)-1-[6-(3-Chlorophenoxymethyl)-2-phenyl-7H-pyrrolo[2,3-d]pyrimidin-4-ylamino]-propan-2-ol (9.31)

¹H NMR (200 MHz, CD₃OD): δ 1.25 (d, 3H, J=6.2 Hz), 3.54-3.79 (m, 2H), 4.12 (m, 1H), 5.15 (s, 2H), 6.60 (s, 1H), 6.95 (m, 2H), 7.07 (dd, 1H, J=7.8, 7.8 Hz), 7.42 (m, 3H), 8.32 (m, 2H); MS (ES): 409.0 (M⁺+1); $t_R$ (method A)=8.7 min.

(2S)-1-[6-(3-Chlorophenoxymethyl)-2-phenyl-7H-pyrrolo[2,3-d]pyrimidin-4-ylamino]-propan-2-ol (9.32)

¹H NMR (200 MHz, CD₃OD): δ 1.25 (d, 3H, J=6.2 Hz), 3.54-3.79 (m, 2H), 4.12 (m, 1H), 5.15 (s, 2H), 6.60 (s, 1H), 6.95 (m, 2H), 7.07 (dd, 1H, J=7.8, 7.8 Hz), 7.42 (m, 3H), 8.32 (m, 2H); MS (ES): 409.0 (M⁺+1); $t_R$ (method A)=8.7 min.

2-[6-(3-Chlorophenoxymethyl)-2-phenyl-7H-pyrrolo[2,3-d]pyrimidin-4-ylamino]-propane-1,3-diol (9.33)

¹H NMR (200 MHz, CD₃OD): δ 3.86 (d, 4H, J=5.8 Hz), 4.57 (t, 1H, J=5.4 Hz), 5.18 (s, 2H), 6.64 (s, 1H), 6.95 (m, 2H), 7.07 (dd, 1H, J=2.2, 2.2 Hz), 8.20 (dd, 1H, J=8.2, 8.2 Hz), 7.43 (m, 3H), 8.32 (m, 2H); MS (ES): 425.0 (M$^+$+1); $t_R$(method A)=7.7 min.

1-{2-[6-(3-Chlorophenoxymethyl)-2-phenyl-7H-pyrrolo[2,3-d]pyrimidin-4-ylamino]-ethyl}-3-methylurea (9.34)

$^1$H NMR (200 MHz, CDCl$_3$): δ 2.57 (d, 3H, J=4.8 Hz), 3.55 (m, 2H), 3.83 (m, 2H), 4.85 (s, 2H), 5.52 (brs, 1H), 6.00 (brs, 1H), 6.38 (s, 1H), 6.64 (m, 1H), 6.73 (dd, 1H, J=1.8, 1.8 Hz), 6.92 (d, 1H, J=8.8 Hz), 7.14 (dd, 1H, J=8.0, 8.0 Hz), 7.40 (m, 3H), 8.34 (m, 2H), 10.64 (brs, 1H); MS (ES): 451.0 (M$^+$+1); $t_R$ (method A)=8.0 min.

2-{[6-(3-Chlorophenoxymethyl)-2-phenyl-7H-pyrrolo[2,3-d]pyrimidin-4-ylamino]-methyl}-piperidine-1-carboxylic acid methylamide (9.35)

$^1$H NMR (200 MHz, CD$_3$OD+DMSO-d$_6$): δ 1.40-1.70 (m, 6H), 2.43 (s, 3H), 3.50-3.90 (m, 2H), 4.10 (m, 1H), 4.45 (m, 2H), 3.83 (m, 2H), 5.20 (s, 2H), 6.58 (s, 1H), 7.04 (m, 2H), 7.10 (dd, 1H, J=2.2, 2.2 Hz), 7.29 (dd, 1H, J=8.2, 8.2 Hz), 7.44 (m, 3H), 8.38 (m, 2H); MS (ES): 505.0 (M$^+$+1); $t_R$ (method A)=9.7 min.

trans-2-{[6-(3-Chlorophenoxymethyl)-2-phenyl-7H-pyrrolo[2,3-d]pyrimidin-4-ylamino]-methyl}-cyclohexanol (9.36)

$^1$H NMR (200 MHz, CDCl$_3$): δ 1.00-2.00 (m, 9H), 2.93 (m, 1H), 3.66 (m, 2H), 4.73 (d, 2H, J=2.8 Hz), 4.90 (brs, 1H), 6.00 (brs, 1H), 5.41 (brs, 1H), 6.37 (s, 1H), 6.57 (ddd, 1H, J=1.0, 2.6, 8.2 Hz), 6.66 (dd, 1H, J=2.6, 2.6 Hz), 6.93 (ddd, 1H, J=0.8, 1.8, 7.9 Hz), 7.13 (dd, 1H, J=8.0, 8.0 Hz), 7.38 (m, 3H), 8.23 (m, 2H), 11.23 (brs, 1H); MS (ES) 463/465 (MH$^+$); $t_R$ (method A)=10.0 min.

(R)-2-[6-(3-Chlorophenoxymethyl)-2-phenyl-7H-pyrrolo[2,3-d]pyrimidin-4-ylamino]-propan-1-ol (9.37)

$^1$H NMR (CDCl$_3$, 200 MHz): δ 1.36 (d, 3H, J=7 Hz), 1.44 (s, 1H), 3.71 (dd, 1H, J=7.2, 3.8 Hz), 3.90 (dd, 1H, J=8.2, 2.8 Hz), 4.44-4.67 (m, 3H), 5.17-5.35 (m, 1H), 6.32 (s, 1H), 6.42-6.57 (m, 2H), 6.76-6.94 (m, 2H), 7.00-7.14 (m, 1H), 7.29-7.44 (m, 3H), 8.14-8.32 (m, 2H); MS (ES) 409.0/411.1 (100/35) [MH$^+$]; $t_R$ (method A)=8.9 min.

(S)-2-[6-(3-Chlorophenoxymethyl)-2-phenyl-7H-pyrrolo[2,3-d]pyriimidin ylamino]-propan-1-ol (9.38)

$^1$H NMR (CDCl$_3$, 200 MHz): δ 1.37 (d, 3H, J=7 Hz), 1.44 (s, 1H), 3.72 (dd, 1H, J=7.4, 3.6 Hz), 3.90 (dd, 1H, J=8, 3 Hz), 4.40-4.70 (m, 3H), 5.28 (brd, 1H, J=5.4 Hz), 6.33 (s, 1H), 6.43-6.60 (m, 2H), 6.76-6.94 (m, 2H), 7.02-7.14 (m, 1H), 7.30-7.45 (m, 3H), 8.14-8.32 (m, 2H); MS (ES) 409/411 (100/35) [MH$^+$]; $t_R$(method A)=8.9 min.

3-[6-(3-Chlorophenoxymethyl)-2-phenyl-7H-pyrrolo[2,3-d]pyrimidin-4-ylamino]-propan-1-ol (9.39)

MS (ES) 409/411 [MH$^+$]; $t_R$ (method A)=8.4 min.

(R)-2-[6-(3-Chlorophenoxymethyl)-2-phenyl-7H-pyrrolo[2,3-d]pyrimidin-4-ylamino]-3-methyl-butan-1-ol (9.40)

MS (ES) 437/439 [MH$^+$]; $t_R$ (method A)=9.7 min.

(S)-2-[6-(3-Chlorophenoxymethyl)-2-phenyl-7H-pyrrolo[2,3-d]pyrimidin-4-ylamino]-3-methyl-butan-1-ol (9.41)

MS (ES) 437/439 [MH$^+$]; $t_R$ (method A)=9.7 min.

(R)-2-[6-(3-Chlorophenoxymethyl)-2-phenyl-7H-pyrrolo[2,3-d]pyrimidin-4-ylamino]-2-phenylethanol (9.42)

MS (ES) 471/473 [MH$^+$]; $t_R$ (method A)=9.8 min.

(S)-2-[6-(3-Chlorophenoxymethyl)-2-phenyl-7H-pyrrolo[2,3-d]pyriimidin-4-ylamino]-2-phenylethanol (9.43)

MS (ES) 471/473 [MH$^+$]; $t_R$ (method A)=9.8 min.

{1-[6-(3-Chlorophenoxymethyl)-2-phenyl-7H-pyrrolo[2,3-d]pyrimidin-4-yl]-piperidin-3-yl}-methanol (9.44)

$^1$H NMR (CDCl$_3$, 200 MHz): δ 1.4-2.00 (m, 5H), 3.52 (d, 2H, J=7.6 Hz), 3.78-3.86 (m, 1H), 4.02-4.22 (m, 2H), 4.50 (dd, 2H, J=11.6, 3.2 Hz), 6.35-6.50 (m, 2H), 6.54 (brs, 1H), 6.83-6.94 (m, 1H), 7.05 (t, 1H, J=8.2 Hz), 7.28-7.44 (m, 3H), 8.18-8.31 (m, 2H); MS (ES) 449/451 [MH$^+$]; $t_R$ (method A)=10.3 min.

N-{2-[6-(3-Chlorophenoxymethyl)-5-dimethylaminomethyl-2-phenyl-7H-pyrrolo[2,3-d]pyrimidin-4-ylamino]-ethyl}-acetamide (9.45)

$^1$H NMR (CDCl$_3$, 200 MHz): δ 1.61 (s, 3H), 2.30 (s, 6H), 3.43-3.60 (m, 4H), 3.74-3.93 (m, 2H), 4.53 (brs, 2H), 6.34-6.50 (m, 2H), 6.83-6.95 (m, 1H), 7.07 (t, 1H, J=8.4 Hz), 7.25-7.45 (m, 3H), 7.53-7.71 (m, 1H), 8.22-8.40 (m, 2H), 9.57-9.78 (m, 1H); MS (ES) 493/495 [MH$^+$]; $t_R$ (method A)=7.2 min.

2-[6-(3-Chlorophenoxymethyl)-5-dimethylaminomethyl-2-phenyl-7H-pyrrolo[2,3-d]pyrimidin-4-ylamino]-ethanol (9.46)

$^1$H NMR (CDCl$_3$, 200 MHz): δ 2.29 (s, 6H), 3.50 (s, 2H), 3.71-3.84 (m, 2H), 3.85-3.97 (m, 2H), 4.44 (s, 2H), 6.33-6.49 (m, 2H), 6.83-6.95 (m, 1H), 7.07 (t, 1H, J=8.2 Hz), 7.20-7.42 (m, 4H), 8.18-8.31 (m, 2H), 9.77 (brs, 1H); MS (ES) 452/454 [MH$^+$]; $t_R$ (method A)=7.0 min.

N-[6-(3-Chlorophenoxymethyl)-2-phenyl-7H-pyrrolo[2,3-d]pyrimidin-4-yl]ethane-diamine (9.47)

MS (ES): 394/396 [MH$^+$].

3-{2-[6-(3-Chlorophenoxymethyl)-2-phenyl-7H-pyrrolo[2,3-d]pyrinmidin-4-ylamino]ethyl}-1,1-dimethylurea (9.48)

To a solution of 9.47 (20 mg) and TEA (100 mg) in DCM (5 mL) and DMF (1 mL) was added dropwise the solution of ClC(O)N(CH$_3$)$_2$ (100 mg) in DCM (3 mL) at 0° C. while stirring. After adding, the stirring was continued for 2 h and the reaction mixture was washed with saturated NaHCO$_3$ aqueous solution twice, brine once, dried over MgSO$_4$, and then concentrated. The residue was purified by preparative TLC (silica gel, EtOAc/Hexane=2/1), yielding an off-white foam (7 mg, 31%). $^1$H-NMR (200 MHz, CDCl$_3$): δ 2.70 (s, 6H), 3.55-3.68 (m, 2H), 3.82-3.94 (m, 2H), 4.82 (s, 2H), 5.40 (t, 1H, J=5.2 Hz), 6.30 (brs, 1H), 6.42 (s, 1H), 6.55-6.78 (m, 2H), 6.90-6.95 (m, 1H), 7.08-7.20 (m, 1H), 7.18-7.48 (m, 3H), 8.28-8.40 (m, 2H), 10.90 (brs, 1H); MS (ES): 465/467 [MH$^+$].

1-{4-[6-(3-Chlorophenoxymethyl)-2-phenyl-7H-pyrrolo[2,3-d]pyrimidin-4-yl]-piperazin-1-yl}-ethanone (9.49)

$^1$H NMR (CDCl$_3$, 200 MHz) δ 2.18 (s, 3H), 3.61-3.77 (m, 2H), 3.77-3.90 (m, 2H), 4.00-4.10 (m, 2H), 4.10-4.20 (m, 2H), 4.62 (brs, 2H), 6.40-6.54 (m, 3H), 6.86-6.95 (m, 1H), 7.08 (t, 1H, J=8.2 Hz), 7.32-7.45 (m, 3H), 8.25-8.39 (m, 2H); MS (ES) 462/464 [MH$^+$]; t$_R$ (method A)=9.8 min.

1-[6-(3-Chlorophenoxymethyl)-2-phenyl-7H-pyrrolo[2,3-d]pyrimidin-4-yl]azetidin-3-ol (9.50)

MS (ES): 407/409 [MH$^+$]; t$_R$ (method A)=8.6 min.

N-(2-{[6-(3-Chlorophenoxymethyl)-2-phenyl-7H-pyrrolo[2,3-d]pyrimidin-4-yl]methylamino}ethyl) acetamide (9.51)

MS (ES): 450/452 [MH$^+$]; t$_R$ (method A)=8.5 min.

EXAMPLE 6

C-6 Alkoxymethylene Derivatives

Alkoxymethylene derivatives are conveniently prepared by silver-mediated displacement of the bromide in 7 with alcohols. A series of piperidine sulfonamides 15 was prepared from the intermediate 10 by Boc removal, C-4 chloride displacement, and sulfonylation (scheme 6).

Scheme 6: Silver-mediated bromide displacement and synthesis of sulfonamides 15.

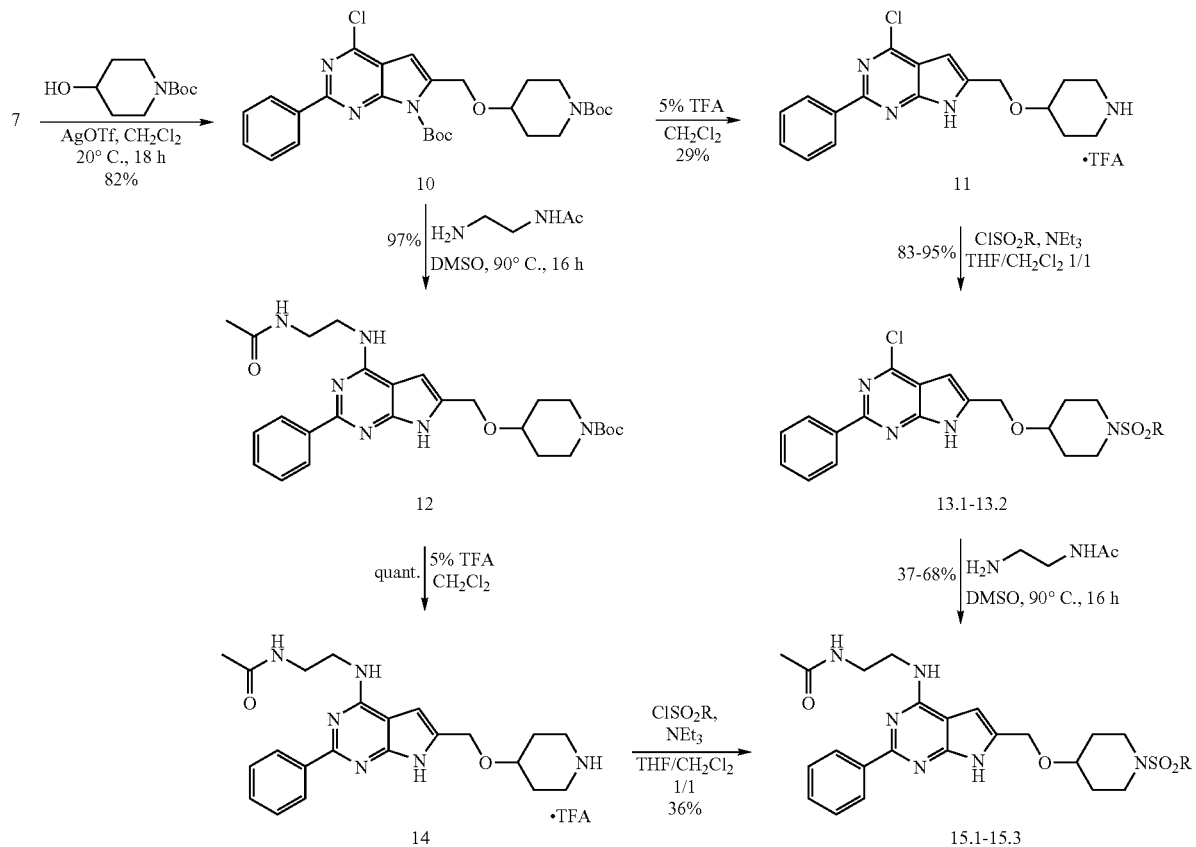

General Procedure for Silver-Mediated Bromide Displacement:

6-(1-tert-Butoxycarbonylpiperidin-4-yloxymethyl)-4-chloro-2-phenzylpyrrolo[2,3-d]pyrimidine-7-carboxylic acid tert-butyl ester (10)

Bromide 7 (4.54 g, 10 mmol) and N-Boc-piperidin-4-ol (13.32 g) were dissolved in DCM (120 mL) and treated with AgOTf (3.55 g) under N$_2$ at rt for 18 h. The solid in the reaction mixture was removed by filtration and washed with DCM (2×20 mL). The filtrate was washed with saturated NaHCO$_3$ solution and brine, dried over MgSO$_4$, filtered and concentrated. The crude product was purified by flash chromatography (silica gel, EtOAc/Hexane=1:2) to give 4.339 g (82%) of the title compound as white solid. $^1$H-NMR (200 MHz, CDCl$_3$): δ 1.45 (s, 9H), 1.50-1.65 (m, 2H), 1.70-1.98 (m, 11H), 3.30-3.50 (m, 2H), 3.70-3.90 (m, 3H), 4.95 (s, 2H), 6.70 (s, 1H), 7.46-7.49 (m, 3H), 8.49-8.53 (m, 2H).

4-Chloro-2-phenyl-6-(piperidin-4-yloxymethyl)-7H-pyrrolo[2,3-d]pyrimidine (11)

Following the procedure to synthesize 14, 11 was prepared in 29% yield.

4-[2-Acetylaminoethylamino)-2-phenyl-7H-pyrrolo[2,3-d]pyrimidin-6-ylmethoxy]piperidine-1-carboxylic acid tert-butyl ester (12)

Aryl chloride 10 (1.3 g), DMSO (20 mL), N-acetylethylenediamine (3.0 g) and NaHCO$_3$ (2 g) were stirred and heated to 90° C. under nitrogen overnight. The reaction mixture is then cooled to room temperature and diluted with water (60 ml). The resulted slurry is extracted with EtOAc three times. The combined organic layers was washed with saturated NaHCO$_3$ solution and brine, dried over MgSO$_4$, filtered and concentrated to give 1.46 g (97%) of a brown solid. $^1$H-NMR (200 MHz, CDCl$_3$): δ 1.44 (s, 9H), 1.50-1.64 (m, 2H), 1.80 (s, 2H), 1.82-1.92 (m, 2H), 2.84-3.08 (m, 3H), 3.18-3.42 (m, 4H), 3.45-3.70 (m, 4H), 3.78-3.95 (m, 3H), 4.46 (s, 2H), 5.76 (t, 1H, J=5.6 Hz), 6.25 (s, 2H), 7.19 (t, 1H, J=6.2), 7.38-7.56 (m, 3H), 8.43-8.46 (m, 2H), 10.19 (brs, 1H); MS (ES): 509.0 [MH$^+$].

6-(1-Benzenesulfonylpiperidin-4-yloxymethyl)-4-chloro-2-phenyl-7H-pyrrolo[2,3-d]pyrimidine (13.1)

Following the procedure to synthesize 15.3, 13.1 was prepared in 95% yield. $^1$H-NMR (200 MHz, CDCl$_3$): δ 1.50-1.70 (m, 2H), 1.70-1.90 (m, 2H), 2.75-2.90 (m, 2H), 3.03-3.36 (m, 3H), 4.45 (s, 2H), 6.40 (s, 1H), 7.30-7.70 (m, 6H), 7.71-7.77 (m, 2H), 8.01-8.06 (m, 2H), 10.08 (brs, 1H).

6-(1-Benzylsulfonylpiperidin-4-yloxymethyl)-4-chloro-2-phenyl-7H-pyrrolo[2,3-d]pyrimidine (13.2)

Following the procedure to synthesize 15.3, 13.2 was prepared in 83% yield. $^1$H-NMR (200 MHz, CDCl$_3$) δ 1.50-1.70 (m, 2H), 1.70-1.90 (m, 2H), 2.90-3.00 (m, 2H), 3.15-3.30 (m, 2H), 3.30-3.45 (m, 1H), 4.19 (s, 2H), 4.52 (s, 2H), 6.45 (s, 1H), 7.30-7.45 (m, 5H), 7.45-7.53 (m, 3H), 8.01-8.06 (m, 2H), 10.08 (brs, 1H).

N-{2-[2-Phenyl-6-(piperidin-4-yloxymethyl)-7H-pyrrolo[2,3-d]pyrimidin-4-ylamino}ethyl)acetamide trifluoroacetic acid salt (14)

Compound 12 (0.23 g) was stirred in 5% TFA/DCM (4 mL). A white foam (0.19 g) was obtained after drying in vacuo in quantitative yield. $^1$H-NMR (200 MHz, CDCl$_3$): δ 1.63 (s, 3H), 1.66-2.00 (m, 2H), 2.78-3.00 (m, 2H), 3.00-3.20 (m, 2H), 3.30-3.48 (m, 2H), 3.50-3.60 (m, 1H), 3.63-3.75 (m, 2H), 4.13 (s, 2H), 6.30 (s, 1H), 7.20-7.40 (m, 3H), 8.13-8.17 (m, 2H); MS (ES): 408.8 [MH$^+$].

N-(2-{6-[1-(Benzenesulfonyl)piperidin-4-yloxymethyl]-2-phenyl-7H-pyrrolo[2,3-d]pyrimidin-4-ylamino}ethyl)acetamide (15.1)

Following the general procedure for C-4 chloride displacement, 15.1 was prepared from 13.1 in 37% yield. $^1$H-NMR (200 MHz, CDCl$_3$): δ 1.45-1.59 (m, 2H), 1.67 (s, 3H), 2.75-2.87 (m, 2H), 3.03-3.26 (m, 4H), 3.27-3.35 (m, 1H), 3.57-3.62 (m, 2H), 3.83-3.92 (m, 2H), 4.36 (s, 2H), 5.74 (t, 1H, J=5.6 Hz), 6.22 (s, 1H), 6.96 (t, 1H, J=5.6 Hz), 7.40-7.54 (m, 3H), 7.55-7.62 (m, 3H), 7.68-7.72 (m, 2H), 8.37-8.45 (m, 2H), 10.09 (brs, 1H); MS (ES): 546.8 [MH$^+$].

N-(2-[6-[1-(Benzylsulfonyl)piperidin-4-yloxymethyl]-2-phenyl-7H-pyrrolo[2,3-d]pyrimidin-4-ylamino]ethyl)acetamide (15.2)

Following the general procedure for C-4 chloride displacement, 15.2 was prepared from 13.2 in 68% yield. $^1$H-NMR (200 MHz, CDCl$_3$): δ 1.41-1.51 (m, 2H), 1.57-1.67 (m, 2H), 1.84 (s, 3H), 2.17-2.95 (m, 2H), 3.11-3.23 (m, 2H), 3.27-3.32 (m, 1H), 3.59-3.64 (m, 2H), 3.85 (m, 2H), 4.14 (s, 2H), 4.41 (s, 2H), 6.18 (brs, 1H), 6.28 (s, 1H), 6.92 (t, 1H, J=5.0 Hz), 7.30-7.40 (m, 5H), 7.40-7.58 (m, 3H), 8.40-8.45 (m, 2H), 10.55 (brs, 1H); MS (ES): 562.7 [MH$^+$].

N-(2-{6-[1-(4-Cyanobenzenesulfonyl)piperidin-4-yloxymethyl]-2-phenyl-7H-pyrrolo[2,3-d]pyrimidin-4-ylamino}ethyl)acetamide (15.3)

Amine 14 (62 mg) and NEt$_3$ (0.1 mL) were stirred in THF (6 mL) and DCM (6 mL) and cooled to 5° C. 4-Cyanophenylsulfonyl chloride (30 mg) was added dropwise by syringe, and stirring was continued at rt for 2 h, then the reaction mixture was concentrated. The residue was redissolved in DCM and washed with saturated NaHCO$_3$, brine, and dried over MgSO$_4$. After removal of solvent, the crude product was purified by preparative TLC (silica gel, DCM/MeOH=12/1) to give 16 mg (36%) of 15.3 as an off-white foam. $^1$H-NMR (200 MHz, CDCl$_3$): δ 1.50-1.67 (m, 2H), 1.80 (s, 3H), 2.94-3.20 (m, 4H), 3.32-3.46 (m, 1H), 3.50-3.70 (m, 2H), 3.80-3.95 (m, 2H), 4.47 (s, 2H), 5.72 (brs, 1H), 6.22 (s, 1H), 6.81 (brs, 1H), 7.20-7.38 (m, 3H), 7.75-7.90 (m, 4H), 8.37-8.40 (m, 2H), 9.37 (brs, 1H); MS (ES): 574.1 [MH$^+$].

EXAMPLE 7

N-alkylpiperidine Derivatives

N-Alkylpiperidine derivatives 17.1-17.19 were prepared by alkylation of 11 and by reductive amination of 14 using NaBH(OAc)$_3$ as reducing agent (scheme 7).

Scheme 7. Synthesis of N-Alkylpiperidine derivatives 17.1-17.19.

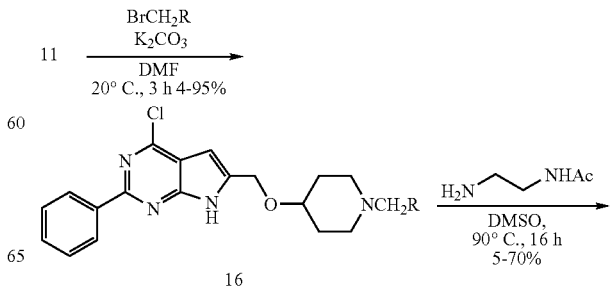

-continued

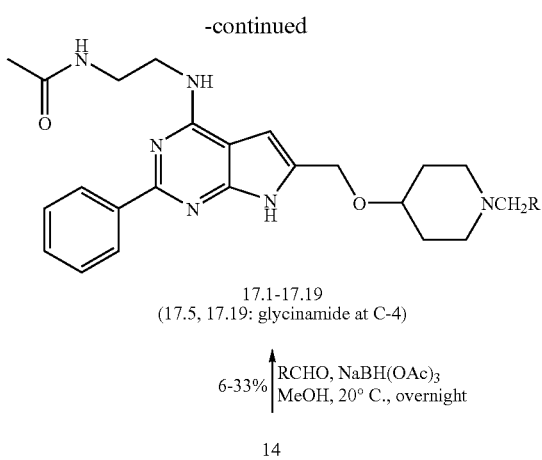

17.1-17.19
(17.5, 17.19: glycinamide at C-4)

6-33% | RCHO, NaBH(OAc)$_3$
MeOH, 20° C., overnight

14

General Procedure for the Alkylation 11→16:

Compound 11 (49 mg), the alkyl bromide, and potassium carbonate (100 mg) were stirred in anhydrous DMF under N$_2$ at rt for 3 h. The DMF was then removed in vacuo. The residue was partitioned between DCM and water. The aqueous layer was separated and extracted with DCM twice. The combined DCM layers were washed with an aqueous saturated sodium bicarbonate solution and brine, and dried over MgSO$_4$. After removal of solvent, the crude product was purified by TLC (silica gel, 100% EtOAc).

The following compounds were prepared in this manner:

4-Chloro-2-phenyl-6-(1-benzylpiperidin-4-yloxymethyl)-7H-pyrrolo[2,3-d]pyrimidine (16.1): 57% yield.

4-Chloro-2-phenyl-6-(1-phenethylpiperidin-4-yloxymethyl)-7H-pyrrolo[2,3-d]pyrimidine (16.2): 31% yield.

4-Chloro-2-phenyl-6-[1-(3-phenylpropyl)piperidin-4-yloxymethyl]-7H-pyrrolo[2,3-d]pyrimidine (16.3): 55% yield.

4-Chloro-2-phenyl-6-[1-(4-bromobenzyl)piperidin-4-yloxymethyl]-7H-pyrrolo[2,3-d]pyrimidine (16.4): 95% yield.

N-{2-[6-(1-Benzylpiperidin-4-yloxymethyl)-2-phenyl-7H-pyrrolo[2,3-d]pyrimidin-4-ylamino]ethyl}acetamide (17.1)

Following the general procedure for C-4 chloride displacement, 17.1 was prepared from 16.1 in 5% yield. $^1$H-NMR (200 MHz, CDCl$_3$): δ 1.52-1.65 (m, 2H), 1.74-1.92 (m, 5H), 2.15-2.25 (m, 2H), 2.62-2.78 (m, 2H), 3.20-3.30 (m, 1H), 3.45 (s, 2H), 3.56-3.68 (m, 2H), 3.82-3.95 (m, 2H), 4.20 (s, 2H), 5.67 (t, 1H, J=5.4 Hz), 6.25 (s, 1H), 7.09 (brs, 1H), 7.20-7.38 (m, 5H), 7.42-7.48 (m, 3H), 8.38-8.43 (m, 2H), 9.34 (brs, 1H); MS (ES): 499.2 (M$^+$+1).

N-{2-[6-(1-Phenethylpiperidin-4-yloxymethyl)-2-phenyl-7H-pyrrolo[2,3-d]-pyrimidin-4-ylamino]ethyl}acetamide (17.2)

Following the general procedure for C-4 chloride displacement, 17.2 was prepared from 16.2 in 23% yield. $^1$H-NMR (200 MHz, CDCl$_3$): δ 1.41-1.58 (m, 2H), 1.57-1.67 (m, 2H), 1.77 (s, 3H), 1.80-2.00 (m, 2H), 2.16-2.26 (m, 2H), 2.53-2.61 (m, 2H), 2.76-2.84 (m, 4H), 3.34-3.42 (m, 1H), 3.57-3.63 (m, 2H), 3.86-3.94 (m, 2H), 4.60 (s, 2H), 5.57 (t, 1H, J=5.8 Hz), 6.25 (s, 1H), 7.06 (brs, 1H), 7.20-7.38 (m, 5H), 7.40-7.58 (m, 3H), 8.40-8.44 (m, 2H), 9.15 (brs, 1H); MS (ES): 513.0 (M$^+$+1).

N-[2-{6-[1-(3-Phenylpropyl)piperidin-4-yloxymethyl]-2-phenyl-7H-pyrrolo[2,3-d]pyrimidin-4-ylamino}ethyl]acetamide (17.3)

Following the general procedure for C-4 chloride displacement, 17.3 was prepared from 16.2 in 18% yield. $^1$H-NMR (200 MHz, CDCl$_3$): δ 1.57-1.67 (m, 2H), 1.77 (s, 3H), 1.80-1.98 (m, 4H), 2.00-2.18 (m, 2H), 2.34 (t, 2H, J=7.6 Hz), 2.62 (t, 2H, J=8.4 Hz), 2.68-2.84 (m, 2H), 3.34-3.46 (m, 1H), 3.57-3.64 (m, 2H), 3.86-3.94 (m, 2H), 4.61 (s, 2H), 5.53 (t, 1H, J=5.4 Hz), 6.24 (s, 1H), 7.07 (brs, 1H), 7.20-7.38 (m, 5H), 7.40-7.58 (m, 3H), 8.40-8.44 (m, 2H), 8.97 (brs, 1H); MS (ES): 527.2 (M$^+$+1).

N-(2-{6-[1-(4-Bromobenzyl)piperidin-4-yloxymethyl]-2-phenyl-7H-pyrrolo[2,3-d]pyrimidin-4-ylamino}ethyl)acetamide (17.4)

Following the general procedure for C-4 chloride displacement, 17.4 was prepared from 16.4 in 32% yield. $^1$H-NMR (200 MHz, CDCl$_3$): δ 1.50-1.65 (m, 2H), 1.76-1.96 (m, 5H), 2.05-2.20 (m, 2H), 2.60-2.75 (m, 2H), 3.25-3.35 (m, 1H), 3.43 (s, 2H), 3.54-3.62 (m, 2H), 3.85-3.93 (m, 2H), 4.50 (s, 2H), 5.67 (t, 1H, J=5.4 Hz), 6.25 (s, 1H), 7.09 (brs, 1H), 7.21 (d, 2H, J=8.4 Hz), 7.40-7.51 (m, 5H), 8.39-8.44 (m, 2H), 9.70 (brs, 1H); MS (ES): 576.9 (M$^+$+1).

2-[6-(1-Benzylpiperidin-4-yloxymethyl)-2-phenyl-7H-pyrrolo[2,3-d]pyrimidin-4-ylamino]acetamide (17.5)

Following the general procedure for C-4 chloride displacement using glycinamide as amine, 17.5 was prepared from 16.1 in 43% yield.

$^1$H-NMR (200 MHz, CDCl$_3$): δ 1.60-1.78 (m, 2H), 1.80-1.95 (m, 2H), 2.08-2.16 (m, 2H), 2.60-2.75 (m, 2H), 3.28-3.39 (m, 1H), 3.47 (s, 2H), 4.38 (d, 2H, J=5.4 Hz), 4.57 (s, 2H), 5.50-5.70 (m, 2H), 6.25 (s, 1H), 6.47 (brs, 1H), 7.20-7.40 (m, 5H), 7.42-7.48 (m, 3H), 8.38-8.43 (m, 2H), 9.34 (brs, 1H).

N-(2-{2-Phenyl-6-[1-(3-phenylallyl)piperidin-4-yloxymethyl]-7H-pyrrolo[2,3-d]pyrimidin-4-ylamino}ethyl]acetamide (17.6)

Following the procedure for the alkylation 11→16, 17.6 was prepared from 14 in 4% yield. $^1$H-NMR (200 MHz, CDCl$_3$) δ 1.57-1.76 (m, 2H), 1.78 (s, 3H), 1.82-2.00 (m, 2H), 2.74-2.92 (m, 2H), 3.20-3.38 (m, 2H), 3.40-3.50 (m, 1H), 3.52-3.64 (m, 2H), 3.82-3.94 (m, 2H), 4.56 (s, 2H), 5.29 (s, 2H), 5.69 (brs, 1H), 6.16-6.34 (m, 2H), 6.59 (d, 1H, J=15.4 Hz), 7.01 (brs, 1H), 7.30-7.40 (m, 5H), 7.40-7.50 (m, 3H), 8.39-8.44 (m, 2H), 9.40 (brs, 1H); MS (ES): 525.2 [MH$^+$].

N-[2-(6-{1-[2-(2-Chlorophenyl)ethyl]piperidin-4-yloxymethyl}-2-phenyl-7H-pyrrolo[2,3-d]pyrimidin-4-ylamino)ethyl]acetamide (17.7)

Following the general procedure for C-4 chloride displacement, 17.7 was prepared in 70% yield. $^1$H-NMR (200 MHz, CDCl$_3$) δ 1.48-1.67 (m, 2H), 1.70-1.90 (m, 5H), 2.23 (t, 2H, J=9.2 Hz), 2.50-2.61 (m, 2H), 2.78-2.94 (m, 4H), 3.18-3.26 (m, 1H), 3.54-3.60 (m, 2H), 3.83-3.91 (m, 2H), 4.44 (s, 2H), 5.73 (t, 1H, J=6.0 Hz), 6.26 (s, 1H), 7.11-7.34 (m, 5H), 7.42-7.51 (m, 3H), 8.40-8.45 (m, 2H), 10.30 (brs, 1H); MS (ES): 546.8 (M$^+$+1).

N-[2-(-6-{1-[2-(2-Chlorophenyl)ethyl]piperidine-4-yloxymethyl}-2-phenyl-7H-pyrrolo[2,3-d]pyrimidin-4-ylamino)ethyl]acetamide methanesulfonic acid salt (17.7.MsOH)

17.7 (315 mg) was dissolved in methanol (5 mL) and cooled to 5° C. 25. Methanesulfonic acid (57 mg) in methanol (5 mL) was added. The resulted solution was then diluted with isopropyl ether (20 mL) and set in freezer overnight. A white solid (82 mg) was obtained after filtration. The mother liquid was concentrated in vacuo (bath temperature 10° C.) to give a slightly brownish oil. The resulting oil was stirred in anhydrous isopropyl ether for 1 h to give 246 mg of a slightly brownish solid. The two batches of product were combined and stirred in anhydrous ethyl ether to give 324 mg (88% yield) of a slightly brownish solid, mp. 153-156° C. $^1$H-NMR (200 MHz, CD$_3$OD) δ 1.80-2.18 (m, 5H), 2.20-2.40 (m, 2H), 2.65-2.90 (m, 5H), 3.20-3.60 (m 10H), 3.70-3.85 (m, 1H), 4.75 (s, 2H), 6.80 (brs, 1H), 7.25-7.40 (m, 2H), 7.40-7.51 (m, 2H), 7.6 7.80 (m, 3H), 8.16-8.35 (m, 2H); t$_R$ (method A)=11.15 min; MS (ES): 546.9 [MH$^+$].

General Procedure for Reductive Amination of 14:

Piperidine 14 (60 mg, 0.15 mmol), aldehyde (45 mg, 0.29 mmol), and NaBH(OAc)$_3$ (67 mg, 0.32 mmol) are stirred in MeOH (6 mL) at rt overnight. The reaction mixture is filtered, and the filtrate is directly charged onto a TLC plate and developed with DCM/MeOH=4/1.

The amines 17.8-17.18 were prepared according to this procedure.

N-[2-(6-{1-[2-(3-Chlorophenyl)ethyl]piperidin-4-yloxymethyl}-2-phenyl-7H-pyrrolo[2,3-d]pyrimidin-4-ylamino)ethyl]acetamide (17.8)

10% yield. $^1$H-NMR (200 MHz, CDCl$_3$): δ 1.50-1.72 (m, 2H), 1.80 (s, 3H), 1.82-1.96 (m, 2H), 2.26-2.42 (m, 2H), 2.55-2.68 (m, 2H), 2.70-2.86 (m, 4H), 3.22-3.40 (m, 1H), 3.55-3.65 (m, 2H), 3.83-3.91 (m, 2H), 4.49 (s, 2H), 5.75 (t, 1H, J=6.0 Hz), 6.26 (s, 1H), 7.00-7.15 (m, 2H), 7.15-7.25 (m, 3H), 7.40-7.55 (m, 3H), 8.40-8.44 (m, 2H), 9.98 (brs, 1H); MS (ES): 546.80 (M$^+$+1).

N-(2-{6-[1-(3-Chlorobenzyl)piperidin-4-yloxymethyl]-2-phenyl-7H-pyrrolo[2,3-d]pyrimidin-4-ylamino}ethyl)acetamide (17.9)

33% yield. $^1$H-NMR (200 MHz, CDCl$_3$): δ 1.50-1.65 (m, 2H), 1.76 (s, 3H), 2.00-2.20 (m, 2H), 2.60-2.69 (m, 2H), 3.28-3.35 (m, 1H), 3.42 (s, 2H), 3.49-3.58 (m, 2H), 3.85-3.93 (m, 2H), 4.54 (s, 2H), 5.59 (t, 1H, J=5.8 Hz), 6.23 (s, 1H), 7.08 (t, 1H, J=5.8 Hz), 7.16-7.25 (m, 3H), 7.30 (s, 1H), 7.40-7.51 (m, 5H), 8.38-8.43 (m, 2H), 9.39 (brs, 1H); MS (ES): 532.8 (M$^+$+1).

N-[2-(6-{1-[2-(4-Chlorophenyl)ethyl]piperidin-4-yloxymethyl}-2-phenyl-7H-pyrrolo[2,3-d]pyrimidin-4-ylamino)ethyl]acetamide (17.10)

10% yield. $^1$H-NMR (200 MHz, CDCl$_3$) δ 1.50-1.72 (m, 2H), 1.78 (s, 3H), 1.82-1.96 (m, 2H), 2.16-2.30 (2H), 2.1-2.30 (m, 2H), 2.48-2.60 (m, 2H), 2.71-2.86 (m, 4H), 3.22-3.40 (m, 1H), 3.55-3.65 (m, 2H), 3.86-3.91 (m, 2H), 4.60 (s, 2H), 5.58 (t, 1H, J=5.0 Hz), 6.24 (s, 1H), 7.03 (t, 1H, J=5.0 Hz), 7.13 (d, 2H, J=8.4 Hz), 7.26 (d, 2H, J=8.4 Hz), 7.43-7.51 (m, 3H), 8.38-8.43 (m, 2H), 9.11 (brs, 1H); MS (ES): 546.8 (M$^+$+1).

N-[2-{1-[2-(2-Methoxyphenyl)ethyl]piperidin-4-yloxymethyl}-2-phenyl-7H-pyrrolo[2,3-d]pyrimidin-4-ylamino)ethyl]acetamide (17.11)

18% yield. $^1$H-NMR (200 MHz, CDCl$_3$) δ 1.50-1.70 (m, 2H), 1.79 (s, 3H), 1.80-1.96 (m, 2H), 2.40-2.62 (m, 2H), 2.65-2.75 (m, 2H), 2.76-2.86 (m, 4H), 3.27-3.34 (m, 1H), 3.55-3.61 (m, 2H), 3.76-3.83 (m, 5H), 4.22 (s, 2H), 5.82 (t, 1H, J=6.0 Hz), 6.27 (s, 1H), 6.80-6.92 (m, 2H), 7.10-7.20 (m, 3H), 7.43-7.51 (m, 3H), 8.41-8.45 (m, 2H), 10.25 (brs, 1H); MS (ES): 542.9 (M$^+$+1).

N-[2-(6-{1-[2-(3-Methoxyphenyl)ethyl]piperidin-4-yloxymethyl}-2-phenyl-7H-pyrrolo[2,3-d]pyrimidin-4-ylamino)ethyl]acetamide (17.12)

7% yield. $^1$H-NMR (200 MHz, CDCl$_3$) δ 1.50-1.80 (m, 2H), 1.81 (s, 3H), 1.90-2.10 (m, 4H), 2.65-2.75 (m, 2H), 2.76-2.96 (m, 4H), 3.27-3.50 (m, 1H), 3.55-3.63 (m, 2H), 3.79 (s, 3H), 3.80-3.93 (m, 2H), 4.51 (s, 2H), 5.78 (brs, 1H), 6.27 (s, 1H), 6.74-6.79 (m, 3H), 6.98 (brs, 1H), 7.17-7.20 (m, 1H), 7.45-7.48 (m, 3H), 8.40-8.45 (m, 2H), 10.00 (brs, 1H); MS (ES): 542.9 (M$^+$+1).

N-[2-(6-{1-[2-(4-Methoxyphenyl)ethyl]piperidin-4-yloxymethyl}-2-phenyl-7H-pyrrolo[2,3-d]pyriinidin-4-ylamino)ethyl]acetamide (17.13)

6% yield. $^1$H-NMR (200 MHz, CDCl$_3$) δ 1.54-1.72 (m, 2H), 1.82 (s, 3H), 1.83-1.96 (m, 2H), 2.71-2.86 (m, 8H), 3.22-3.40 (m, 1H), 3.50-3.65 (m, 2H), 3.76 (s, 3H), 3.80-3.91 (m, 2H), 4.35 (s, 2H), 6.11 (t, 1H, J=5.0 Hz), 6.31 (s, 1H), 6.83 (d, 2H, J=8.4 Hz), 7.14 (t, 1H, J=5.0 Hz), 7.26 (d, 2H, J=8.4 Hz), 7.43-7.46 (m, 3H), 8.40-8.43 (m, 2H), 10.90 (brs, 1H); MS (ES): 543.0 (M$^+$+1).

N-[2-(6-[1-[2-(4-Fluorophenyl)ethyl]piperidin-4-yloxymethyl]-2-phenyl-7H-pyrrolo[2,3-d]pyrimidin-4-ylamino)ethyl]acetamide (17.14)

14% yield. $^1$H-NMR (200 MHz, CDCl$_3$) δ 1.58-1.78 (m, 2H), 1.80 (s, 3H), 1.82-2.10. (m, 2H), 2.44-2.60 (m, 2H), 2.60-2.80 (m, 2H), 2.80-2.92 (m, 4H), 3.38-3.48 (m, 1H), 3.50-3.65 (m, 2H), 3.82-3.94 (m, 2H), 4.53 (s, 2H), 5.77 (t, 1H, J=5.4 Hz), 6.27 (s, 1H), 6.90-7.06 (m, 3H), 7.08-7.20 (m, 2H), 7.40-7.60 (m, 3H), 8.38-8.43 (m, 2H), 9.90 (brs, 1H); MS (ES): 530.8 (M$^+$+1).

N-[2-(6-{1-[2-(2-Chloro-4-fluorophenyl)ethyl]piperidin-4-yloxymethyl}-2-phenyl-7H-pyrrolo[2,3-d]pyrimidin-4-ylamino)ethyl]acetamide (17.15)

10% yield. $^1$H-NMR (200 MHz, CDCl$_3$) δ 1.48-1.70 (m, 2H), 1.77 (s, 3H), 1.82-1.90 (m, 2H), 2.24-2.40 (m, 2H), 2.46-2.64 (m, 2H), 2.74-2.94 (m, 4H), 3.18-3.24 (m, 1H), 3.48-3.60 (m, 2H), 3.83-4.00 (m, 2H), 4.57 (s, 2H), 5.64 (t, 1H, J=6.0 Hz), 6.25 (s, 1H), 6.84-7.20 (m, 4H), 8.38-8.45 (m, 2H), 9.40 (brs, 1H).

N-[2-(6-{1-[2-(2-Chloro-6-fluorophenyl)ethyl]piperidin-4-yloxymethyl}-2-phenyl-7H-pyrrolo[2,3-d]pyrimidin-4-ylamino)ethyl]acetamide (17.16)

13% yield. $^1$H-NMR (200 MHz, CDCl$_3$) δ 1.48-1.64 (m, 2H), 1.77 (s, 3H), 1.78-1.94 (m, 2H), 1.95-2.08 (m, 2H), 2.50-2.55 (m, 2H), 2.70-3.01 (m, 6H), 3.33-3.39 (m, 1H), 3.54-3.62 (m, 2H), 3.86-3.94 (m, 2H), 4.55 (s, 2H), 5.59 (t, 1H, J=5.8 Hz), 6.25 (s, 1H), 6.90-7.00 (m, 1H), 7.04-7.20 (m, 3H), 7.42-7.52 (m, 3H), 8.39-8.44 (m, 2H), 9.55 (brs, 1H).

N-[2-(6-{1-[2-(2-Trifluoromethylphenyl)ethyl]piperidin-4-yloxymethyl}-2-phenyl-7H-pyrrolo[2,3-d]pyrimidin-4-ylamino)ethyl]acetamide (17.17)

7% yield. $^1$H-NMR (200 MHz, CDCl$_3$) δ 1.58-1.76 (m, 2H), 1.78 (s, 3H), 1.84-1.90 (m, 2H), 2.26-2.50 (m, 2H), 2.61-2.67 (m, 2H), 2.78-2.90 (m, 2H), 2.92-3.10 (m, 2H), 3.35-3.45 (m, 1H), 3.57-3.63 (m, 2H), 3.86-3.91 (m, 2H), 4.60 (s, 2H), 5.64 (t, 1H, J=5.2 Hz), 6.26 (s, 1H), 7.03 (t, 1H, J=5.2 Hz), 7.24-7.40 (m, 2H), 7.42-7.60 (m, 5H), 8.39-8.44 (m, 2H), 9.50 (brs, 1H).

N-[2-(6-{1-[2-(2-Bromophenyl)ethyl]piperidin-4-yloxymethyl}-2-phenyl-7H-pyrrolo[2,3-d]pyrimidin-4-ylamino)ethyl]acetamide (17.18)

MS (ES): 590.9 (M$^+$+1).

2-(6-{1-[2-(4-Chlorophenyl)-ethyl]-piperidin-4-yloxymethyl}-2-phenyl-7H-pyrrolo-[2,3-d]pyrimidin-4-ylamino)-acetamide (17.19)

Obtained by the same route using glycinamide. MS (ES): 518.8 (M$^+$+1).

EXAMPLE 8

Open-chain Analogs of Piperidine Derivatives 17

A series of open-chain analogs 19.1-19.5 of the piperidine derivatives 17 was prepared from 7 in two steps (scheme 8).

Scheme 8. Synthesis of open-chain N-alkyl derivatives 19.1-19.5.

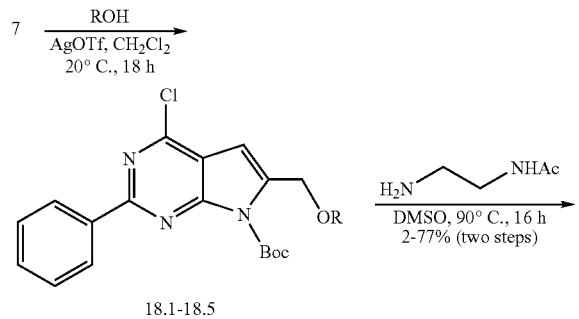

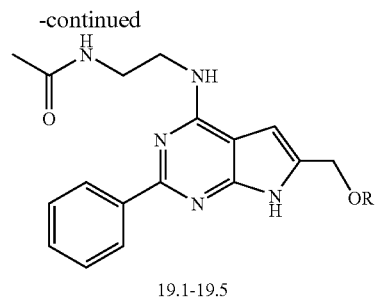

19.1-19.5

The following amines 19.1-19.5 were prepared according to the general procedures for silver-mediated bromide displacement and C-4 chloride displacement:

N-(2-(6-{2-[Methyl-(3-phenylallyl)amino]ethoxymethyl}-2-phenyl-7H-pyrrolo[2,3-d]pyrimidin-4-ylamino}ethyl]acetamide (19.1)

2% yield. $^1$H-NMR (200 MHz, CDCl$_3$): δ 1.78 (s, 3H), 2.45 (s, 3H), 2.79 (t, 2H, J=4.8 Hz), 3.38-3.48 (m, 2H), 3.53-3.58 (m, 2H), 3.70 (t, 2H, J=4.8 Hz), 3.82-3.94 (m, 2H), 4.65 (s, 2H), 5.60 (brs, 1H), 6.23 (s, 1H), 6.36-6.47 (m, 1H), 6.62 (d, 1H, J=15.8 Hz), 7.20-7.32 (m, 6H), 7.38-7.50 (m, 3H), 8.39-8.44 (m, 2H), 9.60 (brs, 1H); MS (ES): 499.1 (M$^+$+1).

N-(2-{2-Phenyl-6-[2-(3-phenylpropylamino)ethoxymethyl]-7H-pyrrolo[2,3-d]-pyrimidin-4-ylamino}ethyl)acetamide TFA salt (19.2)

77% yield. $^1$H-NMR (200 MHz, CDCl$_3$) δ 1.78-2.10 (m, 5H), 2.55-2.60 (m, 2H), 2.80-3.00 (m, 2H), 3.55-3.70 (m, 2H), 3.78-3.95 (m, 2H), 4.16-4.19 (m, 2H), 4.28-4.30 (m, 2H), 4.95 (s, 2H), 6.55 (s, 1H), 7.10-7.25 (m, 5H), 7.45-7.60 (m, 3H), 7.85 (brs, 3H), 8.21-8.25 (m, 2H), 10.13 (brs, 1H).

N-(2-{6-[3-(4-Methoxyphenyl)propoxymethyl]-2-phenyl-7H-pyrrolo[2,3-d]pyrimidin-4-ylamino}ethyl)acetamide (19.3)

40% yield. $^1$H-NMR (200 MHz, CDCl$_3$) δ 1.70-1.90 (m, 5H), 2.53 (t, 2H, J=8.0 Hz), 3.30 (t, 2H, J=6.2 Hz), 3.78 (s, 3H), 3.88-3.90 (m, 2H), 4.42 (s, 2H), 5.64 (t, 1H, J=5.2 Hz), 6.22 (s, 1H), 6.80 (d, 2H, J=8.4 Hz), 6.95-7.20 (m, 3H), 7.40-7.51 (m, 3H), 8.40-8.45 (m, 2H), 10.00 (brs, 1H). MS (ES): 474.0 (M$^+$+1).

N-{2-[6-(3-Hydroxy-3-phenylpropoxymethyl)-2-phenyl-7H-pyrrolo[2,3-d]pyrimidin-4-ylamino}ethyl)acetamide (19.4)

31% yield. $^1$H-NMR (200 MHz, CDCl$_3$) δ 2.61 (s, 3H), 3.05-3.18 (m, 2H), 3.30-3.39 (m, 2H), 3.60-3.70 (m, 2H), 3.87-3.95 (m, 2H), 5.29 (brs, 1H), 5.95 (brs, 1H), 6.05 (brs, 2H), 7.17 (s, 1H), 7.40-7.60 (m, 8H), 7.83-7.88 (m, 1H), 8.41-8.46 (m, 2H), 9.30 (brs, 1H). MS (ES): 460.0 (M$^+$+1).

N-[2-(6-Cyclopentyloxymethyl-2-phenyl-7H-pyrrolo[2,3-d]pyrimidin-4-ylamino)-ethyl]-acetamide (19.5)

$^1$H NMR (200 MHz, CDCl$_3$): δ 1.40-1.70 (m, 8H), 1.76 (s, 3H), 3.58 (m, 2H), 3.87 (m, 3H), 4.44 (s, 2H), 5.65 (brt, 1H), 6.24 (s, 1H), 7.20 (brs, 1H), 7.44 (m, 3H), 8.41 (m, 2H); MS (ES): 393.9 [MH$^+$].

TABLE 2

A₂B antagonists 15, 17, and 19.

| Comp. # | Structure | MW |
|---|---|---|
| 15.1 | 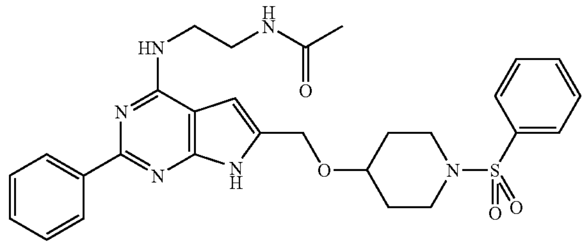 | 548.67 |
| 15.2 | 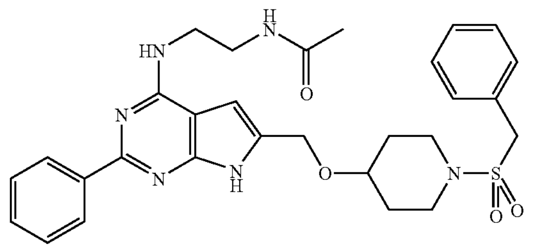 | 562.70 |
| 15.3 | 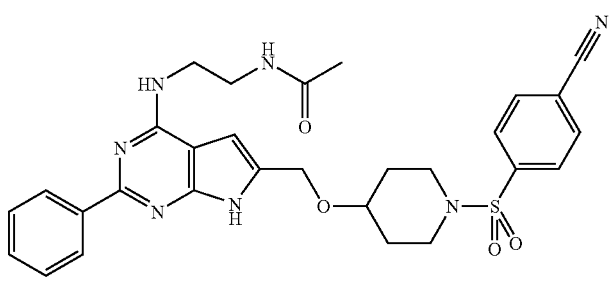 | 573.68 |
| 17.1 | 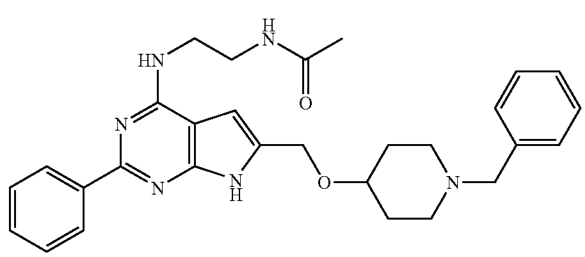 | 498.63 |
| 17.2 | 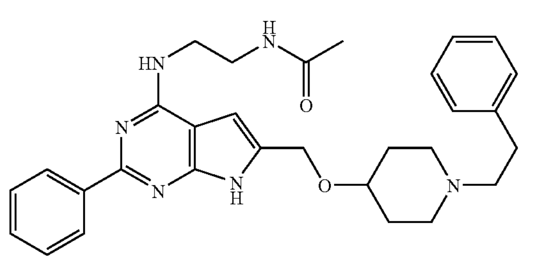 | 512.66 |

TABLE 2-continued

A$_{2B}$ antagonists 15, 17, and 19.

| Comp. # | Structure | MW |
|---|---|---|
| 17.3 | 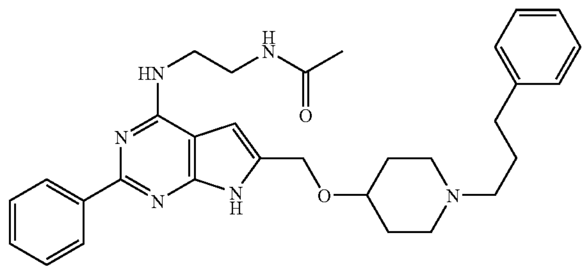 | 526.69 |
| 17.4 | 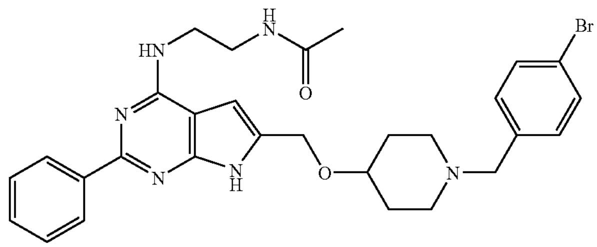 | 577.53 |
| 17.5 | 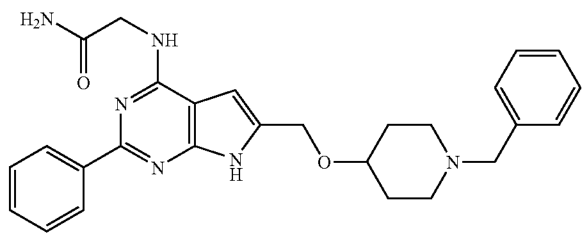 | 470.58 |
| 17.6 | 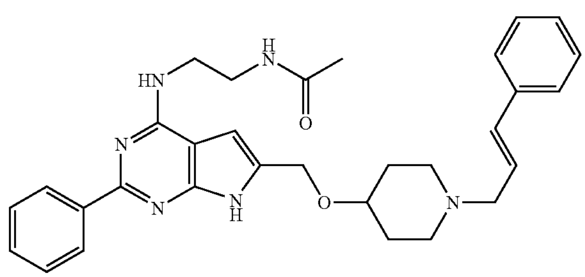 | 524.67 |
| 17.7 | 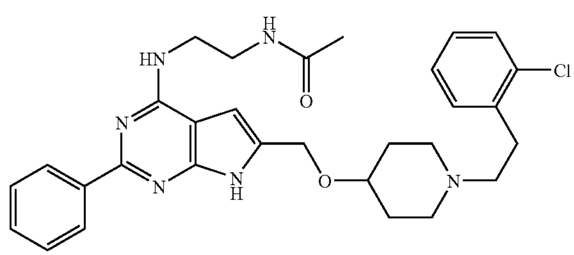 | 547.11 |
| 17.8 | 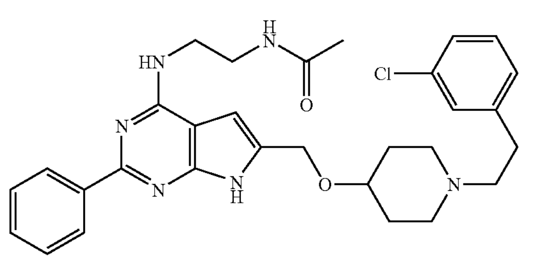 | 547.11 |

TABLE 2-continued

A$_{2B}$ antagonists 15, 17, and 19.

| Comp. # | Structure | MW |
|---|---|---|
| 17.9 | 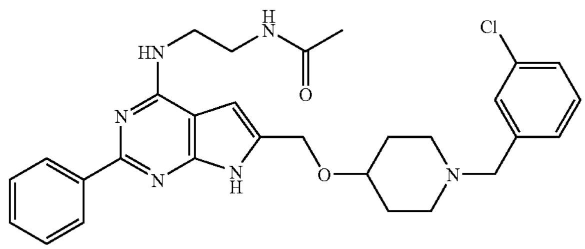 | 533.08 |
| 17.10 | 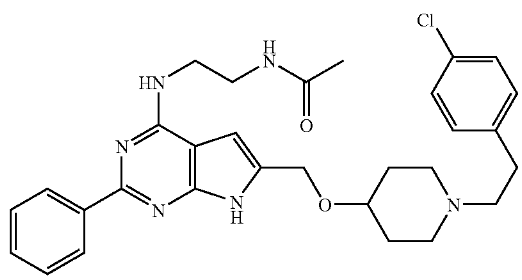 | 547.11 |
| 17.11 | 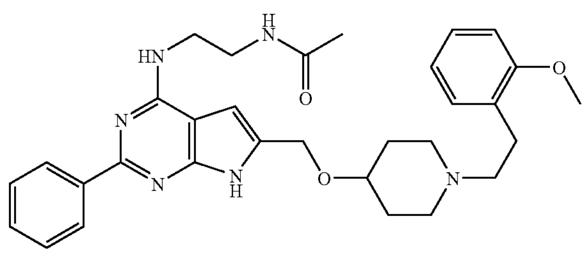 | 542.69 |
| 17.12 | 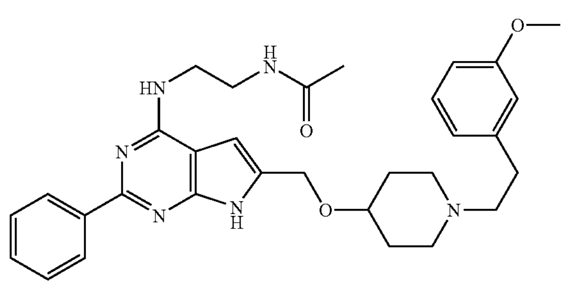 | 542.69 |
| 17.13 | 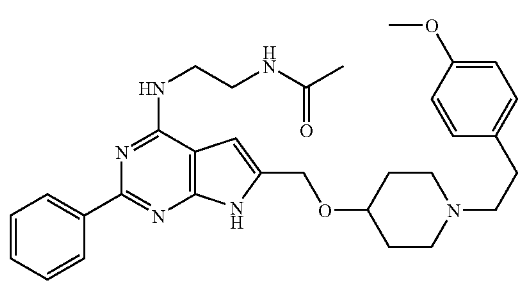 | 542.69 |

TABLE 2-continued

A_{2B} antagonists 15, 17, and 19.

| Comp. # | Structure | MW |
|---|---|---|
| 17.14 | 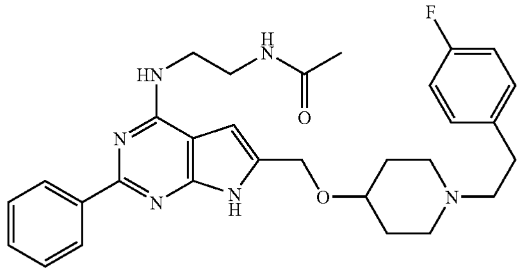 | 530.65 |
| 17.15 | 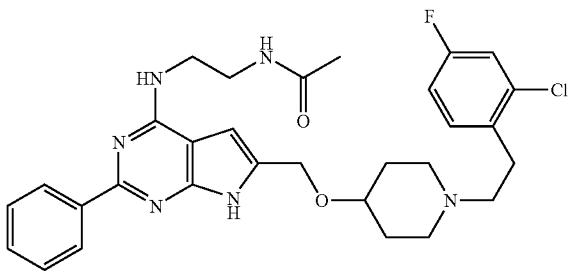 | 565.10 |
| 17.16 | 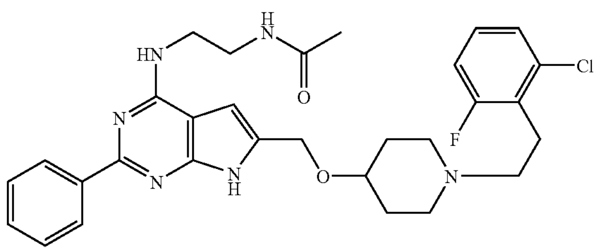 | 565.10 |
| 17.17 | 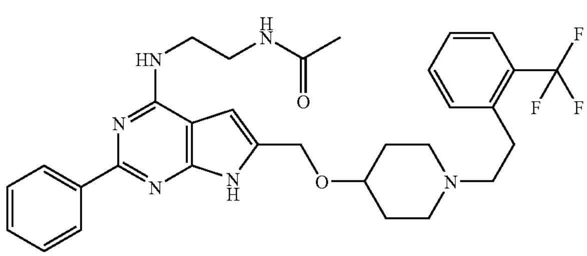 | 580.66 |
| 17.18 | 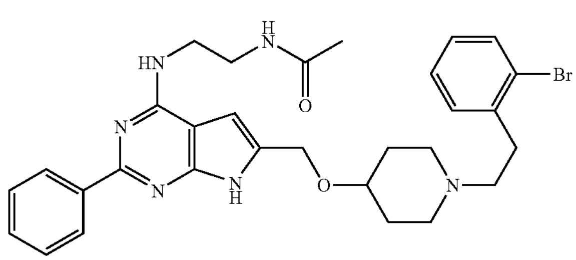 | 591.56 |

TABLE 2-continued
A$_{2B}$ antagonists 15, 17, and 19.
| Comp. # | Structure | MW |
|---|---|---|
| 17.19 | 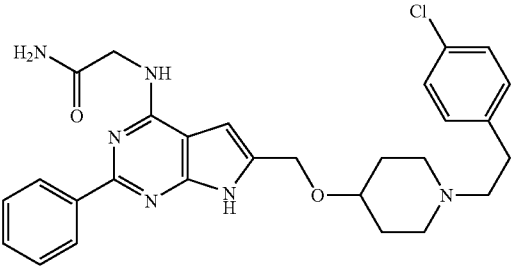 | 519.05 |
| 19.1 | 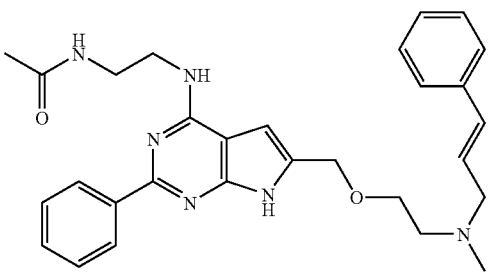 | 498.63 |
| 19.2 | 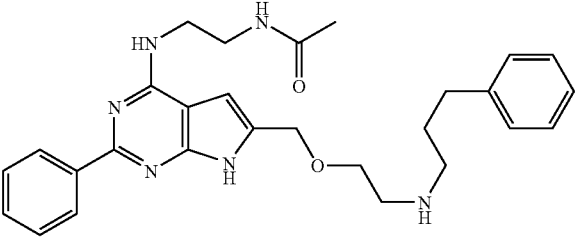 | 486.62 |
| 19.3 | 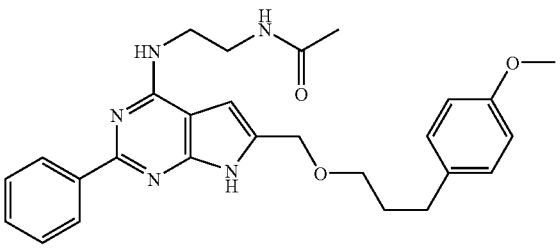 | 473.58 |
| 19.4 | 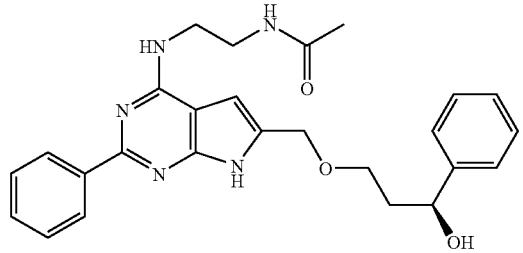 | 459.55 |

TABLE 2-continued

A_{2B} antagonists 15, 17, and 19.

| Comp. # | Structure | MW |
|---|---|---|
| 19.5 | 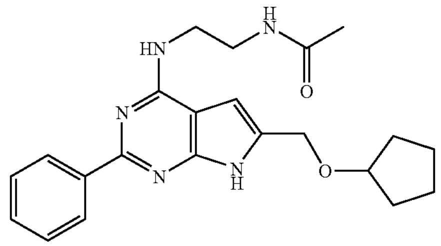 | 393.49 |

EXAMPLE 9
C-6 Oxime Ethers

Oxime ethers 22 were prepared from the bromide 7 via Kornblum oxidation to the aldehyde 20, followed by oxime ether formation and C-4 chloride displacement (scheme 9).

Scheme 9. Synthesis of oxime ethers 22.

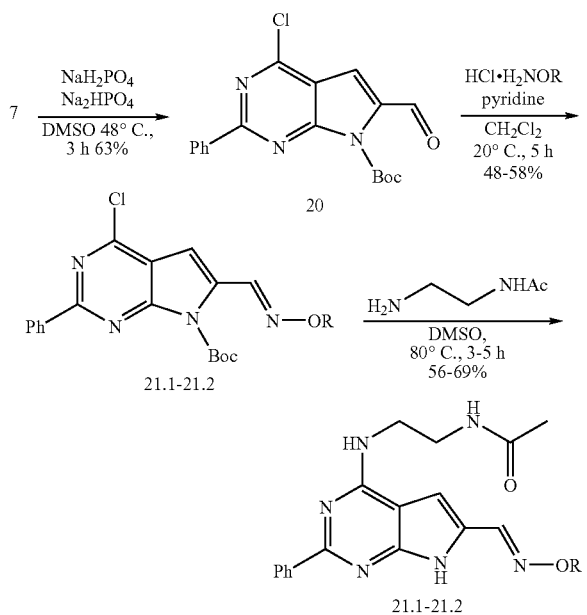

4-Chloro-6-formyl-2-phenylpyrrolo[2,3-d]pyrimidine-7-carboxylic acid tert-butyl ester (20)

A suspension of the bromide 7 (2.00 g, 4.73 mmol), Na$_2$HPO$_4$ (806 mg, 5.68 mmol) and NaH$_2$PO$_4$ (227 mg, 1.89 mmol) in DMSO (50 mL) is heated under nitrogen to 48° C. After 1 h, all solids are dissolved, and the reaction is continued for 2 h. The solution is then poured in H$_2$O (600 mL), and the mixture is extracted with EtOAc (2×150 mL). The combined EtOAc layers are washed with H$_2$O (3×400 mL) and brine and dried over MgSO$_4$. Filtration and concentration yields a yellow solid, which is triturated with EtOH giving 1.06 g (2.97 mmol, 63%) of the title compound as a yellow solid. MS (ES): m/z 304.7/306.7 (33/10) [MH$^+$-Boc-H$_2$O+2 MeOH], 272.7/274.7 (100/32) [MH$^+$-Boc-H$_2$O+MeOH]. $^1$H NMR (200 MHz, CDCl$_3$): δ=1.79 (s, 9H), 7.44 (s, 1H), 7.48-7.55 (m, 3H), 8.51-8.60 (m, 2H), 10.39 (s, 1H). t$_R$ (method A)=10.4 min.

6-(Benzyloxyiminomethyl)-4-chloro-2-phenylpyrrolo[2,3-d]pyrimidine-7-carboxylic acid tert-butyl ester (21.1)

A solution of the aldehyde 20 (50 mg, 0.14 mmol), O-benzylhydroxylamine hydrochloride (26 mg, 0.16 mmol), and pyridine (12 mg, 0.15 mmol) in CH$_2$Cl$_2$ (2 mL) is stirred at ambient temp. for 5 h, then sat. NH$_4$Cl solution is added, and the mixture is extracted with EtOAc (3×5 mL). The combined extracts are washed with brine and dried over MgSO$_4$. Crystallization of the crude solid from hexanes gives 31 mg (0.067 mmol, 48%) of the title compound as colorless solid, single oxime isomer. MS (ES): m/z 463.0/465.0 (90/48) [MH$^+$], 363.1/365.2 (100/32) [MH$^+$-Boc].

6-(tert-Butoxyiminomethyl)-4-chloro-2-phenylpyrrolo[2,3-d]pyrimidine-7-carboxylic acid tert-butyl ester (21.2)

Following the procedure for the corresponding benzyloxyiminomethyl compound, the title compound was obtained in 58% yield as pale yellow solid. $^1$H NMR (200 MHz, CDCl$_3$): (E) isomer (85%): δ=1.39 (s, 9H), 1.77 (s, 9H), 7.06 (s, 1H), 7.45-7.52 (m, 3H), 8.48-8.56 (m, 2H), 8.61 (s, 1H); (Z) isomer (15%): δ=1.45 (s, 9H), 1.78 (s, 9H), 7.05 (s, 1H), 7.45-7.52 (m, 3H), 8.48-8.56 (m, 2H), 8.62 (s, 1H).

N-{2-[6-(Benzyloxyiminomethyl)-2-phenyl-7H-pyrrolo[2,3-d]pyrimdin-4-ylamino]-ethyl}-acetamide (22.1)

Following the general procedure for C-4 chloride displacements, the title compound was obtained after purification by prep. TLC as yellow foam in 69% yield, single oxime isomer, mp. 83-87° C. (decomp.). MS (ES): m/z 429.1 (100) [MH$^+$]. $^1$H NMR (200 MHz, CDCl$_3$): δ=1.82 (s, 3H), 3.53-3.65 (m, 2H), 3.84-3.96 (m, 2H), 5.18 (s, 2H), 5.94 (brs, 1H), 6.51 (s, 1H), 6.84 (brs, 1H), 7.31-7.52 (m, 8H), 8.05 (s, 1H), 8.37-8.45 (m, 2H), 9.16 (brs, 1H). t$_R$ (method A)=8.7 min.

N-{2-[6-(tert-Butoxyiminomethyl)-2-phenyl-7H-pyrrolo[2,3-d]pyrimidin-4-ylamino]-ethyl}-acetamide (22.2)

Following the general procedure for C-4 chloride displacements, the title compound was obtained after purification by prep. TLC as colorless oil in 56% yield. MS (ES): m/z 395.2 (100) [MH$^+$]. t$_R$ (method A)=8.5 min.

TABLE 3

$A_{2B}$ antagonists 22.

| Comp. # | Structure | MW |
|---|---|---|
| 22.1 | 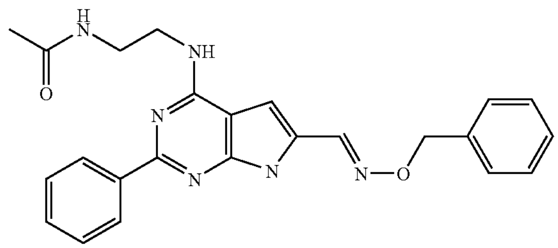 | 428.50 |
| 22.2 | 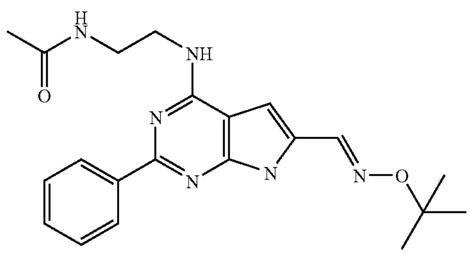 | 394.48 |

EXAMPLE 10

C-6 Amides

The key intermediate for pyrrolo[2,3-d]pyrimidines 26 with an amide moiety at C-6 is the N-benzenesulfonyl-protected pyrrolopyrimidine 24. The amide moiety can be introduced directly by metalation and quench with carbamoyl chlorides or isocyanates, followed by displacement of the chloride at C-4 with amines and concomitant removal of the benzenesulfonyl group (scheme 10).

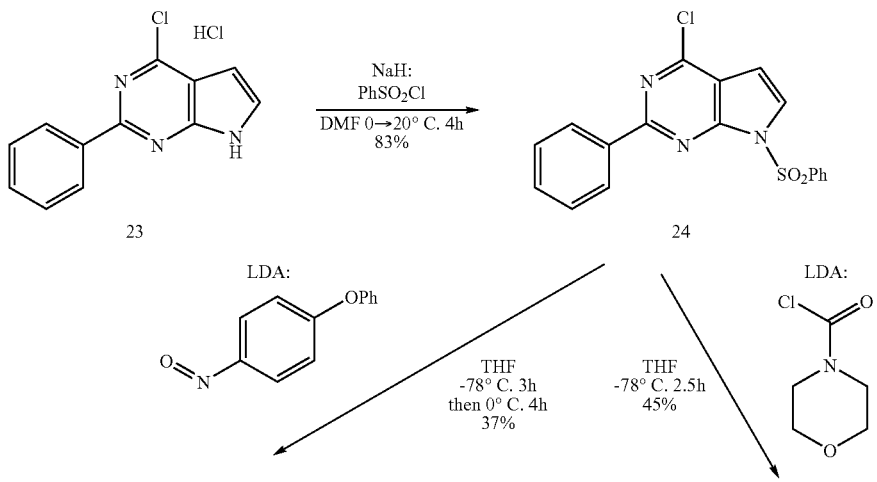

Scheme 10. Synthetic routes to C-6 amides 26: direct amide formation.

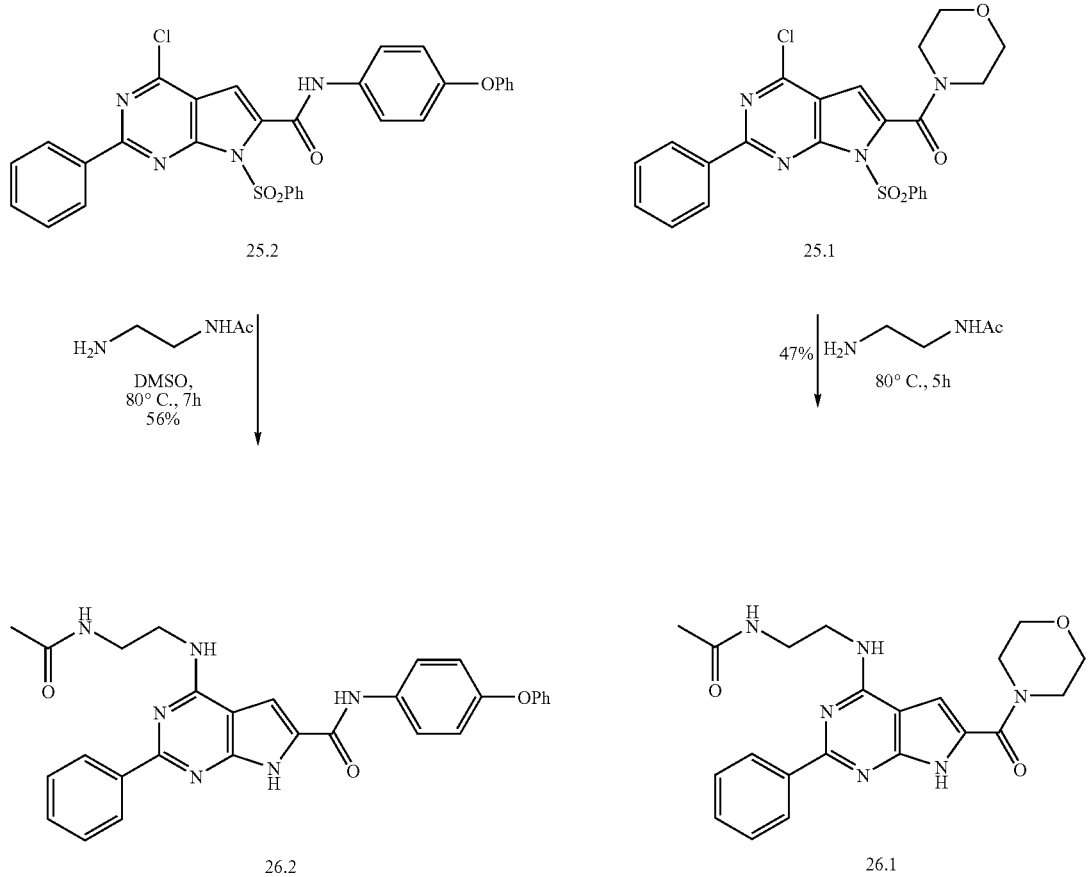

Alternatively, the anion of 24 is reacted with carbon dioxide to give the lithium salt 27, which is used as such because the free acid decarboxylates readily. Chloride displacement at C-4 with amines followed by removal of the sulfonyl group and amide coupling using PyBOP, TBTU, or EDC yields the $A_{2B}$ antagonists 26. The amide formation could be accomplished very conveniently by reacting the hydroxysuccinimide ester 32 (prepared from the acid 30 using EDC and HOBt for the coupling) with the amines. The order of the last two steps (i.e., pyrrole deprotection and amide formation) can be reversed (scheme 11a). Selected amides were converted to their methanesulfonic acid salts.

Schemes 11a-11c. Synthetic routes to C-6 amides 26: $CO_2$ quench.

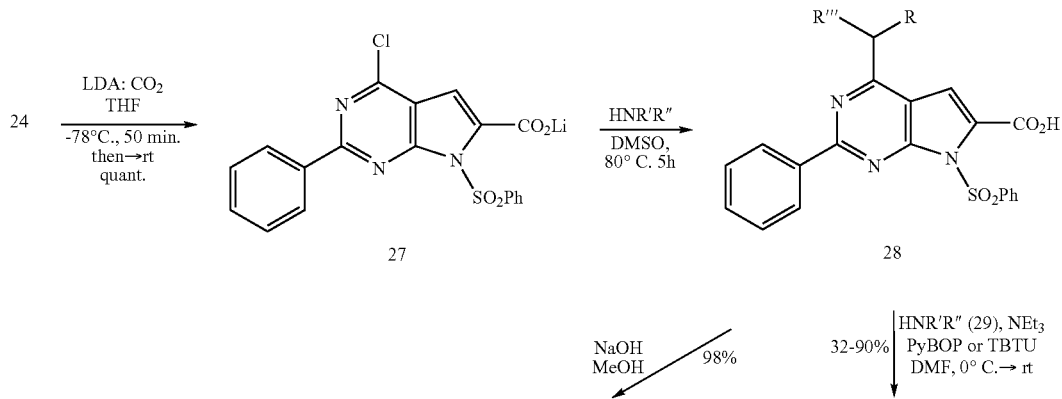

117 118
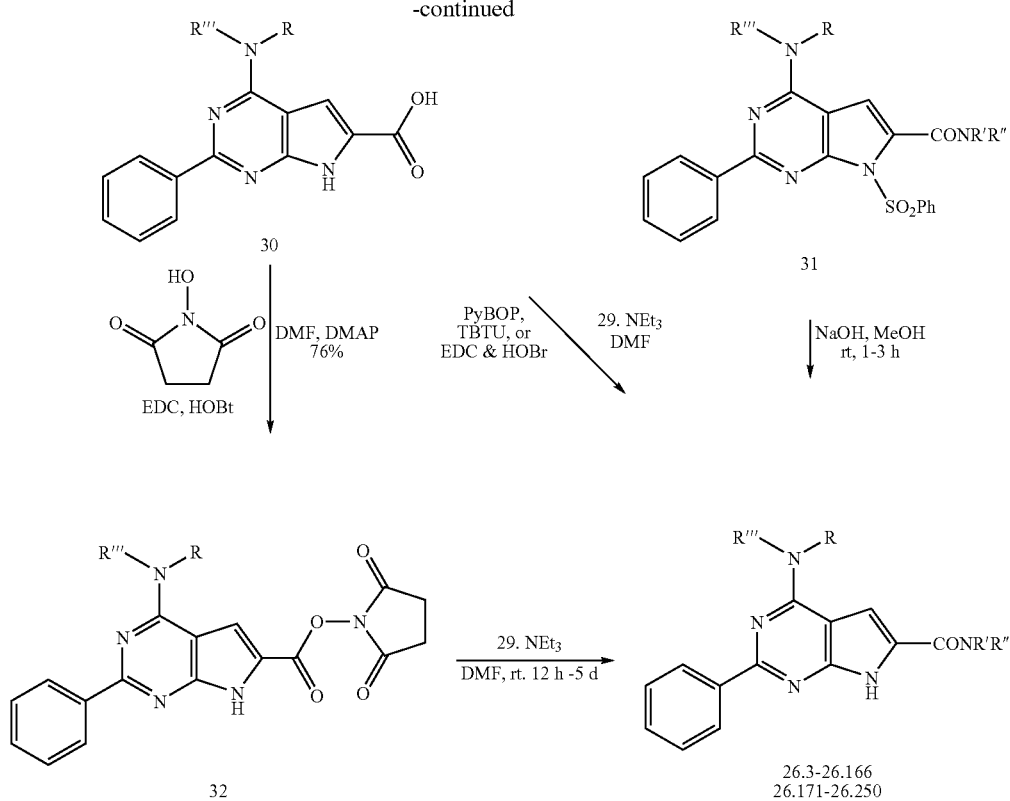
Scheme 11b
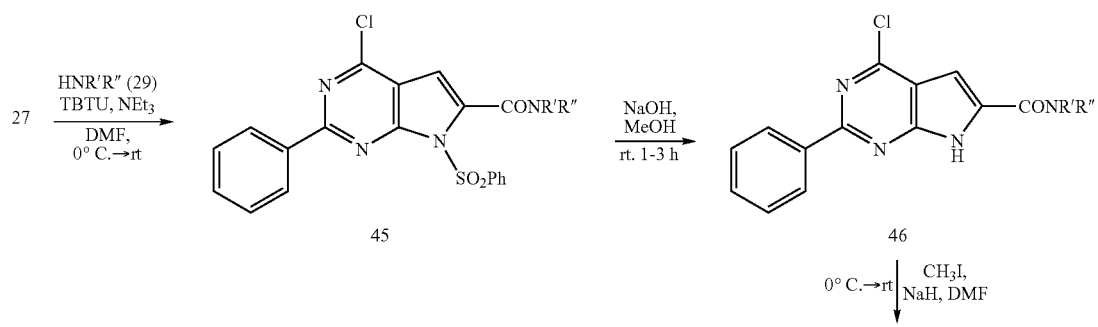
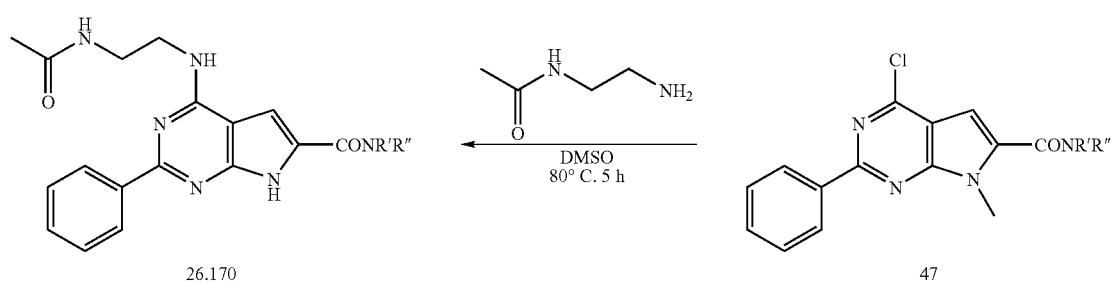

Scheme 11c

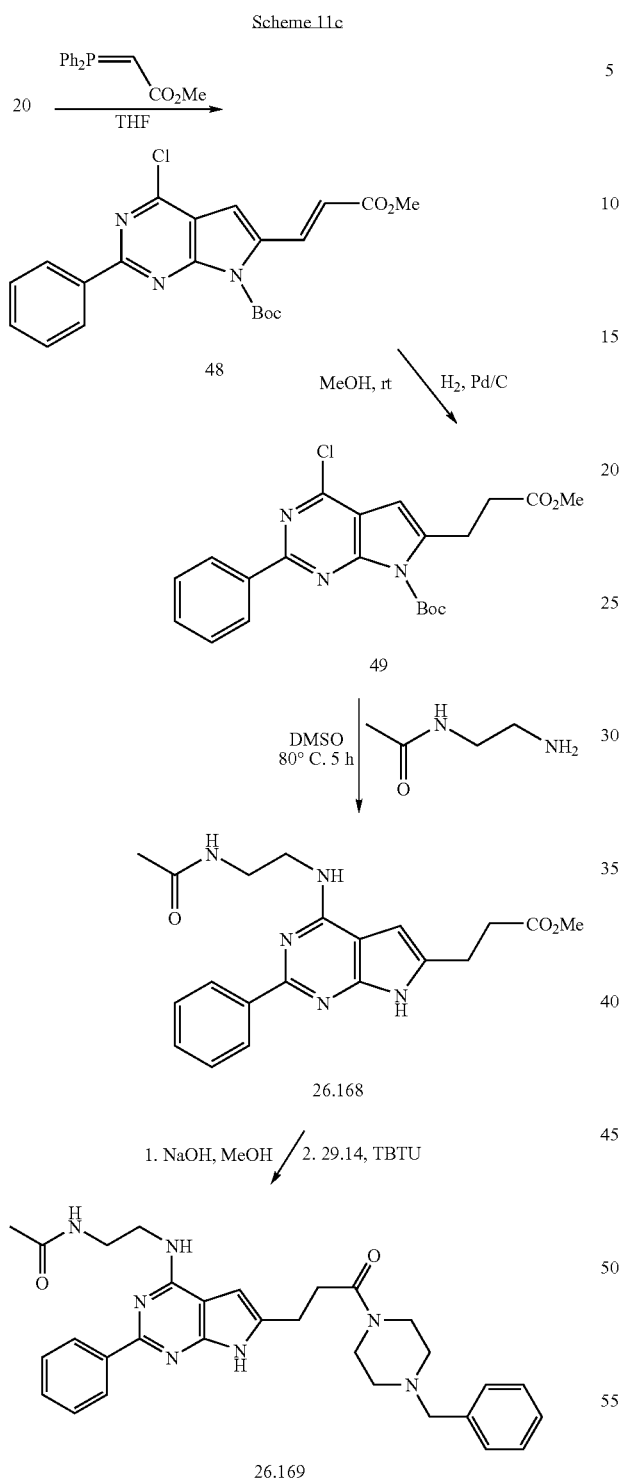

26.167 was prepared in a similar manner starting form 5.

Several amides 26 were derivatized further (scheme 12). Boc-protected 26.66 was deprotected to 26.65 and reacted with sulfonyl chlorides to give 26.67-26.68. The acetylene 26.83 underwent Sonogashira coupling with aryl iodides to yield 26.89-26.91. The acid 26.85 was coupled with a series of primary and secondary amines using TBTU in DMF to yield amides 26.97-26.107. The ketal 26.87 was deprotected and reacted with a series of primary and secondary amines using polymer-supported cyanoborohydride as reducing agent in 45-95% yield.

Scheme 12. Further derivatization of selected C-6 amides 26.

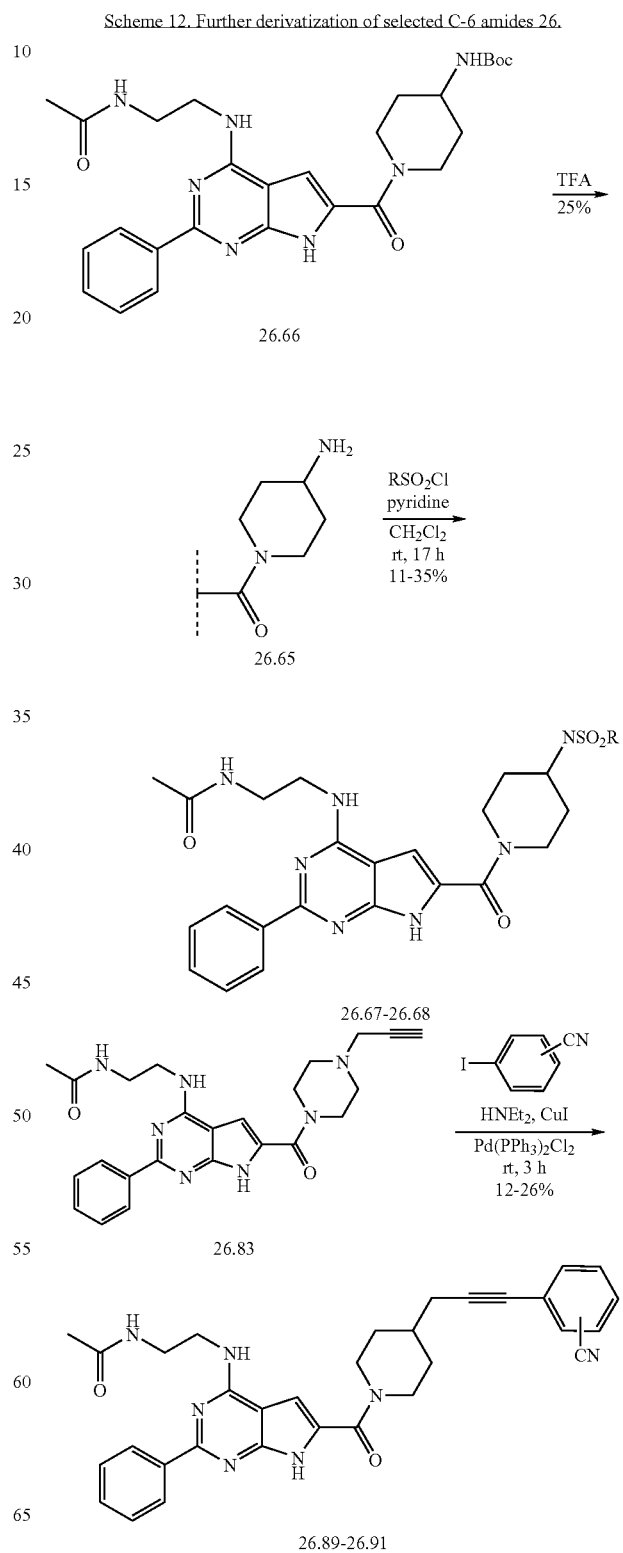

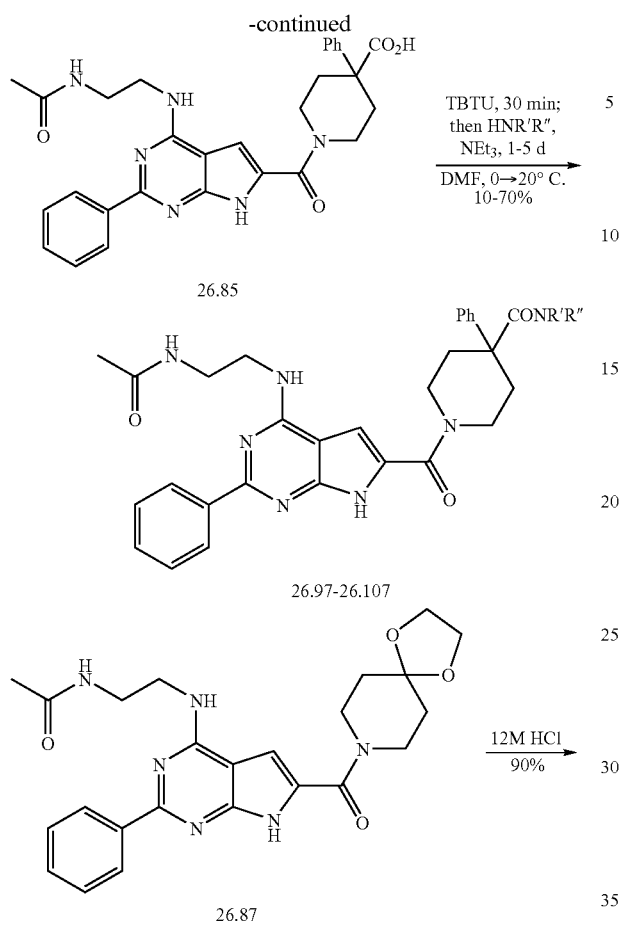
TABLE 4
$A_{2B}$ antagonists 26.1-26.250.
| Comp. # | Structure | MW |
|---|---|---|
| 26.1 | 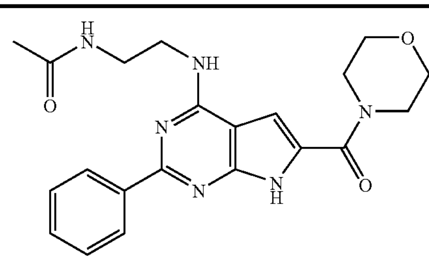 | 408.46 |
| 26.2 | 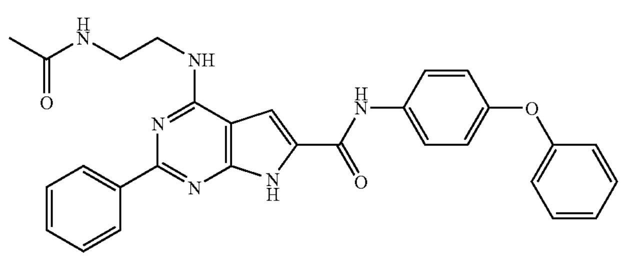 | 506.57 |

TABLE 4-continued
A$_{2B}$ antagonists 26.1-26.250.
| Comp. # | Structure | MW |
|---|---|---|
| 26.3 | 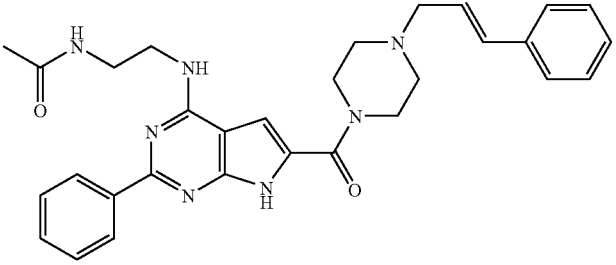 | 523.64 |
| 26.4 | 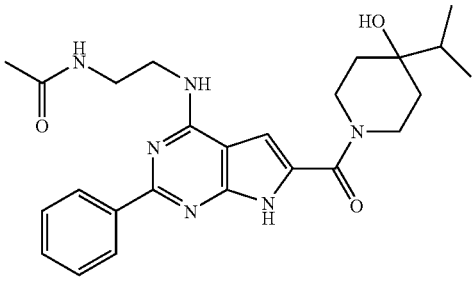 | 464.57 |
| 26.5 | 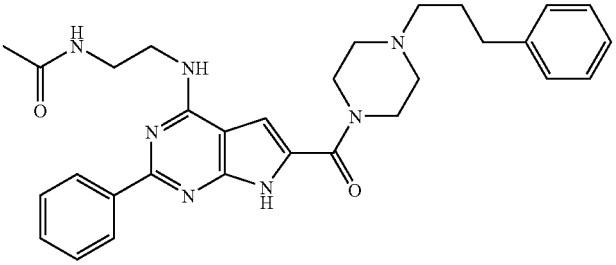 | 525.66 |
| 26.6 | 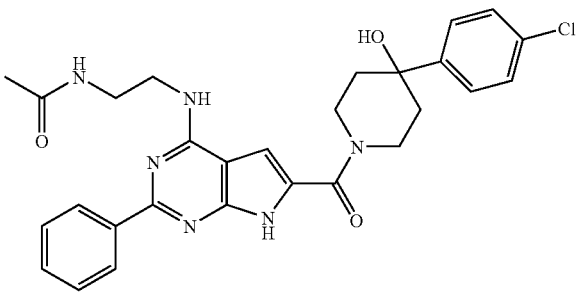 | 533.03 |
| 26.7 | 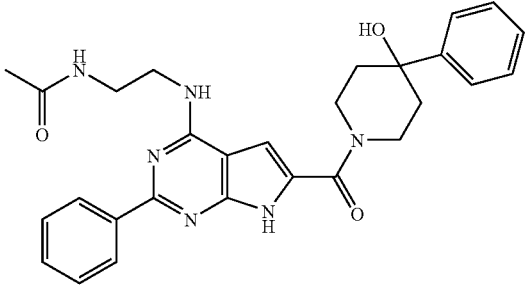 | 498.59 |

TABLE 4-continued

A_{2B} antagonists 26.1-26.250.

| Comp. # | Structure | MW |
| --- | --- | --- |
| 26.8 | 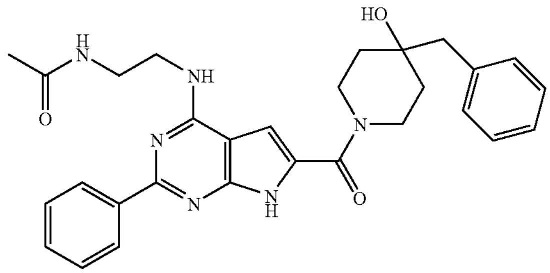 | 512.62 |
| 26.9 | 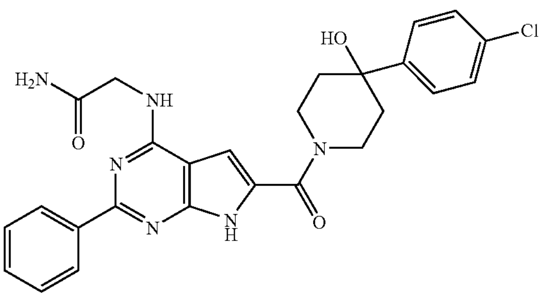 | 504.98 |
| 26.10 | 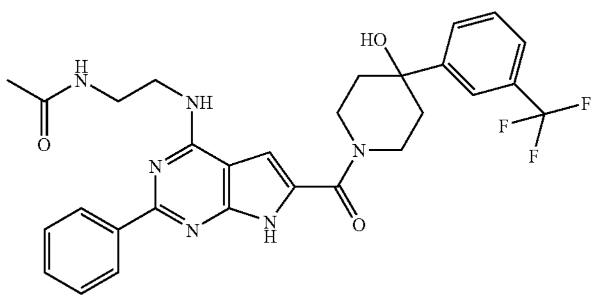 | 566.59 |
| 26.11 | 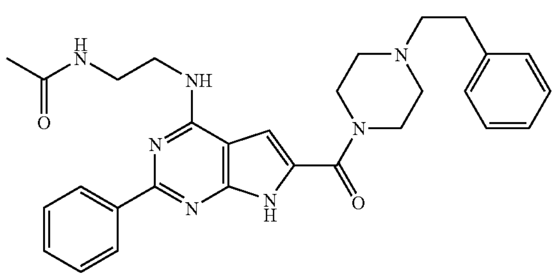 | 511.63 |
| 26.12 | 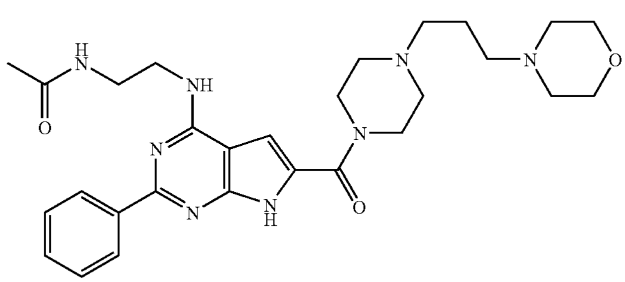 | 534.67 |

TABLE 4-continued

A$_{2B}$ antagonists 26.1-26.250.

| Comp. # | Structure | MW |
|---|---|---|
| 26.13 | 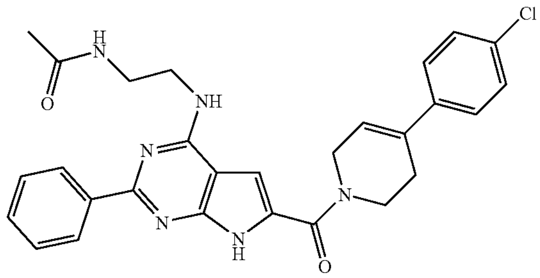 | 515.02 |
| 26.14 | 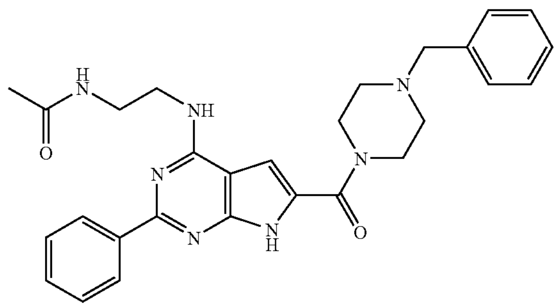 | 497.60 |
| 26.15 | 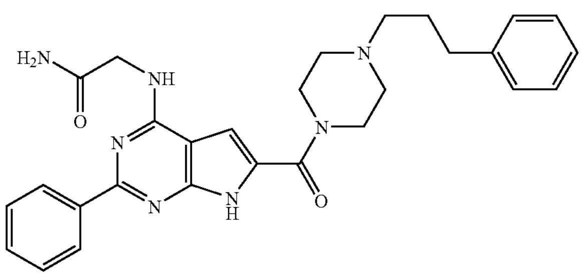 | 497.60 |
| 26.16 | 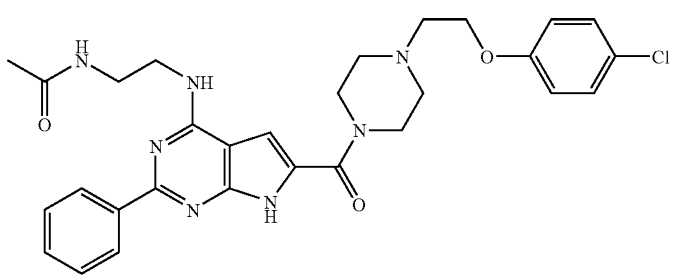 | 562.08 |
| 26.17 | 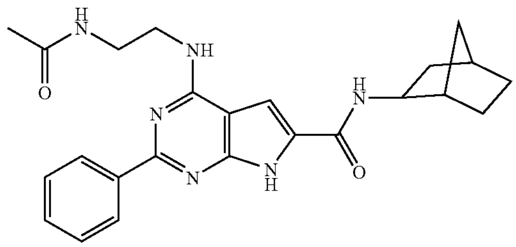 | 432.53 |

TABLE 4-continued

A$_{2B}$ antagonists 26.1-26.250.

| Comp. # | Structure | MW |
|---|---|---|
| 26.18 | 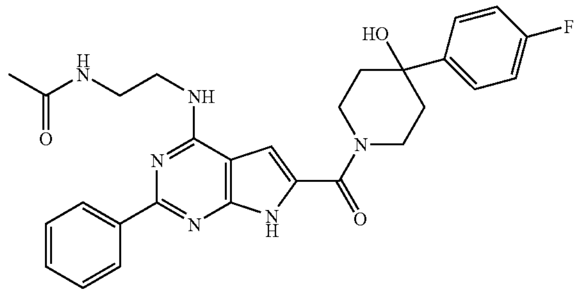 | 516.58 |
| 26.19 | 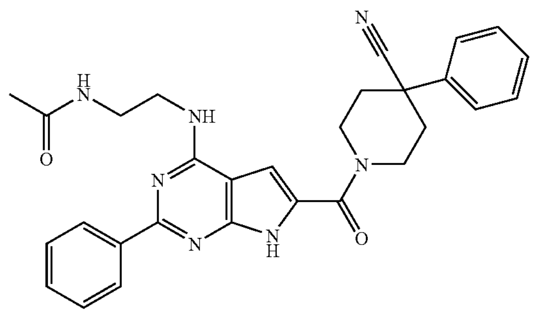 | 507.60 |
| 26.20 | 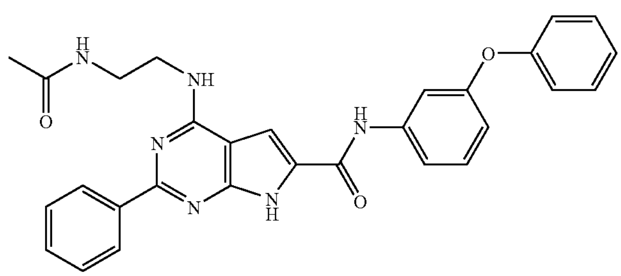 | 506.57 |
| 26.21 | 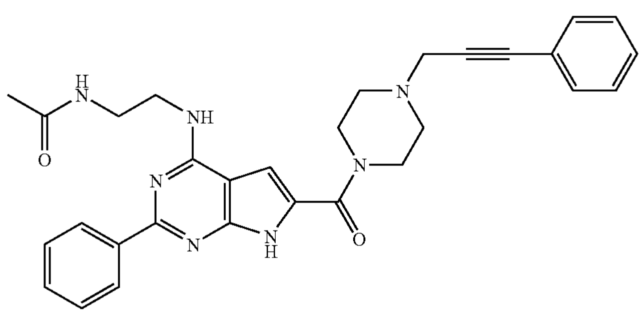 | 521.63 |
| 26.22 | 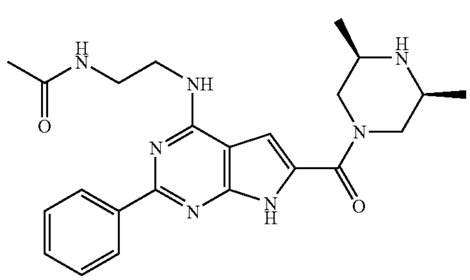 | 435.53 |

TABLE 4-continued

A$_{2B}$ antagonists 26.1-26.250.

| Comp. # | Structure | MW |
|---------|-----------|-----|
| 26.23 | 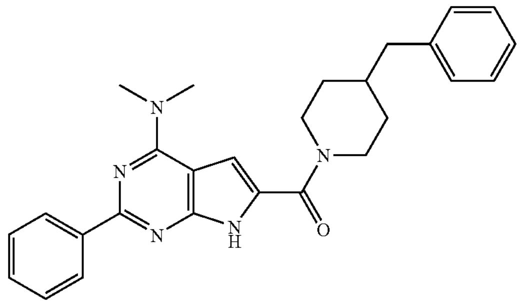 | 439.57 |
| 26.24 | 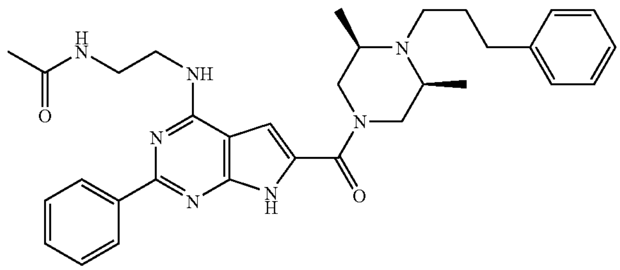 | 553.71 |
| 26.25 | 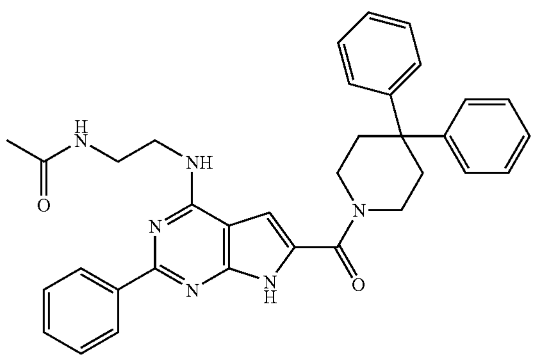 | 558.69 |
| 26.26 | 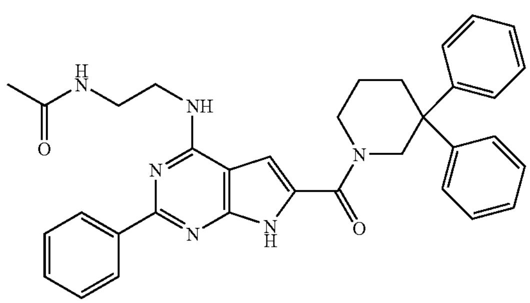 | 558.69 |
| 26.27 | 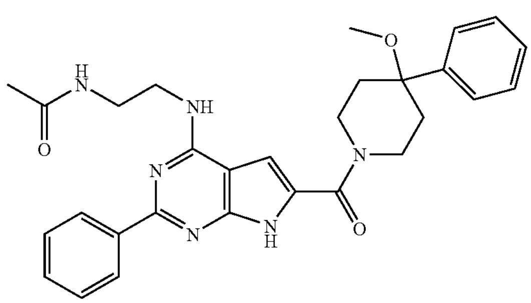 | 512.62 |

TABLE 4-continued

A$_{2B}$ antagonists 26.1-26.250.

| Comp. # | Structure | MW |
|---------|-----------|-----|
| 26.28   | 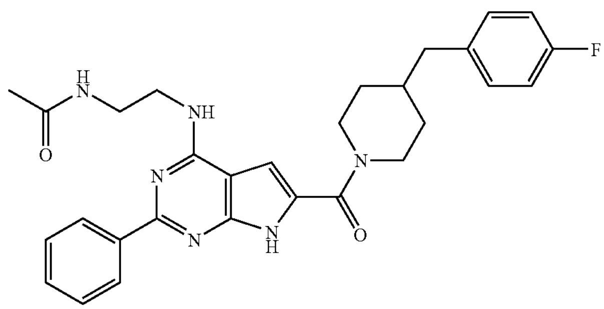          | 514.61 |
| 26.29   | 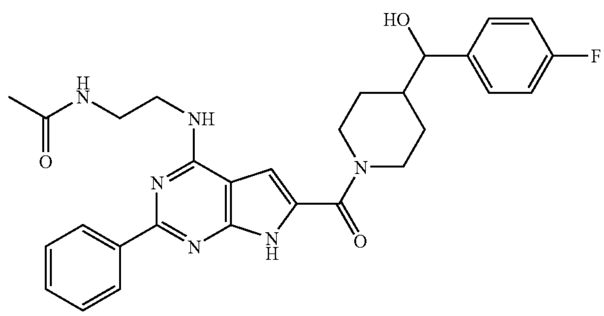          | 530.61 |
| 26.30   | 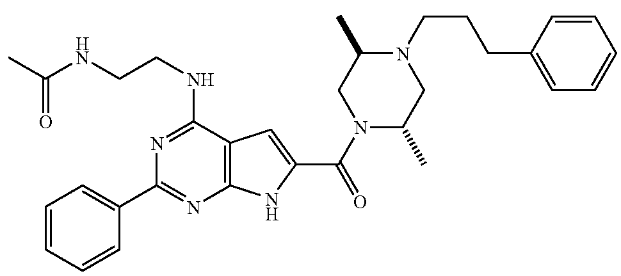          | 553.71 |
| 26.31   | 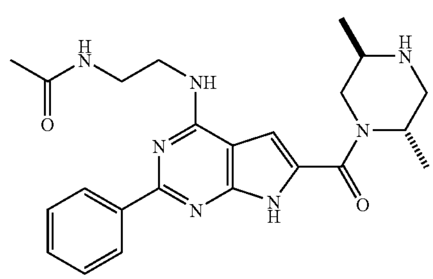          | 435.53 |
| 26.32   | 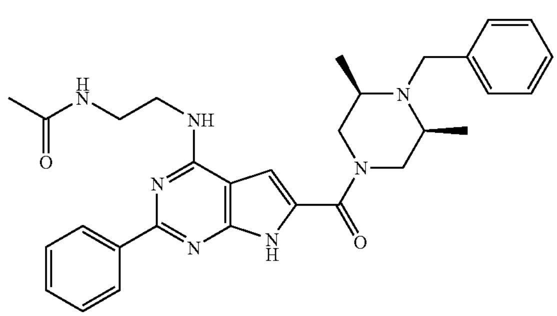          | 525.66 |

TABLE 4-continued

A$_{2B}$ antagonists 26.1-26.250.

| Comp. # | Structure | MW |
|---|---|---|
| 26.33 | 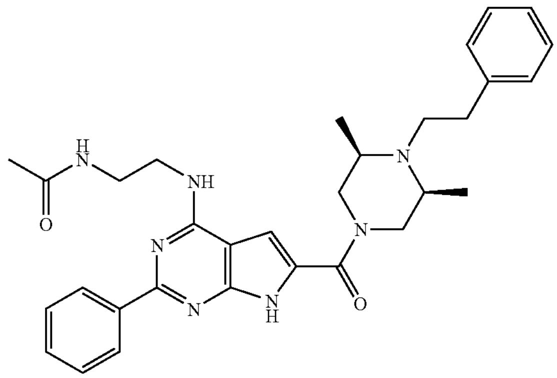 | 539.69 |
| 26.34 | 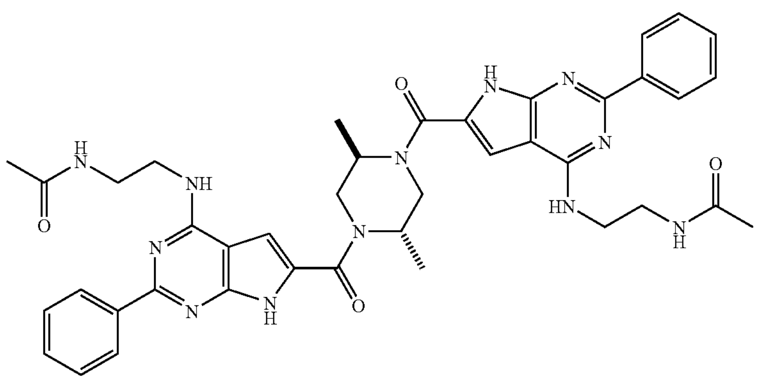 | 756.87 |
| 26.35 | 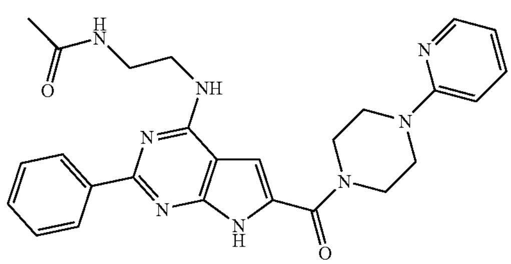 | 484.57 |
| 26.36 | 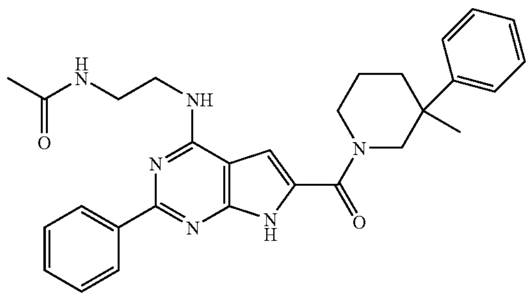 | 496.62 |

TABLE 4-continued
A$_{2B}$ antagonists 26.1-26.250.
| Comp. # | Structure | MW |
|---|---|---|
| 26.37 | 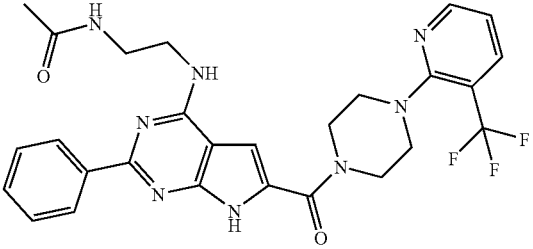 | 552.56 |
| 26.38 | 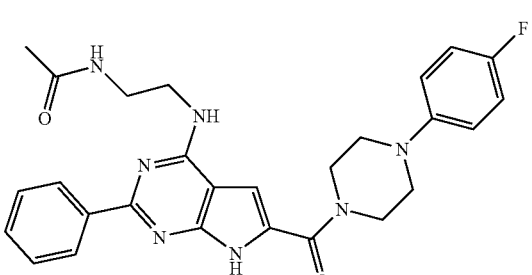 | 501.57 |
| 26.39 | 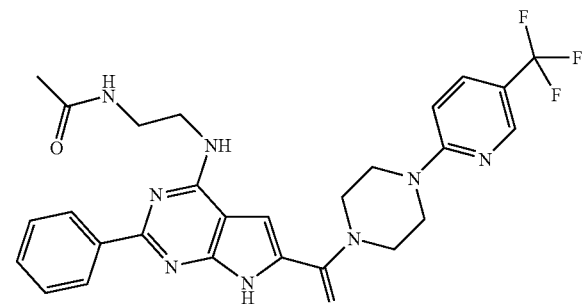 | 552.56 |
| 26.40 | 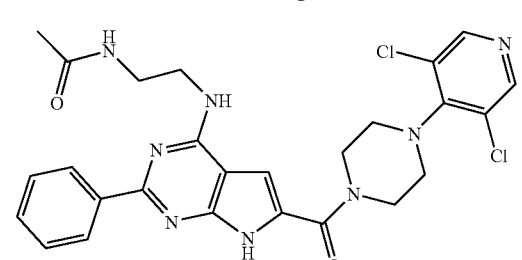 | 553.46 |
| 26.41 | 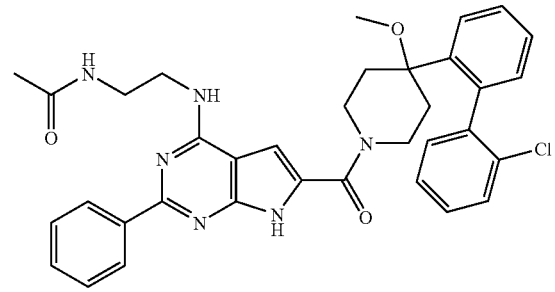 | 623.16 |

TABLE 4-continued

A$_{2B}$ antagonists 26.1-26.250.

| Comp. # | Structure | MW |
|---|---|---|
| 26.42 | 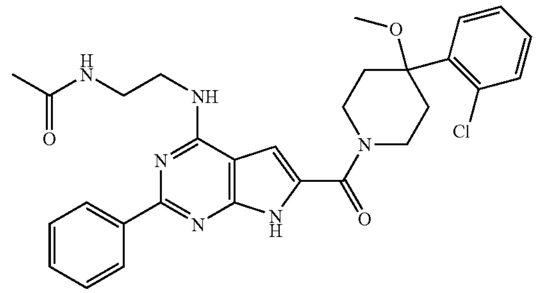 | 547.06 |
| 26.43 | 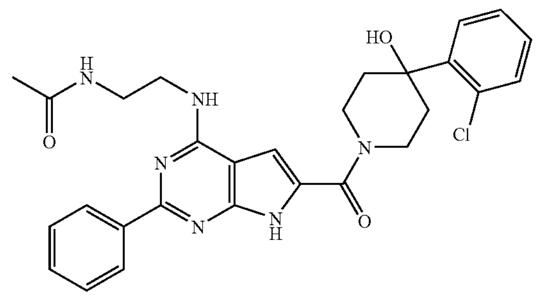 | 533.03 |
| 26.44 | 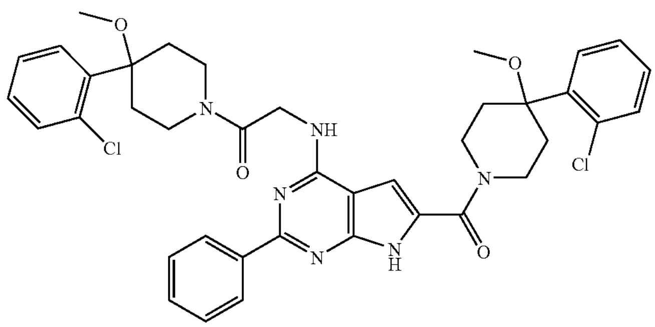 | 727.70 |
| 26.45 | 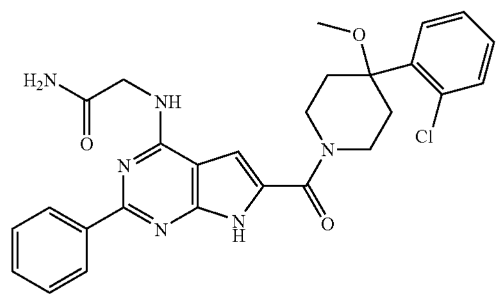 | 519.01 |
| 26.46 | 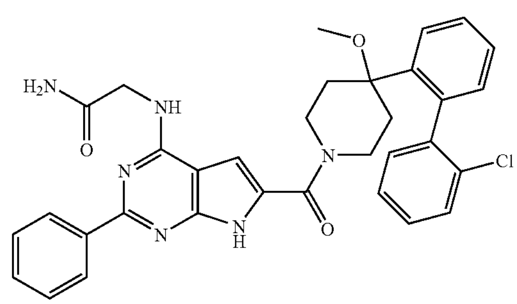 | 595.11 |

TABLE 4-continued

A$_{2B}$ antagonists 26.1-26.250.

| Comp. # | Structure | MW |
|---|---|---|
| 26.47 | 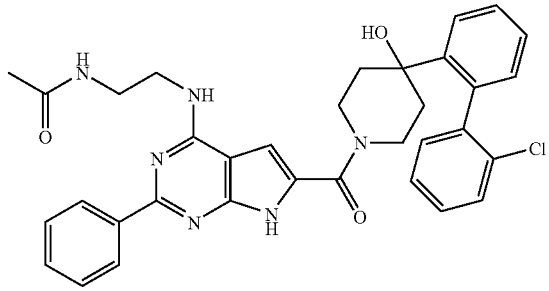 | 609.13 |
| 26.48 | 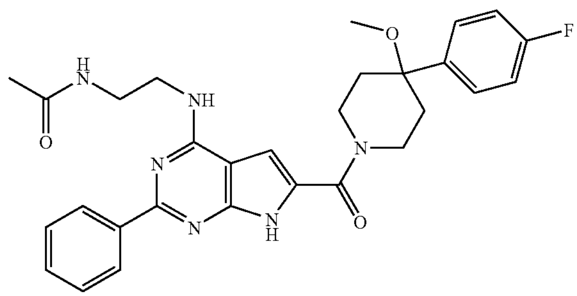 | 530.61 |
| 26.49 | 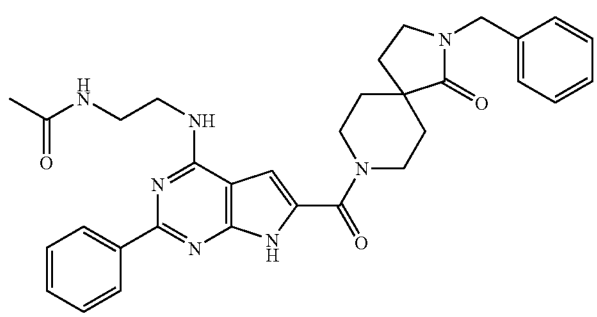 | 565.68 |
| 26.50 | 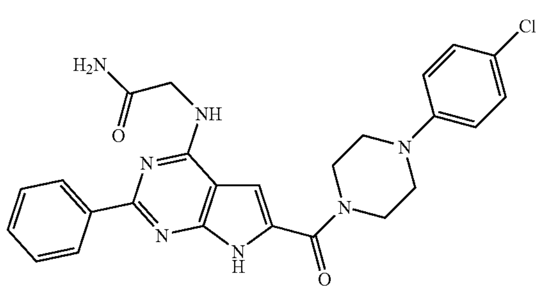 | 489.97 |

TABLE 4-continued
A$_{2B}$ antagonists 26.1-26.250.
| Comp. # | Structure | MW |
| --- | --- | --- |
| 26.51 | 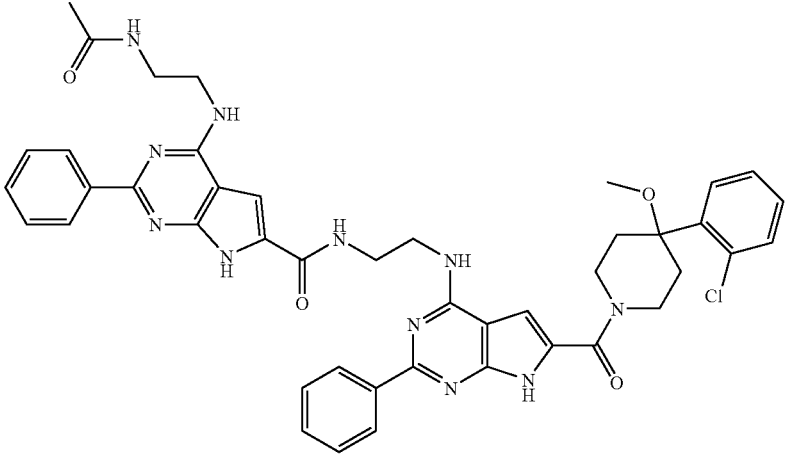 | 826.37 |
| 26.52 | 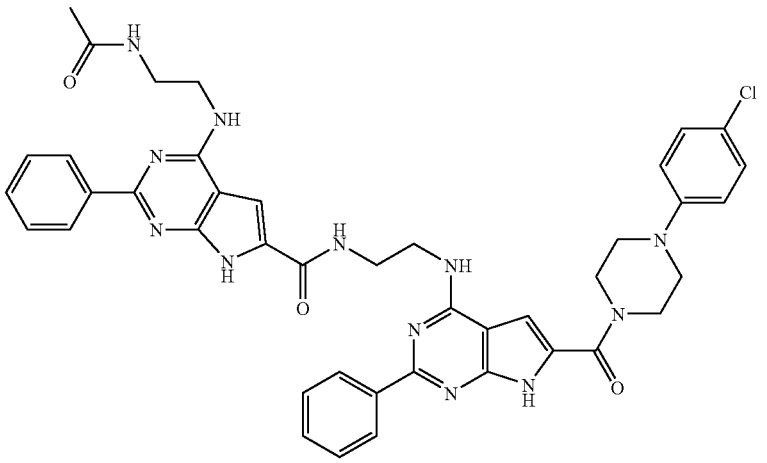 | 797.33 |
| 26.53 | 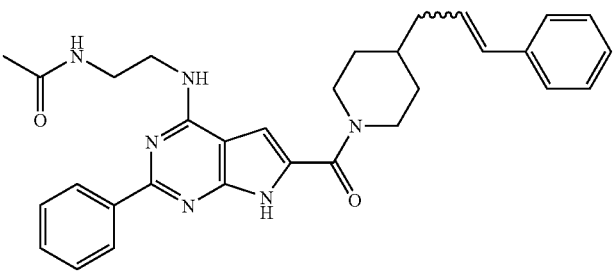 | 522.66 |
| 26.54 | 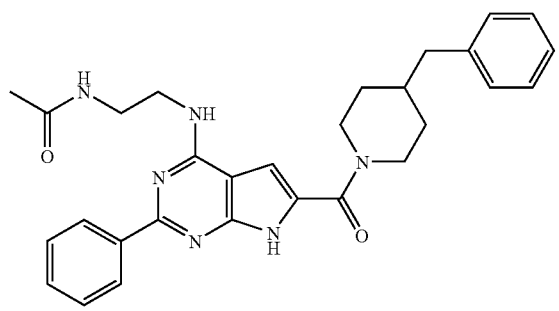 | 496.62 |

TABLE 4-continued

A$_{2B}$ antagonists 26.1-26.250.

| Comp. # | Structure | MW |
|---|---|---|
| 26.55 | 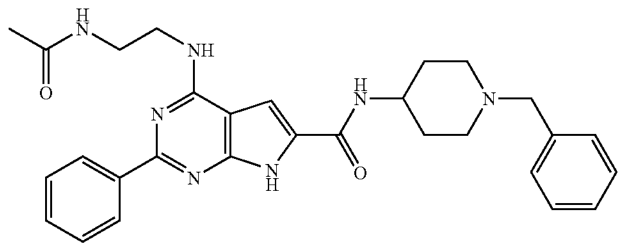 | 511.63 |
| 26.56 | 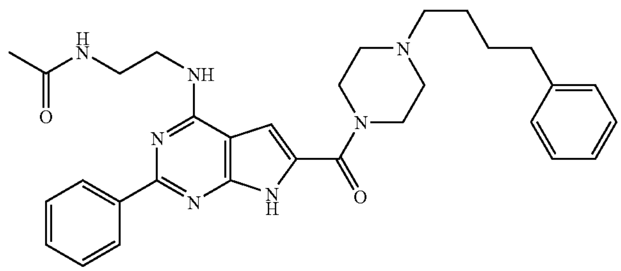 | 539.69 |
| 26.57 | 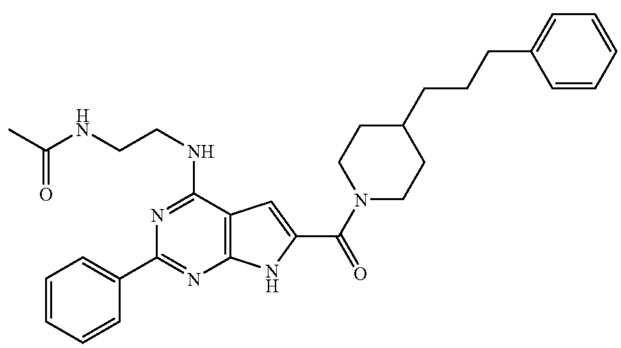 | 524.67 |
| 26.58 | 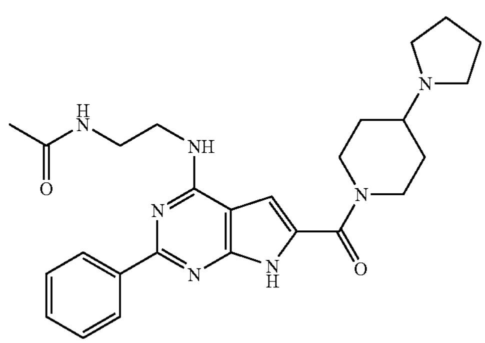 | 475.60 |
| 26.59 | 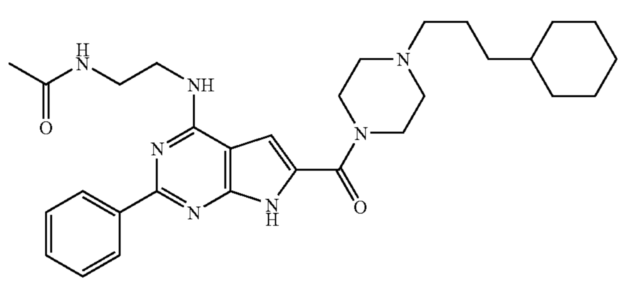 | 531.71 |

TABLE 4-continued

A$_{2B}$ antagonists 26.1-26.250.

| Comp. # | Structure | MW |
|---|---|---|
| 26.60 | 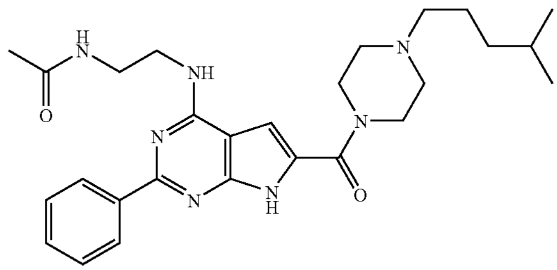 | 491.64 |
| 26.61 | 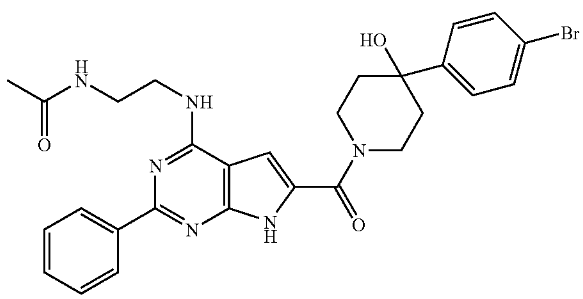 | 577.49 |
| 26.62 | 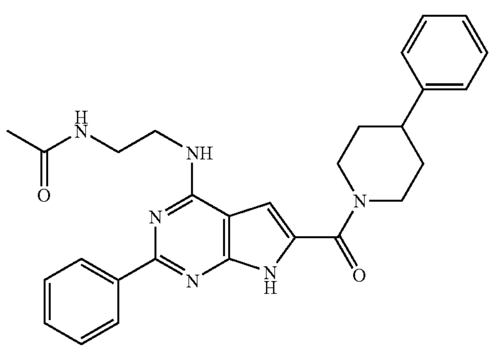 | 482.59 |
| 26.63 | 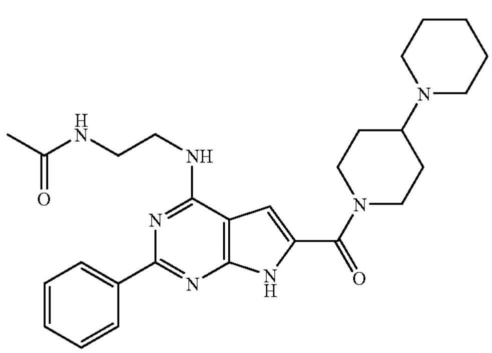 | 489.63 |

TABLE 4-continued

A_{2B} antagonists 26.1-26.250.

| Comp. # | Structure | MW |
|---|---|---|
| 26.64 | 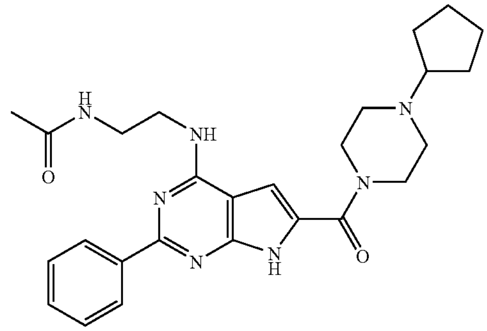 | 475.60 |
| 26.65 | 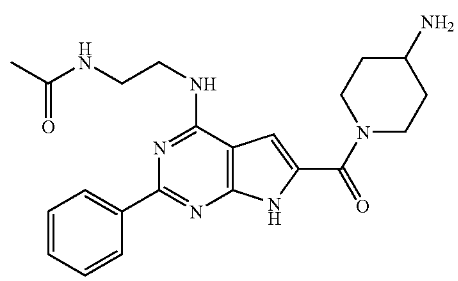 | 421.51 |
| 26.66 | 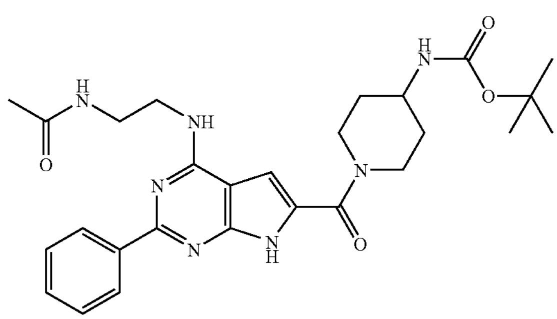 | 521.62 |
| 26.67 | 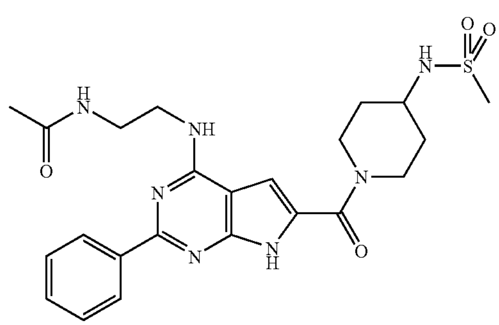 | 499.60 |

TABLE 4-continued
A$_{2B}$ antagonists 26.1-26.250.
| Comp. # | Structure | MW |
|---|---|---|
| 26.68 | 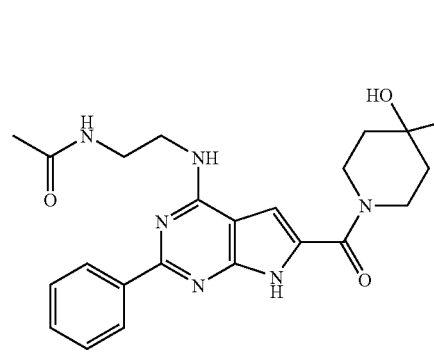 | 475.69 |
| 26.69 | 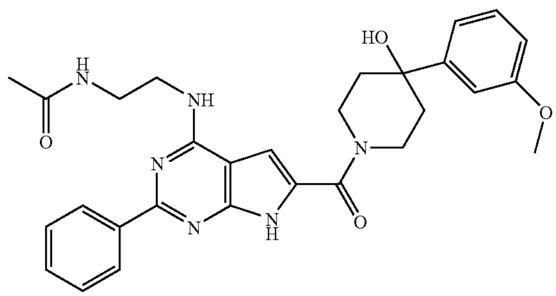 | 528.62 |
| 26.70 | 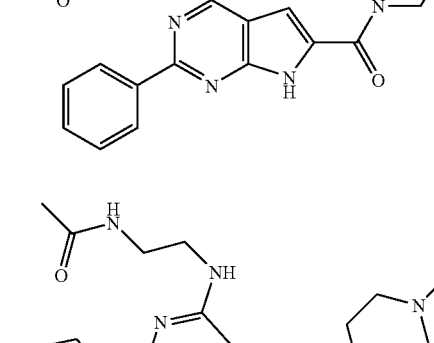 | 528.62 |
| 26.71 | 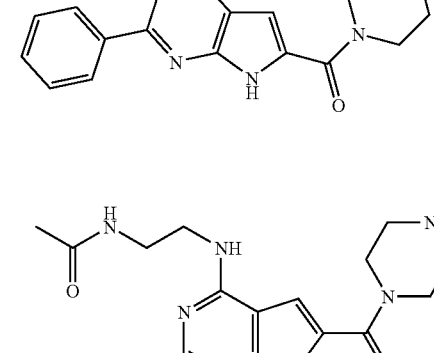 | 518.02 |
| 26.72 | 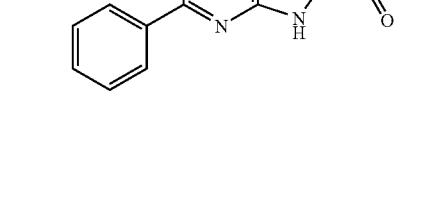 | 451.53 |

TABLE 4-continued

A$_{2B}$ antagonists 26.1-26.250.

| Comp. # | Structure | MW |
|---|---|---|
| 26.73 | 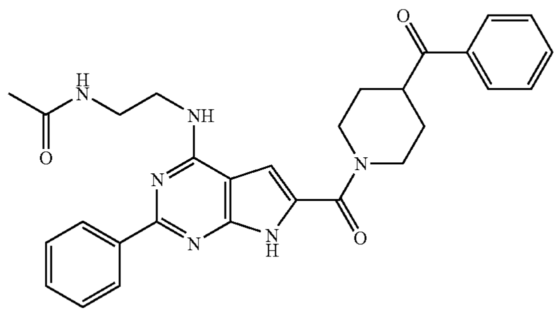 | 510.60 |
| 26.74 | 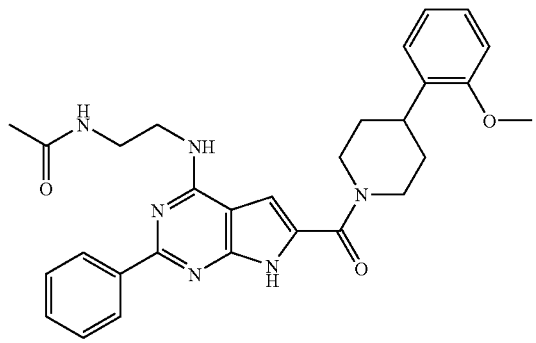 | 512.62 |
| 26.75 | 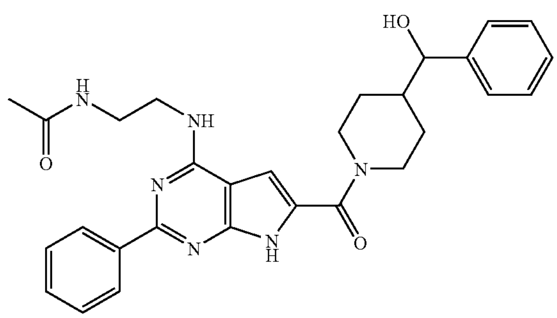 | 512.62 |
| 26.76 | 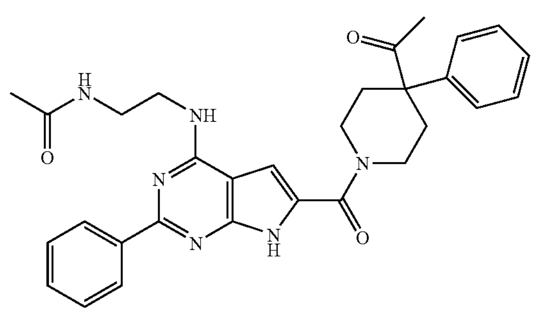 | 524.62 |
| 26.77 | 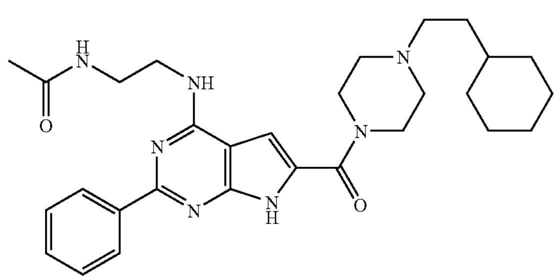 | 517.68 |

TABLE 4-continued

A_{2B} antagonists 26.1-26.250.

| Comp. # | Structure | MW |
|---|---|---|
| 26.78 | 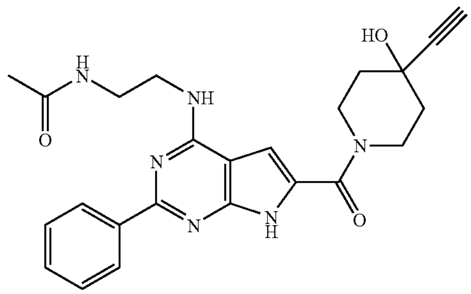 | 446.51 |
| 26.79 | 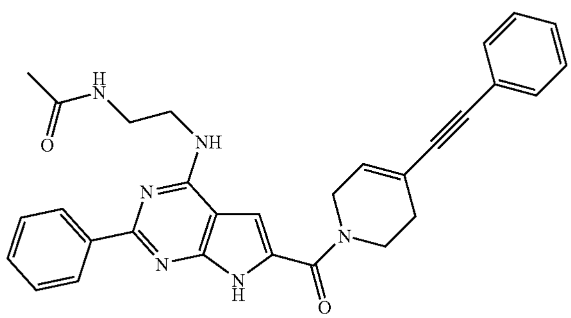 | 504.60 |
| 26.80 | 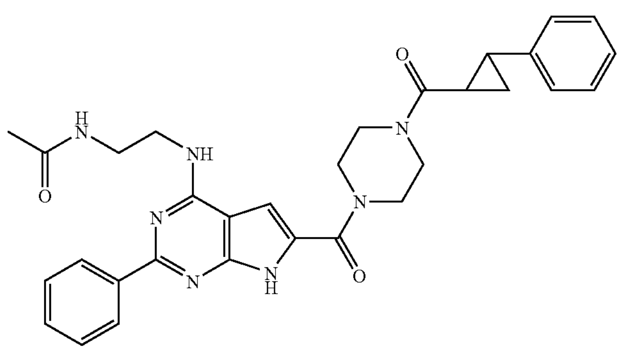 | 551.65 |
| 26.81 | 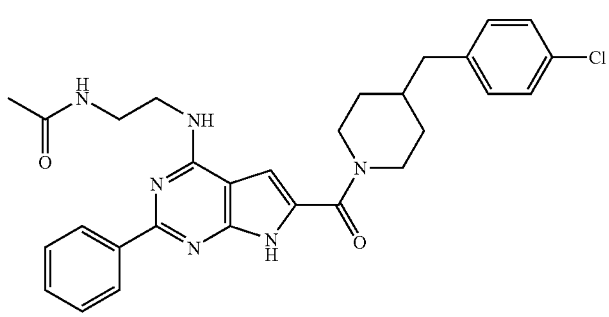 | 531.06 |

TABLE 4-continued
A$_{2B}$ antagonists 26.1-26.250.
| Comp. # | Structure | MW |
|---|---|---|
| 26.82 | 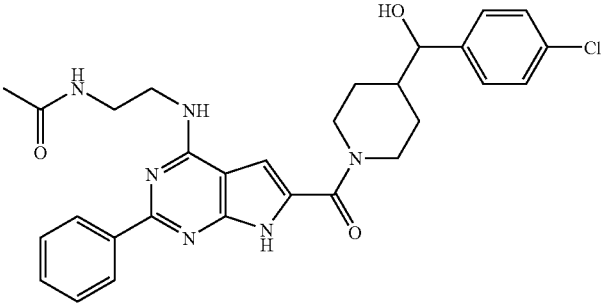 | 547.06 |
| 26.83 | 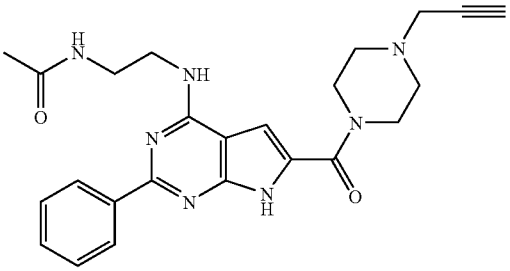 | 445.53 |
| 26.84 | 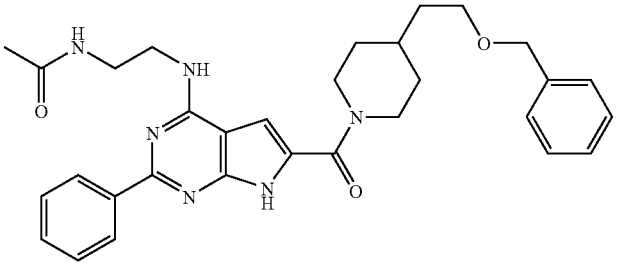 | 540.67 |
| 26.85 | 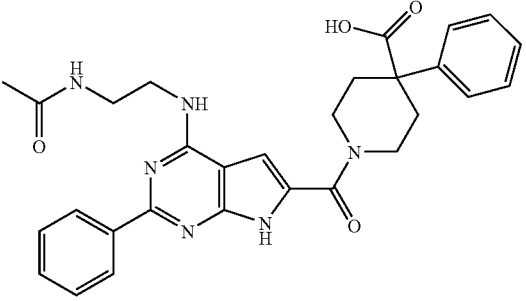 | 526.60 |
| 26.86 | 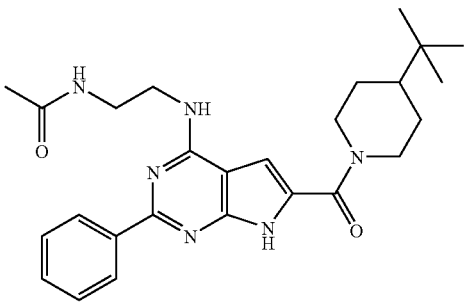 | 462.60 |

TABLE 4-continued

A$_{2B}$ antagonists 26.1-26.250.

| Comp. # | Structure | MW |
|---|---|---|
| 26.87 | 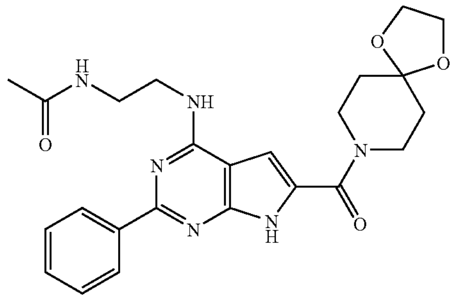 | 464.53 |
| 26.88 | 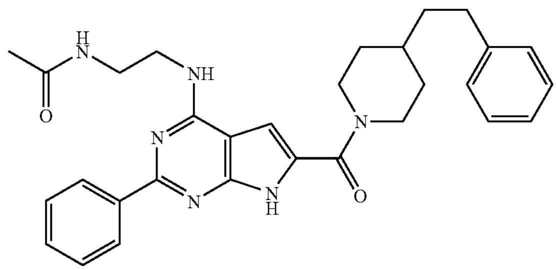 | 510.64 |
| 26.89 | 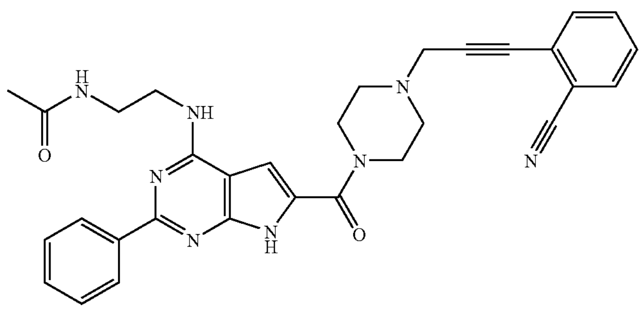 | 546.64 |
| 26.90 | 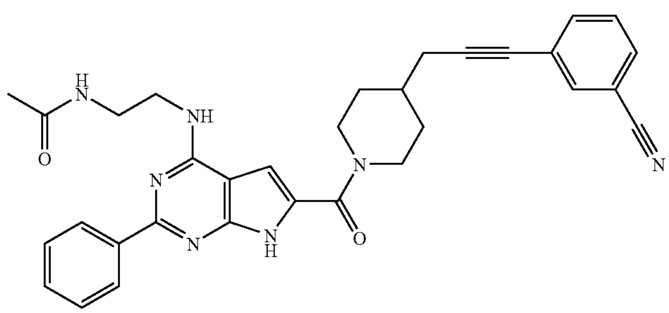 | 546.64 |
| 26.91 | 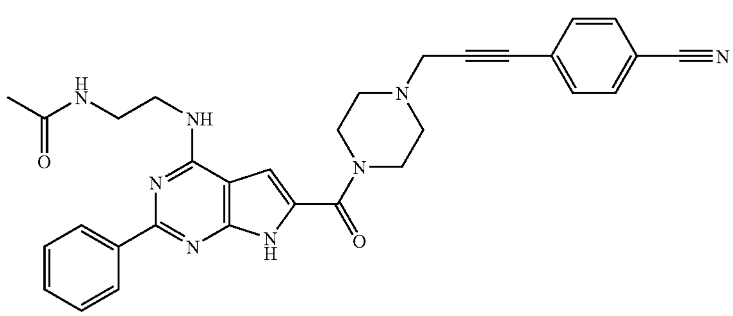 | 546.64 |

TABLE 4-continued

A_{2B} antagonists 26.1-26.250.

| Comp. # | Structure | MW |
|---------|-----------|-----|
| 26.92 | 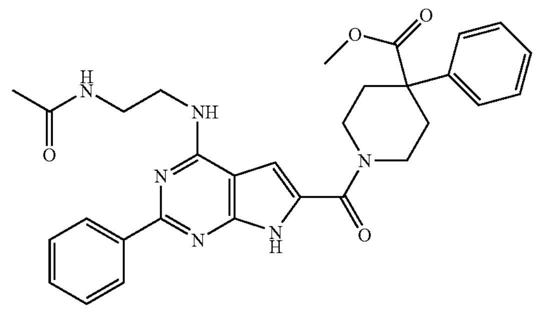 | 540.63 |
| 26.93 | 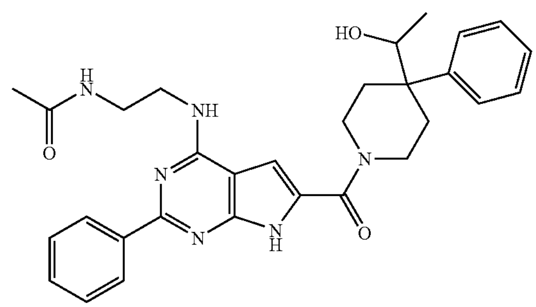 | 526.64 |
| 26.94 | 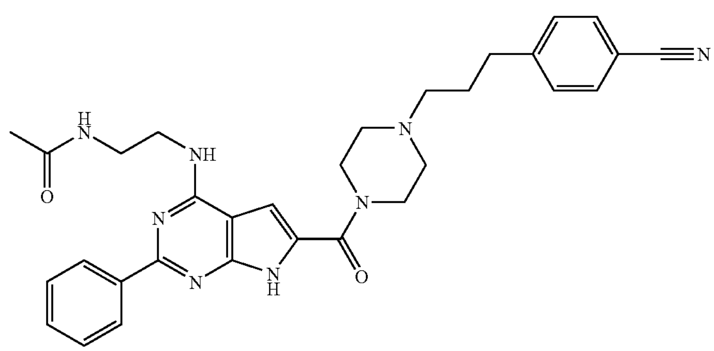 | 550.67 |
| 26.95 | 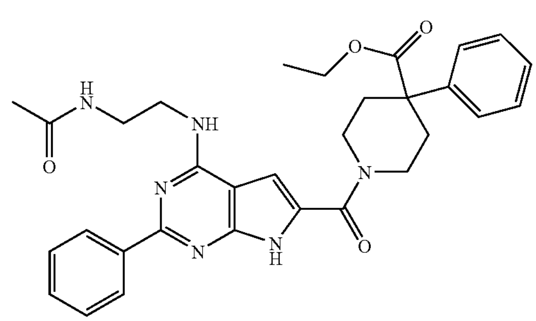 | 554.65 |

TABLE 4-continued

A$_{2B}$ antagonists 26.1-26.250.

| Comp. # | Structure | MW |
|---|---|---|
| 26.96 | 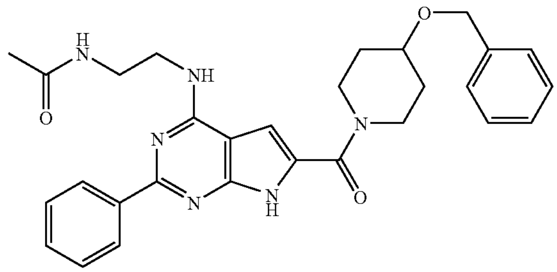 | 512.62 |
| 26.97 | 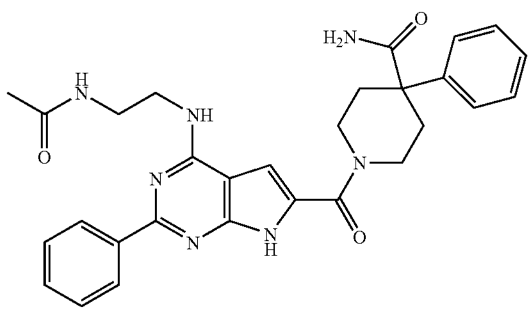 | 525.62 |
| 26.98 | 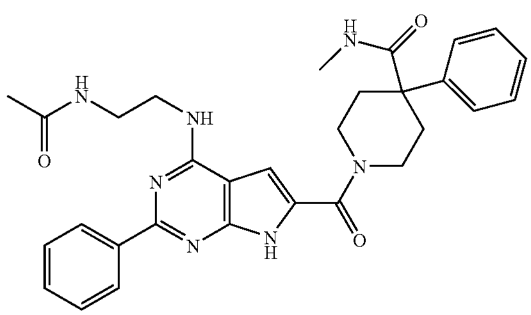 | 539.64 |
| 26.99 | 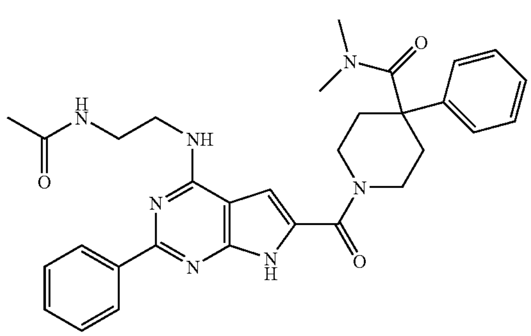 | 553.67 |

TABLE 4-continued

A$_{2B}$ antagonists 26.1-26.250.

| Comp. # | Structure | MW |
| --- | --- | --- |
| 26.100 | 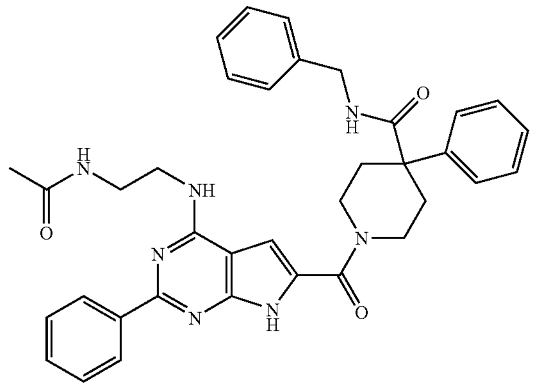 | 615.74 |
| 26.101 | 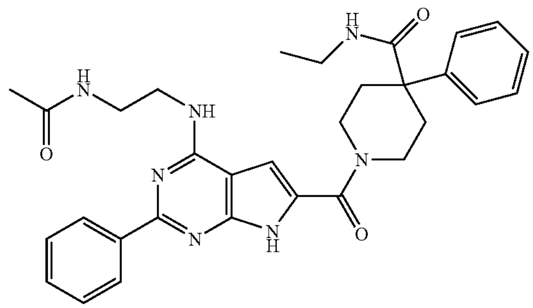 | 553.67 |
| 26.102 | 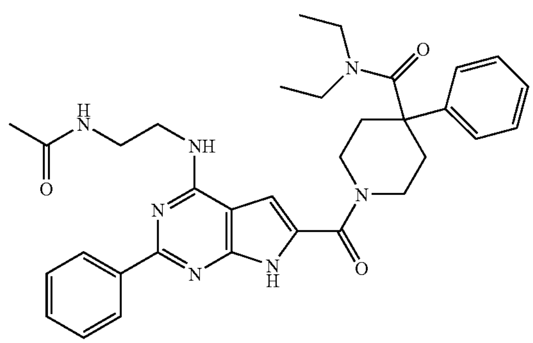 | 581.72 |
| 26.103 | 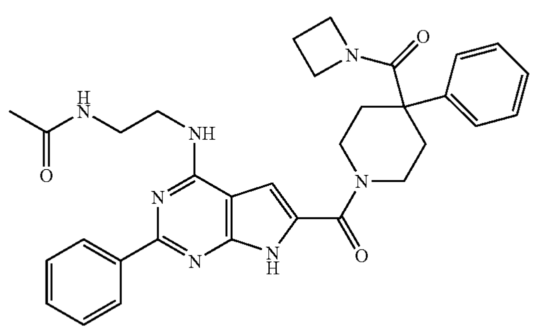 | 565.68 |

TABLE 4-continued
A$_{2B}$ antagonists 26.1-26.250.
| Comp. # | Structure | MW |
|---|---|---|
| 26.104 | 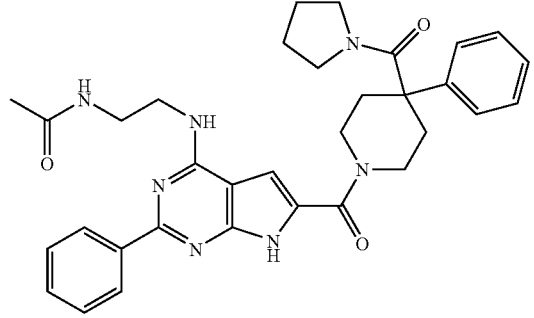 | 579.71 |
| 26.105 | 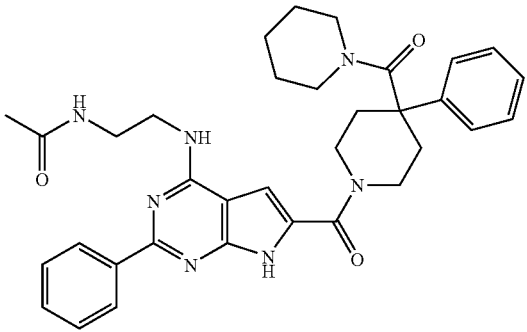 | 593.74 |
| 26.106 | 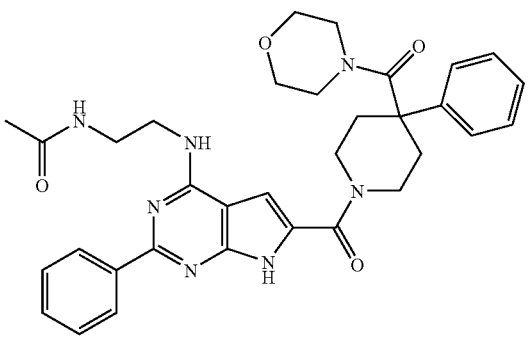 | 595.71 |
| 26.107 | 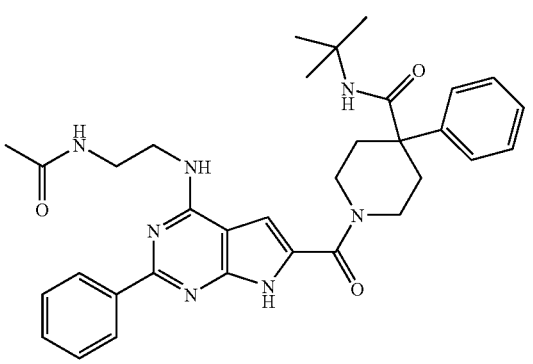 | 581.72 |

TABLE 4-continued

A$_{2B}$ antagonists 26.1-26.250.

| Comp. # | Structure | MW |
|---|---|---|
| 26.108 | 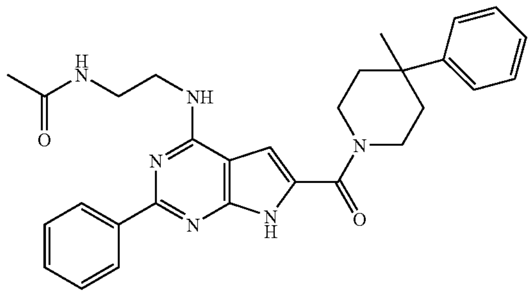 | 496.62 |
| 26.109 | 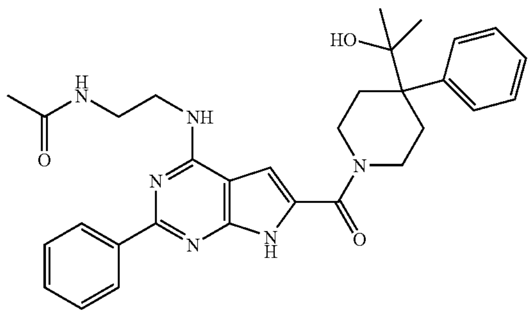 | 540.67 |
| 26.110 | 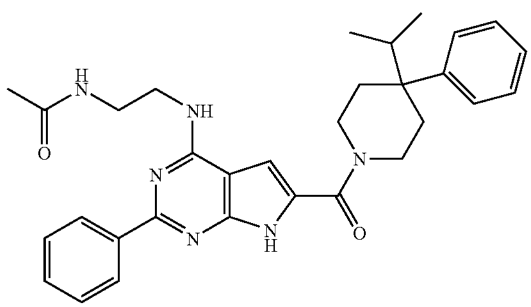 | 524.67 |
| 26.111 | 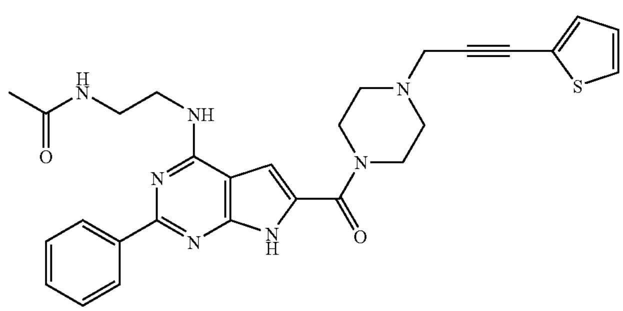 | 527.65 |
| 26.112 | 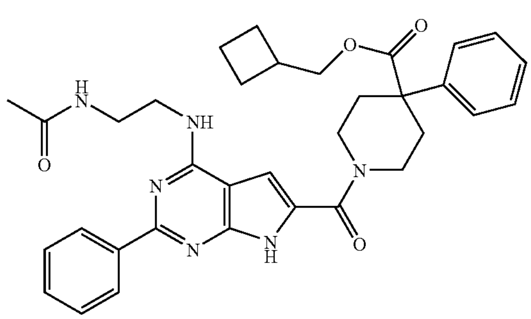 | 594.72 |

TABLE 4-continued

A$_{2B}$ antagonists 26.1-26.250.

| Comp. # | Structure | MW |
|---|---|---|
| 26.113 | 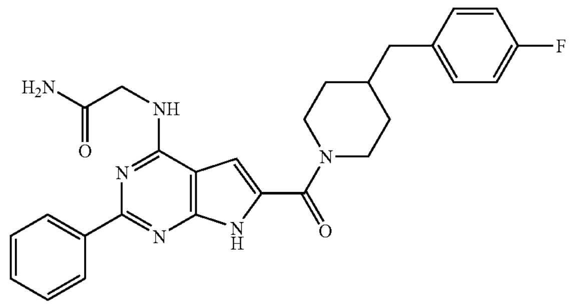 | 486.55 |
| 26.114 | 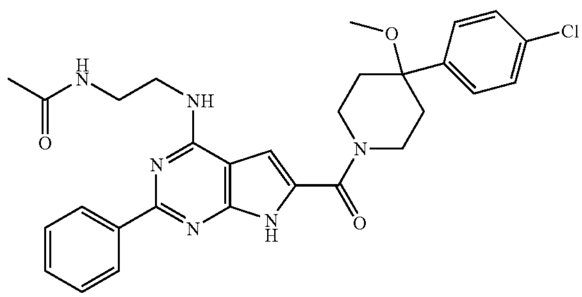 | 547.06 |
| 26.115 | 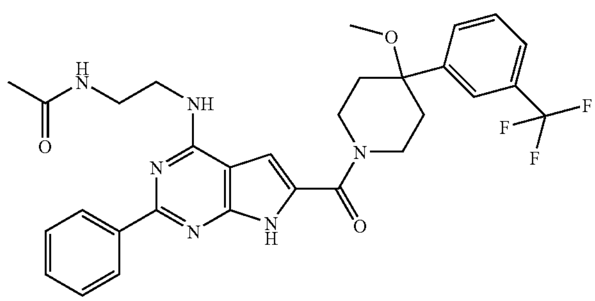 | 580.62 |
| 26.116 | 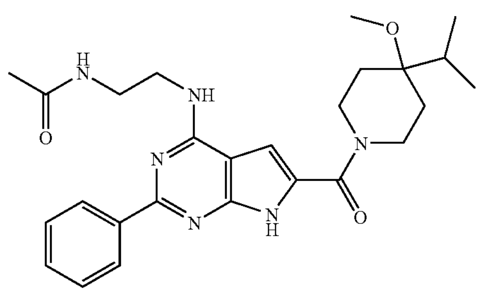 | 478.60 |
| 26.117 | 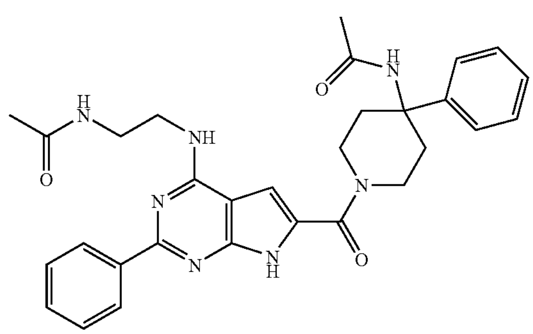 | 539.64 |

TABLE 4-continued

A$_{2B}$ antagonists 26.1-26.250.

| Comp. # | Structure | MW |
|---|---|---|
| 26.118 | 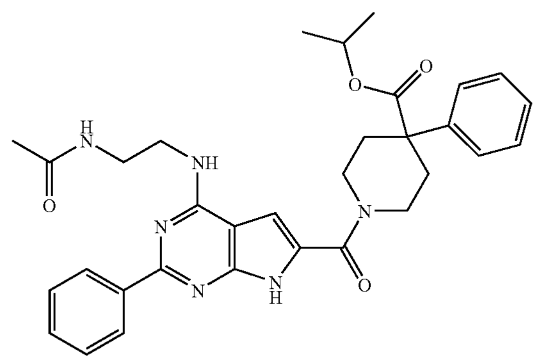 | 568.68 |
| 26.119 | 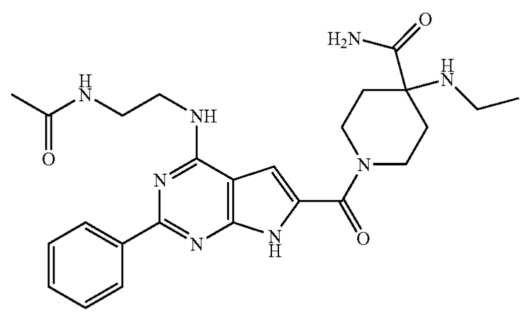 | 492.59 |
| 26.120 | 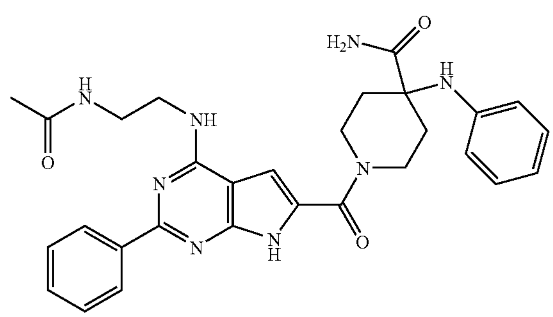 | 540.63 |
| 26.121 | 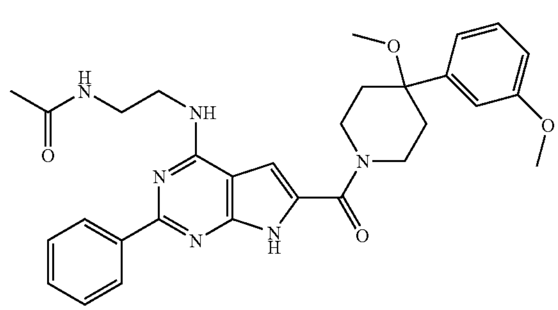 | 542.64 |

TABLE 4-continued
A$_{2B}$ antagonists 26.1-26.250.
| Comp. # | Structure | MW |
|---|---|---|
| 26.122 | 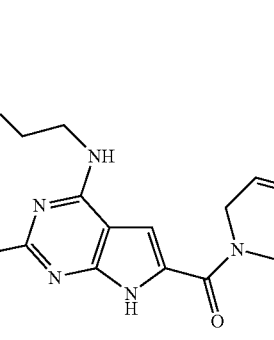 | 518.62 |
| 26.123 | 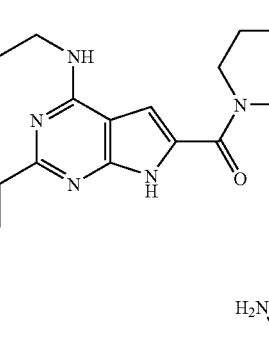 | 510.60 |
| 26.124 | 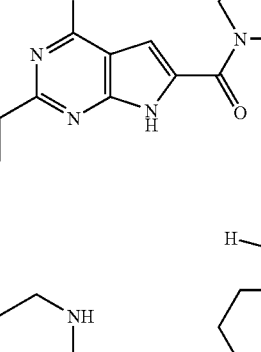 | 542.64 |
| 26.125 | 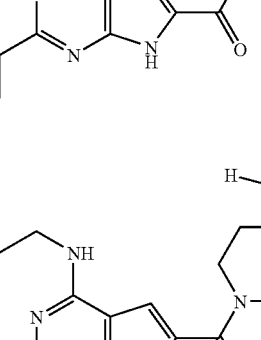 | 597.60 |
| 26.126 | 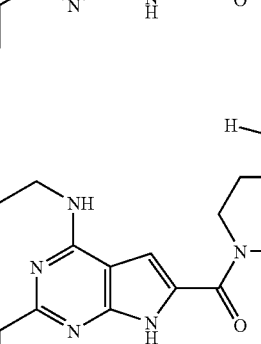 | 510.60 |

TABLE 4-continued
A$_{2B}$ antagonists 26.1-26.250.
| Comp. # | Structure | MW |
|---|---|---|
| 26.127 | 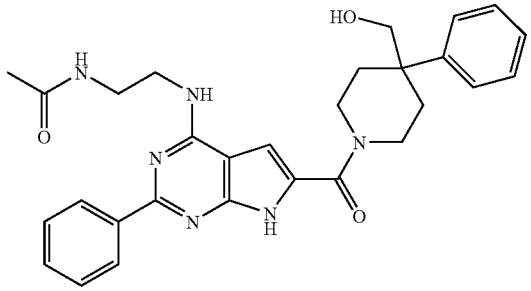 | 512.62 |
| 26.128 | 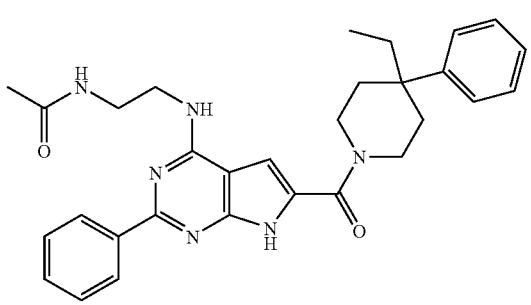 | 510.64 |
| 26.129 | 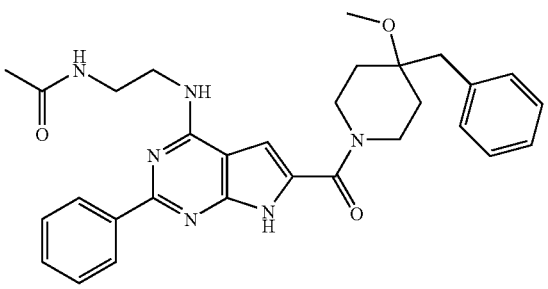 | 526.64 |
| 26.130 | 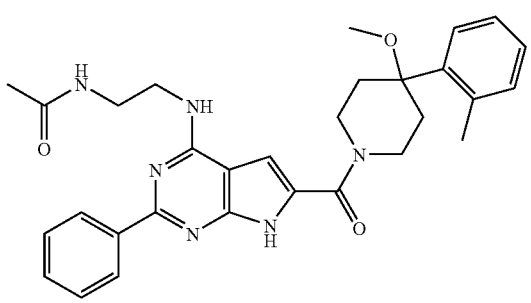 | 526.64 |
| 26.131 | 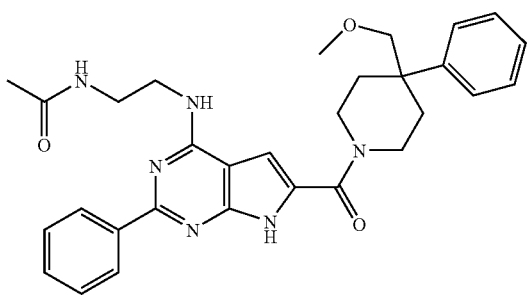 | 526.64 |

TABLE 4-continued

A$_{2B}$ antagonists 26.1-26.250.

| Comp. # | Structure | MW |
|---|---|---|
| 26.132 | 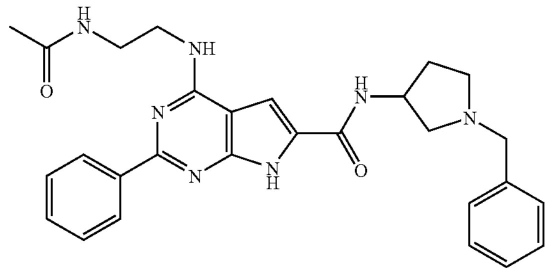 | 497.60 |
| 26.133 | 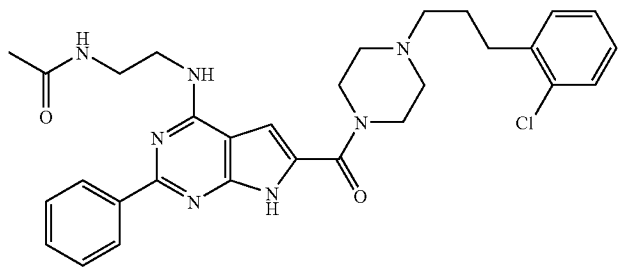 | 560.10 |
| 26.134 | 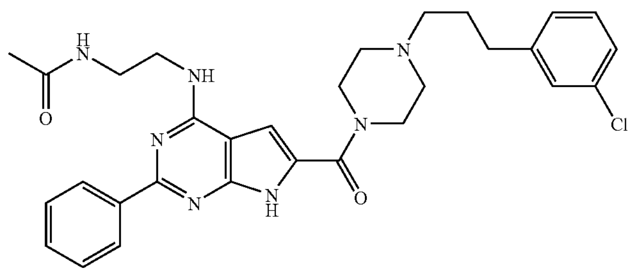 | 560.10 |
| 26.135 | 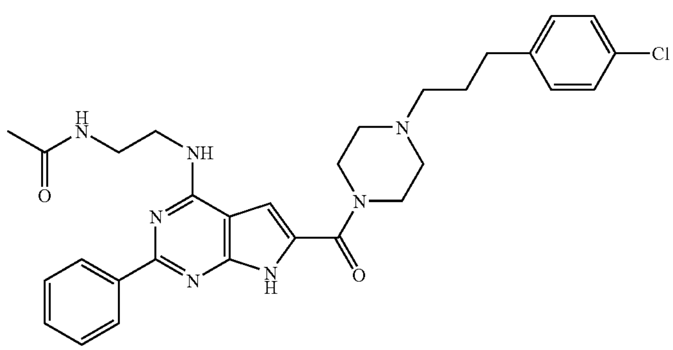 | 560.10 |
| 26.136 | 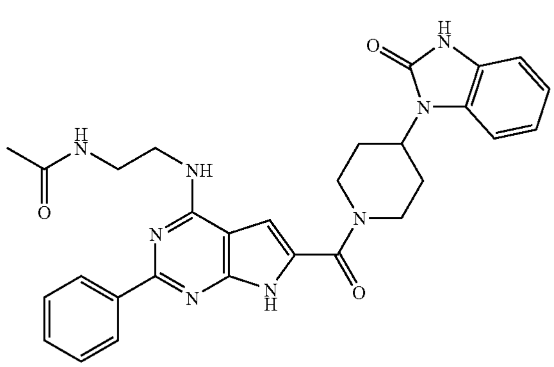 | 538.61 |

TABLE 4-continued
A_{2B} antagonists 26.1-26.250.
| Comp. # | Structure | MW |
|---|---|---|
| 26.137 | 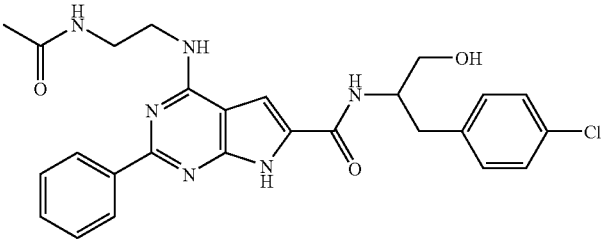 | 507.00 |
| 26.138 | 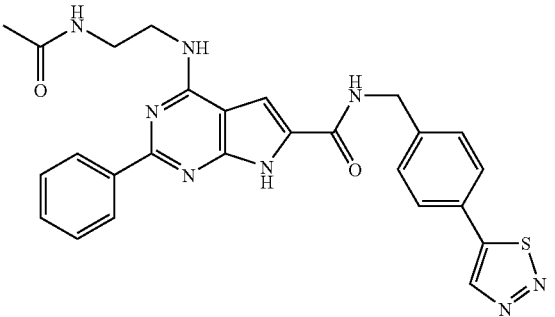 | 512.60 |
| 26.139 | 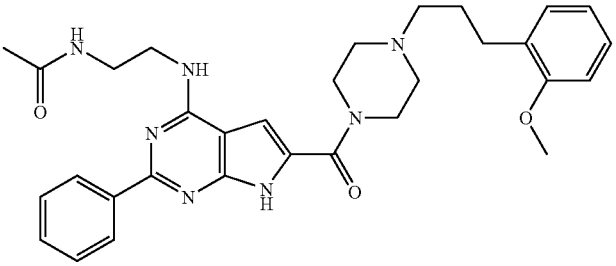 | 555.69 |
| 26.140 | 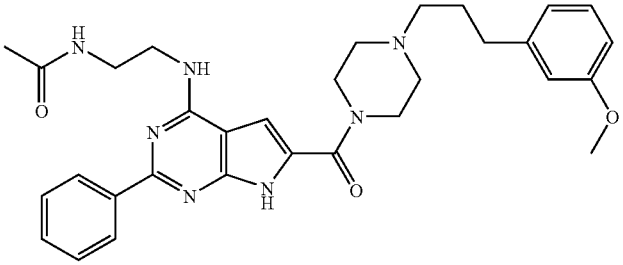 | 555.69 |
| 26.141 | 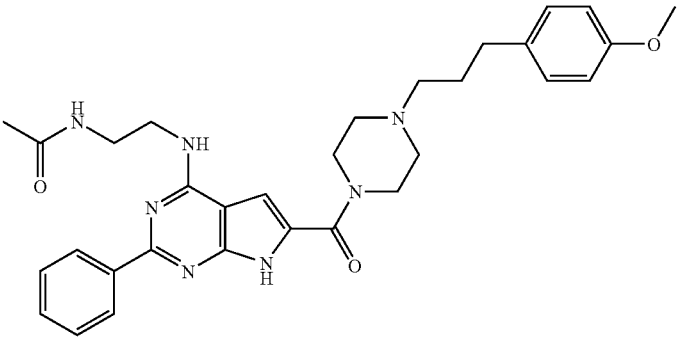 | 555.69 |

TABLE 4-continued

A₂ᵦ antagonists 26.1-26.250.

| Comp. # | Structure | MW |
|---|---|---|
| 26.142 | 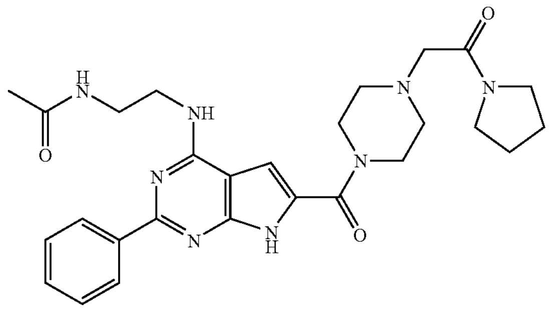 | 518.62 |
| 26.143 | 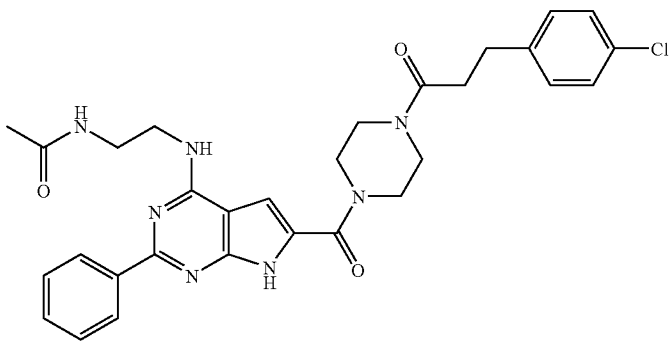 | 574.09 |
| 26.144 | 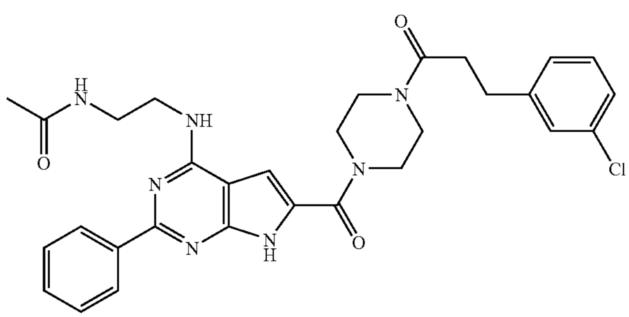 | 574.09 |
| 26.145 | 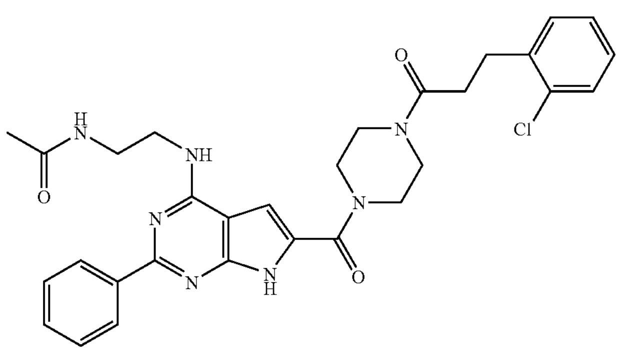 | 574.09 |

TABLE 4-continued
A$_{2B}$ antagonists 26.1-26.250.
| Comp. # | Structure | MW |
|---|---|---|
| 26.146 | 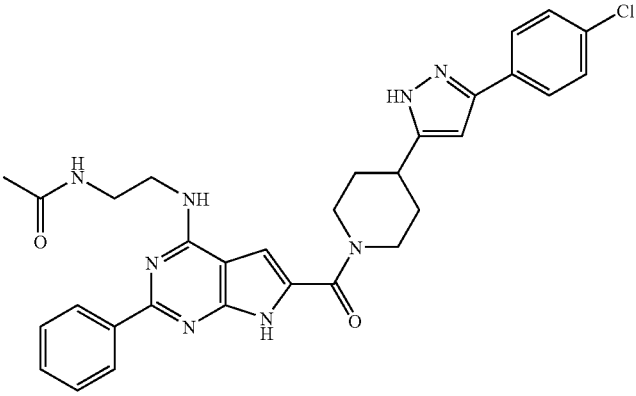 | 583.10 |
| 26.147 | 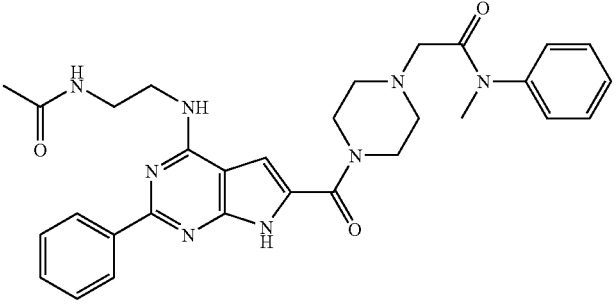 | 554.66 |
| 26.148 | 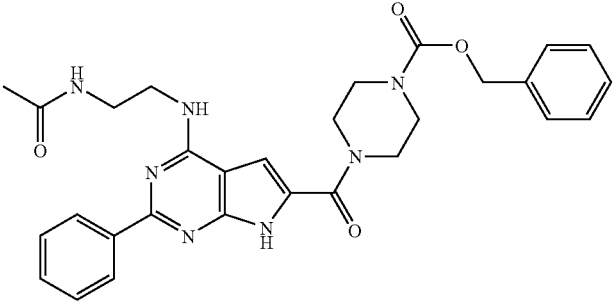 | 541.61 |
| 26.149 | 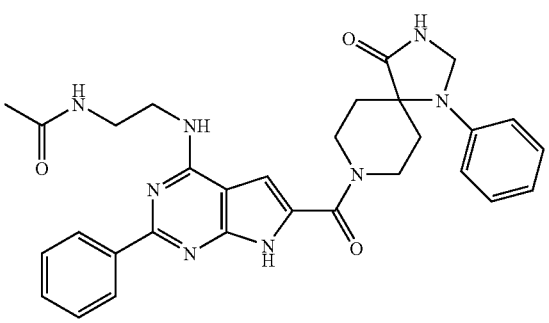 | 552.64 |

TABLE 4-continued

A$_{2B}$ antagonists 26.1-26.250.

| Comp. # | Structure | MW |
|---|---|---|
| 26.150 | 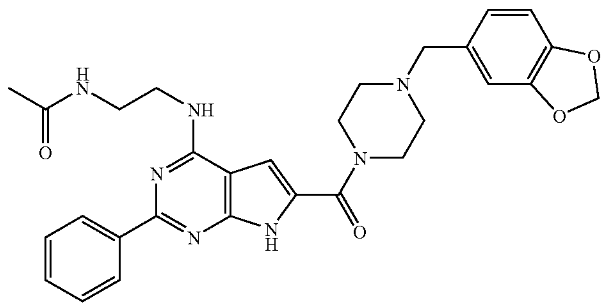 | 541.61 |
| 26.151 | 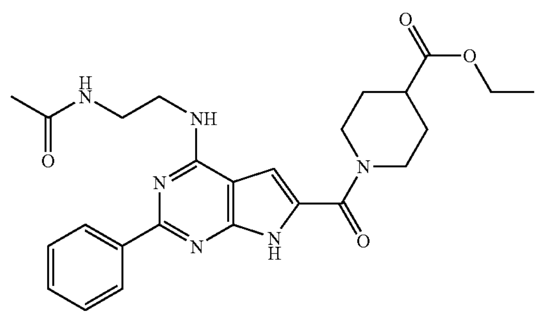 | 478.56 |
| 26.152 | 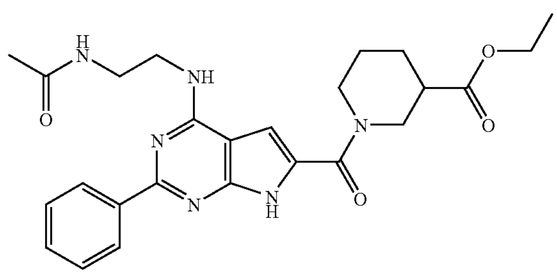 | 478.56 |
| 26.153 | 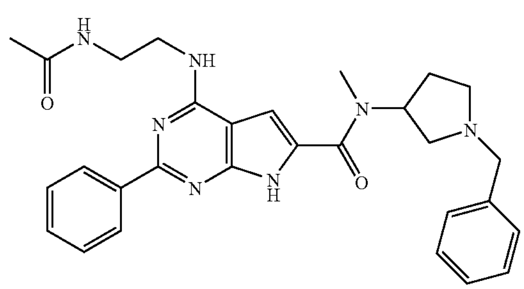 | 511.63 |
| 26.154 | 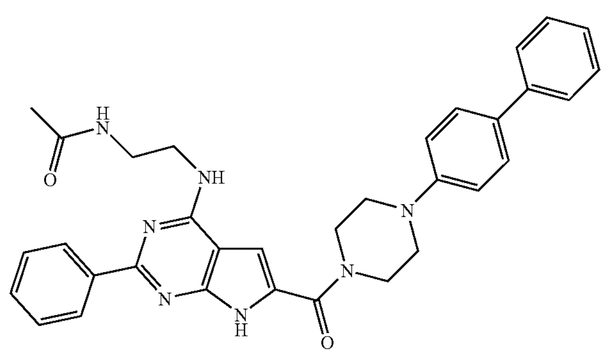 | 559.68 |

TABLE 4-continued

A₂B antagonists 26.1-26.250.

| Comp. # | Structure | MW |
|---|---|---|
| 26.155 | 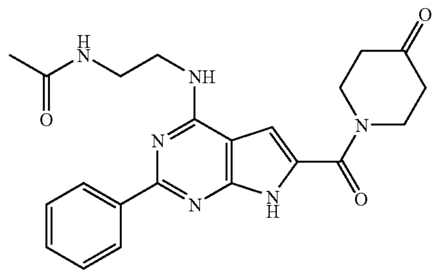 | 420.47 |
| 26.156 | 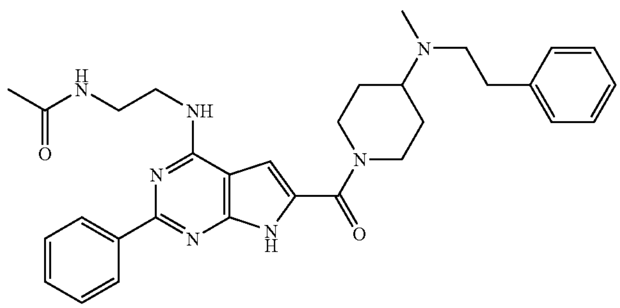 | 539.69 |
| 26.157 | 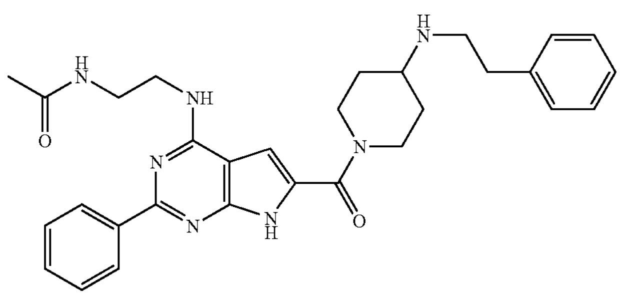 | 525.66 |
| 25.158 | 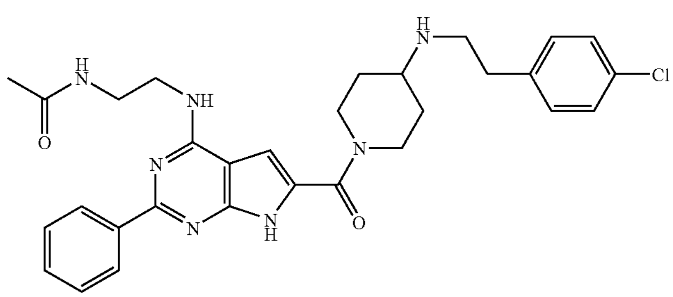 | 560.10 |
| 26.159 | 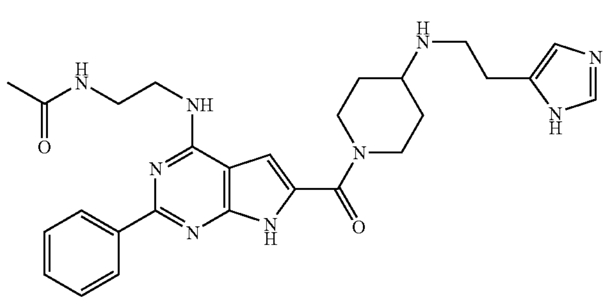 | 515.62 |

TABLE 4-continued

A$_{2B}$ antagonists 26.1-26.250.

| Comp. # | Structure | MW |
|---|---|---|
| 26.160 | 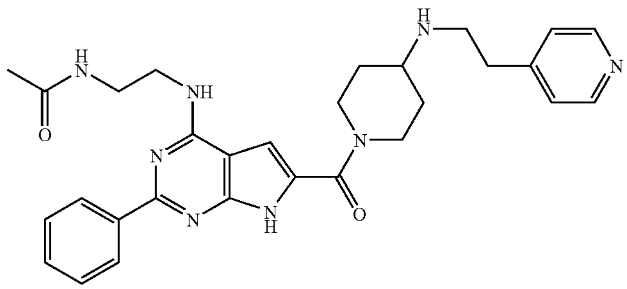 | 526.65 |
| 26.161 | 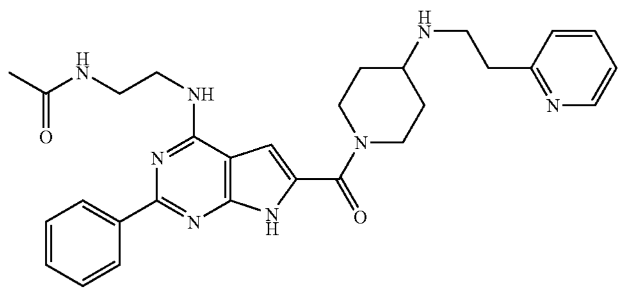 | 526.65 |
| 26.162 | 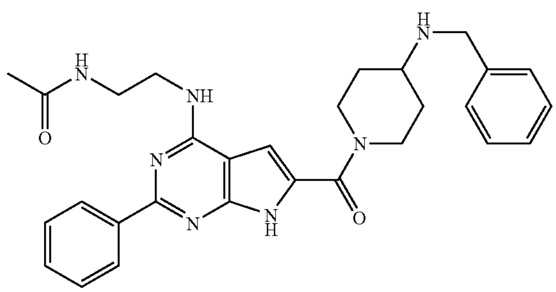 | 511.63 |
| 26.163 | 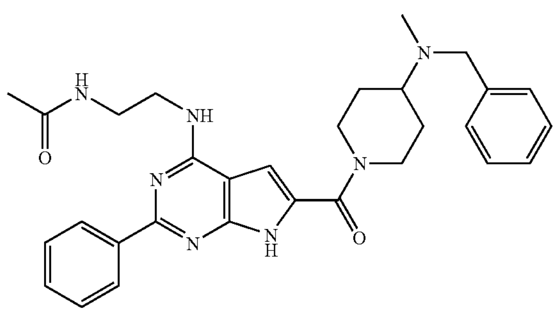 | 525.66 |
| 26.164 | 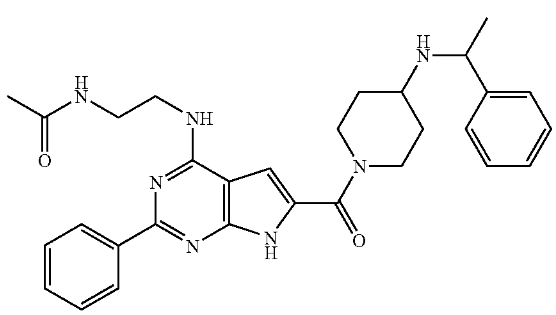 | 525.66 |

TABLE 4-continued

A$_{2B}$ antagonists 26.1-26.250.

| Comp. # | Structure | MW |
|---|---|---|
| 26.165 | 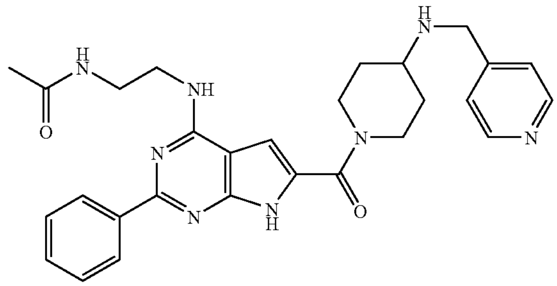 | 512.62 |
| 26.166 | 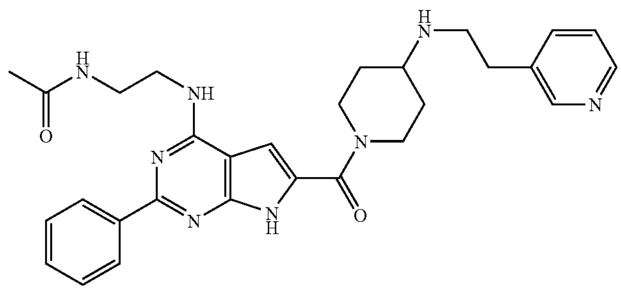 | 526.65 |
| 26.167 | 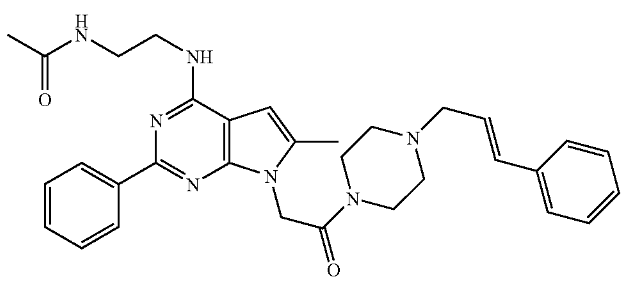 | 551.70 |
| 26.168 | 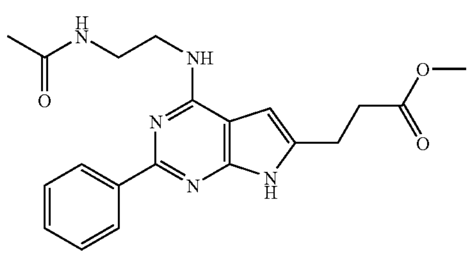 | 381.44 |
| 26.169 | 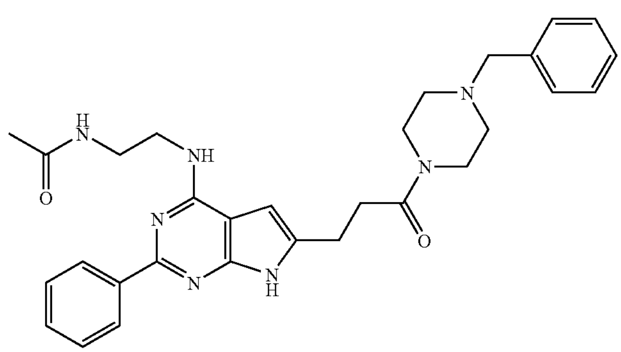 | 525.66 |

TABLE 4-continued
A$_{2B}$ antagonists 26.1-26.250.
| Comp. # | Structure | MW |
|---|---|---|
| 26.170 | 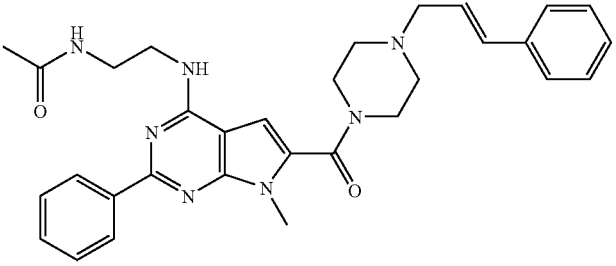 | 537.67 |
| 26.171 | 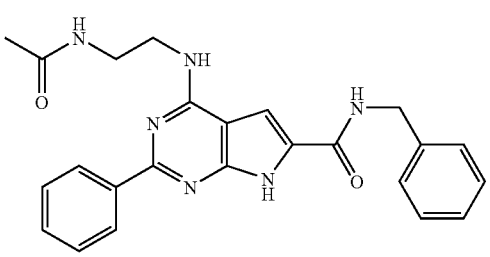 | 428.50 |
| 26.172 | 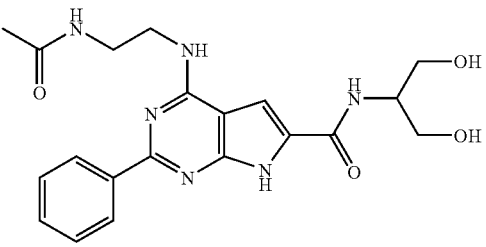 | 412.45 |
| 26.173 | 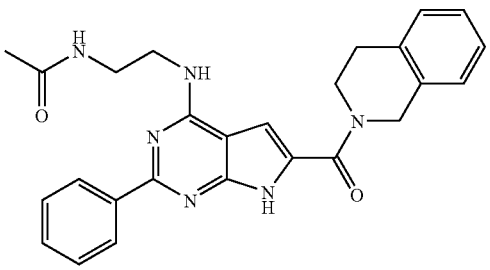 | 454.54 |
| 26.174 | 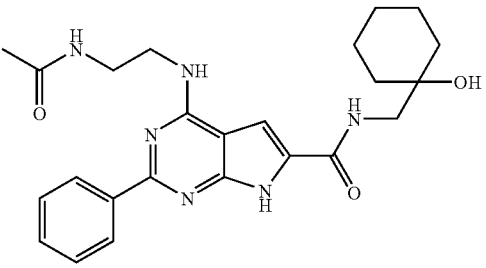 | 450.55 |

TABLE 4-continued

A$_{2B}$ antagonists 26.1-26.250.

| Comp. # | Structure | MW |
| --- | --- | --- |
| 26.175 | 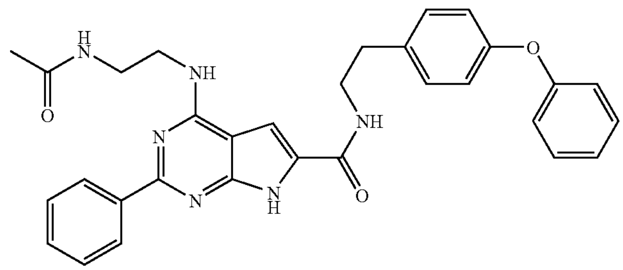 | 534.62 |
| 26.176 | 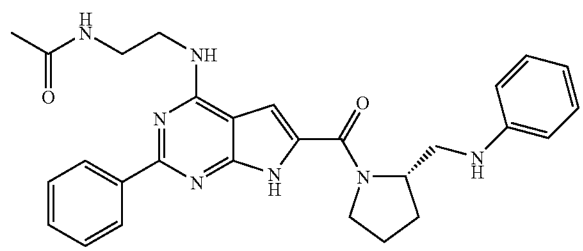 | 497.60 |
| 26.177 | 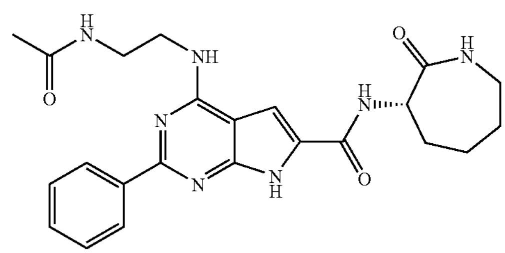 | 449.52 |
| 26.178 | 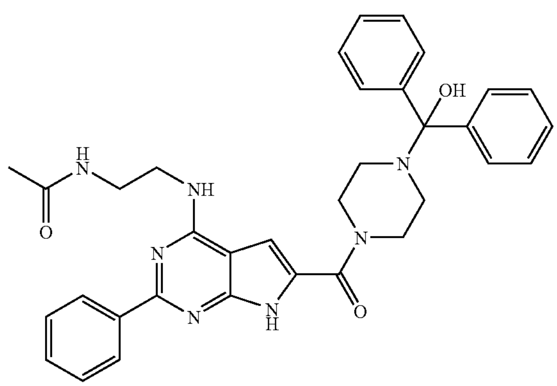 | 588.72 |
| 26.179 | 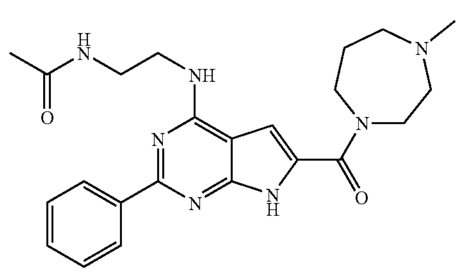 | 435.53 |

TABLE 4-continued

A$_{2B}$ antagonists 26.1-26.250.

| Comp. # | Structure | MW |
|---|---|---|
| 26.180 | 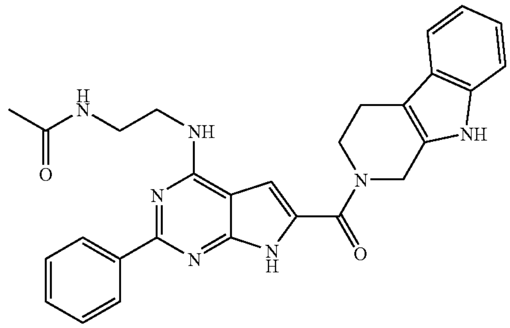 | 493.57 |
| 26.181 | 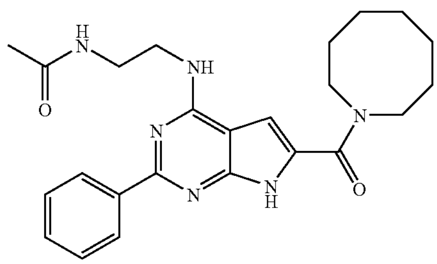 | 434.55 |
| 26.182 | 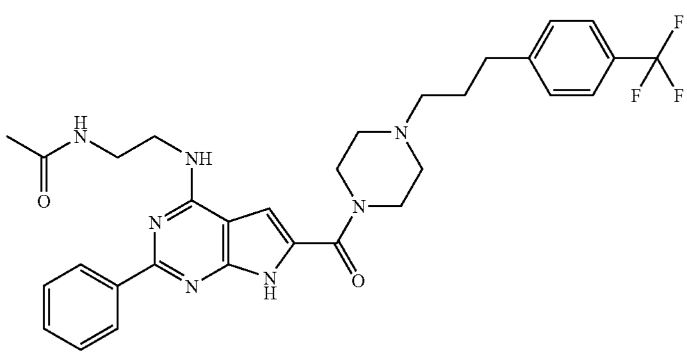 | 593.66 |
| 26.183 | 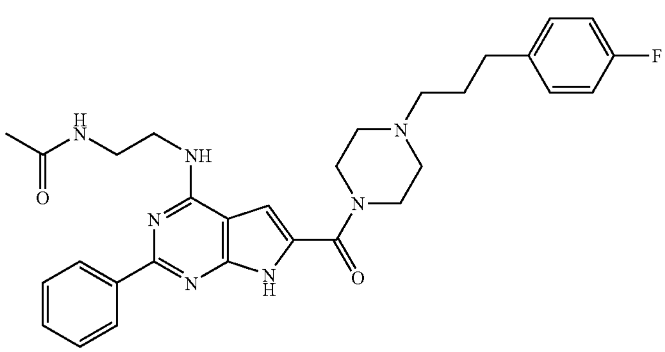 | 543.65 |

TABLE 4-continued

A$_{2B}$ antagonists 26.1-26.250.

| Comp. # | Structure | MW |
|---|---|---|
| 26.184 | 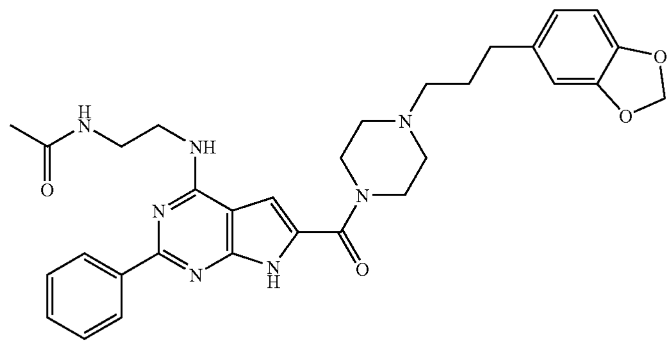 | 569.67 |
| 26.185 | 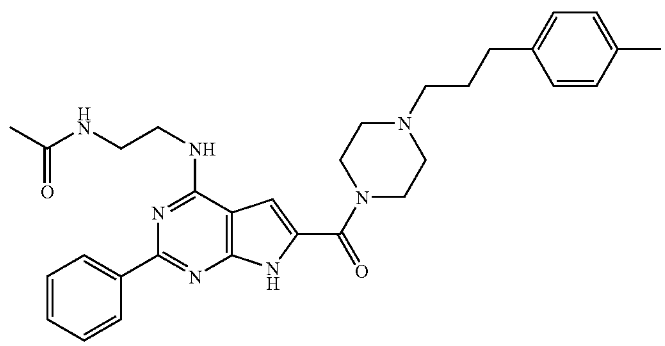 | 539.69 |
| 26.186 | 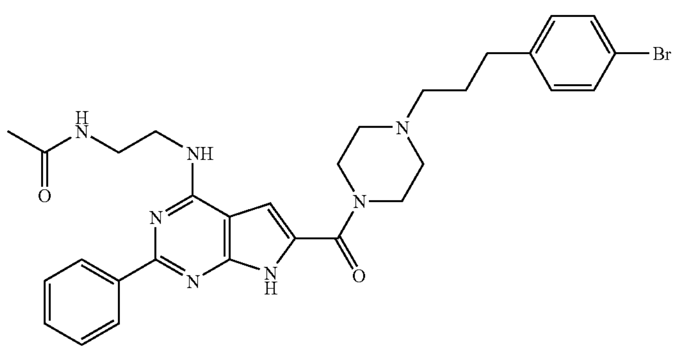 | 604.56 |
| 26.187 | 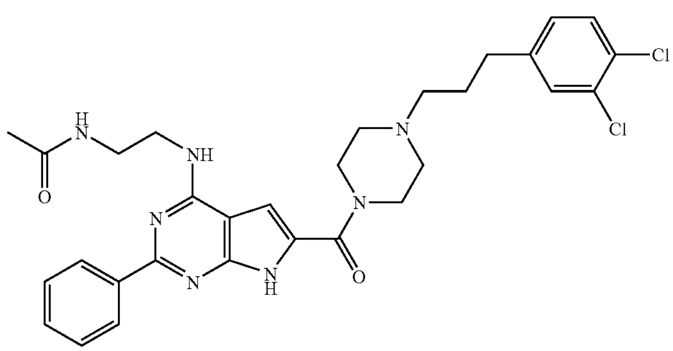 | 594.55 |

TABLE 4-continued
A$_{2B}$ antagonists 26.1-26.250.
| Comp. # | Structure | MW |
|---|---|---|
| 26.188 | 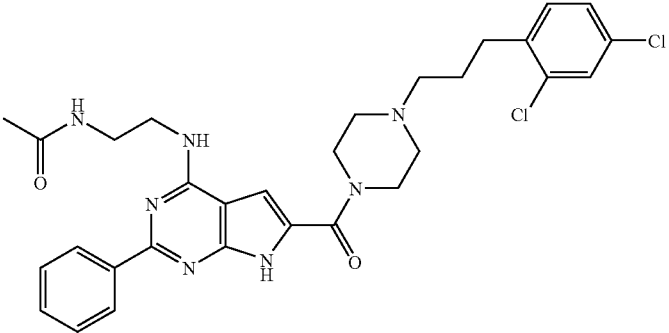 | 594.55 |
| 26.189 | 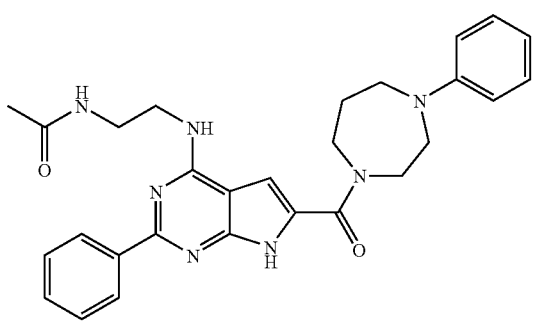 | 497.61 |
| 26.190 | 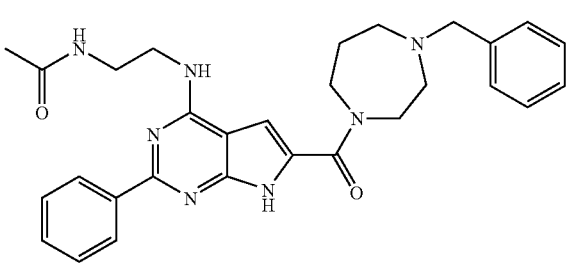 | 511.63 |
| 26.191 | 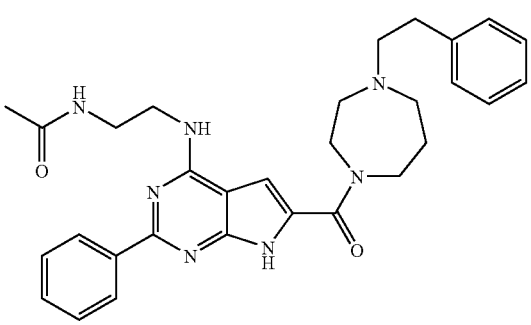 | 525.66 |

TABLE 4-continued
A$_{2B}$ antagonists 26.1-26.250.
| Comp. # | Structure | MW |
|---|---|---|
| 26.192 | 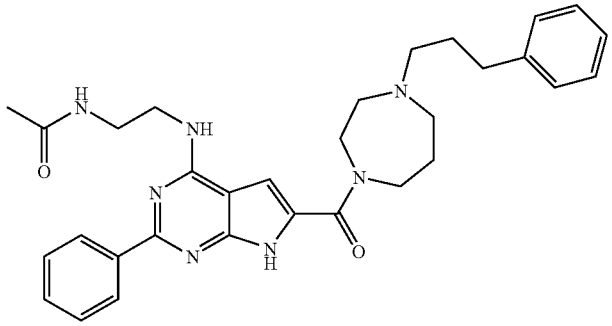 | 539.69 |
| 26.193 | 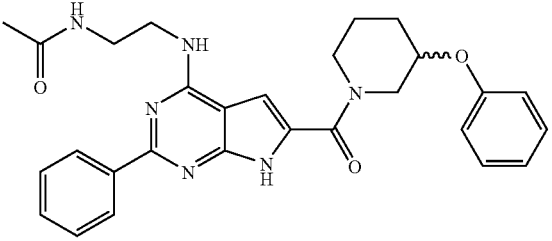 | 498.59 |
| 26.194 | 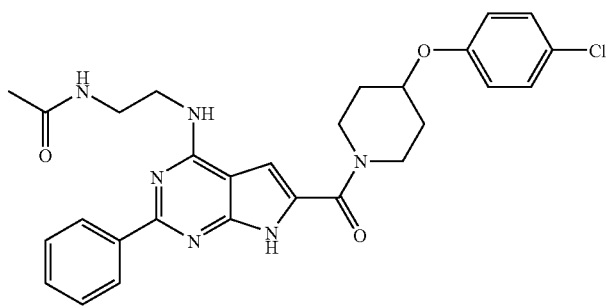 | 533.03 |
| 26.195 | 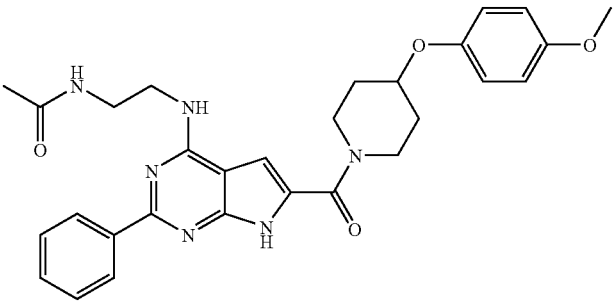 | 528.62 |
| 26.196 | 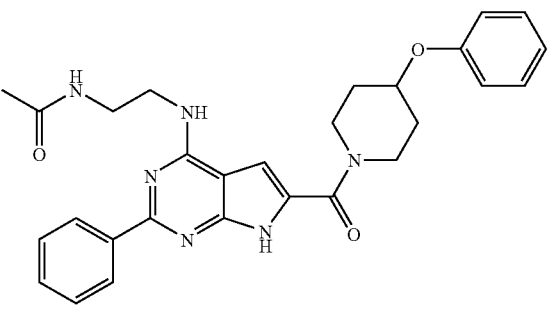 | 498.59 |

TABLE 4-continued
A_{2B} antagonists 26.1-26.250.
| Comp. # | Structure | MW |
|---|---|---|
| 26.197 | 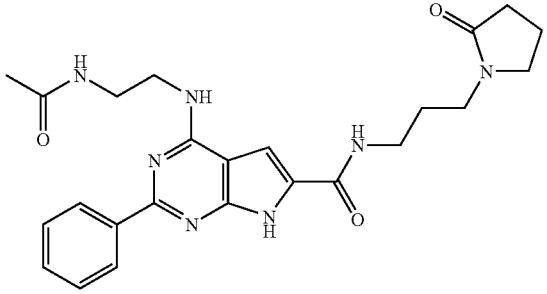 | 463.54 |
| 26.198 | 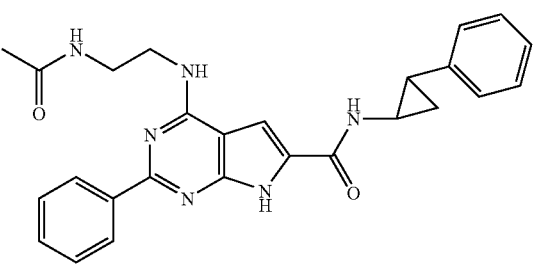 | 454.54 |
| 26.199 | 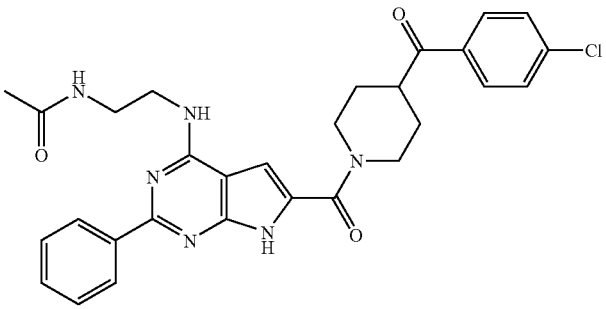 | 545.05 |
| 26.200 | 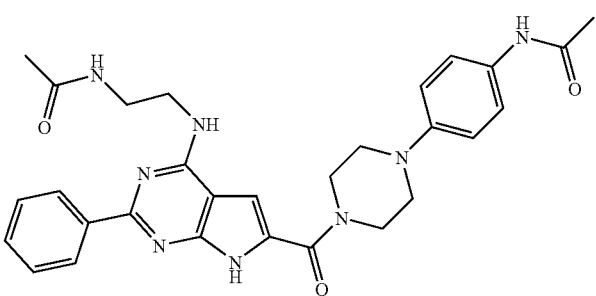 | 540.63 |
| 26.201 | 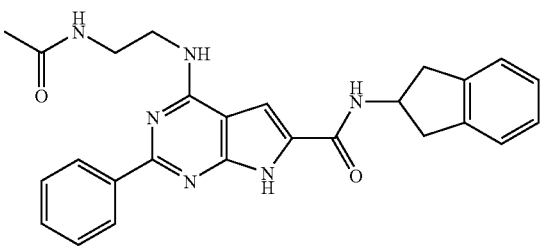 | 454.54 |

TABLE 4-continued
A$_{2B}$ antagonists 26.1-26.250.
| Comp. # | Structure | MW |
|---|---|---|
| 26.202 | 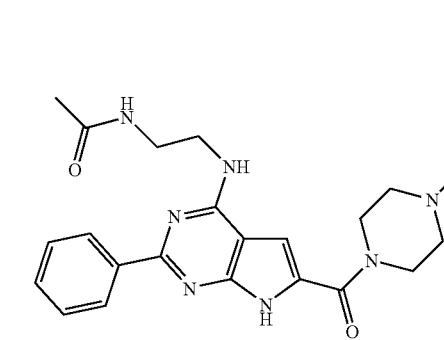 | 508.59 |
| 26.203 | 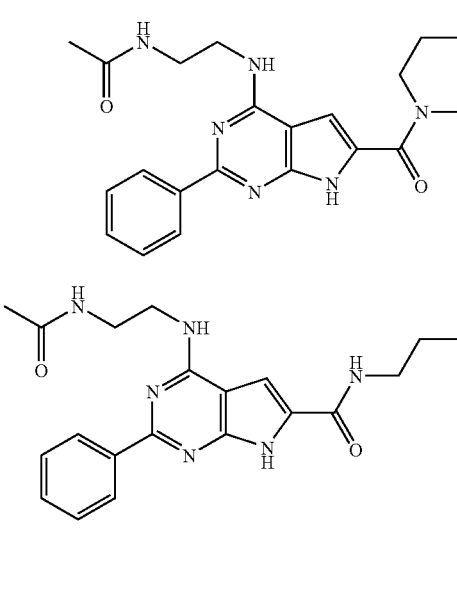 | 508.59 |
| 26.204 | 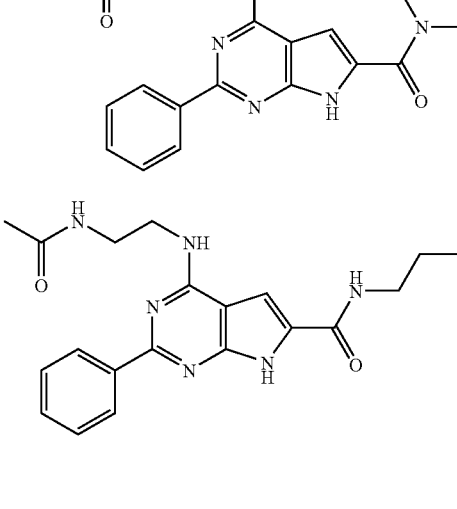 | 436.52 |
| 26.205 | 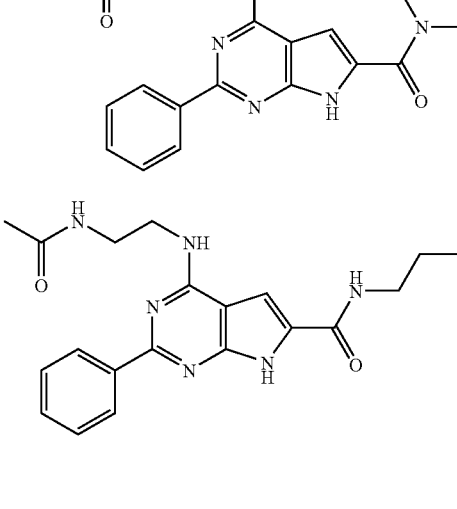 | 472.55 |
| 26.206 | 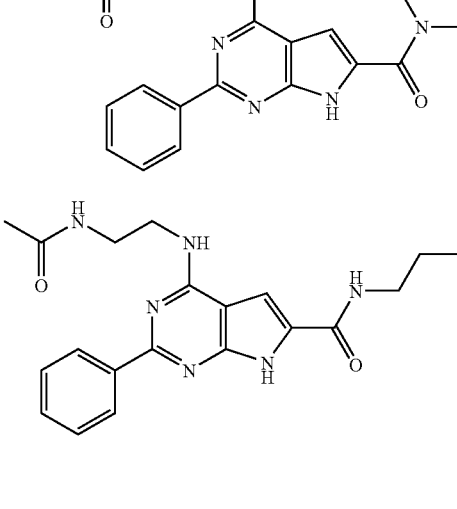 | 554.66 |

TABLE 4-continued
A$_{2B}$ antagonists 26.1-26.250.
| Comp. # | Structure | MW |
|---|---|---|
| 26.207 | 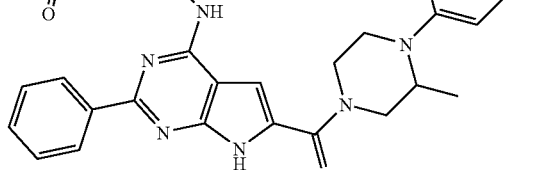 | 527.63 |
| 26.208 | 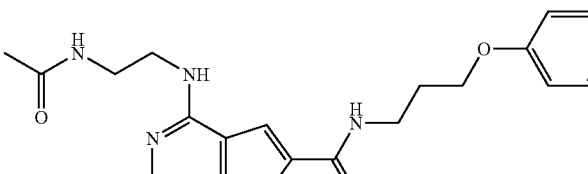 | 458.52 |
| 26.209 | 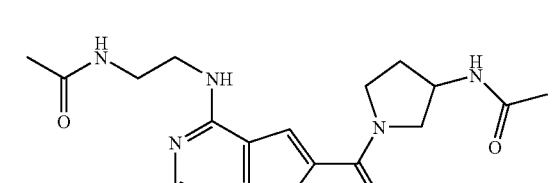 | 449.52 |
| 26.210 | 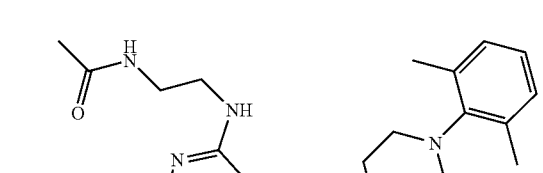 | 511.63 |
| 26.211 | 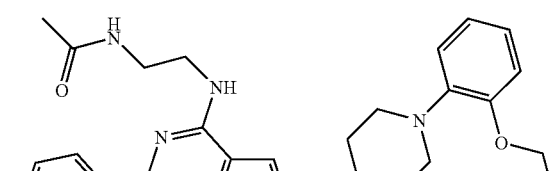 | 527.63 |

TABLE 4-continued

A_{2B} antagonists 26.1-26.250.

| Comp. # | Structure | MW |
|---|---|---|
| 26.212 | 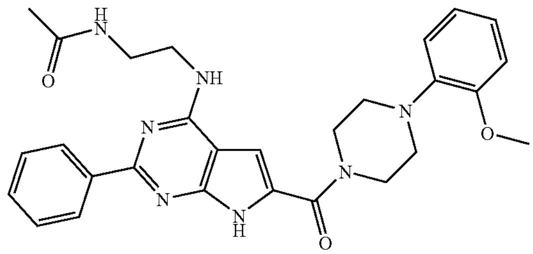 | 513.60 |
| 26.213 | 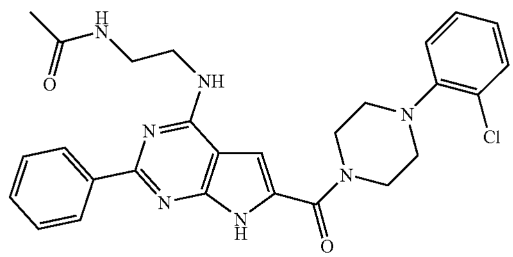 | 518.02 |
| 26.214 | 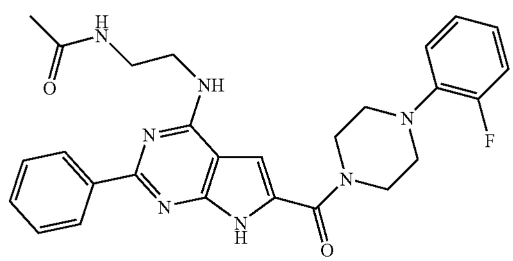 | 501.57 |
| 26.215 | 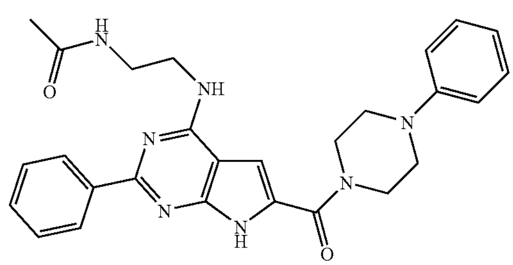 | 483.58 |
| 26.216 | 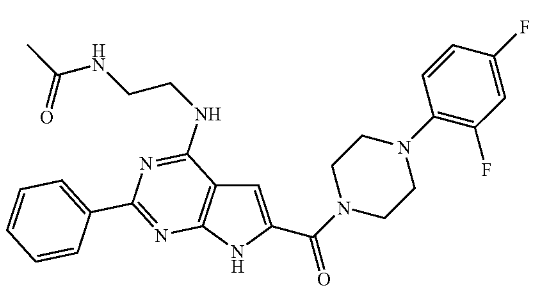 | 519.56 |

TABLE 4-continued
A$_{2B}$ antagonists 26.1-26.250.
| Comp. # | Structure | MW |
|---|---|---|
| 26.217 | 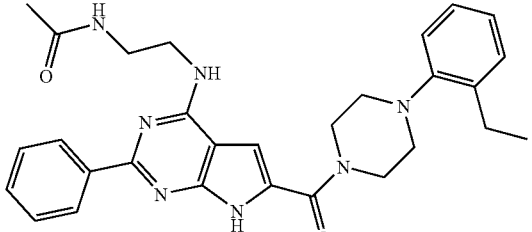 | 511.63 |
| 26.218 | 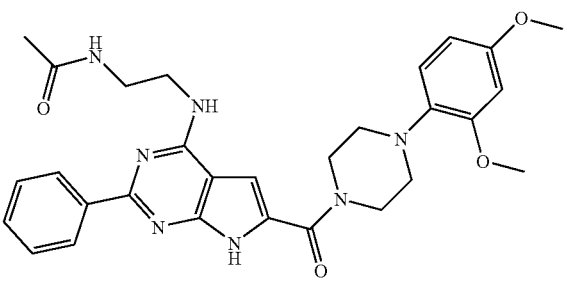 | 543.63 |
| 26.219 | 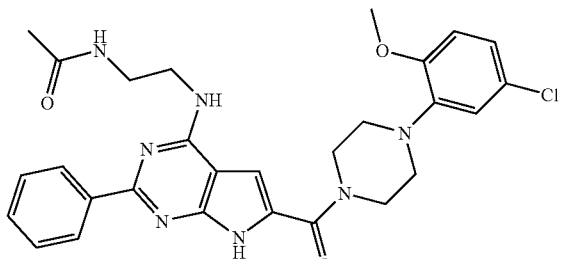 | 548.05 |
| 26.220 | 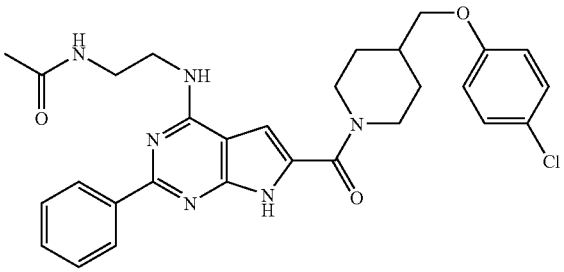 | 547.06 |
| 26.221 | 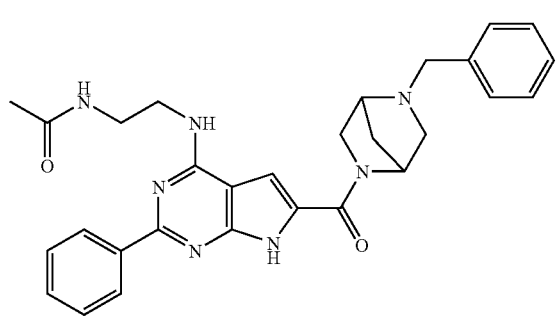 | 509.62 |

TABLE 4-continued
A$_{2B}$ antagonists 26.1-26.250.
| Comp. # | Structure | MW |
|---|---|---|
| 26.222 | 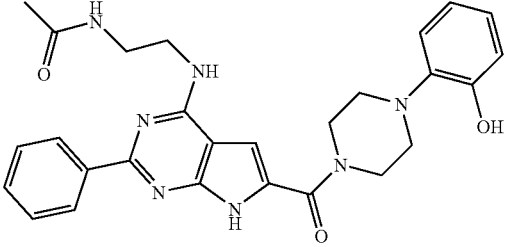 | 499.58 |
| 26.223 | 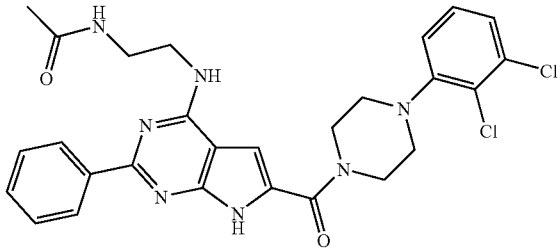 | 552.47 |
| 26.224 | 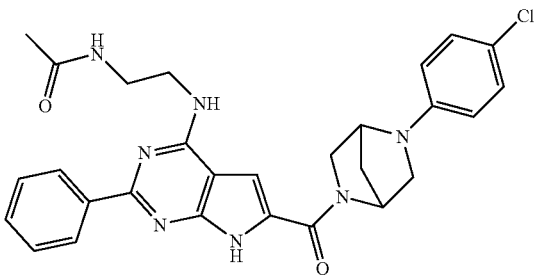 | 530.03 |
| 26.225 | 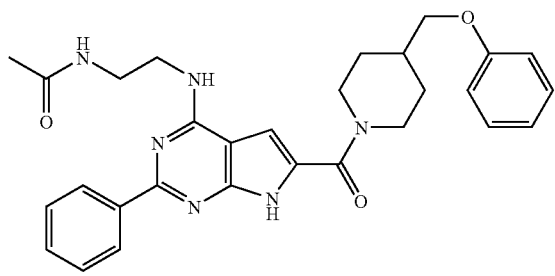 | 512.62 |
| 25.226 | 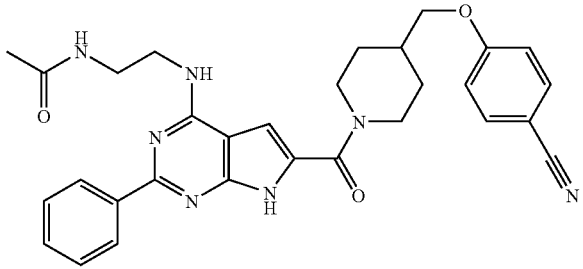 | 537.63 |

TABLE 4-continued

A$_{2B}$ antagonists 26.1-26.250.

| Comp. # | Structure | MW |
|---|---|---|
| 26.227 | 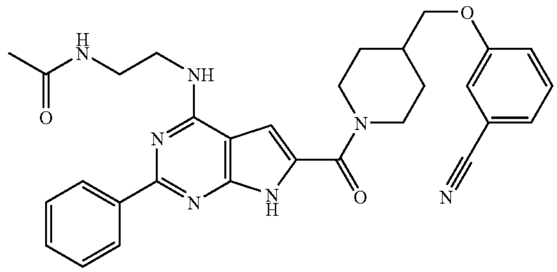 | 537.63 |
| 26.228 | 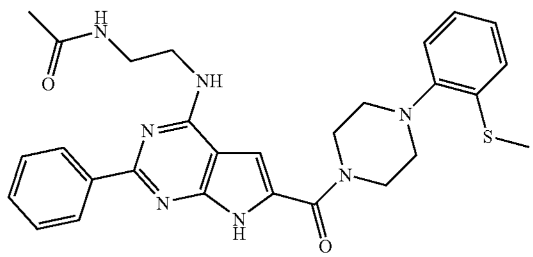 | 529.67 |
| 26.229 | 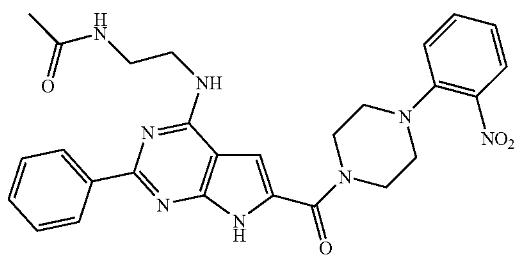 | 528.58 |
| 26.230 | 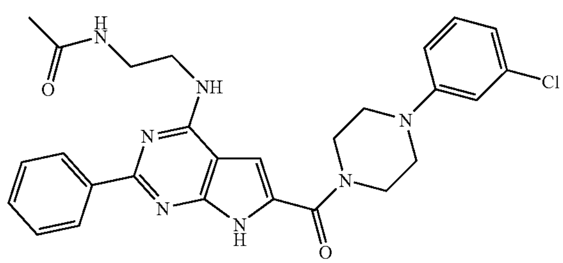 | 518.02 |
| 26.231 | 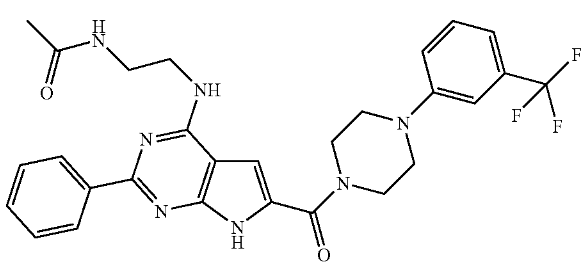 | 551.58 |

TABLE 4-continued
A$_{2B}$ antagonists 26.1-26.250.
| Comp. # | Structure | MW |
|---|---|---|
| 26.232 | 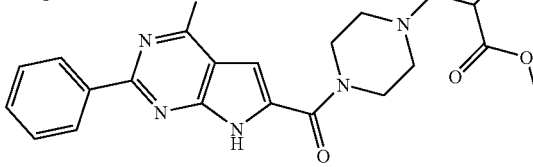 | 541.61 |
| 26.233 | 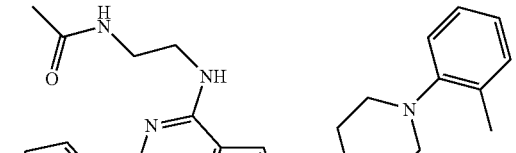 | 497.60 |
| 26.234 | 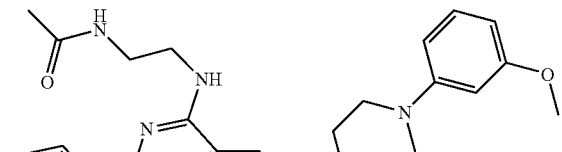 | 513.60 |
| 26.235 | 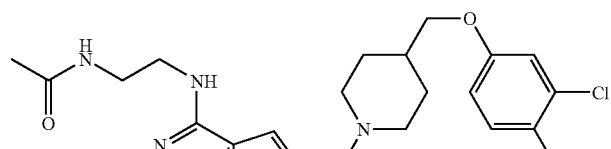 | 581.51 |
| 26.236 | 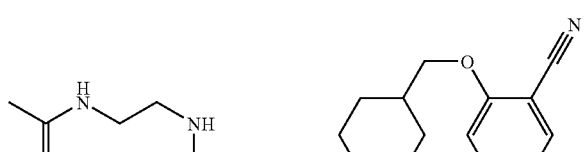 | 537.63 |

TABLE 4-continued

A$_{2B}$ antagonists 26.1-26.250.

| Comp. # | Structure | MW |
|---|---|---|
| 26.237 | 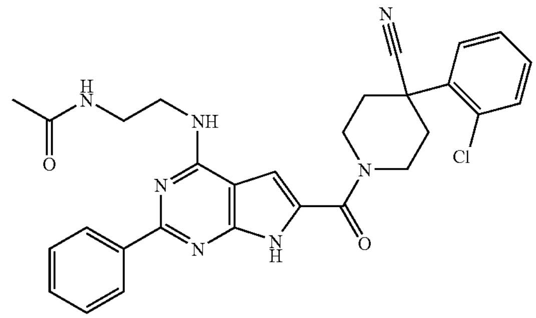 | 542.05 |
| 26.238 | 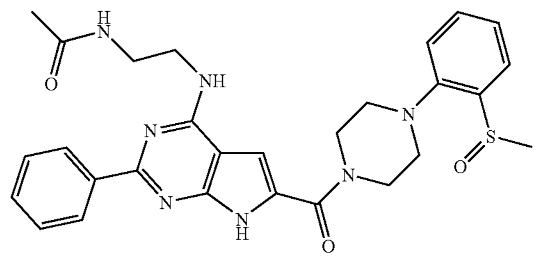 | 545.67 |
| 26.239 | 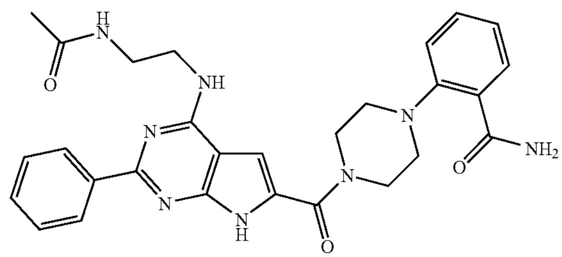 | 526.60 |
| 26.240 | 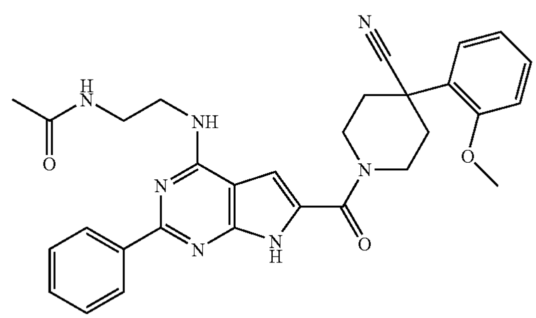 | 537.63 |
| 26.241 | 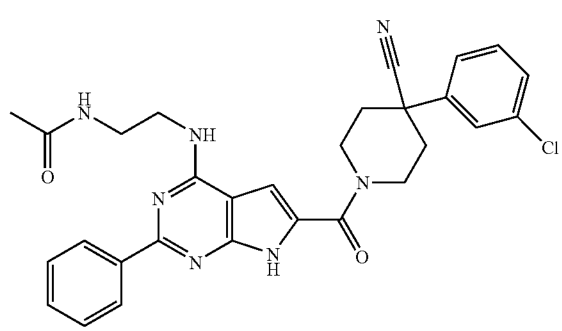 | 542.05 |

TABLE 4-continued

A$_{2B}$ antagonists 26.1-26.250.

| Comp. # | Structure | MW |
|---|---|---|
| 26.242 | 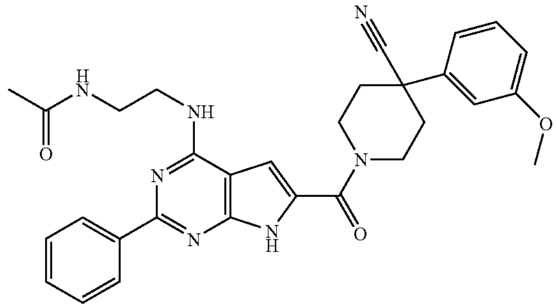 | 537.63 |
| 26.243 | 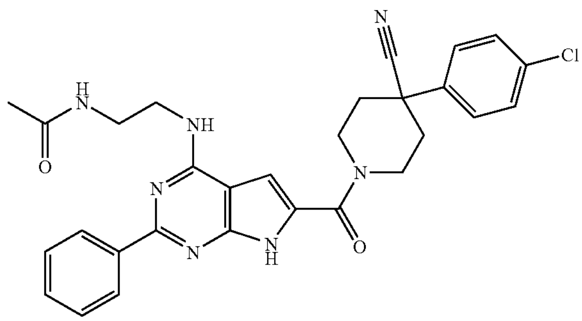 | 542.05 |
| 26.244 | 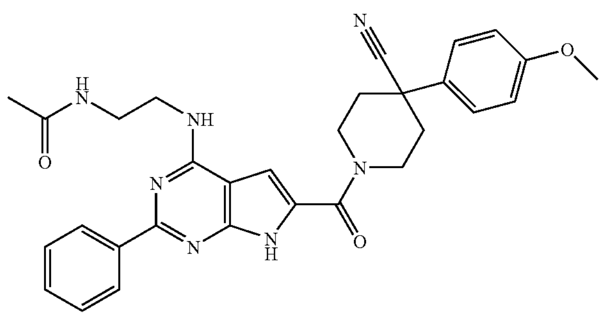 | 537.63 |
| 26.245 | 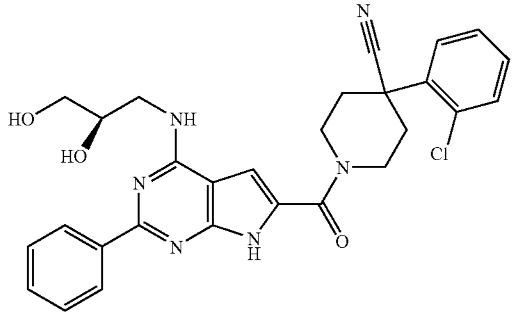 | 531.02 |

TABLE 4-continued
A$_{2B}$ antagonists 26.1-26.250.
| Comp. # | Structure | MW |
|---|---|---|
| 26.246 | 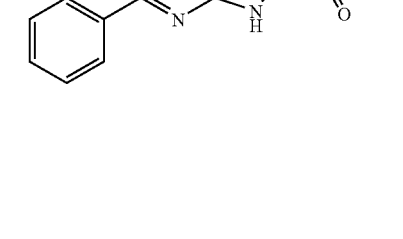 | 549.08 |
| 26.247 | 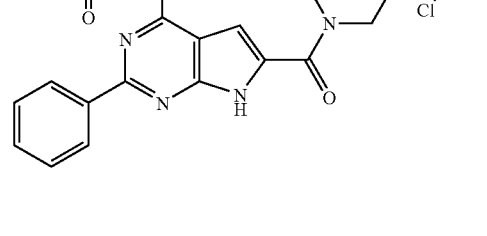 | 513.99 |
| 26.248 | 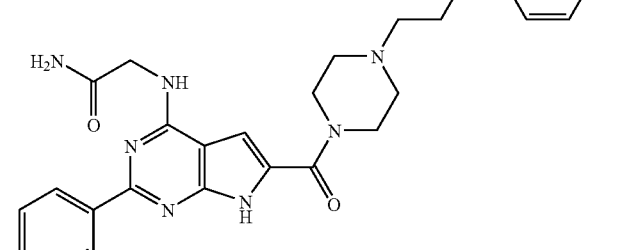 | 532.05 |
| 26.249 | 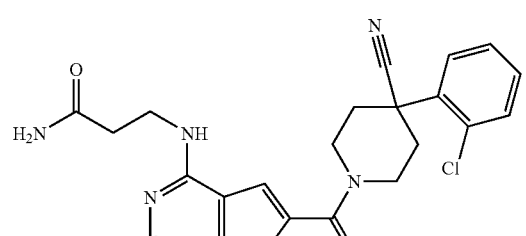 | 528.02 |

TABLE 4-continued

A$_{2B}$ antagonists 26.1-26.250.

| Comp. # | Structure | MW |
|---|---|---|
| 26.250 | 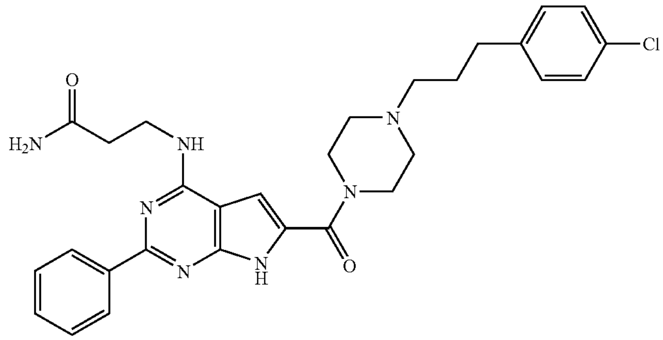 | 546.08 |

7-Benzenesulfonyl-4-chloro-2-phenyl-7H-pyrrolo[2,3-d]pyrimidine (24)

To a suspension of sodium hydride (780 mg of a 60% oil suspension, 19.5 mmol) in dry DMF (20 mL), cooled by an ice/water bath, under nitrogen, is added a solution of the pyrrolopyrimidine 23 (2.00 g, 7.52 mmol) in DMF (10 mL) over 5 min. After 15 min, benzenesulfonyl chloride (1.2 mL, 9.40 mmol) is added, then the cooling bath is removed. After 4 h, the reaction mixture is poured into a mixture of ice and sat. NaHCO$_3$ sol., the precipitated solid is filtered off and triturated with acetone (3×) and methanol (2×), yielding 2.37 g of a beige solid. This solid contains approx. 10 mol-% DMF (based on that 83% yield) and can be used in the next step; a pure sample can be obtained by chromatography on silica gel using acetone as eluent. $^1$H-NMR (CDCl$_3$): δ 6.70 (d, J=4.2 Hz, 1H), 7.47-7.68 (m, 6H), 7.76 (d, J=4.2 Hz, 1H), 8.24-8.32 (m, 2H), 8.48-8.56 (m, 2H); IR (solid): ν=3146 cm$^{-1}$, 1585, 1539, 1506, 1450, 1417, 1386, 1370, 1186, 1176, 1154, 1111, 1015, 919, 726, 683, 616, 607; MS (ES): 372/370 (MH$^+$); mp=226-227° C. C$_{18}$H$_{12}$ClN$_3$O$_2$S (369.83): calcd. C, 58.46; H, 3.27; N, 11.36; Cl, 9.59. Found C, 58.17; H, 3.24; N, 11.36; Cl, 9.48.

7-Benzenesulfonyl-4-chloro-2-phenyl-7H-pyrrolo[2,3-d]pyrimidin-6-yl)-morpholin-4-yl-methanone (25.1)

To a solution of the N-sulfonyl compound 24 (100 mg, 0.270 mmol) in dry THF (10 mL), cooled by dry ice/acetone, is added LDA-THF (270 μL, 1.5M solution in cyclohexane, 0.405 mmol). After 60 min, morpholinecarbamoyl chloride (47 μL, 0.405 mmol) is added. After 1.5 h, the reaction is quenched by adding sat. NH$_4$Cl solution, the mixture is extracted with EtOAc (3×15 mL), combined EtOAc layers are washed with water and brine and dried over MgSO$_4$. Chromatography on silica gel yields 59 mg (0.12 mmol, 45%) of the title compound as white solid, mp. 259-260° C. MS (ES): m/z 483.0/485.0 (100) [MH$^+$]. t$_R$ (method A)=10.8 min.

7-Benzenesulfonyl-4-chloro-2-phenyl-7H-pyrrolo[2,3-d]pyrimidine-6-carboxylic acid (4-phenoxyphenyl)-amide (25.2)

Following the above procedure, 25.2 was obtained in 37% yield as white solid, mp. 250-253° C. MS (ES): m/z 581.0/583.0 (100) [MH$^+$]. t$_R$(method A)=12.8 min.

Lithium 7-benzenesulfonyl-4-chloro-2-phenyl-7H-pyrrolo[2,3-d]pyrimidine-6-carboxylate (27)

To a solution of the N-sulfonyl compound 24 (1.504 g, 4.07 mmol) in dry THF (150 mL), cooled by dry ice/acetone, is added LDA-THF (3.8 mL, 1.5M solution in cyclohexane, 5.7 mmol). After 45 min, carbon dioxide is bubbled into the solution for 5 min, then the cooling bath is removed. When the solution has reached ambient temp., the solvents are evaporated, yielding 1.73 g of the salt 27 [containing (iPr)$_2$NCO$_2$Li] as pale yellow solid. The salt is used without purification in the next step. $^1$H-NMR (D$_6$-DMSO): δ=6.44 (s, 1H), 7.50-7.75 (m, 6H), 8.33-8.40 (m, 2H), 8.53 (dd, J=8.0, 1.6 Hz, 2H).

4-(2-Acetylaminoethylamino)-7-benzenesulfonyl-2-phenyl-7H-pyrrolo[2,3-d]-pyrimidine-6-carboxylic acid (28a)

A solution of the lithium salt 3 (2.02 g, ≈4.8 mmol) and N-acetylethylenediamine (4.91 g, 48.1 mmol) in dry DMSO (20 mL) is heated under nitrogen to 80° C. for 4.5 h. DMSO and the excess amine are evaporated, 2N NaOH (30 mL) is added, and the mixture is extracted with EtOAc (4×30 mL). The aqueous layer is acidified to pH≈3-4 with aq. HCl (first with 12N HCl until some solid has precipitated, then with 2N HCl until pH 3-4 is reached and no more solid precipitates). The beige solid is filtered off and dried, giving 1.59 g of 28a, which is used without further purification in the next step. LC/MS analysis of this material: 83% of 28a, 10% of 30a (desulfonylated material), 6% of desacetyl-28a. $^1$H-NMR (D$_6$-DMSO): δ=1.78 (s, 3H), 3.3 (m, 2H; hidden under water peak), 3.62 (m, 2H), 7.35 (s, 1H), 7.5-7.6 (m, 3H), 7.6-7.8 (m, 3H), 8.0-8.1 (brm, 2H, NH), 8.34 (d, J=8.6 Hz, 2H), 8.40-8.50 (m, 2H). MS (ES): 480 (MH$^+$)

7-Benzenesulfonyl-4-(carbamoylmethylamino)-2-phenyl-7H-pyrrolo[2,3-d]-pyrimidine-6-carboxylic acid (28b)

Prepared according to the procedure for 28a. MS (ES): m/z 451.7 (100) [MH$^+$]. t$_R$ (method A)=7.1 min.

4-(2-Acetylaminoethylamino)-2-phenyl-7H-pyrrolo[2,3-d]pyrimidine-6-carboxylic acid (30a)

A solution of sodium hydroxide in methanol (65 mL, 5M, 325 mmol) is added to a solution of the pyrrolopyrimidine 28a (6.3 g, 13.1 mmol) in methanol (35 mL). After 1.5 h, MeOH is evaporated. The residue is dissolved in 2N NaOH (200 mL) and extracted with $Et_2O$ (2×30 mL). The aqueous layer is acidified to pH≈3-4 with aq. HCl (first with 12N HCl until some solid has precipitated, then with 2N HCl until pH 3-4 is reached and no more solid precipitates). The beige solid is filtered off and dried, giving 4.345 g (12.8 mmol, 98% yield) of 30a. LC/MS analysis of this material: 95% of 30a, 3% of desacetyl-30a. This material is used without further purification. $^1$H-NMR ($D_6$-DMSO): δ=1.81 (s, 3H), 3.3 (m, 2H; hidden under water peak), 3.62 (m, 2H), 7.29 (s, 1H), 7.44-7.50 (m, 3H), 8.0-8.1 (brm, 2H, NH), 8.40-8.45 (m, 2H). $^1$H NMR ($CDCl_3/CD_3OD$, 200 MHz): δ=1.82 (s, 3H), 3.53 ($m_c$, 2H), 3.87 (t, J=5.7 Hz, 2H), 7.24 (s, 1H), 7.44-7.50 (m, 3H), 8.33-8.40 (m, 2H). $^{13}$C NMR ($d_6$-DMSO, 50.3 MHz, DEPT135): δ=22.66 (+), 38.45 (−), 39.53 (−), 102.22 ($C_{quart}$), 106.11 ($C_{quart}$), 124.94 (+), 127.65 (+, 2C), 128.09 (+, 2C), 129.53 ($C_{quart}$), 138.98 (+), 152.02 ($C_{quart}$), 157.15 ($C_{quart}$), 159.21 ($C_{quart}$), 162.14 ($C_{quart}$), 169.47 ($C_{quart}$). MS (ES): m/z 339.9 (100) [$MH^+$]. $t_R$(method A)=5.0 min.

4-(Carbamoylmethylamino)-2-phenyl-7H-pyrrolo[2,3-d]pyrimidine-6-carboxylic acid (30b): Prepared according to the procedure for 30a. MS (ES)

m/z 311.9 (100) [$MH^+$]. $t_R$ (method A)=4.6 min.

4-(2-Acetylaminoethylamino)-2-phenyl-7H-pyrrolo[2,3-d]pyrimidine-6-carboxylic acid 2,5-dioxopyrrolidin-1-yl ester ("succinimide") (32)

Acid 30a (3.0 g, 8.84 mmol), EDC (5.1 g, 26.0 mmol), hydroxybenzotriazole hydrate (1.35 g, 8.84 mmol) and hydroxysuccinimide (3.1 g, 26 mmol) were dissolved in DMF (70 mL). 4-Dimethylamino-pyridine (216 mg, 0.2 mmol) was added and the reaction was stirred at room temperature. After 19 h, the reaction mixture was partitioned between EtOAc and water. The layers were separated and the aqueous layer was re-extracted with EtOAc (3×). The combined EtOAc extracted are washed with water (2×) and brine, dried over $MgSO_4$, filtered and concentrated to yield a yellow foam. The solid was triturated twice, once with $Et_2O$ and once with DCM, to yield 2.92 g of a pale yellow solid (76%). An analytical sample was obtained by chromatography on silica gel eluting with $CHCl_3$→15% iPrOH in $CHCl_3$, mp. 230-234° C. (decomp.). $C_{21}H_{20}N_6O_5$ (436.4): calcd. C, 57.79; H, 4.62; N 19.26. Found C 58.06; H, 4.81; N, 18.99. $^1$H NMR ($d_6$-DMSO, 200 MHz): δ=1.78 (s, 3H), 2.87 (s, 4H), 3.35 (m, 2H), 3.60 (m, 2H), 7.45 (m, 3H), 7.69 (s, 1H), 8.03 (brs, 1H), 8.25 (brs, 1H), 8.42 (m, 2H). MS (ES): 436.7 ($MH^+$). $t_R$ (method A)=6.6 min.

General Procedure for the synthesis of amides 26 from succinimide 32: A solution of succinimide 32 (52 mg, 0.12 mmol), amine 29 or its hydrochloride salt (0.14 mmol) and triethylamine (22 μL, 0.16 mmol if free amine is used, twice the amount if the hydrochloride salt is used) in dry DMF (2 mL) is stirred at ambient temperature for 24-48 h. The solvent is then evaporated, the residue is partitioned between EtOAc (15 mL) and water (10 mL), and the aqueous layer is extracted with more EtOAc (3×15 mL). The combined organic layers are washed with 2N NaOH, water (2×) and brine, dried over $MgSO_4$, filtered and concentrated. The crude material is purified by chromatography followed by trituration or crystallization.

General Procedure for the synthesis of amides 26 from acid 30a: TBTU (48 mg, 0.15 mmol) is added to a solution of acid 30a (41 mg, 0.12 mmol) in DMF (1.5 mL), cooled by ice/water. After 30 min, amine 29 or its hydrochloride salt (0.14 mmol) and triethylamine (22 μL, 0.16 mmol if free amine is used, twice the amount if the hydrochloride salt is used) are added, the cooling bath is removed, and the reaction mixture is stirred at ambient temperature until TLC indicates complete consumption of the acid. DMF is then evaporated, the residue is partitioned between EtOAc (15 mL) and water (10 mL), and the aqueous layer is extracted with more EtOAc (3×15 mL). The combined organic layers are washed with 2N NaOH, water (2×) and brine, dried over $MgSO_4$, filtered and concentrated. The crude material is purified by chromatography followed by trituration or crystallization.

N-{2-[6-(Morpholine-4-carbonyl)-2-phenyl-7H-pyrrolo[2,3-d]pyrimidin-4-ylamino]-ethyl}-acetamide (26.1)

Following the general procedure for C-4 chloride displacement, 26.1 was prepared from 25.1 as an off-white solid, mp 250° C. MS (ES): m/z 409.2 (100) [$MH^+$]. $^1$H NMR ($CDCl_3$, 200 MHz): δ=1.82 (s, 3H), 3.59 (q, J=5.4 Hz, 2H), 3.72-3.80 (m, 4H), 3.83-3.92 (m, 6H), 6.08 (brs, 1H), 6.68 (s, 1H), 6.80 (brs, 1H), 7.43-7.49 (m, 3H), 8.38-8.45 (m, 2H), 9.81 (brs, 1H). $t_R$ (method A)=5.2 min.

4-(2-Acetylaminoethylamino)-2-phenyl-7H-pyrrolo[2,3-d]pyrimidine-6-carboxylic acid (4-phenoxyphenyl)-amide (26.2)

Following the general procedure for C-4 chloride displacement, 26.2 was prepared from 26.1 as a white solid, mp 250-257° C. (decomp.). MS (ES): m/z 506.9 (100) [$MH^+$]. $^1$H NMR (DMSO-$D_6$, 200 MHz): δ=1.79 (s, 3H), 3.40 ($m_c$, 2H), 3.65 (q, J=6.2 Hz, 2H), 6.89-7.13 (m, 5H), 7.29-7.48 (m, 6H), 7.76 (d, J=9.2 Hz, 2H), 7.88 (brs, 1H), 8.04 (brs, 1H), 8.37-8.44 (m, 2H), 10.16 (s, 1H), 12.13 (s, 1H). $t_R$ (method A)=8.5 min.

N-(2-{2-Phenyl-6-[4-(3-phenylallyl)-piperazine-1-carbonyl]-7H-pyrrolo[2,3-d]-pyrimidin-4-ylamino}-ethyl)-acetamide (26.3)

off-white solid. MS (ES): m/z 524.2 (10) [$MH^+$], 408.2 (100) [$MH^+$-$PhC_3H_3$]. $^1$H NMR ($CDCl_3$, 200 MHz): δ=1.81 (s, 3H), 2.61 ($m_c$, 4H), 3.22 (d, J=6.6 Hz, 2H), 3.60 (q, J=5.2 Hz, 2H), 3.88-3.98 (m, 6H), 5.87 (brs, 1H), 6.28 (dt, J=15.7, 6.6 Hz, 1H), 6.54 (d, J=15.7 Hz, 1H), 6.66 (s, 1H), 6.80 (brs, 1H), 7.20-7.50 (m, 8H), 8.40-8.45 (m, 2H), 9.45 (brs, 1H). $t_R$ (method A) 6.0 min.

N-{2-[6-(4-Hydroxy-4-isopropylpiperidine-1-carbonyl)-2-phenyl-7H-pyrrolo[2,3-d]-pyrimidin-4-ylamino]-ethyl}-acetamide (26.4)

white solid, mp 140-145° C. (decomp.). MS (ES): m/z 465.2 (100) [$MH^+$]. IR (film): ν=3332 $cm^{-1}$, 2964, 2877, 1654, 1590, 1574, 1532, 1438, 1387, 1327, 1278, 1255, 1170, 1071, 1026, 936, 776, 750, 706. $^1$H NMR ($CD_3OD$, 200 MHz): δ=0.96 (d, J=7.0 Hz, 6H), 1.55-1.70 (m, 5H), 1.85 (s, 3H), 3.40-3.56 (m, 4H), 3.83 (t, J=6.0 Hz, 2H), 4.37 (brd, J=12.0 Hz, 2H), 6.92 (s, 1H), 7.40-7.46 (m, 3H), 8.37-8.45 (m, 2H). $t_R$ (method A)=5.8 min.

N-(2-{2-Phenyl-6-[4-(3-phenylpropyl)-piperazine-1-carbonyl]-7H-pyrrolo[2,3-d]-pyrimidin-4-ylamino}-ethyl)-acetamide (26.5)

Mp 198-200° C. MS (ES): m/z 526.1 (51) [MH$^+$]. IR (film): ν=3295 cm$^{-1}$, 3062, 3024, 2929, 2857, 1654, 1589, 1573, 1530, 1454, 1432, 1387, 1328, 1297, 1170, 1132, 1027, 1001, 776, 749, 703. $^1$H NMR (CDCl$_3$, 400 MHz): δ=1.79 (s, 3H), 1.83 (quint, J=7.4 Hz, 2H), 2.39 (t, J=7.6 Hz, 2H), 2.47 (m$_c$, 4H), 2.65 (t, J=7.6 Hz, 2H), 3.52-3.56 (m, 2H), 3.80-3.90 (m, 6H), 6.19 (brs, 1H), 6.67 (s, 1H), 7.01 (brs, 1H), 7.16-7.42 (m, 8H), 8.37-8.40 (m, 2H), 10.12 (brs, 1H). $^{13}$C NMR (CDCl$_3$/CD$_3$OD, 80.3 MHz, additional DEPT135): δ=22.97 (+), 28.31 (−), 33.50 (−), 40.85 (−), 41.19 (−), 41.35 (−), 53.01 (−), 57.66 (−), 101.95 (2C, +, $C_{quart}$), 125.85 (+), 126.35 ($C_{quart}$), 127.96 (+), 128.33 (+), 129.91 (+), 138.64 ($C_{quart}$), 141.84 ($C_{quart}$), 150.95 ($C_{quart}$), 157.59 ($C_{quart}$), 160.07 ($C_{quart}$), 161.49 ($C_{quart}$), 171.42 ($C_{quart}$). $t_R$ (method A)=4.4 min. $C_{30}H_{35}N_7O_2$ (525.66): calcd. C, 68.55; H, 6.71; N, 18.65. Found C, 68.93; H, 6.78; N, 18.26.

N-(2-{6-[4-(4-Chlorophenyl)-4-hydroxypiperidine-1-carbonyl]-2-phenyl-7H-pyrrolo[2,3-d]pyrimidin-4-ylamino}-ethyl)-acetamide (26.6)

pale yellow solid. MS (ES): m/z 533/535 (100/37) [MH$^+$]. IR (film): ν=3354 cm$^{-1}$, 3062, 2928, 2869, 1653, 1589, 1573, 1529, 1493, 1437, 1388, 1327, 1275, 1208, 1170, 1095, 1026, 1012, 934, 776, 749, 706. $^1$H NMR (CD$_3$OD, 200 MHz): δ=1.82 (brd, J=13.0 Hz, 2H), 1.85 (s, 3H), 2.11 (dt, J=13.0, 3.8 Hz, 2H), 3.42-3.62 (m, 4H), 3.83 (t, J=6.1 Hz, 2H), 4.48 (brd, J=13.6 Hz, 2H), 6.97 (s, 1H), 7.30-7.54 (m, 7H), 8.38-8.45 (m, 2H). $t_R$ (method A)=7.0 min.

N-{2-[6-(4-Hydroxy-4-phenylpiperidine-1-carbonyl)-2-phenyl-7H-pyrrolo[2,3-d]pyrimidin-4-ylamino]-ethyl}-acetamide (26.7)

off-white solid, mp 158-162° C. (decomp.). MS (ES): m/z 499.0 (100) [MH$^+$]. IR (film): ν=3308 cm$^{-1}$, 3062, 2948, 2925, 2853, 1653, 1591, 1575, 1534, 1447, 1385, 1328, 1277, 1172, 1108, 1037, 1016, 950, 802, 776, 759, 702. $^1$H NMR (CD$_3$OD, 200 MHz): δ=1.82 (brd, J=13.0 Hz, 2H), 1.84 (s, 3H), 2.11 (dt, J=13.0, 3.8 Hz, 2H), 3.41-3.65 (m, 4H), 3.82 (t, J=5.8 Hz, 2H), 4.46 (brd, J=11.8 Hz, 2H), 6.96 (s, 1H), 7.18-7.54 (m, 8H), 8.38-8.45 (m, 2H). $t_R$ (method A)=6.7 min.

N-[2-[6-(4-Benzyl-4-hydroxypiperidine-1-carbonyl)-2-phenyl-7H-pyrrolo[2,3-d]pyrimidin-4-ylamino]-ethyl]-acetamide (26.8)

off-white solid, mp 140-145° C. (decomp.). MS (ES): m/z 512.9 (100) [MH$^+$]. IR (film): ν=3281 cm$^{-1}$, 3065, 2922, 2852, 1654, 1589, 1574, 1532, 1432, 1385, 1327, 1272, 1170, 1084, 1026, 992, 951, 803, 776, 703. $^1$H NMR (CD$_3$OD, 200 MHz): δ=1.5-01.75 (m, 4H), 1.85 (s, 3H), 2.80 (s, 2H), 3.30-3.56 (m, 4H), 3.82 (t, J=6.2 Hz, 2H), 4.30 (brd, J=13.2 Hz, 2H), 6.89 (s, 1H), 7.18-7.35 (m, 5H), 7.35-7.55 (m, 3H), 8.38-8.45 (m, 2H). $t_R$ (method A)=6.9 min.

2-{6-[4-(4-Chlorophenyl)-4-hydroxypiperidine-1-carbonyl]-2-phenyl-7H-pyrrolo[2,3-d]pyrimidin-4-ylamino}-acetamide (26.9)

off-white solid, mp 200-205° C. (decomp.). MS (ES): m/z 504.8/506.9 (100/37) [MH$^+$]. IR (film): ν=3309 cm$^{-1}$, 2954, 2926, 2853, 1684, 1613, 1569, 1532, 1455, 1445, 1430, 1383, 1326, 1265, 1203, 1094, 1010, 950, 911, 824, 760, 737, 705. $^1$H NMR (CD$_3$OD, 200 MHz): δ=1.80-1.90 (m, 2H), 2.08-2.21 (m, 2H), 3.50-3.65 (m, 2H), 4.29 (s, 2H), 4.42-4.55 (m, 2H), 7.01 (s, 1H), 7.32-7.43 (m, 3H), 7.53 (d, J=8.4 Hz, 2H), 8.38-8.45 (m, 2H). $t_R$ (method A)=7.1 min.

N-(2-{6-[4-Hydroxy-4-(3-trifluoromethylphenyl)-piperidine-1-carbonyl]-2-phenyl-7H-pyrrolo[2,3-d]pyrimidin-4-ylamino}-ethyl)-acetamide (26.10)

off-white solid, mp 145-150° C. MS (ES): m/z 566.9 (100) [MH$^+$]. IR (film): ν=3284 cm$^{-1}$, 2933, 1654, 1591, 1574, 1533, 1435, 1387, 1329, 1278, 1165, 1124, 1075, 1026, 931, 803, 776, 751, 703. $^1$H NMR (CD$_3$OD, 200 MHz): δ=1.82 (brd, J=13.0 Hz, 2H), 1.84 (s, 3H), 2.15 (dt, J=13.0, 3.8 Hz, 2H), 3.42-3.70 (m, 4H), 3.82 (t, J=6.2 Hz, 2H), 4.47 (brd, J=12.8 Hz, 2H), 6.97 (s, 1H), 7.40-7.50 (m, 3H), 7.50-7.60 (m, 2H), 7.70-7.80 (m, 1H), 7.88 (s, 1H), 8.37-8.45 (m, 2H). $t_R$ (method A)=7.8 min.

N-{2-[6-(4-Phenethylpiperazine-1-carbonyl)-2-phenyl-7H-pyrrolo[2,3-d]pyrimidin-4-ylamino]-ethyl}-acetamide (26.11)

white solid, mp 226-228° C. MS (ES): m/z 511.8 (15) [MH$^+$], 407.8 (48) [MH$^+$–PhCH=CH$_2$]. IR (film): ν=3295 cm$^{-1}$, 3066, 3027, 2934, 2809, 1654, 1598, 1574, 1533, 1453, 1432, 1387, 1327, 1297, 1170, 1132, 1029, 1000, 776, 749, 703. $^1$H NMR (CD$_3$OD/CDCl$_3$, 200 MHz): δ=1.84 (s, 3H), 2.52-2.78 (m, 6H), 2.78-2.90 (m, 2H), 3.52-3.60 (m, 2H), 3.80-4.00 (m, 6H), 6.19 (brs, 1H), 6.92 (s, 1H), 7.1-67.38 (m, 5H), 7.38-7.50 (m, 3H), 8.35-8.40 (m, 2H). $t_R$ (method A)=4.5 min.

N-(2-{6-[4-(3-Morpholin-4-ylpropyl)-piperazine-1-carbonyl]-2-phenyl-7H-pyrrolo-[2,3-d]pyrimidin-4-ylamino}-ethyl)-acetamide (26.12)

white solid, mp 225-230° C. (decomp.). MS (ES): m/z 535.3 (10) [MH$^+$], 322.0 (52) [MH$^+$-1-(3-morpholin-4-ylpropyl)piperazine]. $t_R$ (method B)=5.3 min.

N-(2-{6-[4-(4-Chlorophenyl)-3,6-dihydro-2H-pyridine-1-carbonyl]-2-phenyl-7H-pyrrolo[2,3-d]pyrimidin-4-ylamino]-ethyl}-acetamide (26.13)

beige solid, mp 172-175° C. MS (ES): m/z 515.2/517.3 (50/20) [MH$^+$]. $t_R$ (method A)=8.9 min.

N-{2-[6-(4-Benzylpiperazine-1-carbonyl)-2-phenyl-7H-pyrrolo[2,3-d]pyrimidin-4-ylamino]-ethyl}-acetamide (26.14)

off-white solid, mp 235-240° C. (decomp.). MS (ES): m/z 497.9 (10) [MH$^+$], 407.9 (100) [MH$^+$-PhCH$_2^+$]. $t_R$ (method A)=4.3 min.

2-{2-Phenyl-6-[4-(3-phenylpropyl)-piperazine-1-carbonyl]-7H-pyrrolo[2,3-d]-pyrimidin-4-ylamino}-acetamide (26.15)

white solid, mp 213-217° C. MS (ES): m/z 498.0 (100) [MH$^+$]. t$_R$ (method A)=4.3 min.

N-[2-(6-{4-[2-(4-Chlorophenoxy)-ethyl]-piperazine-1-carbonyl}-2-phenyl-7H-pyrrolo[2,3-d]pyrimidin-4-ylamino)-ethyl]-acetamide (26.16)

off-white solid, mp 227-228° C. MS (ES): m/z 561.9/563.9 (50/22) [MH$^+$], 321.9 (85) [MH$^+$-2-(4-chlorophenoxy)ethylpiperazine]. t$_R$ (method A)=5.0 min.

4-(2-Acetylaminoethylamino)-2-phenyl-7H-pyrrolo[2,3-d]pyrimidine-6-carboxylic acid bicyclo[2.2.1]hept-2-ylamide (26.17)

off-white solid, mp 280-285° C. (decomp.). MS (ES): m/z 432.9 (100) [MH$^+$]. t$_R$ (method A)=7.3 min.

N-(2-{6-[4-(4-Fluorophenyl)-4-hydroxypiperidine-1-carbonyl]-2-phenyl-7H-pyrrolo[2,3-d]pyrimidin-4-ylamino}-ethyl)-acetamide (26.18)

pale yellow solid, mp 150-153° C. MS (ES): m/z 516.9 (100) [MH$^+$]. t$_R$ (method A)=6.9 min.

N-{2-[6-(4-Cyano-4-phenylpiperidine-1-carbonyl)-2-phenyl-7H-pyrrolo[2,3-d]-pyrimidin-4-ylamino]-ethyl}-acetamide (26.19)

off-white solid, mp 150-155° C. (decomp.). MS (ES): m/z 508.0 (100) [MH$^+$]. t$_R$ (method A)=7.7 min.

4-(2-Acetylaminoethylamino)-2-phenyl-7H-pyrrolo[2,3-d]pyrimidine-6-carboxylic acid (3-phenoxyphenyl)-amide (26.20)

pale yellow solid, mp 140-142° C. MS (ES): m/z 506.9 (100) [MH$^+$]. t$_R$ (method A)=8.8 min.

N-(2-{2-Phenyl-6-[4-(3-phenylprop-2-ynyl)-piperazine-1-carbonyl]-7H-pyrrolo [2,3-d]pyrimidin-4-ylamino}-ethyl)-acetamide (26.21)

off-white solid, mp 213-215° C. MS (ES): m/z 521.8 (100) [MH$^+$], 321.8 (100) [MH$^+$-(3-phenylprop-2-ynyl)piperazine]. IR (film): ν=3302 cm$^{-1}$, 3061, 3022, 2924, 2850, 1654, 1589, 1573, 1531, 1455, 1429, 1386, 1367, 1327, 1298, 1270, 1171, 1135, 1027, 999, 970, 803, 776, 755, 704, 691. $^1$H NMR (CDCl$_3$, 200 MHz): δ=1.80 (s, 3H), 2.73 (m, 4H), 3.50-3.61 (m, 4H), 3.80-4.00 (m, 6H), 5.93 (brs, 1H), 6.68 (s, 1H), 6.82 (brs, 1H), 7.25-7.35 (m, 3H), 7.35-7.55 (m, 5H), 8.37-8.47 (m, 2H), 9.63 (brs, 1H). $^{13}$C NMR (CDCl$_3$, 50.3 MHz, DEPT135): δ=23.03 (+), 29.66 (−), 40.60 (−), 41.70 (−), 47.67 (−), 51.93 (−), 83.63 (C$_{quart}$), 85.81 (C$_{quart}$), 101.97 (+), 102.20 (C$_{quart}$), 122.70 (C$_{quart}$), 126.40 (C$_{quart}$), 128.04 (+), 128.28 (+, 4C), 129.81 (+), 131.69 (+, 4C), 138.70 (C$_{quart}$), 151.13 (C$_{quart}$), 157.67 (C$_{quart}$), 159.89 (C$_{quart}$), 161.60 (C$_{quart}$), 171.17 (C$_{quart}$). t$_R$ (method A)=7.5 min.

N-{2-[6-(cis-3,5-Dimethylpiperazine-1-carbonyl)-2-phenyl-7H-pyrrolo[2,3-d]pyrimidin-4-ylamino]-ethyl}-acetamide (26.22)

off-white solid, mp 138-140° C. MS (ES): m/z 435.8 (100) [MH$^+$]. t$_R$ (method A)=3.1 min.

(4-Benzylpiperidin-1-yl)-(4-dimethylamino-2-phenyl-7H-pyrrolo[2,3-d]pyrimidin-6-yl)methanone (26.23)

pale yellow solid. MS (ES): m/z 439.8 (100) [MH$^+$]. t$_R$ (method A) 11.3 min.

N-(2-[6-[cis-3,5-Dimethyl-4-(3-phenylpropyl)-piperazine-1-carbonyl]-2-phenyl-7H-pyrrolo[2,3-d]pyrimidin-4-ylamino]-ethyl)-acetamide (26.24)

pale yellow solid, mp 86-89° C. MS (ES): m/z 554.0 (18) [MH$^+$], 321.9 (48) [MH$^+$-cis-3,5-dimethyl-4-(3-phenylpropyl)-piperazine]. t$_R$ (method A)=5.8 min.

N-{2-[6-(4,4-Diphenylpiperidine-1-carbonyl)-2-phenyl-7H-pyrrolo[2,3-d]pyrimidin-4-ylamino]-ethyl}-acetamide (26.25)

off-white solid, mp 254-256° C. MS (ES): m/z 558.9 (100) [MH$^+$]. t$_R$ (method A)=8.7 min.

N-{2-[6-(3,3-Diphenylpiperidine-1-carbonyl)-2-phenyl-7H-pyrrolo[2,3-d]pyrimidin-4-ylamino]-ethyl}-acetamide (26.26)

white solid, mp 156-159° C. (decomp.). MS (ES): m/z 558.9 (100) [MH$^+$]. t$_R$ (method A)=8.8 min.

N-{2-[6-(4-Methoxy-4-phenylpiperidine-1-carbonyl)-2-phenyl-7H-pyrrolo[2,3-d]-pyrimidin-4-ylamino]-ethyl}-acetamide (26.27)

white solid, mp 135-138° C. MS (ES): m/z 512.9 (100) [MH$^+$]. t$_R$ (method A)=7.7 min.

N-(2-{6-[4-(4-Fluorobenzyl)-piperidine-1-carbonyl]-2-phenyl-7H-pyrrolo[2,3-d]-pyrimidin-4-ylamino}-ethyl)-acetamide (26.28)

off-white solid, mp 283-284° C. (decomp.). MS (ES): m/z 515.0 (100) [MH$^+$]. IR (film): ν=3286 cm$^{-1}$, 3059, 2940, 2868, 1649, 1589, 1573, 1531, 1509, 1447, 1432, 1386, 1327, 1299, 1271, 1220, 1168, 1105, 1068, 954, 837, 803, 776, 732, 705. $^1$H NMR (CDCl$_3$/CD$_3$OD, 200 MHz): δ=1.20-1.40 (m, 2H), 1.75-1.90 (m, 3H), 1.78 (s, 3H), 2.58 (d, J=7.0 Hz, 2H), 2.99 (brs, 2H), 3.48-3.55 (m, 2H), 3.82-3.90 (m, 2H), 4.57 (brd, J=12.0 Hz, 2H), 6.78 (s, 1H), 6.94-7.16 (m, 4H), 7.44-7.52 (m, 3H), 7.80 (brs, 1H), 8.30-8.39 (m, 2H). t$_R$ (method A)=8.1 min.

N-[2-(6-{4-[(4-Fluorophenyl)-hydroxymethyl]-piperidine-1-carbonyl}-2-phenyl-7H-pyrrolo[2,3-d]pyrimidin-4-ylamino)-ethyl]-acetamide (26.29)

off-white solid, mp 135-145° C. (decomp.). MS (ES): m/z 530.8 (100) [MH$^+$]. t$_R$ (method A)=6.9 min.

N-(2-[{6-trans-2,5-Dimethyl-4-(3-phenylpropyl)-piperazine-1-carbonyl]-2-phenyl-7H-pyrrolo[2,3-d]pyrimidin-4-ylamino}-ethyl)-acetamide (26.30)

off-white solid, mp 98-100° C. MS (ES): m/z 553.9 (48) [MH$^+$], 321.8 (79) [MH$^+$-trans-2,5-dimethyl-4-(3-phenylpropyl)-piperazine]. t$_R$ (method A)=5.7 min.

N-{2-[6-(trans-2,5-Dimethylpiperazine-1-carbonyl)-2-phenyl-7H-pyrrolo[2,3-d]-pyrimidin-4-ylamino]-ethyl}-acetanide (26.31)

yellowish solid, mp 120-125° C. MS (ES): m/z 436.0 (18) [MH$^+$], 321.9 (100) [MH$^+$-trans-2,5-dimethylpiperazine]. t$_R$(method B)=8.8 min.

N-{2-[6-(4-Benzyl-cis-3,5-dimethylpiperazine-1-carbonyl)-2-phenyl-7H-pyrrolo[2,3-d]pyrimidin-4-ylamino]-ethyl}-acetamide (26.32):

white solid, mp 196-198° C. MS (ES): m/z 526.0 (29) [MH$^+$], 435.9 (100) [MH$^+$-PhCH$_2$+]. t$_R$ (method A)=5.1 min.

N-{2-[6-(cis-3,5-Dimethyl-4-phenethylpiperazine-1-carbonyl)-2-phenyl-7H-pyrrolo-[2,3-d]pyrimidin-4-ylamino]-ethyl}-acetamide (26.33)

off-white solid, mp 110-115° C. (decomp.). MS (ES): m/z 540.0 (82) [MH$^+$], 435.8 (73) [MH$^+$-PhCHCH$_2$], 321.8 (100) [MH$^+$-cis-3,5-dimethyl-4-phenethylpiperazine]. t$_R$ (method A)=5.4 min.

N-[2-(6-{4-[4-(2-Acetylaminoethylamino)-2-phenyl-7H-pyrrolo[2,3-d]pyrimidine-6-carbonyl]-trans-2,5-dimethylpiperazine-1-carbonyl}-2-phenyl-7H-pyrrolo[2,3-d]-pyrimidin-4-ylamino)-ethyl]-acetamide (26.34)

white solid. MS (ES): m/z 757.1 (10) [MH$^+$], 436.0 (9) [N-{2-[6-(cis-3,5-dimethyl-4-phenethylpiperazine-1-carbonyl)-2-phenyl-7H-pyrrolo[2,3-d]pyrimidin-4-ylamino]-ethyl}-acetamide-H$^+$], 379.1 (100) [MH$^+$—N-{2-[6-(cis-3,5-dimethyl-4-phenethylpiperazine-1-carbonyl)-2-phenyl-7H-pyrrolo[2,3-d]pyrimidin-4-ylamino]-ethyl}-acetamide]. t$_R$ (method A)=6.6 min.

N-{2-[2-Phenyl-6-(4-pyridin-2-yl-piperazine-1-carbonyl)-7H-pyrrolo[2,3-d]-pyrimidin-4-ylamino]-ethyl}-acetamide (26.35)

off-white solid, mp 223-226° C. (decomp.). MS (ES): m/z 484.9 (22) [MH$^+$], 321.9 (100) [MH$^+$-pyridin-2-yl-piperazine]. t$_R$ (method A)=4.8 min.

N-{2-[6-(3-Methyl-3-phenylpiperidine-1-carbonyl)-2-phenyl-7H-pyrrolo[2,3-d]-pyrimidin-4-ylamino]-ethyl}-acetamide (2636)

Mp 140-145° C. MS (ES): m/z 497.0 (100) [MH$^+$]. IR (film): ν=3294 cm$^{-1}$, 3063, 2936, 2861, 1654, 1590, 1573, 1531, 1432, 1386, 1327, 1296, 1271, 1168, 908, 776, 762, 730, 701. $^1$H NMR (CDCl$_3$, 200 MHz): δ=1.2-1.3 (m, 1H), 1.31 (s, 3H), 1.6-1.8 (m, 2H), 1.79 (s, 3H), 2.15-2.25 (m, 1H), 3.5-3.7 (m, 3H), 3.8-4.1 (m, 5H), 5.85 (brs, 1H), 6.63 (s, 1H), 6.87 (brs, 1H), 7.2-7.5 (m, 10H), 8.40-8.50 (m, 2H), 9.40 (s, 1H). t$_R$ (method A)=8.1 min.

N-(2-{2-Phenyl-6-[4-(3-trifluoromethylpyridin-2-yl)-piperazine-1-carbonyl]-7H-pyrrolo[2,3-d]pyrimidin-4-ylamino}-ethyl)-acetamide (26.37)

off-white solid, mp 225-228° C. MS (ES): m/z 553.0 (100) [MH$^+$]. $^1$H NMR (DMSO-d$_6$, 400 MHz): δ=1.79 (s, 3H), 3.26 (m$_c$, 4H), 3.30-3.38 (m, 2H), 3.60-3.67 (m, 2H), 3.85 (brs, 4H), 7.00 (s, 1H), 7.24 (dd, J=4.8, 7.6 Hz, 1H), 7.40-7.48 (m, 3H), 7.83 (brs, 1H), 8.05 (t, J=5.2 Hz, 1H), 8.11 (dd, J=1.6, 7.6 Hz, 1H), 8.38-8.42 (m, 2H), 8.55 (d, J=4.8 Hz, 1H). t$_R$(method A)=7.6 min.

N-(2-{6-[4-(4-Fluorophenyl)-piperazine-1-carbonyl]-2-phenyl-7H-pyrrolo[2,3-d]pyrimidin-4-ylamino}-ethyl)-acetamide (26.38)

Mp 234° C. MS (ES): m/z 502.0 (100) [MH$^+$], 321.9 (84) [MH$^+$-1-(4-fluorophenyl)piperazine]. IR (film): ν=3301 cm$^{-1}$, 3049, 2923, 2861, 1654, 1590, 1574, 1532, 1508, 1430, 1387, 1328, 1277, 1232, 1164, 1027, 916, 828, 816, 776, 731, 706. $^1$H NMR (CDCl$_3$/CD$_3$OD, 200 MHz): δ=1.79 (s, 3H), 3.21 (m, 4H), 3.54 (m, 2H), 3.86 (t, J=6.2 Hz, 2H), 4.04 (m$_c$, 4H), 6.86 (s, 1H), 6.9-7.1 (m, 4H), 7.45-7.55 (m, 3H), 7.75 (brs, 1H), 8.30-8.40 (m, 2H). t$_R$ (method A)=7.5 min.

N-(2-{2-Phenyl-6-[4-(5-trifluoromethylpyridin-2-yl)-piperazine-1-carbonyl]-7H-pyrrolo[2,3-d]pyrimidin-4-ylamino}-ethyl)-acetamide (26.39)

off-white solid, mp 270-273° C. MS (ES): m/z 553.0 (100) [MH$^+$]. t$_R$ (method A)=8.0 min.

N-(2-{6-[4-(3,5-Dichloropyridin-4-yl)-piperazine-1-carbonyl]-2-phenyl-7H-pyrrolo-[2,3-d]pyrimidin-4-ylamino}-ethyl)-acetamide (26.40)

MS (ES): m/z 552.9/554.9/556.9 (100/71/14) [MH$^+$], 321.9 (83) [MH$^+$-pyridinylpiperazine]. IR (film): ν=3282 cm$^{-1}$, 3080, 2962, 2926, 2854, 1652, 1598, 1574, 1532, 1434, 1383, 1328, 1282, 1241, 1149, 1026, 933, 806, 777, 750, 706. $^1$H NMR (CDCl$_3$/CD$_3$OD, 200 MHz): δ=1.80 (s, 3H), 3.45 (m$_c$, 4H), 3.54 (m, 2H), 3.88 (t, J=6.2 Hz, 2H), 4.04 (m$_c$, 4H), 6.82 (s, 1H), 7.30-7.55 (m, 3H), 8.30-8.40 (m, 4H). t$_R$ (method A)=7.2 min.

N-(2-{6-[4-(2'-Chlorobiphenyl-2-yl)-4-methoxypiperidine-1-carbonyl]-2-phenyl-7H-pyrrolo[2,3-d]pyrimidin-4-ylamino}-ethyl)-acetamide (26.41)

MS (ES): m/z 623.0/625.0 (100/38) [MH$^+$]. IR (film): ν=3306 cm$^{-1}$, 3022, 2945, 2924, 1652, 1591, 1574, 1537, 1434, 1384, 1328, 1286, 1243, 1071, 1016, 776, 753, 704. $^1$H NMR (CDCl$_3$, 200 MHz): δ=1.80 (s, 3H), 1.8-2.3 (m, 4H), 3.08 (s, 3H), 3.3-3.6 (m, 4H), 3.80-3.90 (m, 2H), 4.31 (m$_c$, 2H), 5.81 (m$_c$, 1H), 6.53 (s, 1H), 6.88 (brs, 1H), 7.01-7.10 (m, 1H), 7.25-7.50 (m, 9H), 7.64 (d, J=7.6 Hz, 1H), 8.35-8.45 (m, 2H), 9.47 (brs, 1H). t$_R$(method A)=8.9 min.

N-(2-{6-[4-(2-Chlorophenyl)-4-methoxypiperidine-1-carbonyl]-2-phenyl-7H-pyrrolo[2,3-d]pyrimidin-4-ylamino}-ethyl)-acetaimide (26.42)

white solid, mp. 201-202° C. MS (ES): m/z 547.0/549.0 (100/38) [MH$^+$]. IR (film): ν=3312 cm$^{-1}$, 3034, 2934, 1653, 1599, 1574, 1534, 1433, 1390, 1328, 1286, 1252, 1071, 1016, 776, 754, 705. $^1$H NMR (CDCl$_3$/CD$_3$OD, 200 MHz): δ=1.78 (s, 3H), 1.99 (m, 2H), 2.52 (brd, J=12.8 Hz, 2H), 3.05 (s, 3H), 3.4-3.6 (m, 4H), 3.80-3.90 (m, 2H), 4.51 (brd, J=11.2 Hz, 2H), 6.75 (s, 1H), 7.25-7.40 (m, 3H), 7.40-7.50 (m, 4H), 8.35-8.45 (m, 2H). t$_R$ (method A)=7.2 min. C$_{29}$H$_{31}$ClN$_6$O$_3$ (547.06): calcd. C, 63.67; H, 5.71; N 15.36; Cl, 6.48. Found C, 63.54; H, 5.74; N, 15.40; Cl, 6.65.

N-(2-{6-[4-(2-Chlorophenyl)-4-methoxypiperidine-1-carbonyl]-2-phenyl-7H-pyrrolo[2,3-d]pyrimidin-4-ylamino}-ethyl)-acetamide methanesulfonic acid salt (26.42.MsOH)

26.42 (1.570 g, 2.87 mmol) is dissolved in dry MeOH (25 mL), the solution is filtered, and the flask and the filter are rinsed with additional MeOH (5 mL). Methanesulfonic acid (290 mg, 3.01 mmol) is added, 10 mL of MeOH are evaporated, and $Et_2O$ is added until a persistent precipitate just forms (85 mL). After standing for 1 h at ambient temp., crystallization is completed by cooling to −20° C. overnight. The solid is filtered off and dried, giving 1.613 g (2.508 mmol, 87%) of the salt as white solid, mp. 190-191° C.

N-(2-{6-[4-(2-Chlorophenyl)-4-hydroxypiperidine-1-carbonyl]-2-phenyl-7H-pyrrolo[2,3-d]pyrimidin-4-ylamino}-ethyl)-acetamide (26.43):

MS (ES): m/z 533.0/535.0 (100/36) [MH$^+$]. IR (film): $\nu$=3312 cm$^{-1}$, 3054, 2961, 2924, 2857, 1658, 1598, 1574, 1533, 1431, 1388, 1328, 1274, 1170, 1016, 776, 756, 705. $^1$H NMR (CDCl$_3$, 200 MHz): $\delta$=1.78 (s, 3H), 2.09 (brd, J=12.8 Hz, 2H), 2.38 (brdt, J=3.6, 12.6 Hz, 2H), 3.4-3.6 (m, 4H), 3.80-3.90 (m, 2H), 4.54 (brd, J=13.2 Hz, 2H), 6.31 (brs, 1H), 6.75 (s, 1H), 7.15-7.60 (m, 8H), 8.35-8.45 (m, 2H). $t_R$ (method A)=6.5 min.

2-{6-[4-(2-Chlorophenyl)-4-methoxypiperidine-1-carbonyl]-2-phenyl-7H-pyrrolo-[2,3-d]pyrimidin-4-ylamino}-1-[4-(2-chlorophenyl)-4-methoxypiperidin-1-yl]-ethanone (26.44)

off-white solid. MS (ES): m/z 727.1/729.1/731.1 (100/69/14) [MH$^+$]. $t_R$ (method A)=11.3 min.

2-{6-[4-(2-Chlorophenyl)-4-methoxypiperidine-1-carbonyl]-2-phenyl-7H-pyrrolo-[2,3-d]pyrimidin-4-ylamino}-acetamide (26.45)

MS (ES): m/z 519.0/521.0 (100/37) [MH$^+$]. IR (film): $\nu$=3310 cm$^{-1}$, 3024, 2960, 2936, 2873, 1673, 1590, 1573, 1532, 1446, 1431, 1389, 1324, 1298, 1285, 1199, 1071, 1016, 776, 754, 705. $^1$H NMR (CDCl$_3$/CD$_3$OD, 200 MHz): $\delta$=2.05 (m, 2H), 2.57 (brd, J=13.6 Hz, 2H), 3.09 (s, 3H), 3.45-3.65 (m, 2H), 4.36 (s, 2H), 4.45-4.60 (m, 2H), 6.81 (s, 1H), 7.25-7.50 (m, 7H), 8.32-8.40 (m, 2H). $t_R$ (method A)=7.5 min.

2-{6-[4-(2'-Chlorobiphenyl-2-yl)-4-methoxypiperidine-1-carbonyl]-2-phenyl-7H-pyrrolo[2,3-d]pyrimidin-4-ylamino}-acetamide (26.46)

m/z 595.0/597.0 (100/38) [MH$^+$]. IR (film): $\nu$=3362 cm$^{-1}$, 3023, 2924, 2850, 1669, 1594, 1573, 1532, 1463, 1438, 1388, 1324, 1284, 1071, 1017, 803, 755, 705. $^1$H NMR (CDCl$_3$/CD$_3$OD, 200 MHz): $\delta$=1.75-2.25 (m, 4H), 3.09 (s, 3H), 3.3-3.6 (m, 2H), 4.20-4.35 (m, 2H), 4.39 (s, 2H), 6.58 (s, 1H), 7.01-7.10 (m, 1H), 7.25-7.50 (m, 9H), 7.64 (d, J=7.4 Hz, 1H), 8.35-8.45 (m, 2H). $t_R$ (method A)=8.9 min.

N-(2-{6-[4-(2'-Chlorobiphenyl-2-yl)-4-hydroxypiperidine-1-carbonyl]-2-phenyl-7H-pyrrolo[2,3-d]pyrimidin-4-ylamino}-ethyl)-acetamide (26.47)

MS (ES): m/z 609.0/611.0 (100/38) [MH$^+$]. IR (film): $\nu$=3352 cm$^{-1}$, 3022, 2924, 1652, 1599, 1575, 1538, 1463, 1451, 1382, 1328, 1272, 1112, 1015, 754, 705. $^1$H NMR (CDCl$_3$, 200 MHz): $\delta$=1.79 (s, 3H), 1.8-2.2 (m, 4H), 3.3-3.5 (m, 2H), 3.60 (m, 2H), 3.80-3.90 (m, 2H), 4.43 (m$_c$, 2H), 5.96 (brs, 1H), 6.62 (s, 1H), 6.91 (brs, 1H), 6.90-7.07 (m, 1H), 7.25-7.57 (m, 10H), 8.35-8.45 (m, 2H), 9.62 (brs, 1H). $t_R$ (method A)=7.8 min.

N-(2-{6-[4-(4-Fluorophenyl)-4-methoxypiperidine-1-carbonyl]-2-phenyl-7H-pyrrolo[2,3-d]pyrimidin-4-ylamino}-ethyl)-acetamide (26.48)

white solid, mp 134-137° C. MS (ES): m/z 531.0 (100) [MH$^+$]. IR (film): $\nu$=3305 cm$^{-1}$, 3056, 2932, 2824, 1651, 1599, 1574, 1533, 1447, 1432, 1387, 1327, 1280, 1223, 1163, 1071, 1025, 900, 834, 776, 751, 706. $^1$H NMR (CDCl$_3$/CD$_3$OD, 200 MHz): $\delta$=1.78 (s, 3H), 1.92 (dt, J=4.8, 12.8 Hz, 2H), 2.14 (brd, J=13.2 Hz, 2H), 3.01 (s, 3H), 3.4-3.6 (m, 4H), 3.86 (t, J=5.4 Hz, 2H), 4.49 (brd, J=13.2 Hz, 2H), 6.75 (s, 1H), 7.06 (app t, J=8.8. Hz, 2H), 7.25-7.40 (m, 2H), 7.40-7.50 (m, 3H), 8.35-8.45 (m, 2H). $t_R$ (method A)=7.4 min.

N-{2-[6-(2-Benzyl-1-oxo-2,8-diazaspiro[4.5]decane-8-carbonyl)-2-phenyl-7H-pyrrolo[2,3-d]pyrimidin-4-ylamino]-ethyl}-acetamide (26.49)

white solid, mp 140° C. (decomp.). MS (ES): m/z 565.9 (100) [MH$^+$]. $t_R$ (method A)=6.9 min.

2-{6-[4-(4-Chlorophenyl)-piperazine-1-carbonyl]-2-phenyl-7H-pyrrolo[2,3-d]pyrimidin-4-ylamino}-acetamide (26.50)

MS (ES): m/z 489.9/491.9 (100/34) [MH$^+$]. $t_R$ (method A)=7.6 min.

4-(2-Acetylaminoethylamino)-2-phenyl-7H-pyrrolo[2,3-d]pyrimidine-6-carboxylic acid (2-{6-[4-(2-chlorophenyl)-4-methoxypiperidine-1-carbonyl]-2-phenyl-7H-pyrrolo[2,3-d]-pyrimidin-4-ylamino}-ethyl)-amide (26.51)

white solid, mp. 180-185° C. (decomp.). MS (ES): m/z 826.0/828.0 (52/21) [MH$^+$]. $t_R$ (method A)=8.2 min.

4-(2-Acetylaminoethylamino)-2-phenyl-7H-pyrrolo[2,3-d]pyrimidine-6-carboxylic acid (2-{(6-[4-(4-chlorophenyl)-piperazine-1-carbonyl]-2-phenyl-7H-pyrrolo[2,3-d]-pyrimidin-4-ylamino}-ethyl)-amide (26.52)

off-white solid. MS (ES): m/z 797.0/799.0 (6/3) [MH$^+$]. $t_R$ (method A)=8.3 min.

N-(2-{2-Phenyl-6-[4-(3-phenylallyl)-piperidine-1-carbonyl]-7H-pyrrolo[2,3-d]-pyrimidin-4-ylamino}-ethyl)-acetamide (26.53)

$^1$H NMR (CDCl$_3$, 200 MHz) $\delta$ 1.79 (m, 7H), 2,21 (t, 1H, J=6.6 Hz), 2.33 (m, 1H), 3.00 (brs, 2H), 3.15 (m, 1H), 3.59 (brs, 2H), 3.90 (brs, 2H), 4.58 (brs 2H), 5.99 (brs, 1H), 6.23 (m, 1H), 6.37 (m, 1H), 6.66 (d, 1H), 6.99 (brs, 1H), 7.24-7.46 (m, 8H), 8.40 (m, 2H), 9.70 (brs, 1H). MS (ES) 522.8 [MH$^+$]. $t_R$ (method A)=9.2 min.

N-{2-[6-(4-Benzylpiperidine-1-carbonyl)-2-phenyl-7H-pyrrolo[2,3-d]pyrimidin-4-ylamino]-ethyl}-acetamide (26.54)

white solid, mp. 260-261° C. $^1$H NMR (CDCl$_3$, 200 MHz): δ=1.78 (m, 7H), 2.54 (d, 2H, J=6.6 Hz), 2.91 (brs, 2H), 3.56 (brs, 2H), 3.84 (brs, 2H), 4.53 (d, 2H, J=13.6 Hz), 6.40 (brs, 1H), 6.71 (s, 1H), 7.12-7.45 (m, 9H), 8.40 (q, 2H, J=2.2 Hz), 9.98 (brs, 1H). MS (ES) 496.8 [MH$^+$]. $t_R$ (method A)=8.6 min. C$_{29}$H$_{32}$N$_6$O$_2$.0.33H$_2$O (502.57): calcd. C 69.30; H, 6.55; N, 16.72. Found C, 69.46; H, 6.48; N, 16.70.

4-(2-Acetylaminoethylamino)-2-phenyl-7H-pyrrolo[2,3-d]pyrimidine-6-carboxylic acid (1-benzylpiperidin-4-yl)-amide (26.55)

$^1$H NMR (CDCl$_3$, 200 MHz) δ 1.61-2.05 (m, 7H), 2.18 (m, 2H), 2.89 (d, 2H, J=12 Hz), 3.56 (s, 2H), 3.60 (d, 2H, J=4.8 Hz), 3.87 (brs, 2H), 3.99 (brs, 1H), 6.22 (brs, 1H), 6.33 (brs, 1H), 6.68 (b, 1H), 6.86 (brs, 1H), 7.26-7.45 (m, 9H), 8.40 (q, 2H, J=3.2 Hz), 9.64 (brs, 1H). MS (ES) 512.1 [MH$^+$]. $t_R$ (method A)=4.9 min.

N-(2-{2-Phenyl-6-[4-(4-phenylbutyl)-piperazine-1-carbonyl]-7H-pyrrolo[2,3-d]-pyrimidin-4-ylamino}-ethyl)-acetamide (26.56)

$^1$H NMR (CDCl$_3$, 200 MHz) δ 1.52-1.68 (m, 4H), 1.78 (s, 3H), 2.37 (t, 2H, J=7 Hz), 2.44 (brs, 4H), 2.63 (t, 2H, J=7.6 Hz), 3.54 (brs, 2H), 3.81 (brs, 6H), 6.28 (brs, 1H), 6.66 (s, 1H), 7.12-7.44 (m, 9H), 8.40 (q, 2H, J=4.2 Hz), 10.40 (brs, 1H). MS (ES) 540.1 [MH$^+$]. $t_R$ (method A)=4.9 min.

N-(2-{2-Phenyl-6-[4-(3-phenylpropyl)-piperidine-1-carbonyl]-7H-pyrrolo[2,3-d]-pyrimidin-4-ylamino}-ethyl)-acetamide (26.57)

$^1$H NMR (CDCl$_3$, 200 MHz) δ 1.17-1.38 (m, 5H), 1.58-1.69 (m, 4H), 1.79 (s, 3H), 2.61 (t, 2H, J=7.6 Hz), 3.00 (brs, 2H), 3.55 (q, 2H, J=5.4 Hz), 3.86 (brs, 2H), 4.53 (d, 2H, J=13.2 Hz), 6.05 (brs, 1H), 6.65 (s, 1H), 7.03 (brs, 1H), 7.16-7.32 (m, 5H), 7.33-7.48 (m, 3H), 8.40 (q, 2H, J=3.2 Hz), 9.81 (brs, 1H). MS (ES) 524.9 [MH$^+$]. $t_R$ (method A)=9.6 min.

N-{2-[2-Phenyl-6-(4-pyrrolidin-1-yl-piperidine-1-carbonyl)-7H-pyrrolo[2,3-d]-pyrimidin-4-ylamino]-ethyl}-acetamide (26.58)

$^1$H NMR (CDCl$_3$, 200 MHz) δ 1.62-2.00 (m, 7H), 1.84 (s, 3H), 2.74 (brs, 4H), 3.03 (t, 2H, J=14 Hz), 3.62 (m, 2H), 3.91 (brs, 2H), 4.49 (d, 2H, J=13.6 Hz), 6.57 (brs, 1H), 6.87 (s, 1H), 7.20 (m, 1H), 7.33-7.45 (m, 3H), 8.42 (q, 2H, J=3.2 Hz), 9.90 (brs, 1H). MS (ES) 475.9 [MH$^+$]. $t_R$ (method A)=3.7 min.

N-(2-{6-[4-(3-Cyclohexylpropyl)-piperazine-1-carbonyl]-2-phenyl-7H-pyrrolo[2,3-d]pyrimidin-4-ylamino}-ethyl)-acetamide (26.59)

$^1$H NMR (CDCl$_3$, 200 MHz) δ 0.90 (t, 2H, J=10.1 Hz), 1.19 (d, 6H, J=7.4 Hz), 1.50 (brs, 2H), 1.67 (d, 5H, J=10.6 Hz), 1.77 (s, 3H), 2.33 (t, 2H, J=7.7 Hz), 2.47 (brs, 4H), 3.48 (m, 2H), 3.82 (brs, 6H), 6.28 (brs, 1H), 6.67 (s, 1H), 7.16 (brs, 1H), 7.42 (m, 3H), 8.37 (m, 2H), 10.44 (brs, 1H). MS (ES) 532.0 [MH$^+$]. $t_R$ (method A)=5.1 min.

N-(2-{6-[4-(4-Methylpentyl)-piperazine-1-carbonyl]-2-phenyl-7H-pyrrolo[2,3-d]-pyrimidin-4-ylamino}-ethyl)-acetamide (26.60)

$^1$H NMR (CDCl$_3$, 200 MHz) δ 0.87 (d, 6H, J=6.6 Hz), 1.20 (m, 2H), 1.49 (m, 3H), 1.74 (s, 3H), 2.33 (t, 2H, J=7.5 Hz), 2.44 (brs, 4H), 3.47 (brs, 2H), 3.78 (brs, 6H), 6.60 (brs, 1H), 6.68 (s, 1H), 7.41 (brs, 4H), 8.35 (brs, 2H), 11.11 (brs, 1H). MS (ES) 492.3 [MH$^+$]. $t_R$ (method A)=4.5 min.

N-(2-{6-[4-(4-Bromophenyl)-4-hydroxypiperidine-1-carbonyl]-2-phenyl-7H-pyrrolo-[2,3-d]pyrimidin-4-ylamino}-ethyl)-acetamide (26.61)

$^1$H NMR (CD$_3$OD, 200 MHz) δ 1.80 (brs, 2H), 1.85 (s, 3H), 2.11 (m, 2H), 3.52 (m, 4H), 3.83 (t, 2H, J=6 Hz), 4.51 (d, 2H, J=12.4 Hz), 6.97 (s, 1H), 7.43-7.48 (m, 7H), 8.42 (m, 2H). MS (ES) 576.5/578.4 [MH$^+$]. $t_R$ (method A)=7.5 min.

N-{2-[2-Phenyl-6-(4-phenylpiperidine-1-carbonyl)-7H-pyrrolo[2,3-d]pyrimidin-4-ylamino]-ethyl}-acetamide (26.62)

$^1$H NMR (CDCl$_3$, 200 MHz) δ 1.63-1.89 (m, 4H), 1.71 (s, 3H), 2.73 (t, 1H, J=10.7 Hz), 2.94 (brs, 2H), 3.46 (brs, 2H), 3.71 (brs, 2H), 4.63 (d, 2H, J=12.6 Hz), 6.34 (brs, 1H), 6.74 (s, 1H), 7.15-7.41 (m, 9H), 8.37 (brs, 2H), 11.12 (brs, 1H). MS (ES) 483.0 [MH$^+$]. $t_R$ (method A)=7.7 min.

N-{2-[6-([1,4']Bipiperidinyl-1'-carbonyl)-2-phenyl-7H-pyrrolo[2,3-d]pyrimidin-4-ylamino]-ethyl}-acetamide (26.63)

$^1$H NMR (CDCl$_3$, 200 MHz) δ 1.44 (brs, 2H), 1.70 (brs, 6H), 1.83 (s, 3H), 1.96 (d, 2H), 2.63 (brs, 4H), 2.91 (brs, 3H), 3.62 (brs, 2H), 3.91 (brs, 2H), 4.60 (d, 2H, J=11.4 Hz), 6.74 (brs, 1H), 6.94 (s, 1H), 7.42 (m, 4H), 8.40 (m, 2H), 10.30 (brs, 1H). MS (ES) 489.8 [MH$^+$]. $t_R$ (method A)=3.9 min.

N-{2-[6-(4-Cyclopentylpiperazine-1-carbonyl)-2-phenyl-7H-pyrrolo[2,3-d]pyrimidin-4-ylamino]-ethyl}-acetamide (26.64)

$^1$H NMR (CDCl$_3$, 200 MHz) δ 1.51-1.71 (m, 8H), 1.80 (s, 3H), 2.56 (brs, 4H), 3.33 (t, 1H), 3.59 (m, 6H), 6.12 (brs, 1H), 6.67 (s, 1H), 7.01 (brs, 1H), 7.44 (m, 3H), 8.41 (m, 2H), 9.98 (brs, 1H). MS (ES) 475.9 [MH$^+$]. $t_R$ (method A)=4.0 min.

N-{2-[6-(4-Aminopiperidine-1-carbonyl)-2-phenyl-7H-pyrrolo[2,3-d]pyrimidin-4-ylamino]-ethyl}-acetamide (26.65)

Prepared from 26.66 by stirring in TFA followed by basic workup; 25% yield. $^1$H NMR (CD$_3$OD, 200 MHz) δ 1.42 (m, 2H), 1.86 (s, 3H), 1.97 (brs, 2H), 3.15 (m, 3H), 3.53 (t, 2H, J=6 Hz), 3.83 (t, 2H, J=6 Hz), 4.50 (d, 2H, J=13.6 Hz), 6.92 (s, 1H), 7.42 (m, 3H), 8.40 (m, 2H), 9.98 (brs, 1H). MS (ES) 421.8 [MH$^+$]. $t_R$ (method A)=3.2 min.

{1-[4-(2-Acetylaminoethylamino)-2-phenyl-7H-pyrrolo[2,3-d]pyrimidin-6-carbonyl]piperidin-4-yl}-carbamic acid tert-butyl ester (26.66)

$^1$H NMR (CDCl$_3$, 200 MHz) δ 1.46 (s, 9H), 1.61 (brs, 4H), 1.82 (s, 3H), 2.11 (m, 1H), 3.19 (t, 2H, J=11.2 Hz), 3.60 (q, 2H, J=5 Hz), 3.74 (brs, 1H), 3.91 (m, 2H), 4.50 (d, 2H, J=13.2

Hz), 5.97 (brs, 1H), 6.65 (s, 1H), 6.79 (brs, 1H), 7.45 (m, 3H), 8.43 (m, 2H), 9.44 (brs, 1H). MS (ES) 522.0 [MH$^+$]. $t_R$ (method A)=7.2 min.

N-{2-[6-(4-Methanesulfonylaminopiperidine-1-carbonyl)-2-phenyl-7H-pyrrolo[2,3-d]pyrimidin-4-ylamino]-ethyl}-acetamide (26.67)

Prepared from 26.65 and methanesulfonyl chloride in 11% yield. $^1$H NMR (CDCl$_3$, 200 MHz) δ 1.49 (m, 2H), 1.76 (s, 3H), 1.97 (m, 2H), 2.90 (s, 3H), 3.25 (brs, 2H), 3.43 (t, 2H, J=6.1 Hz), 3.50 (m, 1H), 3.74 (t, 2H, J=6.1 Hz), 4.31 (d, 2H, J=13.6 Hz), 6.83 (s, 1H), 7.33-7.38 (m, 3H), 8.43 (m, 2H). MS (ES) 500.0 [MH$^+$]. $t_R$ (method A)=5.4 min.

N-(2-{2-Phenyl-6-[4-(toluene-4-sulfonylamino)-piperidine-1-carbonyl]-7H-pyrrolo-[2,3-d]pyrimidin-4-ylamino}-ethyl)-acetamide (26.68)

Prepared from 26.65 and tosyl chloride in 35% yield. $^1$H NMR (CD$_3$OD, 200 MHz) δ 1.80 (m, 2H), 1.89 (s, 3H), 2.35 (s, 1H), 2.43 (brs, 2H), 2.49 (s, 3H), 3.54 (t, 2H, J=6.2 Hz), 3.89 (t, 2H, J=6.2 Hz), 4.23 (d, 2H, J=14.4 Hz), 7.07-7.97 (m, 8H), 8.21 (m, 2H). MS (ES) 576.1 [MH$^+$]. $t_R$ (method A)=7.2 min.

N-(2-{6-[4-Hydroxy-4-(3-methoxyphenyl)-piperidine-1-carbonyl]-7H-pyrrolo[2,3-d]-pyrimidin-4-ylamino}-ethyl)-acetamide (26.69)

$^1$H NMR (CD$_3$OD, 200 MHz) δ 1.80 (brs, 1H), 1.85 (s, 3H), 1.97 (s, 1H), 2.14 (m, 2H), 2.49 (brs, 4H), 3.80 (s, 3H), 3.83 (d, 2H, J=5.8 Hz), 4.44 (d, 2H, J=12.8 Hz), 6.78-6.84 (m, 1H), 6.97 (s, 1H), 7.05-7.13 (m, 2H), 7.26 (t, 1H, J=7.9 Hz), 7.42-7.47 (m, 3H), 8.41 (m, 2H). MS (ES) 529 [MH$^+$]. $t_R$ (method A)=7.2 min.

N-(2-{6-[4-Hydroxy-4-(2-methoxyphenyl)-piperidine-1-carbonyl]-2-phenyl-7H-pyrrolo[2,3-d]pyrimidin-4-ylamino}-ethyl)-acetamide (26.70)

$^1$H NMR (CD$_3$OD, 200 MHz) δ 1.74 (d, 1H, J=0.8 Hz), 1.81 (brs, 1H), 1.85 (s, 3H), 2.56 (m, 2H), 0.52 (brs, 4H), 3.80 (d, 2H, J=6.6 Hz), 3.85 (s, 3H), 4.43 (d, 2H, J=13.2 Hz), 6.92-7.01 (m, 3H), 7.25 (m, 1H), 7.42-7.47 (m, 3H), 7.53 (m, 1H), 8.41 (m, 2H). MS (ES) 529.0 [MH$^+$]. $t_R$(method A)=6.7 min.

N-(2-{6-[4-(4-Chlorophenyl)-piperazine-1-carbonyl]-2-phenyl-7H-pyrrolo[2,3-d]-pyrimidin-4-ylamino}-ethyl)-acetamide (26.71)

$^1$H NMR (CD$_3$OD, 200 MHz) δ 1.86 (s, 3H), 3.23 (m, 4H), 3.53 (t, 2H, J=6.2 Hz), 3.84 (t, 2H, J=6.3 Hz), 3.99 (t, 4H, J=4.8 Hz), 6.95-6.99 (m, 3H), 7.20 (d, 2H, J=9.2 Hz), 7.42-7.44 (m, 3H), 8.41 (m, 2H). MS (ES) 517.9/519.9 [MH$^+$]. $t_R$ (method A)=8.8 min. C$_{27}$H$_{28}$ClN$_7$O$_2$ (518.02): calcd. C, 62.60; H, 5.45; N, 18.93; Cl, 6.84. Found C, 62.66; H, 5.46; N, 18.39; Cl, 6.49.

N-(2-{6-[4-(2-Hydroxyethyl)-piperazine-1-carbonyl]-2-phenyl-7H-pyrrolo[2,3-d]-pyrimidin-4-ylamino}-ethyl)-acetamide (26.72)

$^1$H NMR (CD$_3$OD, 200 MHz) δ 1.86 (s, 3H), 2.62 (m, 4H), 3.52 (t, 2H, J=6 Hz), 3.71 (t, 2H, J=5.6 Hz), 3.85 (m, 4H), 6.92 (s, 1H), 7.41-7.44 (m, 3H), 8.39 (m, 2H). MS (ES) 451.9 [MH$^+$]. $t_R$(method A)=3.6 min.

N-{2-[6-(4-Benzoylpiperidine-1-carbonyl)-2-phenyl-7H-pyrrolo[2,3-d]pyrimidin-4-ylamino]-ethyl}-acetamide (26.73)

$^1$H NMR (CDCl$_3$, 200 MHz) δ 1.76 (s, 3H), 1.89 (brs, 3H), 3.19 (brs, 2H), 3.49 (brs, 4H), 3.77 (brs, 2H), 4.45 (d, 2H, J=13.2 Hz), 6.55 (brs, 3H), 6.74 (s, 1H), 7.43-7.62 (m, 6H), 7.90 (d, 2H, J=7.4 Hz), 8.38 (brs, 2H), 10.67 (brs, 1H). MS (ES) 510.9 [MH$^+$]. $t_R$(method A)=7.5 min.

N-(2-{6-[4-(2-Methoxyphenyl)-piperidine-1-carbonyl]-2-phenyl-7H-pyrrolo[2,3-d]-pyrimidin-4-ylamino}-ethyl)-acetamide (26.74)

$^1$H NMR (CDCl$_3$, 200 MHz) δ 1.68 (brs, 2H), 1.78 (s, 3H), 1.90 (d, 2H, J=11.6 Hz), 3.20 (m, 3H), 3.55 (brs, 2H), 3.83 (brs, 5H), 4.77 (brs, 2H), 6.22 (brs, 1H), 6.74 (brs, 1H), 6.89 (q, 2H, J=6.9 Hz), 7.16 (t, 3H, J=8.8 Hz), 7.43 (brs, 3H), 8.40 (brs, 2H), 10.20 (brs, 1H). MS (ES) 512.9 [MH$^+$]. $t_R$(method A)=8.3 min.

N-(2-{6-[4-(Hydroxyphenylmethyl)-piperidine-1-carbonyl]-2-phenyl-7H-pyrrolo[2,3-d]pyrimidin-4-ylamino}-ethyl)-acetamide (26.75)

$^1$H NMR (CDCl$_3$, 200 MHz) δ 1.29 (brs, 3H), 1.75 (s, 3H), 1.83-2.08 (m, 2H), 2.87 (brs, 2H), 3.53 (brs, 2H), 3.81 (brs, 2H), 4.33 (d, 1H, J=7 Hz), 4.52 (t, 2H, J=15 Hz), 6.43 (brs, 1H), 6.67 (s, 1H), 7.16 (brs, 1H), 7.26-7.31 (m, 5H), 7.42 (t, 3H, J=2.9 Hz), 8.32 (m, 2H). MS (ES) 512.9 [MH$^+$]. $t_R$(method A)=6.8 min.

N-{2-[6-(4-Acetyl-4-phenylpiperidine-1-carbonyl)-2-phenyl-7H-pyrrolo[2,3-d]-pyrimidin-4-ylamino]-ethyl}-acetamide (26.76)

$^1$H NMR (CDCl$_3$, 200 MHz) δ 1.82 (s, 3H), 1.96 (s, 3H), 2.01 (brs, 2H), 2.45 (brs, 2H), 3.58 (brs, 4H), 3.87 (brs, 2H), 4.20 (brs, 2H), 6.24 (brs, 1H), 6.70 (s, 1H), 6.90 (brs, 1H), 7.21-7.43 (m, 7H), 8.37 (brs, 2H), 9.74 (brs, 1H). MS (ES) 524.9 [MH$^+$]. $t_R$ (method A)=7.6 min.

N-(2-{6-[4-(2-Cyclohexylethyl)-piperazine-1-carbonyl]-2-phenyl-7H-pyrrolo[2,3-d]-pyrimidin-4-ylamino}-ethyl)-acetamide (26.77)

$^1$H NMR (CDCl$_3$, 200 MHz) δ 0.94 (t, 2H, J=10.8 Hz), 1.20-1.44 (m, 7H), 1.67-1.73 (m, 4H), 1.77 (s, 3H), 2.46 (m, 6H), 3.53 (brs, 2H), 3.81 (brs, 6H), 6.31 (brs, 1H), 6.67 (s, 1H), 7.18 (brs, 1H), 7.40-7.44 (t, 3H, J=3.1 Hz), 8.38 (m, 2H), 10.56 (brs, 1H). MS (ES) 517.9 [MH$^+$]. $t_R$(method A)=4.8 min.

N-{2-[6-(4-Ethynyl-4-hydroxypiperidine-1-carbonyl)-2-phenyl-7H-pyrrolo[2,3-d]-pyrimidin-4-ylamino]-ethyl}-acetamide (26.78)

$^1$H NMR (CDCl$_3$, 200 MHz) δ 1.83 (s, 3H), 1.89 (m, 2H), 2.04 (m, 2H), 2.61 (s, 1H), 3.64 (m, 2H), 3.74 (m, 2H), 3.91 (s, 2H), 4.20 (m, 2H), 6.68 (brs, 1H), 6.74 (s, 1H), 7.45-7.48 (m, 3H), 8.42 (m, 2H). MS (ES) 446.8 [MH$^+$]. $t_R$(method A)=5.5 min.

N-{2-[2-Phenyl-6-(4-phenylethynyl-3,6-dihydro-2H-pyridine-1-carbonyl)-7H-pyrrolo[2,3-d]pyrimidin-4-ylamino]-ethyl}-acetamide (26.79)

$^1$H NMR (CDCl$_3$, 200 MHz) δ 1.83 (s, 3H), 2.50 (brs, 2H), 3.56 (q, 2H, J=6 Hz), 3.84 (t, 2H, J=5.2 Hz), 4.00 (t, 2H, J=5.7 Hz), 4.44 (brs, 2H), 6.25 (brs, 1H), 7.07 (s, 1H), 7.37-7.45 (m, 10H), 8.54 (m, 2H). MS (ES) 504.9 [MH$^+$]. t$_R$(method A)=8.7 min.

N-(2-{2-Phenyl-6-[4-(2-phenylcyclopropanecarbonyl)-piperazine-1-carbonyl]-7H-pyrrolo[2,3-d]pyrimidin-4-ylamino}-ethyl)-acetamide (26.80)

$^1$H NMR (CDCl$_3$, 200 MHz) δ 1.32 (m, 1H), 1.68 (p, 1H, J=4.6 Hz), 1.95 (p, 1H, J=3.8 Hz), 2.51 (m, 1H), 3.56 (brs, 2H), 3.70 (brs, 4H), 3.83 (brs, 6H), 6.47 (brs, 1H), 6.74 (brs, 1H), 7.00 (brs, 1H), 7.12 (d, 2H, J=6.6 Hz), 7.21-7.33 (m, 3H), 7.41 (brs, 3H), 8.38 (brs, 2H), 10.39 (brs, 1H). MS (ES) 552.2 [MH$^+$]. t$_R$ (method A)=7.3 min.

N-(2-{6-[4-(4-Chlorobenzyl)-piperidine-1-carbonyl]-2-phenyl-7H-pyrrolo[2,3-d]-pyrimidin-4-ylamino}-ethyl)-acetamide (26.81)

$^1$H NMR (CDCl$_3$, 200 MHz) δ 1.70 (m, 3H), 1.80 (s, 3H), 2.07 (d, 2H, J=5.2 Hz), 2.52 (d, 2H, J=6.2 Hz), 2.94 (brs, 2H), 3.57 (brs, 2H), 3.88 (brs, 2H), 4.54 (d, 2H, J=13.8 Hz), 6.07 (brs, 1H), 6.66 (s, 1H), 6.99-7.46 (m, 8H), 8.41 (q, 2H, J=3.2 Hz), 9.69 (brs, 1H). MS (ES) 530.9/532.9 [MH$^+$]. t$_R$(method A)=9.1 min

N-[2-(6-{4-[(4-Chlorophenyl)-hydroxymethyl]-piperidine-1-carbonyl}-2-phenyl-7H-pyrrolo[2,3-d]pyrimidin-4-ylamino)-ethyl]-acetamide (26.82)

$^1$H NMR (CDCl$_3$, 200 MHz) δ 1.43 (brs, 3H), 1.79 (s, 3H), 1.86 (m, 2H), 2.01 (brs, 2H), 2.93 (brs, 2H), 3.59 (brs, 2H), 3.88 (brs, 2H), 4.39 (d, 1H, J=6.8 Hz), 4.61 (t, 2H, J=2.9 Hz), 6.03 (brs, 1H), 6.65 (s, 1H), 6.89 (brs, 1H), 7.21-7.34 (m, 5H), 7.43 (t, 3H, J=6.2 Hz), 8.41 (m, 2H). MS (ES) 547.1/549.0 [MH$^+$]. t$_R$ (method A)=7.4 min.

N-{2-[2-Phenyl-6-(4-prop-2-ynylpiperazine-1-carbonyl)-7H-pyrrolo[2,3-d]pyrimidin-4-ylamino]-ethyl}-acetamide (26.83)

Prepared from 30a in 43% yield. $^1$H NMR (CD$_3$COCD$_3$, 200 MHz) δ 1.82 (s, 3H), 2.62 (t, 4H, J=5 Hz), 2.74 (t, 2H, J=2.2 Hz), 3.40 (d, 2H, J=2.2 Hz), 3.56 (q, 2H, J=3.1 Hz), 3.84 (m, 6H), 6.95 (s, 1H), 7.43 (m, 4H), 8.54 (m, 2H). MS (ES) 445.9 [MH$^+$]. t$_R$ (method A)=4.5 min.

N-(2-{6-[4-(2-Benzyloxyethyl)-piperidine-1-carbonyl]-2-phenyl-7H-pyrrolo[2,3-d]-pyrimidin-4-ylamino}-ethyl)-acetamide (26.84)

$^1$H NMR (CDCl$_3$, 200 MHz) δ 1.20 (m, 3H), 1.57 (m, 2H), 1.73 (brs, 2H), 1.78 (s, 3H), 2.94 (brs, 2H), 3.50 (m, 4H), 3.83 (brs, 2H), 4.49 (s, 2H), 4.55 (brs, 2H), 6.22 (brs, 1H), 6.66 (s, 1H), 7.13 (brs, 1H), 7.33-7.44 (m, 8H), 8.40 (m, 2H), 10.12 (brs, 1H). MS (ES) 540.9 [MH$^+$]. t$_R$ (method A)=8.5 min.

1-[4-(2-Acetylaminoethylamino)-2-phenyl-7H-pyrrolo[2,3-d]pyrimidine-6-carbonyl]-4-phenylpiperidine-4-carboxylic acid (26.85)

$^1$H NMR (CD$_3$COCD$_3$, 200 MHz) δ 1.82 (s, 3H), 2.68 (d, 2H, J=13.4 Hz), 3.41 (m, 2H), 3.55 (m, 2H), 3.84 (t, 2H, J=5.5 Hz), 4.50 (d, 2H, J=13.6 Hz), 7.00 (s, 1H), 7.42 (m, 9H), 8.52 (m, 2H), 10.82 (brs, 1H). MS (ES) 526.8 [MH$^+$]. t$_R$ (method B)=6.7 min.

N-{2-[6-(4-tert-Butylpiperidine-1-carbonyl)-2-phenyl-7H-pyrrolo[2,3-d]pyrimidin-4-ylamino]-ethyl}-acetamide (26.86)

$^1$H NMR (CDCl$_3$, 200 MHz) δ 1.33 (m, 3H), 1.61 (brs, 9H), 1.81 (s, 3H), 1.85 (brs, 2H), 2.96 (brs, 2H), 3.62 (m, 2H), 3.92 (m, 2H), 4.74 (d, 2H, J=12.4 Hz), 5.82 (brs, 1H), 6.65 (s, 1H), 6.85 (brs, 1H), 7.46 (m, 3H), 8.44 (m, 2H), 9.42 (brs, 1H). MS (ES) 462.9 [MH$^+$]. t$_R$ (method A)=8.6 min.

N-{2-[6-(1,4-Dioxa-8-azaspiro[4.5]decane-8-carbonyl)-2-phenyl-7H-pyrrolo[2,3-d]-pyrimidin-4-ylamino]-ethyl}-acetamide (26.87)

$^1$H NMR (CDCl$_3$, 200 MHz) δ 1.74 (brs, 7H), 3.49 (m, 2H), 3.84 (m, 6H), 3.96 (s, 4H), 6.55 (brs, 1H), 6.69 (s, 1H), 7.30 (brs, 1H), 7.40 (m, 3H), 8.31 (m, 2H), 9.42 (brs, 1H). MS (ES) 464.8 [MH$^+$]. t$_R$(method A)=5.9 min.

N-{2-[6-(4-Phenethylpiperidine-1-carbonyl)-2-phenyl-7H-pyrrolo[2,3-d]pyrimidin-4-ylamino]-ethyl}-acetamide (26.88)

$^1$H NMR (CDCl$_3$, 200 MHz) δ 1.63 (brs, 5H), 1.81 (s, 3H), 1.85 (m, 2H), 2.67 (t, 2H, J=7.8 Hz), 3.03 (brs, 2H), 3.61 (brs, 2H), 3.91 (brs, 2H), 4.65 (brs, 2H), 5.90 (brs, 1H), 6.66 (s, 1H), 6.86 (brs, 1H), 7.17-7.26 (m, 5H), 7.45 (brs, 3H), 8.42 (brs, 2H), 9.58 (brs, 1H). MS (ES) 510.8 [MH$^+$]. t$_R$ (method A)=9.0 min.

General Procedure for Sonogashira Reaction with 26.83:

Combine acetylene 26.83 (20 mg, 0.0449 mmol), 2-iodobenzonitrile (12.4 mg, 1.2 eq.) and diethylamine (1 ml) and stir under N$_2$ at rt for 3 h. Add Pd(PPh$_3$)$_2$Cl$_2$ (1.6 mg, 5% eq.) and CuI (0.5 mg, 5% eq.). After 3 h, remove solvent and pour into 10 ml of H$_2$O. Extracted with 5×8 ml of EtOAc, washed with 2×10 ml of H$_2$O and 10 ml of brine, dried over MgSO$_4$. The crude material is purified by prep. TLC.

The following 3 compounds 26.89-26.91 were synthesized by this method:

N-[2-(6-{4-[3-(2-Cyanophenyl)-prop-2-ynyl]-piperazine-1-carbonyl}-2-phenyl-7H-pyrrolo[2,3-d]pyrimidin-4-ylamino)-ethyl]-acetamide (26.89)

$^1$H NMR (CDCl$_3$, 200. MHz) δ 1.78 (s, 3H), 2.87 (brs, 4H), 3.62 (brs, 2H), 3.76 (s, 2H), 3.93 (brs, 6H), 6.05 (brs, 1H), 6.86 (s, 1H), 7.08 (brs, 1H), 7.46 (brs, 4H), 7.56 (m, 2H), 7.66 (d, 2H, J=8 Hz), 8.44 (brs, 2H), 9.45 (brs, 1H). MS (ES) 546.9 [MH$^+$]. t$_R$ (method A)=6.4 min.

N-[2-(6-{4-[3-(3-Cyanophenyl)-prop-2-ynyl]-piperazine-1-carbonyl}-2-phenyl-7H-pyrrolo-2,3-d]pyrimidin-4-ylamino)-ethyl]-acetamide (26.90): $^1$H NMR (CDCl$_3$, 200 MHz) δ 1.84 (s, 3H), 2.74 (brs, 4H), 3.61 (brs, 4H), 3.96 (brs, 6H), 6.70 (s, 1H), 7.46 (brs, 4H), 7.58-7.78 (m, 4H), 8.42 (m, 2H), 9.40 (brs, 1H). MS (ES) 546.8 [MH$^+$]. t$_R$ (method A)=6.3 min.

N-[2-(6-{4-[3-(4-Cyanophenyl)-prop-2-ynyl]-piperazine-1-carbonyl}-2-phenyl-7H-pyrrolo[2,3-d]pyrimidin-4-ylamino)-ethyl]-acetamide (26.91

¹H NMR (CDCl₃, 200 MHz) δ 1.83 (s, 3H), 2.73 (brs, 4H), 3.62 (brs, 4H), 3.98 (brs, 6H), 5.93 (brs, 1H), 6.69 (brs, 2H), 7.46 (m, 4H), 7.58 (t, 3H, J=9.2 Hz), 8.44 (brs, 2H), 9.40 (brs, 1H). MS (ES) 546.9 [MH⁺]. $t_R$ (method A)=6.4 min.

1-[4-(2-Acetylaminoethylamino)-2-phenyl-7H-pyrrolo[2,3-d]pyrimidine-6-carbonyl]-4-phenylpiperidine-4-carboxylic acid methyl ester (26.92)

¹H NMR (CDCl₃, 200 MHz) δ 1.80 (s, 3H), 1.96 (m, 2H), 2.63 (t, 2H, J=6.9 Hz), 3.35 (brs, 2H), 3.57 (brs, 2H), 3.70 (s, 3H), 3.86 (brs, 2H), 4.46 (brs, 2H), 6.21 (brs, 1H), 6.73 (s, 1H), 7.00 (brs, 1H), 7.34-7.41 (m, 8H), 8.39 (brs, 2H), 9.90 (brs, 1H). MS (ES) 540.8 [MH⁺]. $t_R$(method A)=7.8 min.

N-(2-{6-[4-(1-Hydroxyethyl)-4-phenylpiperidine-1-carbonyl]-2-phenyl-7H-pyrrolo-[2,3-d]pyrimidin-4-ylamino}-ethyl)-acetamide (26.93)

¹H NMR (CDCl₃, 200 MHz) δ 0.98 (d, 3H, J=6.2 Hz), 1.78 (s, 3H), 1.86 (brs, 2H), 2.20 (d, 1H, J=10.2 Hz), 2.44 (d, 1H, J=12.6 Hz), 3.02 (brs, 2H), 3.60 (m, 3H), 3.83 (brs, 2H), 4.40 (d, 2H, J=11 Hz), 6.37 (brs, 1H), 6.66 (s, 1H), 7.12 (brs, 1H), 7.27-7.39 (m, 8H), 8.34 (t, 2H, J=3.7 Hz), 10.50 (brs, 1H). MS (ES) 526.9 [MH⁺]. $t_R$ (method A)=6.9 min.

N-[2-(6-{4-[3-(4-Cyanophenyl)-propyl]-piperazine 1-carbonyl}-2-phenyl-7H-pyrrolo[2,3-d]pyrimidin-4-ylamino)-ethyl]-acetamide (26.94)

¹H NMR (CDCl₃, 200 MHz) δ 1.82 (brs, 5H), 2.39 (t, 2H, J=7 Hz), 2.50 (brs, 4H), 2.72 (t, 2H, J=7.5 Hz), 3.60 (brs, 2H), 3.87 (brs, 6H), 6.13 (brs, 1H), 6.68 (s, 1H), 6.88 (brs, 1H), 7.31 (brs, 2H), 7.44 (brs, 3H), 7.60 (d, 2H, J=8 Hz), 8.40 (m, 2H), 9.78 (brs, 1H). MS (ES) 550.9 [MH⁺]. $t_R$(method A)=5.4 min.

1-[4-(2-Acetylaminoethylamino)-2-phenyl-7H-pyrrolo[2,3-d]pyrimidine-6-carbonyl]-4-phenylpiperidine-4-carboxylic acid ethyl ester (26.95)

¹H NMR (CDCl₃, 200 MHz) δ 1.21 (t, 3H, J=7.6 Hz), 1.81 (s, 3H), 2.01 (m, 2H), 2.64 (m, 2H), 3.40 (brs, 2H), 3.60 (brs, 2H), 3.91 (brs, 2H), 4.20 (q, 2H, J=7.2), 4.47 (brs, 2H), 6.03 (brs, 1H), 6.71 (s, 1H), 6.91 (brs, 1H), 7.34-7.44 (m, 8H), 8.44 (brs, 2H), 9.70 (brs, 1H). MS (ES) 555.0 [MH⁺]. $t_R$ (method A)=7.8 min.

N-{2-[6-(4-Benzyloxypiperidine-1-carbonyl)-2-phenyl-7H-pyrrolo[2,3-d]pyrimidin-4-ylamino]-ethyl}-acetamide (26.96)

¹H NMR (CDCl₃, 200 MHz) δ 1.22 (m, 1H), 1.71 (s, 3H), 1.82 (brs, 2H), 3.43 (brs, 2H), 3.66 (m, 6H), 3.96 (brs, 2H), 4.53 (s, 2H), 6.66 (brs, 1H), 6.71 (s, 1H), 7.33-7.44 (m, 8H), 8.36 (m, 2H), 11.14 (brs, 1H). MS (ES) 512.9 [MH⁺]. $t_R$(method A)=7.5 min.

Amide Formation with 26.85:
Acid 26.85 (16 mg, 0.0304 mmol) and triethylamine (8.5 µl, 2 eq.) were dissolved in DMF (2 ml) and cooled in ice bath. 5 min. later, TBTU (11.7 mg, 1.2 eq.) was added. 30 min later, pyrrolidine (3.1 µl, 1.2 eq.) was added and then stirred at rt for 2 days. The reaction mixture was poured into 10 ml of 5% HOAc aqueous solution, extracted with 5×8 ml of EtOAc, washed with 8 ml of 5% HOAc aqueous solution, 2×8 ml of H₂O and 8 ml of brine, dried over MgSO₄. Filter out and remove solvent and purify by TLC to obtain 12.6 mg of 26.104 as off-white solid.

The amides 26.97-26.107 were prepared by this method.

1-[4-(2-Acetylaminoethylamino)-2-phenyl-7H-pyrrolo[2,3-d]pyrimidine-6-carbonyl]-4-phenylpiperidine-4-carboxylic acid amide (26.97)

¹H NMR (CDCl₃, 200 MHz) δ 1.80 (s, 3H), 2.17 (brs, 2H), 2.48 (brs, 2H), 3.61 (brs, 2H), 3.90 (brs, 2H), 4.11 (brs, 2H), 5.30 (brs, 1H), 5.52 (brs, 1H), 5.99 (brs, 1H), 6.70 (s, 1H), 6.86 (brs, 1H), 7.32-7.46 (m, 8H), 8.41 (m, 2H), 9.64 (brs, 1H). MS (ES) 525.9 [MH⁺]. $t_R$ (method B)=12.6 min.

1-[4-(2-Acetylaminoethylamino)-2-phenyl-7H-pyrrolo[2,3-d]pyrimidine-6-carbonyl]-4-phenylpiperidine-4-carboxylic acid methylamide (26.98)

¹H NMR (CDCl₃, 200 MHz) δ 1.71 (s, 3H), 2.13 (brs, 2H), 2.41 (brs, 2H), 3.66 (d, 3H, J=4.8 Hz), 3.48 (brs, 2H), 3.81 (m, 4H), 3.93 (brs, 2H), 5.87 (d, 1H, J=4.4 Hz), 6.76 (s, 1H), 7.29-7.39 (m, 8H), 7.64 (brs, 1H), 8.29 (brs, 2H). MS (ES) 539.9 [MH⁺]. $t_R$(method B)=13.0 min.

1-[4-(2-Acetylaminoethylamino)-2-phenyl-7H-pyrrolo[2,3-d]pyrimidine-6-carbonyl]-4-phenylpiperidine-4-carboxylic acid dimethylamide (26.99)

¹H NMR (CDCl₃, 200 MHz) δ 1.75 (s, 3H), 2.41 (d, 2H, J=13.2 Hz), 2.50-3.00 (brs, 6H), 3.35 (brs, 4H), 3.86 (brs, 4H), 4.41 (brs, 2H), 6.38 (t, 1H, J=5.2 Hz), 6.74 (s, 1H), 7.20-7.43 (m, 8H), 8.41 (m, 2H), 10.09 (brs, 1H). MS (ES) 553.9 [MH⁺]. $t_R$(method B)=14.5 min.

1-[4-(2-Acetylaminoethylamino)-2-phenyl-7H-pyrrolo[2,3-d]pyrimidine-6-carbonyl]-4-phenylpiperidine-4-carboxylic acid benzylamide (26.100)

¹H NMR (CDCl₃, 200 MHz) δ 1.80 (s, 3H), 2.17 (brs, 2H), 2.49 (brs, 2H), 3.59 (brs, 2H), 3.89 (brs, 4H), 4.09 (brs, 2H), 4.36 (brs, 2H), 5.57 (brs, 1H), 6.71 (s, 1H), 7.04 (m, 3H), 7.23-7.43 (m, 11H), 8.40 (brs, 2H), 9.59 (brs, 1H). MS (ES) 615.9 [MH⁺]. $t_R$ (method A)=7.7 min.

1-[4-(2-Acetylaminoethylamino)-2-phenyl-7H-pyrrolo[2,3-d]pyrimidine-6-carbonyl]-4-phenylpiperidine-4-carboxylic acid ethylamide (26.101)

¹H NMR (CDCl₃, 200 MHz) δ 1.00 (t, 3H, J=7.2 Hz), 1.78 (s, 3H), 2.20 (brs, 2H), 2.44 (brs, 2H), 3.21 (d, 2H, J=6.4 Hz), 3.56 (brs, 2H), 3.85 (brs, 4H), 4.03 (brs, 2H), 5.30 (brs, 1H), 6.21 (brs, 1H), 6.71 (s, 1H), 7.04 (brs, 1H), 7.37-7.40 (m, 8H), 8.38 (brs, 2H), 9.97 (brs, 1H). MS (ES) 553.9 [MH⁺]. $t_R$ (method A)=6.6 min.

1-[4-(2-Acetylaminoethylamino)-2-phenyl-7H-pyrrolo[2,3-d]pyrimidine-6-carbonyl]-4-phenylpiperidine-4-carboxylic acid diethylamide (26.102)

¹H NMR (CDCl₃, 200 MHz) δ 0.68 (brs, 3H), 1.23 (brs, 3H), 1.76 (s, 3H), 2.39 (d, 2H), 2.91 (brs, 2H), 3.33 (brs, 2H), 3.58 (brs, 4H), 3.88 (brs, 4H), 4.40 (brs, 2H), 6.24 (brs, 1H), 6.74 (s, 1H), 7.15 (brs, 1H), 7.22-7.44 (m, 8H), 8.42 (m, 2H), 9.97 (brs, 1H). MS (ES) 581.9 [MH$^+$]. $t_R$(method B)=16.5 min.

N-(2-{6-[4-(Azetidine-1-carbonyl)-4-phenylpiperidine-1-carbonyl]-2-phenyl-7H-pyrrolo[2,3-d]pyrimidin-4-ylamino}-ethyl)-acetamide (26.103)

$^1$H NMR (CDCl$_3$, 200 MHz) δ 1.76 (s, 3H), 1.80 (brs, 2H), 2.02 (t, 4H, J=7.4 Hz), 2.43 (d, 2H, J=12 Hz), 3.57 (brs, 4H), 3.87 (brs, 2H), 3.99 (brs, 2H), 4.38 (brs, 2H), 6.38 (brs, 1H), 6.74 (s, 1H), 7.22-7.40 (m, 9H), 8.41 (m, 2H), 10.01 (brs, 1H). MS (ES) 556.0 [MH$^+$]. $t_R$ (method B)=14.6 min.

N-(2-{2-Phenyl-6-[4-phenyl-4-(pyrrolidine-1-carbonyl)-piperidine-1-carbonyl]-7H-pyrrolo[2,3-d]pyrimidin-4-ylamino}-ethyl)-acetamide (26.104)

$^1$H NMR (CDCl$_3$, 200 MHz) δ 1.56 (brs, 4H), 1.76 (brs, 4H), 1.78 (s, 3H), 2.47 (d, 2H), 2.82 (brs, 2H), 3.57 (brs, 4H), 3.89 (brs, 2H), 4.40 (brs, 2H), 6.22 (brs, 1H), 6.74 (s, 1H), 7.10 (brs, 1H), 7.22-7.43 (m, 8H), 8.42 (m, 2H), 9.80 (brs, 1H). MS (ES) 580.0 [MH$^+$]. $t_R$ (method B)=15.6 mm.

N-(2-{2-Phenyl-6-[4-phenyl-4-(piperidine-1-carbonyl)-piperidine-1-carbonyl]-7H-pyrrolo[2,3-d]pyrimidin-4-ylamino}-ethyl)-acetamide (26.105)

$^1$H NMR (CDCl$_3$, 200 MHz) δ 1.48 (brs, 4H), 1.68 (brs, 4H), 1.79 (s, 3H), 2.41 (d, 2H), 3.32 (brs, 4H), 3.61 (brs, 4H), 4.46 (brs, 2H), 6.06 (brs, 1H), 6.72 (s, 1H), 7.04 (brs, 1H), 7.24-7.46 (m, 8H), 8.43 (m, 2H), 9.66 (brs, 1H). MS (ES) 593.9 [MH$^+$]. $t_R$ (method A)=7.9 min.

N-(2-{6-[4-(Morpholine-4-carbonyl)-4-phenylpiperidine-1-carbonyl]-2-phenyl-7H-pyrrolo[2,3-d]pyrimidin-4-ylamino}-ethyl)-acetamide (26.106)

$^1$H NMR (CDCl$_3$, 200 MHz) δ 1.80 (s, 3H), 2.38 (d, 2H), 3.35 (brs, 8H), 3.61 (brs, 4H), 3.90 (brs, 4H), 4.47 (brs, 2H), 6.05 (brs, 1H), 6.72 (s, 1H), 6.96 (brs, 1H), 7.24-7.44 (m, 8H), 8.43 (m, 2H), 9.66 (brs, 1H). MS (ES) 595.9 [MH$^+$]. $t_R$(method B)=14.2 min.

1-[4-(2-Acetylaminoethylamino)-2-phenyl-7H-pyrrolo[2,3-d]pyrimidine-6-carbonyl]-4-phenylpiperidine-4-carboxylic acid tert-butylamide (26.107)

$^1$H NMR (CDCl$_3$, 200 MHz) δ 1.24 (s, 9H), 1.81 (s, 3H), 2.40 (d, 2H), 3.61 (brs, 4H), 3.91 (brs, 4H), 4.11 (brs, 2H), 6.01 (brs, 1H), 6.72 (s, 1H), 6.91 (brs, 1H), 7.30-7.45 (m, 8H), 8.41 (m, 2H), 9.56 (brs, 1H). MS (ES) 581.9 [MH$^+$]. $t_R$(method A)=7.8 min.

N-{2-[6-(4-Methyl-4-phenylpiperidine-1-carbonyl)-2-phenyl-7H-pyrrolo[2,3-d]-pyrimidin-4-ylamino]-ethyl}-acetamide (26.108)

$^1$H NMR (CDCl$_3$, 200 MHz) δ 1.30 (s, 3H), 1.77 (m, 5H), 2.18 (brs, 2H), 3.54 (brs, 2H), 3.69 (brs, 2H), 3.81 (brs, 4H), 6.20 (brs, 1H), 6.67 (s, 1H), 7.09 (brs, 1H), 7.23-7.42 (m, 8H), 8.40 (m, 2H), 10.23 (brs, 1H). MS (ES) 496.9 [MH$^+$]. $t_R$ (method A)=7.9 min.

N-(2-{6-[4-(1-Hydroxy-1-methylethyl)-4-phenylpiperidine-1-carbonyl]-2-phenyl-7H-pyrrolo[2,3-d]pyrimidin-4-ylamino}-ethyl)-acetamide (26.109)

$^1$H NMR (CDCl$_3$, 200 MHz) δ 1.09 (s, 6H), 1.79 (s, 3H), 1.97 (t, 2H, J=12.8 Hz), 2.41 (d, 2H, J=13 Hz), 2.87 (brs, 2H), 3.57 (brs, 2H), 3.69 (s, 1H), 3.85 (brs, 2H), 4.50 (d, 2H, J=9.8 Hz), 6.11 (brs, 1H), 6.64 (s, 1H), 7.02 (brs, 1H), 7.29-7.40 (m, 8H), 8.37 (brs, 2H), 10.01 (brs, 1H). MS (ES) 540.9 [MH$^+$]. $t_R$ (method A)=7.0 min.

N-{2-[6-(4-Isopropyl-4-phenylpiperidine-1-carbonyl)-2-phenyl-7H-pyrrolo[2,3-d]-pyrimidin-4-ylamino]-ethyl}-acetamide (26.110)

$^1$H NMR (CDCl$_3$, 200 MHz) δ 1.15 (brs, 2H), 1.24 (s, 6H), 1.48 (d, 2H, J=11.6 Hz), 1.69 (m, 1H), 1.75 (s, 3H), 2.76 (brs, 2H), 3.51 (brs, 2H), 3.79 (brs, 2H), 4.52 (d, 2H, J=11Hz), 6.32 (brs, 1H), 6.64 (s, 1H), 7.13-7.42 (m, 9H), 8.38 (brs, 2H), 10.41 (brs, 1H). MS (ES) 524.9 [MH$^+$]. $t_R$(method A)=8.8 min.

N-(2-{2-Phenyl-6-[4-(3-thiophen-2-yl-prop-2-ynyl)-piperazine-1-carbonyl]-7H-pyrrolo[2,3-d]pyrimidin-4-ylamino}-ethyl)-acetamide (26.111)

$^1$H NMR (CDCl$_3$, 200 MHz) δ 1.81 (s, 3H), 2.71 (brs, 4H), 3.61 (brs, 4H), 3.94 (brm, 6H), 5.94 (brs, 1H), 6.69 (s, 1H), 6.83 (brs, 1H), 6.96 (dd, 1H, J=5 Hz, J=3.8 Hz), 7.22 (m, 2H), 7.45 (brd, 3H), 8.40 (brd, 2H), 9.62 (brs, 1H).

1-[4-(2-Acetylaminoethylamino)-2-phenyl-7H-pyrrolo[2,3-d]pyrimidine-6-carbonyl]-4-phenylpiperidine-4-carboxylic acid cyclobutylmethyl ester (26.112)

$^1$H NMR (CDCl$_3$, 200 MHz) δ 0.89-1.34 (m, 7H), 1.70 (t, 2H, J=10Hz), 1.78 (s, 3H), 2.02 (brt, 2H), 2.53 (d, 2H, J=13.6 Hz), 3.42 (brm, 2H), 3.59 (brs, 2H), 3.89 (brs, 2H), 4.39 (d, 2H, J=12.4 Hz), 6.04 (brs, 1H), 6.15 (brs, 1H), 6.73 (s, 1H), 7.09 (brs, 1H), 7.26-7.45 (m, 7H), 8.42 (m, 2H).

2-{6-[4-(4-Fluorobenzyl)-piperidine-1-carbonyl]-2-phenyl-7H-pyrrolo[2,3-d]-pyrimidin-4-ylamino}-acetamide (26.113)

$^1$H NMR (CDCl$_3$, 200 MHz) δ 1.30 (brs, 2H), 1.75 (s, 3H), 1.81 (brs, 3H), 2.55 (m, 2H), 2.96 (brs, 2H), 4.42 (d, 2H, J=5 Hz), 4.58 (d, 2H, J=14.2 Hz), 5.52 (brs, 1H), 5.89 (brs, 1H), 6.28 (brs, 1H), 6.65 (s, 1H), 6.95-7.15 (m, 4H), 7.46 (m, 3H), 8.41 (m, 2H).

N-(2-{6-[4-(4-Chlorophenyl)-4-methoxypiperidine-1-carbonyl]-2-phenyl-7H-pyrrolo[2,3-d]pyrimidin-4-ylamino}-ethyl)-acetamide (26.114)

$^1$H NMR (CDCl$_3$, 200 MHz) δ 1.77 (s, 3H), 1.87-2.12 (m, 4H), 2.95 (s, 3H), 3.51 (brs, 4H), 3.78 (brs, 2H), 4.40 (d, 2H, J=10.6 Hz), 6.47 (brs, 1H), 6.74 (s, 1H), 7.23-7.41 (m, 8H), 8.35 (m, 2H), 10.83 (brs, 1H). MS (ES) 547.0/549.0 [MH$^+$]. $t_R$ (method A)=8.6 min.

N-(2-{6-[4-Methoxy-4-(3-trifluoromethylphenyl)-piperidine-1-carbonyl]-2-phenyl-7H-pyrrolo[2,3-d]pyrimidin-4-ylamino}-ethyl)-acetamide (26.115)

$^1$H NMR (CDCl$_3$, 200 MHz) δ 1.80 (s, 3H), 1.90-2.18 (m, 4H), 3.03 (s, 3H), 3.59 (brs, 4H), 3.86 (brs, 2H), 4.51 (d, 2H, J=13.4 Hz), 6.10 (brs, 1H), 6.72 (s, 1H), 6.92 (brs, 1H), 7.42-7.64 (m, 8H), 8.38 (m, 2H), 10.05 (brs, 1H). MS (ES) 581 [MH$^+$]. t$_R$(method A)=8.8 min.

N-{2-[6-(4-Isopropyl-4-methoxypiperidine-1-carbonyl)-2-phenyl-7H-pyrrolo[2,3-d]-pyrimidin-4-ylamino]-ethyl}-acetamide (26.116)

$^1$H NMR (CDCl$_3$, 200 MHz) δ 0.91 (d, 6H, J=6.8 Hz), 1.69 (m, 4H), 1.80 (s, 3H), 1.99 (m, 1H), 3.19 (s, 3H), 3.61 (brs, 4H), 3.89 (brs, 2H), 4.41 (d, 2H, J=12.4 Hz), 6.03 (brs, 1H), 6.68 (s, 1H), 6.96 (brs, 1H), 7.45 (m, 3H), 8.39 (m, 2H), 9.89 (brs, 1H). MS (ES) 478.9 [MH$^+$]. t$_R$(method A)=7.0 min.

N-{2-[6-(4-Acetylamino-4-phenylpiperidine-1-carbonyl)-2-phenyl-7H-pyrrolo[2,3-d]pyrimidin-4-ylamino]-ethyl}-acetamide (26.117)

$^1$H NMR (CDCl$_3$, 200 MHz) δ 1.65 (s, 3H), 1.88 (s, 3H), 2.50 (brs, 6H), 3.36 (m, 2H), 3.67 (m, 2H), 4.26 (d, 2H, J=13.2 Hz), 6.76 (s, 1H), 6.94 (brs, 1H), 7.05-7.25 (m, 8H), 7.48 (brs, 1H), 8.28 (m, 2H), 10.34 (brs, 1H). MS (ES) 540 [MH$^+$]. t$_R$(method B)=13.5 min.

1-[4-(2-Acetylaminoethylamino)-2-phenyl-7H-pyrrolo[2,3-d]pyrimidine-6-carbonyl]-4-phenylpiperidine-4-carboxylic acid isopropyl ester (26.118)

$^1$H NMR (CDCl$_3$, 200 MHz) δ 1.19 (d, 6H, J=6.2 Hz), 1.77 (s, 3H), 1.93 (t, 2H, J=11Hz), 2.60 (d, 2H, J=12.8 Hz), 3.32 (brs, 2H), 3.54 (brs, 2H), 3.82 (brs, 2H), 4.42 (d, 2H, J=13.2 Hz), 5.05 (m, 1H, J=6.2 Hz), 6.31 (brs, 1H), 6.72 (s, 1H), 7.12-(brs, 1H), 7.31-7.42 (m, 8H), 8.35 (m, 2H), 10.46 (brs, 1H). MS (ES) 568.9 [MH$^+$]. t$_R$(method A)=8.4 min.

1-[4-(2-Acetylaminoethylamino)-2-phenyl-7H-pyrrolo[2,3-d]pyrimidine-6-carbonyl]-4-ethylaminopiperidine-4-carboxylic acid amide (26.119)

$^1$H NMR (CD$_3$OD, 200 MHz) δ 1.13 (t, 3H, J=7 Hz), 1.74 (m, 2H), 1.85 (s, 3H), 2.09 (m, 2H), 2.55 (q, 2H, J=7.1 Hz), 3.52 (t, 2H, J=6 Hz), 3.83 (t, 4H, J=6 Hz), 3.94 (m, 2H), 6.92 (s, 1H), 7.41-7.47 (m, 3H), 8.39-8.44 (m, 2H). MS (ES) 493.0 [MH$^+$]. t$_R$(method A)=6.6 min.

1-[4-(2-Acetylaminoethylamino)-2-phenyl-7H-pyrrolo[2,3-d]pyrimidine-6-carbonyl]-4-phenylaminopiperidine-4-carboxylic acid amide (26.120)

$^1$H NMR (CD$_3$OD, 200 MHz) δ 1.84 (s, 3H), 2.13 (m, 4H), 3.51 (m, 4H), 3.82 (t, 2H, J=6 Hz), 4.24 (d, 2H, J=6.9 Hz), 6.67-6.74 (m, 3H), 6.92 (s, 1H), 7.13 (t, 2H, J=7.9 Hz), 7.42 (m, 3H), 8.41 (m, 2H). MS (ES) 541.0 [MH$^+$]. t$_R$ (method A)=6.3 min.

N-(2-{6-[4-Methoxy-4-(3-methoxyphenyl)-piperidine-1-carbonyl]-2-phenyl-7H-pyrrolo[2,3-d]pyrimidin-4-ylamino}-ethyl)-acetamide (26.121)

$^1$H NMR (CDCl$_3$, 200 MHz) δ 1.75 (s, 3H), 1.87 (d, 2H, J=11.6 Hz), 2.05 (d, 2H, J=12.8 Hz), 3.00 (s, 3H), 3.48 (brs, 2H), 3.81 (brs, 4H), 4.41 (d, 2H, J=13 Hz), 6.39 (brs, 1H), 6.74 (s, 1H), 6.81 (d, 2H, J=8.2 Hz), 6.93 (brs, 2H), 7.24-7.38 (m, 5H), 8.35 (m, 2H), 10.64 (brs, 1H). MS (ES) 543.0 [MH$^+$]. t$_R$ (method A)=7.3 min.

1-[4-(2-Acetylaminoethylamino)-2-phenyl-7H-pyrrolo[2,3-d]pyrimidine-6-carbonyl]-4-pyrrolidin-1-ylpiperidine-4-carboxylic acid amide (26.122)

$^1$H NMR (CD$_3$OD, 200 MHz) δ 1.78 (brs, 4H), 1.85 (s, 3H), 1.96 (m, 2H), 2.07 (m, 2H), 2.75 (brs, 4H), 3.53 (t, 2H, J=6 Hz), 3.68 (brs, 2H), 3.84 (t, 2H, J=6 Hz), 4.08 (m, 2H), 6.92 (s, 1H), 7.42-7.45 (m, 3H), 8.38-8.42 (m, 2H). MS (ES) 519.0 [MH$^+$]. t$_R$(method A)=3.4 min.

N-(2-{6-[4-(2-Methoxyphenyl)-3,6-dihydro-2H-pyridine-1-carbonyl]-2-phenyl-7H-pyrrolo[2,3-d]pyrimidin-4-ylamino}-ethyl)-acetamide (26.123)

$^1$H NMR (CDCl$_3$, 200 MHz) δ 1.81 (s, 3H), 2.69 (brs, 2H), 3.05 (d, 2H, J=4.8 Hz), 3.63 (m, 2H), 3.82 (d, 3H, J=3.2 Hz), 3.92 (m, 2H), 4.52 (brs, 2H), 5.84 (brs, 1H), 6.75 (s, 1H), 6.94 (m, 3H), 7.15-7.26 (m, 2H), 7.45 (m, 3H), 8.43 (m, 2H), 9.48 (brs, 1H). MS (ES) 511.0 [MH$^+$]. t$_R$(method A)=7.7 min.

N-(2-{6-[4-Methoxy-4-(2-methoxyphenyl)-piperidine-1-carbonyl]-2-phenyl-7H-pyrrolo[2,3-d]pyrimidin-4-ylamino}-ethyl)-acetamide (26.124)

$^1$H NMR (CDCl$_3$, 200 MHz) δ 1.80 (s, 3H), 2.31 (m, 4H), 3.14 (s, 3H), 3.62 (brs, 4H), 3.63 (m, 2H), 3.84 (s, 3H), 3.93 (m, 4H), 4.47 (d, 2H), 5.90 (brs, 1H), 6.70 (s, 1H), 6.96 (m, 3H), 7.30 (m, 2H), 7.45 (m, 3H), 8.41 (m, 2H), 9.47 (brs, 1H). MS (ES) 543.0 [MH$^+$]. t$_R$ (method A)=7.1 min.

N-{2-[6-(4-Amino-4-phenylpiperidine-1-carbonyl)-2-phenyl-7H-pyrrolo[2,3-d]-pyrimidin-4-ylamino]-ethyl}-acetamide (26.125)

$^1$H NMR (CD$_3$OD, 200 MHz) δ 1.85 (s, 3H), 1.94 (brs, 2H), 2.32 (brs, 2H), 3.52 (t, 2H, J=6.2 Hz), 3.83 (t, 2H, J=5.8 Hz), 3.84 (s, 3H), 3.99 (m, 4H), 4.47 (d, 2H), 6.94 (s, 1H), 7.24-7.59 (m, 8H), 8.42 (m, 2H). MS (ES) 498.0 [MH$^+$]. t$_R$ (method B)=8.4 min.

N-{2-[6-(4-Formyl-4-phenylpiperidine-1-carbonyl)-2-phenyl-7H-pyrrolo[2,3-d]-pyrimidin-4-ylamino]-ethyl}-acetamide (26.126)

$^1$H NMR (CDCl$_3$+CD$_3$OD, 200 MHz) δ 1.75 (s, 3H), 2.12 (brs, 2H), 2.46 (brs, 2H), 3.46 (brs, 4H), 3.83 (brs, 2H), 4.31 (brs, 2H), 6.73 (s, 1H), 7.25-7.41 (m, 8H), 8.32 (m, 2H), 9.45 (s, 1H). MS (ES) 511.0 [MH$^+$]. t$_R$(method A)=2.9 min.

N-{2-[6-(4-Hydroxymethyl-4-phenylpiperidine-1-carbonyl)-2-phenyl-7H-pyrrolo-[2,3-d]pyrimidin-4-ylamino]-ethyl}-acetamide (26.127)

$^1$H NMR (CDCl$_3$+CD$_3$OD, 200 MHz) δ 1.79 (s, 3H), 2.02 (brs, 2H), 2.31 (d, 2H, J=12.2 Hz), 3.40 (m, 2H), 3.50 (brs, 2H), 3.57 (s, 2H), 3.87 (m, 2H), 4.27 (d, 2H, J=12.8 Hz), 6.77 (s, 1H), 7.31-7.48 (m, 8H), 8.34 (m, 2H). MS (ES) 511.0 [MH$^+$]. t$_R$ (method A)=2.9 min.

N-{2-[6-(4-Ethyl-4-phenylpiperidine-1-carbonyl)-2-phenyl-7H-pyrrolo[2,3-d]-pyrimidin-4-ylamino]-ethyl}-acetamide (26.128)

$^1$H NMR (CDCl$_3$, 200 MHz) δ 1.16 (m, 2H), 1.24 (d, 3H, J=7 Hz), 1.44 (m, 2H), 1.62 (m, 2H), 1.75 (s, 3H), 2.88 (brs, 2H), 3.56 (brs, 2H), 3.85 (brs, 2H), 4.45 (d, 1H, J=13.4 Hz), 4.60 (d, 1H, J=10.4 Hz), 5.99 (brs, 1H), 6.61 (s, 1H), 6.99 (brs, 1H), 7.11-7.43 (m, 8H), 8.38 (m, 2H) 9.87 (brs, 1H). MS (ES) 511.0 [MH$^+$]. t$_R$ (method A)=8.3 min.

N-{2-[6-(4-Benzylmethoxypiperidine-1-carbonyl)-2-phenyl-7H-pyrrolo[2,3-d]-pyrimidin-4-ylamino]-ethyl}-acetamide (26.129)

$^1$H NMR (CDCl$_3$, 200 MHz) δ 1.48 (t, 2H, J=1.1 Hz), 1.76 (m, 5H), 2.76 (s, 2H), 3.35 (m, 5H), 3.52 (brs, 2H), 3.80 (brs, 2H), 4.24 (d, 2H, J=12.2 Hz), 6.25 (brs, 1H), 6.63 (s, 1H), 7.10-7.43 (m, 9H), 8.35 (m, 2H), 10.41 (brs, 1H). MS (ES) 527.0 [MH$^+$]. t$_R$(method A)=7.3 min.

N-{2-[6-(4-Methoxy-4-o-tolylpiperidine-1-carbonyl)-2-phenyl-7H-pyrrolo[2,3-d]-pyrimidin-4-ylamino]-ethyl}-acetamide (26.130)

$^1$H NMR (CDCl$_3$, 200 MHz) δ 1.77 (s, 3H), 1.88 (t, 2H, J=11.8 Hz), 2.28 (d, 2H, J=14.4 Hz), 2.55 (s, 3H), 2.98 (s, 3H), 3.49 (brs, 4H), 3.79 (brs, 2H), 4.44 (d, 2H, J=12.8 Hz), 6.31 (brs, 1H), 6.73 (s, 1H), 7.18 (brs, 5H), 7.40 (m, 3H), 8.35 (m, 2H), 10.60 (brs, 1H). MS (ES) 527.0 [MH$^+$]. t$_R$(method A)=7.9 min.

N-{2-[6-(4-Methoxymethyl-4-phenylpiperidine-1-carbonyl)-2-phenyl-7H-pyrrolo[2,3-d]pyrimidin-4-ylamino]-ethyl}-acetamide (26.131)

$^1$H NMR (CDCl$_3$, 200 MHz) δ 1.75 (s, 3H), 1.94 (t, 2H, J=10.6 Hz), 2.17 (t, 2H, J=13.0 Hz), 3.21 (brs, 4H), 3.30 (s, 3H), 3.48 (d, 2H, J=4.0 Hz), 3.75 (brs, 2H), 4.15 (d, 2H, J=13.2 Hz), 6.43 (brs, 1H), 6.66 (s, 1H), 7.26-7.42 (m, 9H), 8.32 (m, 2H), 10.76 (brs, 1H). MS (ES) 527.0 [MH$^+$]. t$_R$ (method A)=7.5 min.

4-(2-Acetylaminoethylamino)-2-phenyl-7H-pyrrolo[2,3-d]pyrimidine-6-carboxylic acid (1-benzylpyrrolidin-3-yl)-amide (26.132)

MS (ES): 497.7 (M$^+$+1), t$_R$ (method A)=4.4 min.

N-[2-(6-{4-[3-(2-Chlorophenyl)-propyl]-piperazine-1-carbonyl}-2-phenyl-7H-pyrrolo[2,3-d]pyrimidin-4-ylamino)-ethyl]-acetamide (26.133)

MS (ES): 560.1 (M$^+$+1), t$_R$ (method A)=4.9 min.

N-[2-(6-{4-[3-(3-Chlorophenyl)-propyl]-piperazine1-carbonyl}-2-phenyl-7H-pyrrolo[2,3-d]pyrimidin-4-ylamino)-ethyl]-acetamide (26.134)

MS (ES): 560.1 (M$^+$+1).

N-[2-(6-{4-[3-(4-Chlorophenyl)-propyl]-piperazine-1-carbonyl}-2-phenyl-7H-pyrrolo[2,3-d]pyrimidin-4-ylamino)-ethyl]-acetamide (26.135)

$^1$H NMR (d$_6$-DMSO, 200 MHz): δ=1.72 (tt, J=6.8, 6.8 Hz, 2H), 1.82 (s, 3H), 2.34 (t, J=6.8 Hz, 2H), 2.42 (brs, 4H), 2.59 (t, J=7.0 Hz, 2H), 3.32-3.45 (m, 2H), 3.60-3.80 (m, 6H), 6.95 (d, J=1.8 Hz, 1H), 7.24-7.35 (AA' BB', 4H), 7.40-7.50 (m, 3H), 7.83 (t, J=5.5 Hz, 1H), 8.07 (t, J=5.7 Hz, 1H), 8.40-8.47 (m, 2H), 12.00 (d, J=1.4 Hz, 1H). $^{13}$C NMR (d$_6$-DMSO, 50.3 MHz, DEPT135): δ=22.67 (+), 27.79 (−), 32.07 (−), 38.60 (−), 39.67 (−), 44.63 (−), 52.80 (−), 56.82 (−), 101.54 (C$_{quart}$), 102.33 (+), 126.58 (C$_{quart}$), 127.55 (+), 128.10 (+), 129.33 (+), 130.15 (+), 130.24 (C$_{quart}$), 139.12 (C$_{quart}$), 140.99 (C$_{quart}$), 151.08 (C$_{quart}$), 156.86 (C$_{quart}$), 158.30 (C$_{quart}$), 161.36 (C$_{quart}$), 169.44 (C$_{quart}$). MS (ES): 559.2 (M$^+$+1), t$_R$ (method A)=4.9 min.

N-[2-(6-{4-[3-(4-Chlorophenyl)-propyl]-piperazine-1-carbonyl}-2-phenyl-7H-pyrrolo[2,3-d]pyrimidin-4-ylamino)-ethyl]-acetamide methanesulfonate salt (26.135.MsOH)

Compound 26.135 (5.37 g, 9.59 mmol) is dissolved in a mixture of methanol (50 mL) and THF (100 mL), and methanesulfonic acid (921 mg, 9.59 mmol) is added dropwise. The solution is allowed to stand for 15 minutes and then concentrated in vacuo. The pale yellow foam is dissolved in ethanol and concentrated to give 6.3 g (100%) of a pale yellow amorphous solid, mp. 150-156° C. $^1$H NMR (400 MHz, DMSO-D$_6$): δ=1.79 (s, 3H), 1.96 (m, 2H), 2.30 (s, 3H), 2.64 (t, 2H, J=7.2 Hz), 3.12 (m, 4H), 3.35 (m, 6H), 3.50-3.70 (m, 4H), 4.46 (d, 2H, J=6.8 Hz), 7.02 (s, 1H), 7.26 (d, 2H, J=8.4 Hz), 7.36 (d, 2H, J=8.4 Hz), 7.40-7.48 (m, 3H), 7.87 (brs, 1H), 8.04 (brs, 1H), 8.39 (dd, 2H, J=2.0, 7.2 Hz), 9.68 (brs, 1H), 12.09 (brs, 1H). MS (ES): 560.0/562.0 (100/33) [MH$^+$]. t$_R$ (method B)=10.5 min.

N-(2-{6-[4-(2-Oxo-2,3-dihydrobenzoimidazol-1-yl)-piperidine-1-carbonyl]-2-phenyl-7H-pyrrolo[2,3-d]pyrimidin-4-ylamino}-ethyl)-acetamide (26.136)

$^1$H NMR (d6-DMSO, 400 MHz) δ 1.79 (s, 3H), 1.82 (m, 2H), 2.36 (m, 2H), 3.13 (m, 2H), 3.40 (m, 2H), 3.62 (m, 2H), 4.52 (m, 3H), 6.94 (s, 1H), 6.97 (m, 3H), 7.26 (d, 1H, J=5.2 Hz), 7.43 (m, 3H), 7.85 (brs, 1H), 8.05 (brs, 1H), 8.40 (d, 2H, J=6.8 Hz), 10.9 (brs, 1H), 12.0 (brs, 1H); MS (ES): 538.9 (M$^+$+1), t$_R$ (method B)=12.9 min.

4-(2-Acetylaminoethylamino)-2-phenyl-7H-pyrrolo[2,3-d]pyrimidine-6-carboxylic acid [1-(4-chlorobenzyl)-2-hydroxyethyl]-amide (26.137)

$^1$H NMR (d$_6$-DMSO, 400 MHz) δ 1.79 (s, 3H), 1.82 (m, 2H), 2.75 (m, 2H), 3.35 (m, 2H), 3.40 (m, 2H), 3.45 (m, 2H), 3.62 (m, 2H), 4.11 (brs, 1H), 4.91 (t, 1H, J=5.4 Hz), 7.09 (s, 1H), 7.17 (d, 2H, J=8.8 Hz), 7.43 (m, 3H), 8.01 (d, 2H, J=8.4 Hz), 8.38 (d, 2H, J=8.4 Hz), 11.92 (brs, 1H); MS (ES): 506.9 (M$^+$+1), t$_R$ (method B)=14.5 min.

4-(2-Acetylaminoethylamino)-2-phenyl-7H-pyrrolo[2,3-d]pyrimidine-6-carboxylic acid 4-[1,2,3]thiadiazol-4-yl-benzylamide (26.138)

MS (ES): 512.9 (M$^+$+1), t$_R$(method B)=14.2 min.

N-[2-(6-{4-[3-(2-Methoxyphenyl)-propyl]-piperazine-1-carbonyl}-2-phenyl-7H-pyrrolo[2,3-d]pyrimidin-4-ylamino)-ethyl]-acetamide (26.139)

MS (ES): 555.9 (M$^+$+1), t$_R$ (method B)=11.7 min.

N-[2-(6-{4-[3-(3-Methoxyphenyl)-propyl]-piperazine-1-carbonyl}-2-phenyl-7H-pyrrolo[2,3-d]pyrimidin-4-ylamino)-ethyl]-acetamide (26.140)

MS (ES): 556.0 (M$^+$+1), $t_R$ (method B)=11.4 min.

N-[2-(6-{4-[3-(4-Methoxyphenyl)-propyl]-piperazine-1-carbonyl}-2-phenyl-7H-pyrrolo[2,3-d]pyrimidin-4-ylamino)-ethyl]-acetamide (26.141)

MS (ES): 555.9 (M$^+$+1), $t_R$ (method B)=11.3 min.

N-(2-{6-[4-(2-Oxo-2-pyrrolidin-1-ylethyl)-piperazine-1-carbonyl]-2-phenyl-7H-pyrrolo[2,3-d]pyrimidin-4-ylamino}-ethyl)-acetamide (26.142)

MS (ES): 518.9 (M$^+$+1), $t_R$ (method B)=8.7 min.

N-[2-(6-{4-[3-(4-Chlorophenyl)-propionyl]-piperazine-1-carbonyl}-2-phenyl-7H-pyrrolo[2,3-d]pyrimidin-4-ylamino)-ethyl]-acetamide (26.143)

MS (ES): 573.9 (M$^+$+1), $t_R$ (method B)=15.5 min.

N-[2-(6-{4-[3-(3-Chlorophenyl)-propionyl]-piperazine-1-carbonyl}-2-phenyl-7H-pyrrolo[2,3-d]pyrimidin-4-ylamino)-ethyl]-acetamide (26.144)

MS (ES): 573.9 (M$^+$+1), $t_R$ (method B)=15.5 min.

N-[2-(6-{4-[3-(2-Chlorophenyl)-propionyl]-piperazine-1-carbonyl}-2-phenyl-7H-pyrrolo[2,3-d]pyrimidin-4-ylamino)-ethyl]-acetamide (26.145)

MS (ES): 573.8 (M$^+$+1), $t_R$ (method B)=15.2 min.

N-[2-(6-{4-[5-(4-Chlorophenyl)-2H-pyrazol-3-yl]-piperidine-1-carbonyl}-2-phenyl-7H-pyrrolo[2,3-d]pyrimidin-4-ylamino)-ethyl]-acetamide (26.146)

MS (ES): 582.9 (M$^+$+1), $t_R$ (method B)=16.4 min.

2-{4-[4-(2-Acetylaminoethylamino)-2-phenyl-7H-pyrrolo[2,3-d]pyrimidine-6-carbonyl]-piperazin-1-yl}-N-methyl-N-phenylacetamide (26.147)

MS (ES): 555.0 (M$^+$+1), $t_R$ (method B)=10.4 min.

4-[4-(2-Acetylaminoethylamino)-2-phenyl-7H-pyrrolo[2,3-d]pyrimidine-6-carbonyl]-piperazine-1-carboxylic acid benzyl ester (26.148)

MS (ES): 541.9 (M$^+$+1), $t_R$(method B)=15.3 min.

N-{2-[6-(4-Oxo-1-phenyl-1,3,8-triazaspiro[4.5]decane-8-carbonyl)-2-phenyl-7H-pyrrolo[2,3-d]pyrimidin-4-ylamino]-ethyl}-acetamide (26.149)

MS (ES): 552.9 (M$^+$+1), $t_R$ (method B)=13.9 min.

N-{2-[6-(4-Benzo[1,3]dioxol-5-ylmethylpiperazine-1-carbonyl)-2-phenyl-7H-pyrrolo[2,3-d]pyrimidin-4-ylamino]-ethyl}-acetamide (26.150)

MS (ES): 541.9 (M$^+$+1), $t_R$ (method A)=3.8 min.

1-[4-(2-Acetylaminoethylamino)-2-phenyl-7H-pyrrolo[2,3-d]pyrimidine-carbonyl]-piperidine-4-carboxylic acid ethyl ester (26.151)

MS (ES): 479.0 (M$^+$+1), $t_R$ (method A)=6.7 min.

1-[4-(2-Acetylaminoethylamino)-2-phenyl-7H-pyrrolo[2,3-d]pyrimidine-6-carbonyl]-piperidine-3-carboxylic acid ethyl ester (26.152)

MS (ES): 479.0 (M$^+$+1), $t_R$ (method A)=6.9 min.

4-(2-Acetylaminoethylamino)-2-phenyl-7H-pyrrolo[2,3-d]pyrimidine-6-carboxylic acid (1-benzylpyrrolidin-3-yl)-methylamide (26.153)

MS (ES): 512.0 (M$^+$+1), $t_R$(method A)=4.3 min.

N-{2-[6-(4-Biphenyl-4-yl-piperazine-1-carbonyl)-2-phenyl-7H-pyrrolo[2,3-d]pyrimidin-4-ylamino]-ethyl}-acetamide (26.154)

$^1$H NMR (d$_6$-DMSO, 200 MHz) δ 1.73 (s, 3H), 3.60 (m, 2H), 3.84 (m, 2H), 7.01 (m, 4H), 7.20-7.40 (m, 9H), 7.82 (brs, 1H), 8.02 (brs, 1H), 8.40 (m, 2H), 12.03 (brs, 1H); MS (ES): 559.9 (M$^+$+1), $t_R$ (method A)=9.0 min.

N-{2-[6-(4-Oxopiperidine-1-carbonyl)-2-phenyl-7H-pyrrolo[2,3-d]pyrimidin-4-ylamino]-ethyl}-acetamide (26.155)

Compound 26.87 (400 mg, 0.86 mmol) was dissolved in 5 mL of 12M HCl (aq). After 45 minutes, the reaction was basified by its slow addition to cold NaHCO$_3$ (sat). The solution was then partitioned between EtOAc and water. The layers were separated and the aqueous layer was re-extracted with EtOAc (2×). The combined EtOAc extracts were dried over MgSO$_4$, filtered and concentrated to yield 325 mg of a white solid (90%). $^1$H NMR (CDCl$_3$, 200 MHz) δ 1.83 (s, 3H), 2.59 (m, 4H), 3.60 (m, 2H), 3.88 (m, 2H), 4.20 (m, 4H), 6.17 (brs, 1H), 6.69 (brs, 1H), 6.76 (s, 1H), 7.43 (m, 3H), 8.42 (m, 2H), 9.84 (brs, 1H); MS (ES): 420.9 (M$^+$+1).

General Procedure for the Reductive Amination of 26.155 Using Polymer-Supported Cyanoborohydride:

The amine (0.14 mmol) is dissolved in 1 mL of a DCM/AcOH (100:1) mixture. Ketone 26.155 (40 mg, 0.095 mmol) and polystyrylmethyltrimethylammonium cyanoborohydride (60 mg, loading=3-5 mmol/g) are added and the reaction is placed on an orbital shaker. After 17 h, the reaction mixture is filtered and the resin is washed with DCM.

Alternatively, after filtration the reaction can be worked up with EtOAc and 5% Na$_2$CO$_3$ (aq.). The resulting homogeneous solution is concentrated, yielding the products in 45-95% yield.

The following 11 amines 26.156-26.166 were prepared by this method:

N-(2-{6-[4-(Methylphenethylamino)-piperidine-1-carbonyl]-2-phenyl-7H-pyrrolo-[2,3-d]pyrimidin-4-ylamino}-ethyl)-acetamide (26.156)

$^1$H NMR (d$_6$-DMSO, 200 MHz) δ 1.30-1.50 (m, 2H), 1.77 (m, 2H), 1.87 (s, 3H), 2.26 (s, 3H), 2.67 (m, 5H), 2.80-3.10 (m, 2H), 3.33 (m, 2H), 3.61 (m, 2H), 4.34 (d, 2H, J=13.2 Hz), 6.89 (S, 1H), 7.1-7.3 (6H, m), 7.42 (m, 3H), 7.78 (brs, 1H), 8.02 (brs, 1H), 8.40 (m, 2H). MS (ES): 539.9 (M$^+$+1), $t_R$ (method B)=11.1 min.

N-{2-[6-(4-Phenethylaminopiperidine-1-carbonyl)-2-phenyl-7H-pyrrolo[2,3-d]-pyrimidin-4-ylamino]-ethyl}-acetamide (26.157)

$^1$H NMR (CDCl$_3$, 200 MHz) δ 1.40-1.60 (m, 2H), 1.80 (s, 3H), 2.00 (m, 2H), 2.80-2.90 (m, 3H), 2.94 (d, 2H, J=6.0 Hz), 3.10-3.30 (m, 2H), 3.60 (m, 2H), 3.90 (m, 2H), 4.44 (d, 2H, J=13.8 Hz), 5.98 (brs, 1H), 6.66 (s, 1H), 6.82 (brs, 1H), 7.17-7.30 (m, 5H), 7.45 (m, 3H), 8.40 (d, 1H, J=5.6 Hz) 8.42 (d, 1H, J=7.8 Hz). MS (ES): 526.0 (M$^+$+1), t$_R$ (method B)=10.8 min.

N-[2-(6-{4-[2-(4-Chlorophenyl)-ethylamino]-piperidine-1-carbonyl}-2-phenyl-7H-pyrrolo[2,3-d]pyrimidin-4-ylamino)-ethyl]-acetamide (26.158)

$^1$H NMR (CDCl$_3$, 200 MHz): δ=1.38-1.55 (m, 2H), 1.79 (s, 3H), 1.90-2.10 (m, 2H), 2.70-2.85 (m, 3H), 2.90 (d, 2H, J=6.6 Hz), 3.10-3.30 (m, 2H), 3.61 (m, 2H), 3.90 (m, 2H), 4.45 (d, 2H, J=13.2 Hz), 5.97 (brs, 1H), 6.65 (s, 1H), 6.81 (brs, 1H), 7.14 (d, 2H, J=8.0 Hz), 7.27 (d, 2H, J=7.4 Hz), 7.45 (m, 3H), 8.40 (m, 3H); MS (ES): 560.0 (M$^+$+1), t$_R$ (method B)=12.0 min.

N-[2-(6-{4-[2-(3H-Imidazol-4-yl)-ethylamino]-piperidine-1-carbonyl}-2-phenyl-7H-pyrrolo[2,3-d]pyrimidin-4-ylamino)-ethyl]-acetamide (26.159)

$^1$H NMR (d$_6$-DMSO, 200 MHz): δ=1.20-1.30 (m, 2H), 1.78 (s, 3H), 1.80-1.90 (m, 2H), 2.60 (m, 3H), 2.78 (m, 4H), 3.34 (m, 2H), 3.62 (m, 2H), 4.20 (m, 2H), 6.73 (s, 1H), 6.76 (s, 1H), 6.90 (s, 1H), 7.36-7.52 (m, 5H), 7.79 (brs, 1H), 8.03 (m, 1H), 8.39 (m, 2H); MS (ES): 516.0 (M$^+$+1), t$_R$ (method B)=7.2 min.

N-(2-{2-Phenyl-6-[4-(2-pyridin-4-ylethylamino)-piperidine-1-carbonyl]-7H-pyrrolo-[2,3-d]pyrimidin-4-ylamino}-ethyl)-acetamide (26.160)

$^1$H NMR (d$_6$-DMSO, 200 MHz): δ=1.15-1.30 (m, 2H), 1.78 (s, 3H), 1.82-1.95 (m, 2H), 2.60-2.92 (m, 5H), 3.12 (m, 2H), 3.33 (m, 2H), 3.61 (m, 2H), 4.20 (m, 2H), 6.89 (s, 1H), 6.90-7.20 (brs, 1H), 7.24 (d, 1H, J=5.6 Hz), 7.42 (m, 3H), 7.76 (m, 1H), 8.01 (m, 1H), 8.40 (m, 3H); MS (ES): 527.0 (M$^+$+1), t$_R$ (method B)=7.6 min.

N-(2-{2-Phenyl-6-[4-(2-pyridin-2-ylethylamino)-piperidine-1-carbonyl]-7H-pyrrolo-[2,3-d]pyrimidin-4-ylamino}-ethyl)-acetamide (26.161)

$^1$H NMR (d$_6$-DMSO, 200 MHz): δ=1.15-1.30 (m, 2H), 1.80 (s, 3H), 1.82-1.95 (m, 2H), 2.70-3.00 (m, 5H), 3.15 (m, 2H), 3.33 (m, 2H), 3.63 (m, 2H), 4.20 (m, 2H), 6.87 (s, 1H), 6.90-7.20 (brs, 1H), 7.10-7.30 (m, 2H), 7.42 (m, 3H), 7.60-7.80 (m, 2H), 8.00 (brs, 1H), 8.40 (m, 3H); MS (ES): 526.9 (MH$^+$), t$_R$ (method B)=9.1 min.

N-{2-[6-(4-Benzylaminopiperidine-1-carbonyl)-2-phenyl-7H-pyrrolo[2,3-d]-pyrimidin-4-ylamino]-ethyl}-acetamide (26.162)

$^1$H NMR (CDCl$_3$, 200 MHz): δ=1.40-1.60 (m, 2H), 1.79 (s, 3H), 2.00 (m, 2H), 1.90 (brs, 1H), 3.21 (m, 2H), 3.59 (m, 2H), 3.89 (m, 2H), 4.30 (d, 2H, J=13.6 Hz), 5.95 (m, 1H), 6.66 (s, 1H), 6.85 (brs, 1H), 7.30 (m, 5H), 7.43 (m, 3H), 8.42 (m, 2H); MS (ES): 512.0 (M$^+$+1), t$_R$ (method B)=10.0 min.

N-(2-{6-[4-(Benzylmethylamino)-piperidine-1-carbonyl]-2-phenyl-7H-pyrrolo[2,3-d]pyrimidin-4-ylamino}-ethyl)-acetamide (26.163)

$^1$H NMR (CDCl$_3$, 200 MHz): δ=1.60-1.80 (m, 2H), 1.80 (s, 3H), 1.98 (m, 2H), 2.23 (s, 3H), 2.80 (brs, 1H), 3.10 (m, 2H), 3.60 (m, 4H), 3.90 (m, 2H), 4.66 (d, 2H, J=13.6 Hz), 5.90 (brs, 1H), 6.68 (s, 1H), 7.24-7.35 (m, 5H), 7.44 (m, 3H), 8.42 (m, 2H); MS (ES): 526.0 (M$^+$+1), t$_R$ (method B)=10.2 min.

N-(2-{2-Phenyl-6-[4-(1-phenylethylamino)-piperidine-1-carbonyl]-7H-pyrrolo[2,3-d]pyrimidin-4-ylamino}-ethyl)-acetamide (26.164)

$^1$H NMR (CDCl$_3$, 200 MHz): δ=1.35 (d, 3H, J=5.8 Hz), 1.60-1.80 (m, 2H), 1.79 (s, 3H), 2.00-2.15 (m, 2H), 2.65 (m, 1H), 2.80 (brs, 1H), 3.10 (m, 2H), 3.60 (m, 2H), 3.80-4.20 (m, 3H), 5.92 (brs, 1H), 6.61 (s, 1H), 6.84 (brs, 1H), 7.32 (s, 5H), 7.44 (m, 3H) 8.40 (m, 2H); MS (ES): 526.0 (M$^+$+1), t$_R$ (method B)=10.5 min.

N-[2-(2-Phenyl-6-{4-[(pyridin-4-ylmethyl)-amino]-piperidine-1-carbonyl}-7H-pyrrolo[2,3-d]pyrimidin-4-ylamino)-ethyl]-acetamide (26.165)

$^1$H NMR (d$_6$-DMSO, 200 MHz) δ=1.20-1.40 (m, 2H), 1.78 (s, 3H), 1.80-2.00 (m, 2H), 3.10 (m, 2H), 3.36 (m, 2H), 3.63 (m, 3H), 3.78 (s, 2H), 4.12 (m, 2H), 6.90 (s, 1H), 7.42 (m, 6H), 7.80 (brs, 1H), 8.05 (brs, 1H), 8.40 (m, 2H), 8.47 (m, 2H); MS (ES): 512.9 (M$^+$+1), t$_R$ (method B)=8.4 min.

N-(2-{2-Phenyl-6-[4-(2-pyridin-3-ylethylamino)-piperidine-1-carbonyl]-7H-pyrrolo-[2,3-d]pyrimidin-4-ylamino}-ethyl)-acetamide (26.166)

$^1$H NMR (d6-DMSO, 200 MHz): δ=1.20-1.40 (m, 2H), 1.78 (s, 3H), 1.80-2.00 (m, 2H), 2.60-2.90 (m, 6H), 3.00-3.25 (m, 3H), 3.62 (m, 2H), 4.39 (m, 2H), 6.85 (s, 1H), 7.25 (m, 1H), 7.40 (m, 3H), 7.63 (m, 1H), 7.79 (brs, 1H), 8.02 (m, 1H), 8.39 (m, 3H); MS (ES): 526.9 (M$^+$+1), t$_R$ (method B)=7.7 min.

N-[2-(6-Methyl-{2-oxo-2-[4-(3-phenylallyl)-piperazin-1-yl]-ethyl}-2-phenyl-7H-pyrrolo[2,3-d]pyrimidin-4-ylamino)-ethyl]-acetamide (26.167)

Prepared from 5 by alkylation similar to the preparation of 47 and C-4 chloride displacement according to the general procedure. MS (ES) 552 (MH$^+$); t$_R$ (method B)=3.9 min

3-[4-(2-Acetylaminoethylamino)-2-phenyl-7H-pyrrolo[2,3-d]pyrimidin-6-yl]-propionic acid methyl ester (26.168)

Wittig reaction of 20 followed by double bond reduction using the conditions for 43→44 and C-4 chloride displacement according to the general procedure gave the title compound. $^1$H NMR (CDCl$_3$, 200 MHz) δ 9.95 (s, 1H), 8.39 (m, 2H), 7.43 (m, 3H), 6.05 (m, 1H), 5.52 (m, 1H), 3.89 (m, 2H), 3.65 (s, 3H), 3.58 (m, 2H), 2.90 (t, 2H), 2.62 (t, 2H), 1.76 (s, 3H); t$_R$ (method B)=5.0 min.

N-(2-{6-[3-(4-Benzylpiperazin-1-yl)-3-oxopropyl]-2-phenyl-7H-pyrrolo[2,3-d]-pyrimidin-4-ylamino}-ethyl)-acetamide (26.169)

Prepared by hydrolysis of the methyl ester of 26.128 and amide formation according to the general procedure for 30a→26. $^1$H NMR (CDCl$_3$, 200 MHz) δ 9.99 (s, 1H), 8.41 (m, 2H), 7.42 (m, 3H), 7.30 (m, 5H), 6.05 (s, 1H), 5.45 (m, 1H), 3.88 (m, 2H), 3.63 (m, 2H), 3.56 (m, 2H), 3.45 (s, 2H), 3.38 (m, 2H), 3.05 (t, 2H), 2.61 (t, 2H), 2.39 (m, 2H), 2.34 (m, 2H), 1.75 (s, 3H); t$_R$ (method A)=3.9 min.

N-(2-{7-Methyl-2-phenyl-6-[4-(3-phenylallyl)-piperazine-1-carbonyl]-7H-pyrrolo-[2,3-d]pyrimidin-4-ylamino}-ethyl)-acetamide (26.170)

Amide formation of 27 with 4-(3-phenylallyl)piperazine (29.3) according to the general procedure 30a→26 gave amide 45, MS (ES) 598/600 (MH$^+$). Sulfonyl group removal as described for 28→30, except that the pH was adjusted to 7, yielded 46, MS (ES) 458/460 (MH$^+$). Alkylation with methyl iodide and NaH in DMF according to the procedure for Boc-29.200→Boc-26.206, followed by C-4 chloride displacement according to the general procedure yielded 26.170. $^1$H NMR (CDCl$_3$, 200 MHz) δ 8.51 (m, 2H), 7.5-7.25 (brm, 10H), 7.07 (m, 1H); 5.43 (d, 1H, J=16.0 Hz), 6.48 (s, 1H), 6.25 (dt, 1H, J=16.0, 6.6 Hz), 5.76 (m, 1H), 3.92 (m, 5H), 3.79 (m, 4H), 3.57 (m, 2H), 3.21 (d, 2H, J=6.6 Hz), 2.56 (m, 4H), 1.76 (s, 3H); MS (ES) 537 (MH$^+$); t$_R$ (method A)=5.4 min.

4-(2-Acetylaminoethylamino)-2-phenyl-7H-pyrrolo[2,3-d]pyrimidine-6-carboxylic acid benzylamide (26.171)

MS (ES) 428 (MH$^+$); t$_R$ (method A)=7.0 min.

4-(2-Acetylaminoethylamino)-2-phenyl-7H-pyrrolo[2,3-d]pyrimidine-6-carboxylic acid (2-hydroxy-1-hydroxymethylethyl)-amide (26.172)

MS (ES) 413 (MH$^+$); t$_R$(method A)=9.3 min.

N-{2-[6-(3,4-Dihydro-1H-isoquinoline-2-carbonyl)-2-phenyl-7H-pyrrolo[2,3-d]pyrimidin-4-ylamino]-ethyl}-acetamide (26.173)

MS (ES) 454 (MH$^+$); t$_R$ (method A)=7.4 min.

4-(2-Acetylaminoethylamino)-2-phenyl-7H-pyrrolo[2,3-d]pyrimidine-6-carboxylic acid (1-hydroxycyclohexylmethyl)-amide (26.174)

MS (ES) 451 (MH$^+$); t$_R$ (method A)=6.3 min.

4-(2-Acetylaminoethylamino)-2-phenyl-7H-pyrrolo[2,3-d]pyrimidine-6-carboxylic acid [2-(4-phenoxyphenyl)-ethyl]-amide (26.175)

MS (ES) 535 (MH$^+$).

N-{2-[2-Phenyl-6-((S)-2-phenylaminomethylpyrrolidine-1-carbonyl)-7H-pyrrolo[2,3-d]pyrimidin-4-ylamino]-ethyl}-acetamide (26.176)

MS (ES) 498 (MH$^+$); t$_R$ (method A)=7.7 min.

4-(2-Acetylaminoethylamino)-2-phenyl-7H-pyrrolo[2,3-d]pyrimidine-6-carboxylic acid ((S)-2-oxoazepan-3-yl)-amide (26.177)

MS (ES) 450 (MH$^+$); t$_R$ (method A)=5.6 min.

N-(2-{6-[4-(Hydroxydiphenylmethyl)-piperidine-1-carbonyl]-2-phenyl-7H-pyrrolo-[2,3-d]pyrimidin-4-ylamino}-ethyl)-acetamide (26.178)

MS (ES) 589 (MH$^+$); t$_R$(method A)=8.4 min.

N-{2-[6-(4-Methyl-[1,4]diazepane-1-carbonyl)-2-phenyl-7H-pyrrolo[2,3-d]pyrimidin-4-ylamino]-ethyl}-acetamide (26.179)

MS (ES) 436 (MH$^+$); t$_R$ (method A)=6.9 min.

N-{2-[2-Phenyl-6-(1,3,4,9-tetrahydro-β-carboline-2-carbonyl)-7H-pyrrolo[2,3-d]-pyrimidin-4-ylamino]-ethyl}-acetamide (26.180)

MS (ES) 494 (MH$^+$); t$_R$ (method A)=7.7 min.

N-{2-[6-(Azocane-1-carbonyl)-2-phenyl-7H-pyrrolo[2,3-d]pyrimidin-4-ylamino]-ethyl}-acetamide (26.181)

MS (ES) 435 (MH$^+$); t$_R$ (method A)=7.3 min.

N-[2-(2-Phenyl-6-{4-[3-(4-trifluoromethylphenyl)-propyl]-piperazine-1-carbonyl}-7H-pyrrolo[2,3-d]pyrimidin-4-ylamino)-ethyl]-acetamide (26.182)

MS (ES) 594 (MH$^+$); t$_R$ (method A)=5.1 min.

N-[2-(6-{4-[3-(4-Fluorophenyl)-propyl]-piperazine-1-carbonyl}-2-phenyl-7H-pyrrolo[2,3-d]pyrimidin-4-ylamino)-ethyl]-acetamide (26.183)

MS (ES) 544 (MH$^+$); t$_R$ (method A)=4.6 min.

N-(2-{6-[4-(3-Benzol 1,31-dioxol-5-yl-propyl)-piperazine-1-carbonyl]-2-phenyl-7H-pyrrolo[2,3-d]pyrimidin-4-ylamino}-ethyl)-acetamide (26.184)

MS (ES) 570 (MH$^+$); t$_R$ (method A)=4.4 min.

N-(2-{2-Phenyl-6-[4-(3-ptolylpropyl)-piperazine-1-carbonyl]-7H-pyrrolo[2,3-d]-pyrimidin-4-ylamino}-ethyl)-acetamide (26.185)

MS (ES) 540 (MH$^+$); t$_R$ (method A)=4.8 min.

N-[2-(6-{4-[3-(4-Bromophenyl)-propyl]-piperazine-1-carbonyl}-2-phenyl-7H-pyrrolo[2,3-d]pyrimidin-4-ylamino)-ethyl]-acetamide (26.186)

MS (ES) 606 (MH$^+$); t$_R$ (method A)=5.0 min.

N-[2-(6-{4-[3-(3,4-Dichlorophenyl)-propyl]-piperazine-1-carbonyl}-2-phenyl-7H-pyrrolo[2,3-d]pyrimidin-4-ylamino)-ethyl]-acetamide (26.187)

MS (ES) 596 (M$^+$+H); t$_R$ (method B)=4.4 min.

N-[2-(6-{4-[3-(2,4-Dichlorophenyl)-propyl]-piperazine-1-carbonyl}-2-phenyl-7H-pyrrolo[2,3-d]pyrimidin-4-ylamino)-ethyl]-acetamide (26.188)

MS (ES) 596 (M$^+$+H); t$_R$ (method B)=4.4 min.

N-{2-[2-Phenyl-6-(4-phenyl-[1,4]diazepane-1-carbonyl)-7H-pyrrolo[2,3-d]pyrimidin-4-ylamino]-ethyl}-acetamide (26.189)

MS (ES) 498 (MH$^+$); t$_R$ (method B)=15.5 min.

N-{2-[6-(4-Benzyl-[1,4]diazepane-1-carbonyl)-2-phenyl-7H-pyrrolo[2,3-d]pyrimidin-4-ylamino]-ethyl}-acetamide (26.190)

MS (ES) 512 (MH$^+$); t$_R$ (method B)=10.3 min.

N-{2-[6-(4-Phenethyl-[1,4]diazepane-1-carbonyl)-2-phenyl-7H-pyrrolo[2,3-d]-pyrimidin-4-ylamino]-ethyl}-acetamide (26.191)

MS (ES) 527 (M$^+$+H); t$_R$ (method B)=11.2 min.

N-(2-{2-Phenyl-6-[4-(3-phenylpropyl)-[1,4]diazepane-1-carbonyl]-7H-pyrrolo[2,3-d]-pyrimidin-4-ylamino}-ethyl)-acetamide (26.192)

MS (ES) 540 (MH$^+$); t$_R$ (method B) 11.8 min.

(R,S)—(N-{2-[6-(3-Phenoxypiperidine-1-carbonyl)-2-phenyl-7H-pyrrolo[2,3-d]pyrimidin-4-ylamino]-ethyl}-acetamide (26.193)

MS (ES) 499 (MH$^+$); t$_R$ (method B)=15.6 min.

N-(2-{6-[4-(4-Chlorophenoxy)-piperidine-1-carbonyl]-2-phenyl-7H-pyrrolo[2,3-d]-pyrimidin-4-ylamino}-ethyl)-acetamide (26.194)

MS (ES) 533 (MH$^+$); t$_R$ (method B)=17.1 min.

N-{2-[6-[4-(4-Methoxyphenoxy)-piperidine-1-carbonyl]-2-phenyl-7H-pyrrolo-2,3-d]-pyrimidin-4-ylamino}-ethyl}-acetanide (26.195)

MS (ES) 529 (MH$^+$); t$_R$ (method B)=15.8 min.

N-{2-[6-(4-Phenoxypiperidine-1-carbonyl)-2-phenyl-7H-pyrrolo[2,3-d]pyrimidin-4-ylamino]-ethyl}-acetamide (26.196)

MS (ES) 499 (MH$^+$); t$_R$ (method B)=16.3 min.

4-(2-Acetylaminoethylamino)-2-phenyl-7H-pyrrolo[2,3-d]pyrimidine-6-carboxylic acid [3-(2-oxopyrrolidin-1-yl)-propyl]-amide (26.197)

MS (ES) 464.08 [MH$^+$], t$_R$ (method A)=5.44 min.

4-(2-Acetylaminoethylamino)-2-phenyl-7H-pyrrolo[2,3-d]pyrimidine-6-carboxylic acid (2-phenylcyclopropyl)-amide (26.198)

MS (ES) 455.14 [MH$^+$], t$_R$ (method A)=7.74 min.

N-(2-{6-[4-(4-Chlorobenzoyl)-piperidine-1-carbonyl]-2-phenyl-7H-pyrrolo[2,3-d]-pyrimidin-4-ylamino}-ethyl)-acetamide (26.199)

MS (ES) 545.0 [MH$^+$], t$_R$ (method A)=8.15 min.

N-(2-{6-[4-(4-Acetylaminophenyl)-piperazine-1-carbonyl]-2-phenyl-7H-pyrrolo[2,3-d]pyrimidin-4-ylamino}-ethyl)-acetamide (26.200)

MS (ES) 541.11 [MH$^+$], t$_R$(method A)=5.83 min.

4-(2-Acetylaminoethylamino)-2-phenyl-7H-pyrrolo[2,3-d]pyrimidine-6-carboxylic acid indan-2-ylamide (26.201)

MS (ES) 455.03 [MH$^+$], t$_R$ (method A)=7.52 min.

N-(2-{6-[4-(4-Cyanophenyl)-piperazine-1-carbonyl]-2-phenyl-7H-pyrrolo[2,3-d]-pyrimidin-4-ylamino}-ethyl)-acetamide (26.202)

$^1$H NMR (CDCl$_3$, 200 MHz): δ=1.81 (s, 3H), 2.72 (brs, 3H), 3.42-3.60 (m, 6H), 3.87 (t, 2H, J=4.8 Hz), 3.97-4.10 (m, 4H), 6.86 (s, 2H), 6.89 (s, 1H), 7.4-7.6 (m, 6H), 8.30-8.42 (m, 2H). MS (ES) 509.0 [MH$^+$], t$_R$ (method A)=7.22 min.

N-{2-[6-[4-(2-Cyanophenyl)-piperazine-1-carbonyl]-2-phenyl-7H-pyrrolo[2,3-d]-pyrimidin-4-ylamino]-ethyl}-acetamide (26.203)

$^1$H NMR (CD$_3$OD, 200 MHz): δ=1.86 (s, 3H), 3.20-3.35 (m, 4H), 3.47-3.60 (m, 2H), 3.84 (brt, 2H, J=6.3 Hz), 4.05 (brt, 4H, J=4.4 Hz), 6.67 (s, 1H), 7.08-7.22 (m, 2H), 7.38-7.50 (m, 3H), 7.53-7.70 (m, 2H), 7.90 (s, 1H), 8.37-8.48 (m, 2H). MS (ES) 508.95 [MH$^+$], t$_R$ (method A)=7.43 min.

N-{2-[6-(4-Hydroxymethylpiperidine-1-carbonyl)-O-phenyl-7H-pyrrolo[2,3-d]-pyrimidin-4-ylamino]-ethyl}-acetamide (26.204)

$^1$H NMR (CD$_3$OD, 200 MHz): δ=1.22-1.40 (m, 2H), 1.70-1.94 (m, 6H), 2.9-3.2 (m, 2H), 3.4-3.6 (m, 4H), 3.83 (brt, 2H, J=6.2 Hz), 4.56 (brd, 2H, J=12.2 Hz), 6.90 (s, 1H), 7.38-7.5 (m, 3H), 7.90 (s, 1H), 8.35-8.47 (m, 2H). MS (ES) 437.11 [MH$^+$], t$_R$ (method A)=5.19 min.

4-(2-Acetylaminoethylamino)-2-phenyl-7H-pyrrolo[2,3-d]pyrimidine-6-carboxylic acid [2-(4-methoxyphenyl)-ethyl]-amide (26.205)

MS (ES) 472.93 [MH$^+$], t$_R$ (method A)=7.23 min.

N-[2-(6-{4-[4-(Acetylmethylamino)-phenyl]-piperazine-1-carbonyl}-2-phenyl-7H-pyrrolo[2,3-d]pyrimidin-4-ylamino)-ethyl]-acetamide (26.206)

MS (ES) 554.9 [MH$^+$], t$_R$ (method A)=6.20 min.

N-(2-{6-[4-(4-Methoxyphenyl)-3-methylpiperazine-1-carbonyl]-2-phenyl-7H-pyrrolo[2,3-d]pyrimidin-4-ylamino}-ethyl)-acetamide (26.207)

$^1$H NMR (CDCl$_3$, 200 MHz): δ=0.90 (d, 6H, J=6.2 Hz), 1.77 (s, 3H), 2.91-3.10 (m, 2H), 3.2-3.7 (m, 6H), 3.7-4.5 (m,

7H), 6.53 (m, 1H), 6.73-7.00 (m, 6H), 7.25 (m, 1H), 7.35-7.50 (m, 2H), 8.31-8.47 (m, 1H). MS (ES) 528.0 [MH$^+$], $t_R$ (method A)=6.9 min.

4-(2-Acetylaminoethylamino)-2-phenyl-7H-pyrrolo[2,3-d]pyrimidine-6-carboxylic acid (2-phenoxyethyl)-amide (26.208)

MS (ES) 458.94 [MH$^+$], $t_R$ (method A)=7.3 min.

N-{2-[6-(3-Acetylaminopyrrolidine-1-carbonyl)-2-phenyl-7H-pyrrolo[2,3-d]-pyrimidin-4-ylamino]-ethyl}-acetamide (26.209)

MS (ES) 449.95 [MH$^+$], $t_R$ (method A)=5.1 min.

N-(2-{6-[4-(2,6-Dimethylphenyl)-piperazine-1-carbonyl]-2-phenyl-7H-pyrrolo[2,3-d]pyrimidin-4-ylamino}-ethyl)-acetamide (26.210)

MS (ES) 511.89 [MH$^+$], $t_R$(method A)=9.0 min.

N-(2-{6-[4-(2-Ethoxyphenyl)-piperazine-1-carbonyl]-2-phenyl-7H-pyrrolo[2,3-d]-pyrimidin-4-ylamino}-ethyl)-acetamide (26.211)

$^1$H NMR (CDCl$_3$, 200 MHz): δ=1.75 (s, 3H), 3.09 (brt, 4H, J=4.4 Hz), 3.43-3.57 (m, 2H), 3.70-3.85 (m, 2H), 3.90-4.05 (m, 4H), 6.35-6.45 (m, 1H), 6.74 (s, 1H), 6.8-7.07 (m, 4H), 7.19-7.3 (m, 1H), 7.34-7.49 (m, 3H), 8.31-8.48 (m, 2H), 10.7 (brs, 1H). MS (ES) 527.84 [MH$^+$], $t_R$ (method A)=7.91 min.

N-(2-{6-[4-(2-Methoxyphenyl)-piperazine-1-carbonyl]-2-phenyl-7H-pyrrolo[2,3-d]-pyrimidin-4-ylamino}-ethyl)-acetamide (26.212)

MS (ES) 513.87 [MH$^+$], $t_R$ (method A)=7.33 min.

N-(2-{6-[4-(2-Chlorophenyl)-piperazine-1-carbonyl]-2-phenyl-7H-pyrrolo[2,3-d]-pyrimidin-4-ylamino}-ethyl)-acetamide (26.213)

MS (ES) 517.82 [MH$^+$], $t_R$ (method A)=8.28 min.

N-(2-{6-[4-(2-Fluorophenyl)-piperazine-1-carbonyl]-2-phenyl-7H-pyrrolo[2,3-d]-pyrimidin-4-ylamino}-ethyl)-acetamide (26.214)

MS (ES) 501.88 [MH$^+$], $t_R$ (method A)=7.76 min.

N-{2-[2-Phenyl-6-(4-phenylpiperazine-1-carbonyl)-7H-pyrrolo[2,3-d]pyrimidin-4-ylamino]-ethyl}-acetamide (26.215)

$^1$H NMR (CD$_3$OD, 200 MHz): δ=1.86 (s, 3H), 3.17-3.28 (m, 4H), 3.47-3.61 (m, 2H), 3.84 (brt, 2H, J=5.8 Hz), 3.98 (brt, 4H, J=4.8 Hz), 6.87 (t, 1H, J=7.4 Hz), 6.96 (s, 1H), 6.99 (dd, 2H, J=8.9, 1.0 Hz), 7.25 (dd, 2H, J=7.6, 1.6 Hz), 7.35-7.52 (m, 3H), 8.36-8.49 (m, 2H); MS (ES) 483.84 [MH$^+$], $t_R$ (method A)=7.50 min.

N-(2-{6-[4-(2,4-Difluorophenyl)-piperazine-1-carbonyl]-2-phenyl-7H-pyrrolo[2,3-d]-pyrimidin-4-ylamino}-ethyl)-acetamide (26.216)

$^1$H NMR (CD$_3$OD, 200 MHz): δ=1.86 (s, 3H), 3.10 (brt, 4H, J=5.2 Hz), 3.53 (t, 2H, J=6.2 Hz) 3.83 (t, 2H, J=6.2 Hz), 3.99 (brt, 4H, J=4.8 Hz), 6.80-7.16 (m, 4H), 7.36-7.51 (m, 3H), 8.33-8.49 (m, 2H); MS (ES) 519.81 [MH$^+$], $t_R$ (method A)=7.92 min.

N-(2-{6-[4-(2-Ethylphenyl)-piperazine-1-carbonyl]-2-phenyl-7H-pyrrolo[2,3-d]-pyrimidin-4-ylamino}-ethyl)-acetamide (26.217)

$^1$H NMR (CD$_3$OD, 200 MHz): δ=1.28 (t, 3H, J=7.4 Hz), 1.85 (s, 1H), 2.76 (q, 2H, J=7.2 Hz), 2.87-3.10 (m, 4H), 3.45-3.59 (m, 2H), 3.83 (brt, 2H, J=5.8 Hz), 3.91-4.5 (m, 4H), 6.95 (s, 1H), 6.99-7.19 (m, 3H), 7.20-7.27 (m, 1H), 7.37-7.49 (m, 3H), 8.37-8.48 (m, 2H). MS (ES) 511.86 [MH$^+$], $t_R$ (method A)=8.92 min.

N-(2-{6-[4-(2,4-Dimethoxyphenyl)-piperazine-1-carbonyl]-2-phenyl-7H-pyrrolo-[2,3-d]pyrimidin-4-ylamino}-ethyl)-acetamide (26.218)

$^1$H NMR (CD$_3$OD, 200 MHz): δ=1.85 (s, 3H), 2.93-3.08 (m, 4H), 3.46-3.59 (m, 2H), 3.75 (s, 3H), 3.78-3.88 (m, 5H), 3.90-4.40 (m, 4H), 6.45 (dd, 1H, J=8.6, 2.6 Hz), 6.56 (d, 1H, J=2.6 Hz), 6.90 (d, 1H, J=8.8 Hz), 6.94 (s, 1H), 7.33-7.52 (m, 3H), 8.35-8.48 (m, 2H); MS (ES) 543.86 [MH$^+$], $t_R$(method A)=7.00 min.

N-(2-{6-[4-(5-Chloro-2-methoxyphenyl)-piperazine-1-carbonyl]-2-phenyl-7H-pyrrolo[2,3-d]pyrimidin-4-ylamino}-ethyl)-acetamide (26.219)

$^1$H NMR (d$_6$-DMSO, 200 MHz): δ=1.81 (s, 3H), 3.0-3.12 (m, 4H), 3.34-3.45 (m, 2H), 3.59-3.71 (m, 2H), 3.82 (s, 1H), 3.83-3.92 (m, 4H), 6.89 (d, 1H, J=1.8 Hz), 6.98-7.40 (m, 3H), 7.39-7.51 (m, 3H), 7.76-7.87 (m, 1H), 8.01-8.11 (m, 1H), 8.35-8.47 (m, 2H); MS (ES) 547.83 [MH$^+$], $t_R$(method A)=8.11 min.

N-(2-{6-[4-(4-Chlorophenoxymethyl)-piperidine-1-carbonyl]-2-phenyl-7H-pyrrolo-[2,3-d]pyrimidin-4-ylamino}-ethyl)-acetamide (26.220)

$^1$H NMR (d$_6$-DMSO, 200 MHz): δ=1.22-1.50 (m, 2H), 1.80 (s, 3H), 1.81-1.97 (m, 2H), 2.91-3.17 (m, 2H), 3.30-3.44 (m, 2H), 3.56-3.73 (m, 2H), 3.85-3.96 (m, 2H), 4.33-4.54 (m, 2H), 6.98 (d, 2H, J=9.2 Hz), 7.33 (d, 2H, J=9.0 Hz), 7.38-7.54 (m, 3H), 7.80-7.91 (m, 1H), 8.02-8.13 (m, 1H), 8.36-8.48 (m, 2H); MS (ES) 546.82 [MH$^+$], $t_R$ (method A)=8.96 min.

N-{2-[6-(5-Benzyl-2,5-diazabicyclo[2.2.1]heptane-2-carbonyl)-2-phenyl-7H-pyrrolo-[2,3-d]pyrimidin-4-ylamino]-ethyl}-acetamide (26.221)

MS (ES) 509.87 [MH$^+$], $t_R$(method A)=4.05 min.

N-(2-{6-[4-(2-Hydroxyphenyl)-piperazine-1-carbonyl]-2-phenyl-7H-pyrrolo[2,3-d]-pyrimidin-4-ylamino}-ethyl)-acetamide (26.222)

$^1$H NMR (d$_6$-DMSO, 200 MHz): δ=1.81 (s, 3H), 2.95-3.08 (m, 4H), 3.33-3.45 (m, 2H), 3.58-3.71 (m, 2H), 3.80-3.96 (m, 4H), 6.69-6.96 (m, 4H), 6.99 (s, 1H), 7.39-7.53 (m, 3H), 7.76-7.88 (m, 1H), 8.00-8.11 (m, 1H), 8.35-8.48 (m, 2H); MS (ES) 321.81 [MH$^+$], $t_R$ (method A)=6.86 min.

N-(2-{6-[4-(2,3-Dichlorophenyl)-piperazine-1-carbonyl]-2-phenyl-7-pyrrolo[2,3-d]-pyrimidin-4-ylamino}-ethyl)-acetamide (26.223)

$^1$H NMR (d6-DMSO, 200 MHz): δ=1.81 (s, 3H), 3.00-3.15 (m, 4H), 3.43-3.75 (m, 2H), 3.80-4.00 (m, 4H), 7.01 (s, 1H), 7.18 (t, 1H, J=4.6 Hz), 7.30-7.39 (m, 2H), 7.40-7.53 (m, 3H), 7.76-7.90 (m, 1H), 8.00-8.12 (m, 1H), 8.34-8.48 (m, 1H); MS (ES) 551.73 [MH$^+$], $t_R$ (method A)=8.83 min.

N-(2-{6-[5-(4-Chlorophenyl)-2,5-diazabicyclo[2.2.1]heptane-2-carbonyl]-2-phenyl-7H-pyrrolo[2,3-d]pyrimidin-4-ylamino}-ethyl)-acetamide (26.224)

MS (ES) 529.77 [MH$^+$], $t_R$ (method A)=8.15 min.

N-{2-[6-(4-Phenoxymethylpiperidine-1-carbonyl)-2-phenyl-7H-pyrrolo[2,3-d]-pyrimidin-4-ylamino]-ethyl}-acetamide (26.225):

$^1$H NMR (d$_6$-DMSO, 200 MHz): δ=1.20-1.50 (m, 2H), 1.80 (s, 3H), 1.82-2.00 (m, 2H), 2.10-2.30 (m, 1H), 2.95-3.18 (m, 2H), 3.32-3.45 (m, 2H), 3.57-3.71 (m, 2H), 3.90 (d, 2H, J=5.8 Hz), 4.45 (brd, 2H, J=11.8 Hz), 6.86-7.20 (m, 4H), 7.29 (dd, 2H, J=7.0, 1.4 Hz), 7.38-7.53 (m, 3H), 7.76-7.89 (m, 1H), 8.00-8.11 (m, 1H), 8.35-8.48 (m, 2H); MS (ES) 512.90 [MH$^+$], $t_R$ (method A)=8.12 min.

N-(2-{6-[4-(4-Cyanophenoxymethyl)-piperidine-1-carbonyl]-2-phenyl-7H-pyrrolo-[2,3-d]pyrimidin-4-ylamino}-ethyl)-acetamide (26.226)

$^1$H NMR (d$_6$-DMSO, 200 MHz): δ=1.22-1.49 (m, 2H), 1.80 (s, 3H), 1.82-1.98 (m, 2H), 2.02-2.24 (m, 1H), 2.92-3.17 (m, 2H), 3.32-3.44 (m, 2H), 3.56-3.74 (m, 2H), 4.01 (d, 2H, J=6.0 Hz), 4.35-4.52 (m, 2H), 6.94 (s, 1H), 7.13 (d, 2H, J=9.2 Hz), 7.38-7.52 (m, 3H), 7.77 (d, 2H, J=8.8 Hz), 7.80-7.88 (m, 1H), 7.99-8.10 (m, 1H), 8.33-8.47 (m, 2H); MS (ES) 537.88 [MH$^+$], $t_R$(method A)=7.61 min.

N-(2-{6-[4-(3-Cyanophenoxymethyl)-piperidine-1-carbonyl]-2-phenyl-7H-pyrrolo-[2,3-d]pyrimidin-4-ylamino}-ethyl)-acetamide (26.227)

$^1$H NMR (d$_6$-DMSO, 200 MHz): δ=1.22-1.48 (m, 2H), 1.80 (s, 3H), 1.83-1.98 (m, 2H), 2.03-2.25 (m, 1H), 2.94-3.19 (m, 2H), 3.32-3.45 (m, 2H), 3.56-3.73 (m, 2H), 3.98 (d, 2H, J=6.2 Hz), 4.34-4.54 (m, 2H), 6.94 (s, 1H), 7.26-7.36 (m, 1H), 7.36-7.55 (m, 6H), 7.78-7.89 (m, 1H), 8.00-8.12 (m, 1H), 8.35-8.47 (m, 2H); MS (ES) 537.87 [MH$^+$], $t_R$ (method A)=7.80 min.

N-(2-{6-[4-(2-Methylsulfanylphenyl)-piperazine-1-carbonyl]-2-phenyl-7H-pyrrolo-[2,3-d]pyrimidin-4-ylamino}-ethyl)-acetamide (26.228)

$^1$H NMR (d$_6$-DMSO, 200 MHz): δ=1.78 (s, 3H), 2.38 (s, 3H), 2.89-3.03 (m, 4H), 3.30-3.42 (m, 2H), 3.55-3.70 (m, 2H), 3.77-3.92 (m, 4H), 6.98 (s, 1H), 7.06-7.22 (m, 4H), 7.74-7.87 (m, 1H), 7.97-8.13 (m, 1H), 8.32-8.48 (m, 2H); MS (ES) 529.91 [MH$^+$], $t_R$ (method A)=8.09 min.

N-(2-{6-[4-(2-Nitrophenyl]piperazine-1-carbonyl]-2-phenyl-7H-pyrrolo[2,3-d]-pyrimidin-4-ylamino}-ethyl)-acetamide (26.229)

$^1$H NMR (d$_6$-DMSO, 200 MHz): δ=1.81 (s, 3H), 3.06-3.19 (m, 4H), 3.33-3.45 (m, 2H), 3.58-3.74 (m, 2H), 3.78-3.94 (m, 4H), 7.01 (s, 1H), 7.20 (dd, 1H, J=7.6, 0.8 Hz), 7.34-7.53 (m, 4H), 7.63 (dd, 1H, J=7.7, 1.4 Hz), 7.86 (dd, 1H, J=8.0, 1.4 Hz), 8.00-8.11 (m, 1H), 8.34-8.48 (m, 2H); MS (ES) 528.89 [MH$^+$], $t_R$ (method A)=7.49 min.

N-(2-{6-[4-(3-Chlorophenyl)-piperazine-1-carbonyl]-2-phenyl-7H-pyrrolo[2,3-d]-pyrimidin-4-ylamino}-ethyl)-acetamide (26.230)

$^1$H NMR (d6-DMSO, 200 MHz): δ=1.81 (s, 1H), 3.32-3.45 (m, 6H), 3.58-3.77 (m, 2H), 3.80-3.93 (m, 4H), 6.78-7.04 (m, 4H), 7.26 (t, 1H, J=8 Hz), 7.40-7.53 (m, 3H), 7.80-7.93 (m, 1H), 8.01-8.13 (m, 1H), 8.37-8.49 (m, 2H); MS (ES) 517.85 [MH$^+$], $t_R$ (method A)=8.13 min.

N-(2-{2-Phenyl-6-[4-(3-trifluoromethylphenyl)-piperazine-1-carbonyl]-7H-pyrrolo-[2,3-d]pyrimidin-4-ylamino}-ethyl)-acetamide (26.231)

$^1$H NMR (d$_6$-DMSO, 200 MHz): δ=1.81 (s, 3H), 3.33-3.46 (m, 7H), 3.59-3.74 (m, 2H), 3.81-3.94 (m, 4H), 7.01 (s, 1H), 7.12 (brd, 1H, J=7.4 Hz), 7.20-7.32 (m, 2H), 7.40-7.53 (m, 4H), 7.80-7.91 (m, 1H), 8.00-8.11 (m, 1H), 8.36-8.47 (m, 2H); MS (ES) 551.88 [MH$^+$], $t_R$ (method A)=8.41 min.

2-{4-[4-(2-Acetylaminoethylamino)-2-phenyl-7H-pyrrolo[2,3-d]pyrimidine-6-carbonyl]-piperazin-1-yl}-benzoic acid methyl ester (26.232)

$^1$H NMR (d$_6$-DMSO, 200 MHz): δ=1.81 (s, 3H), 2.99-3.12 (m, 4H), 3.32-3.71 (m, 4H), 3.80-3.91 (m, 7H), 6.94-7.20 (m, 4H), 7.35-7.57 (m, 3H), 7.65 (dd, 1H, J=6.8, 1.4 Hz), 7.76-7.89 (m, 1H), 7.99-8.11 (m, 1H), 8.34-8.47 (m, 2H); MS (ES) 541.89 [MH$^+$], $t_R$ (method A)=7.36 min.

N-{2-[2-Phenyl-6-(4-o-tolylpiperazine-1-carbonyl)-7H-pyrrolo[2,3-d]pyrimidin-4-ylamino]-ethyl}-acetamide (26.233)

$^1$H NMR (d$_6$-DMSO, 200 MHz): δ=1.81 (s, 3H), 2:31 (s, 3H), 2.85-3.00 (m, 4H), 3.33-3.45 (m, 2H), 3.58-3.72 (m, 2H), 3.82-3.93 (m, 4H), 6.92-7.09 (m, 3H), 7.18 (brt, 2H, J=7.4 Hz), 7.39-7.53 (m, 3H), 7.76-7.89 (m, 1H), 8.00-8.12 (m, 1H), 8.36-8.48 (m, 2H); MS (ES) 497.89 [MH$^+$], $t_R$ (method A)=8.15 min.

N-(2-{6-[4-(3-Methoxyphenyl)-piperazine-1-carbonyl]-2-phenyl-7H-pyrrolo[2,3-d]-pyrimidin-4-ylamino}-ethyl)-acetamide (26.234)

$^1$H NMR (d6-DMSO, 200 MHz): δ=1.81 (s, 3H), 3.16-3.45 (m, 6H), 3.57-3.70 (m, 2H), 3.73 (s, 3H), 3.80-3.91 (m, 4H), 6.36-6.63 (m, 3H), 7.00 (s, 1H), 7.15 (t, 1H, J=7.6 Hz), 7.38-7.53 (m, 3H), 7.77-7.91 (m, 1H), 7.99-8.12 (m, 1H), 8.34-8.48 (m, 2H); MS (ES) 513.95 [MH$^+$], $t_R$ (method A)=7.37 min.

N-(2-{6-[4-(3,4-Dichlorophenoxymethyl)-piperidine-1-carbonyl]-2-phenyl-7H-pyrrolo[2,3-d]pyrimidin-4-ylamino}-ethyl)-acetamide (26.235)

$^1$H NMR (d$_6$-DMSO, 200 MHz): δ=1.20-1.45 (m, 2H), 1.80 (s, 3H), 1.81-1.97 (m, 2H), 2.20-2.23 (m, 1H), 2.92-3.17 (m, 2H), 3.32-3.47 (m, 2H), 3.58-3.72 (m, 2H), 3.95 (d, 2H, J=6.8 Hz), 4.35-4.53 (m, 2H), 6.94 (s, 1H), 6.99 (dd, 1H, J=8.8, 3.0 Hz), 7.27 (d, 1H, J=2.8 Hz), 7.39-7.57 (m, 4H), 7.76-7.89 (m, 1H), 7.99-8.12 (m, 1H), 8.35-8.49 (m, 2H); MS (ES) 580.80 [MH$^+$], $t_R$ (method A)=9.40 min.

N-(2-{6-[4-(2-Cyanophenoxymethyl)-piperidine-1-carbonyl]-2-phenyl-7H-pyrrolo-[2,3-d]pyrimidin-4-ylamino}-ethyl)-acetamide (26.236)

$^1$H NMR (d$_6$-DMSO, 200 MHz): δ=1.27-1.48 (m, 2H), 1.78 (s, 3H), 1.82-1.99 (m, 2H), 2.06-2.26 (m, 1H), 2.93-3.16 (m, 2H), 3.31-3.42 (m, 2H), 3.53-3.73 (m, 2H), 4.06 (brd, 2H, J=6.2 Hz), 4.31-4.53 (m, 2H), 6.93 (s, 1H), 7.07 (t, 1H, J=7.7 Hz), 7.26 (d, 1H, J=8.4 Hz), 7.37-7.50 (m, 3H), 7.58-7.76 (m, 2H), 7.77-7.85 (m, 1H), 7.97-8.08 (m, 1H), 8.34-8.45 (m, 2H); MS (ES) 538.12 [MH$^+$], t$_R$ (method A)=6.22 min.

N-(2-{6-[4-(2-Chlorophenyl)-4-cyanopiperidine-1-carbonyl]-2-phenyl-7H-pyrrolo-[2,3-d]pyrimidin-4-ylamino}-ethyl)-acetamide (26.237)

$^1$H NMR (d6-DMSO, 200 MHz): δ=1.80 (s, 3H), 2.02-2.24 (m, 2H), 2.54-2.70 (m, 2H), 3.3-3.5 (m, 4H), 3.56-3.74 (m, 2H), 4.50-4.70 (m, 2H), 7.02 (s, 1H), 7.40-7.53 (m, 5H), 7.54-7.65 (m, 2H), 7.74-7.84 (m, 1H), 7.99-8.10 (m, 1H), 8.35-8.48 (m, 2H); MS (ES) 541.99 [MH$^+$], t$_R$(method A)=6.5 min.

N-(2-{6-[4-(2-Chlorophenyl)-4-cyanopiperidine-1-carbonyl]-2-phenyl-7H-pyrrolo-[2,3-d]pyrimidin-4-ylamino}-ethyl)-acetamide methanesulfonic acid salt (26.237.MsOH)

$^1$H NMR (CD$_3$OD, 200 MHz): δ=1.90 (s, 3H), 2.08-2.32 (m, 2H), 2.66 (brs, 2H), 2.72 (brs, 3H), 3.57 (brt, 2H, J=6.4 Hz), 3.93 (brt, 2H, J=6.2 Hz), 4.73 (brd, 2H, J=12.8 Hz), 7.18 (brs, 1H), 7.35-7.49 (m, 2H), 7.50-7.74 (m, 5H), 8.07-8.31 (m, 2H); MS (ES) 541.8 [MH$^+$], t$_R$ (method A)=7.7 min.

N-(2-{6-[4-(2-Methanesulfinylphenyl)-piperazine-1-carbonyl]-2-phenyl-7H-pyrrolo-[2,3-d]pyrimidin-4-ylamino}-ethyl)-acetamide (26.238)

$^1$H NMR (CD$_3$OD, 200 MHz): δ=1.86 (s, 3H), 2.89 (brs, 5H), 3.13-3.38 (m, 3H), 3.46-3.60 (m, 2H), 3.75-3.90 (m, 2H), 3.91-4.08 (m, 3H), 6.95 (s, 1H), 7.20-7.63 (m, 6H), 7.70-7.96 (m, 1H), 8.30-8.59 (m, 2H); MS (ES) 545.85 [MH$^+$], t$_R$ (method A)=6.12 min.

2-{4-[4-(2-Acetylaminoethylamino)-2-phenyl-7H-pyrrolo[2,3-d]pyrimidine-6-carbonyl]-piperazin-1-yl}-benzamide (26.239)

$^1$H NMR (d$_6$-DMSO, 200 MHz): δ 1.78 (s, 3H), 2.92-3.09 (m, 4H), 3.31-3.42 (m, 2H), 3.54-3.70 (m, 2H), 3.80-3.96 (m, 4H), 6.98 (s, 1H), 7.06-7.22 (m, 2H), 7.35-7.55 (m, 5H), 7.67 (dd, 1H, J=7.6, 1.8 Hz), 7.74-7.86 (m, 1H), 7.97-8.80 (m, 1H), 8.32-8.44 (m, 2H); MS (ES) 526.89 [MH$^+$], t$_R$ (method B)=12.60 min.

N-(2-{6-[4-Cyano-4-(2-methoxyphenyl)-piperidine-1-carbonyl]-2-phenyl-7H-pyrrolo[2,3-d]pyrimidin-4-ylamino}-ethyl)-acetamide (26.240)

$^1$H NMR (CD$_3$OD, 200 MHz) δ=1.85 (s, 3H), 1.98-2.22 (m, 2H), 2.35-2.55 (m, 2H), 3.40-3.64 (m, 4H), 3.83 (t, 2H, J=5.8 Hz), 3.92 (s, 3H), 4.70 (brd, 2H, J=14.2 Hz), 6.96 (s, 1H), 6.98-7.14 (m, 2H), 7.26-7.53 (m, 5H), 8.31-8.51 (m, 2H); MS (ES) 537.93 [MH$^+$], t$_R$ (method A)=7.55 min.

N-(2-{6-[4-(3-Chlorophenyl)-4-cyanopiperidine-1-carbonyl]-2-phenyl-7H-pyrrolo-[2,3-d]pyrimidin-4-ylamino}-ethyl)-acetamide (26.241)

$^1$H NMR (CD$_3$OD, 200 MHz): δ=1.86 (s, 3H), 2.03-2.35 (m, 4H), 3.36-3.63 (m, 4H), 3.83 (brt, 2H, J=6.2 Hz), 4.74 (brd, 2H, J=13.8 Hz), 6.98 (s, 1H), 7.32-7.56 (m, 6H), 7.57-7.66 (m, 1H), 8.34-8.52 (m, 2H); MS (ES) 541.91 [MH$^+$], t$_R$ (method A)=8.14 min.

N-(2-{6-[4-Cyano-4-(3-methoxyphenyl)-piperidine-1-carbonyl]-2-phenyl-7H-pyrrolo[2,3-d]pyrimidin-4-ylamino}-ethyl)-acetamide (26.242)

$^1$H NMR (CD$_3$OD, 200 MHz): δ=1.85 (s, 3H), 2.03-2.28 (m, 4H), 3.36-3.61 (m, 4H), 3.52-3.61 (m, 5H), 4.71 (brd, 2H, J=14.4 Hz), 6.85-7.01 (m, 2H), 7.05-7.16 (m, 2H), 7.28-7.50 (m, 4H), 8.33-8.50 (m, 2H); MS (ES) 537.93 [MH$^+$], t$_R$(method A)=7.66 min.

N-(2-{6-[4-(4-Chlorophenyl)-4-cyanopiperidine-1-carbonyl]-2-phenyl-7H-pyrrolo[2,3-d]pyrimidin-4-ylamino}-ethyl)-acetamide (26.243)

$^1$H NMR (CD$_3$OD, 200 MHz): δ=1.86 (s, 3H), 2.00-2.31 (m, 4H), 3.36-3.62 (m, 4H), 3.83 (brt, 2H, J=6.0 Hz), 4.73 (brd, 2H, J=14 Hz), 6.97 (s, 1H), 7.33-7.49 (m, 5H), 7.50-7.61 (m, 2H), 8.34-8.50 (m, 2H); MS (ES) 541.92 [MH$^+$], t$_R$ (method A)=8.18 min.

N-(2-{6-[4-Cyano-4-(4-methoxyphenyl)-piperidine-1-carbonyl]-2-phenyl-7H-pyrrolo[2,3-d]pyrimidin-4-ylamino}-ethyl)-acetamide (26.244)

$^1$H NMR (CD$_3$OD, 200 MHz): δ=1.87 (s, 3H), 1.97-2.32 (m, 4H), 3.42-3.60 (m, 4H), 3.80 (s, 3H), 3.81-3.89 (m, 2H), 4.72 (brd, 2H, J=14 Hz), 6.88-7.04 (m, 3H), 7.34-7.53 (m, 5H), 8.34-8.49 (m, 2H); MS (ES) 537.94 [MH$^+$], t$_R$ (method A)=7.57 min.

(S)-7-Benzenesulfonyl-4-(2,3-dihydroxypropylamino)-2-phenyl-7H-pyrrolo[2,3-d]-pyrimidine-6-carboxylic acid (28.c)

27 (126 mg) and dihydroxypropyl amine (273 mg) were stirred in anhydrous DMSO (2 mL) at 80° C. under nitrogen for 4 h. The reaction mixture was cooled to rt and diluted with water (10 mL). The resulting mixture was acidified with 0.5N HCl until a white solid formed (pH≈3.5-4.0). The solid was collected by filtration, washed with cold water, and dried in vacuo. A white solid (131 mg) was obtained in 93% yield. $^1$H-NMR (200 MHz, DMSO-d$_6$): δ=3.30-3.33 (m, 2H), 3.57-3.60 (m, 2H), 3.65-6.71 (m, 1H), 3.82-3.97 (m, 2H), 7.32 (s, 1H), 7.46-7.50 (m, 3H), 7.55-7.68 (m, 3H), 8.38-8.49 (m, 4H). MS (ES): 468.9 (M$^+$+1).

(S)-1-[7-Benzenesulfonyl-4-(2,3-dihydroxypropylamino)-2-phenyl-7H-pyrrolo[2,3-d]pyrimidine-6-carbonyl]-4-(2-chlorophenyl)piperidine-4-carbonitrile (31.c)

(s)-7-Benzenesulfonyl-4-(2,3-dihydroxypropylamino)-2-phenyl-7H-pyrrolo[2,3-d]-pyrimidine-6-carboxylic acid (28.c) (47 mg), 29.237 (25 mg, 1.1 eq), and PyBop (100 mg, 2.0 eq) were stirred at rt under nitrogen for 6 h. DMF was removed in vacuo. The residue was partitioned between DCM and saturated NaHCO$_3$ aqueous solution. The aqueous layer was extracted with DCM twice. The combined DCM layers was washed with saturated NaHCO$_3$ aqueous solution, brine, and dried over MgSO$_4$. After removal of solvent, an off-white solid (163 mg) was obtained. Pure product (63 mg) was obtained by TLC purification (silica gel, EtOAc/Hexane=3/1) in 94% yield. $^1$H-NMR (200 MHz, DMSO-d$_6$+MeOH-d$_4$): δ=2.40-2.75 (m, 2H), 2.78-2.90 (m, 4H), 3.30-3.50 (m, 1H), 3.50-3.60 (m, 2H), 3.60-3.97 (m, 4H), 6.70 (s, 1H), 7.20-7.68 (m, 9H), 8.34-8.37 (m, 4H).

(S)-4-(2-Chlorophenyl)-1-[4-(2,3-dihydroxypropylamino)-2-phenyl-7H-pyrrolo[2,3-d]pyrimidine-6-carbonyl]piperidine-4-carbonitrile (26.245)

(S)-1-[7-Benzene-sulfonyl-4-(2,3-dihydroxypropylamino)-2-phenyl-7H-pyrrolo[2,3-d]-pyrimidine-6-carbonyl]-4-(2-chlorophenyl)piperidine-4-carbonitrile 31.c (55 mg) was stirred in MeOH and treated with 1 M NaOH aqueous solution at rt under nitrogen for 2 h. The resulting mixture was neutralized with 3M HCl aqueous solution (pH=7). The solvent was then removed in vacuo. The residue was dissolved in DCM+MeOH and charged onto a TLC plate. A white foam (29 mg) was obtained in 67% yield. $^1$H-NMR (200 MHz, CDCl$_3$+MeOH-d$_4$): δ=1.95-2.20 (m, 2H), 2.50-2.70 (m, 2H), 3.40-3.70 (m, 4H), 3.78-3.95 (m, 3H), 4.65-4.78 (m, 2H), 6.75 (s, 1H), 7.25-7.47 (m, 7H), 8.18-8.23 (m, 4H). MS (ES): 531.0 [MH$^+$].

The following compounds 26.246-26.250 were prepared in the same manner:

(S)-[4-(2,3-dihydroxypropylamino)-2-phenyl-7H-pyrrolo[2,3-d]pyrimidine-6-yl]-{4-[3-(4-chlorophenyl)propyl]piperazin-1-yl}methanone (26.246):

2% yield. $^1$H-NMR (200 MHz, CDCl$_3$): δ=1.50-1.70 (m, 2H), 2.38-2.48 (m, 2H), 2.50-2.60 (m, 4H), 2.60-2.70 (m, 2H), 3.60-3.70 (m, 2H), 3.80-4.02 (m, 8H), 4.18-4.25 (m, 2H), 6.63 (s, 1H), 7.05-7.15 (m, 3H), 7.40-7.60 (m, 5H), 8.18-840 (m, 2H), 9.52 (brs, 1H); MS (ES): 548.9 (M$^+$+1).

2-{6-[4-(2-Chlorophenyl)-4-cyanopiperidine-1-carbonyl]-2-phenyl-7H-pyrrolo[2,3-d]pyrimidin-4-ylamino}acetamide (26.247)

2% yield. $^1$H-NMR (200 MHz, CDCl$_3$+MeOH-d$_4$): δ=2.10-2.30 (m, 2H), 2.60-2.75 (m, 2H), 3.10-3.25 (m, 2H), 3.65-3.75 (m, 2H), 4.30 (s, 2H), 7.02 (s, 1H), 7.38-7.45 (m, 5H), 7.48-7.60 (m, 2H), 8.38-8.40 (m, 2H). MS (ES): 513.9 (M$^+$+1).

3-(6-{4-[3-(4-Chlorophenyl)propyl]piperazine-1-carbonyl}-2-phenyl-7H-pyrrolo[2,3-d]pyrimidin-4-ylamino)acetamide (26.248)

5% yield. $^1$H-NMR (200 MHz, MeOH-d$_4$): δ=1.80-1.95 (m, 2H), 2.40-2.50 (m, 2H), 2.52-2.62 (m, 4H), 2.62-2.72 (m, 2H), 3.82-3.95 (m, 4H), 4.30 (m, 2H), 6.93 (s, 1H), 7.18 (d, 2H, J=8.4 Hz), 7.23 (d, 2H, J=8.4 Hz), 7.55-7.65 (m, 3H), 8.36-842 (m, 2H). MS (ES): 532.0 (M$^+$+1).

3-{6-[4-(2-Chlorophenyl)-4-cyanopiperidine-1-carbonyl]-2-phenyl-7H-pyrrolo[2,3-d]pyrimidin-4-ylamino}propionamide (26.249)

1% yield. $^1$H-NMR (200 MHz, CDCl$_3$): δ=2.00-2.20 (m, 2H), 2.55-2.80 (m, 4H), 3.65-3.75 (m, 2H), 4.00-4.15 (m, 2H), 4.70-4.85 (m, 2H), 6.00 (brs, 1H), 6.20 (brs, 1H), 6.75 (s, 1H), 7.20-7.60 (m, 8H), 8.38-8.48 (m, 2H), 9.77 (brs, 1H). MS (ES): 527.9 (M$^+$+1).

3-(6-{4-[3-(4-Chlorophenyl)propyl]piperazine-1-carbonyl}-2-phenyl-7H-pyrrolo[2,3-d]pyrimidin-4-ylamino)propionamide (26.250)

2% yield. $^1$H-NMR (200 MHz, CDCl$_3$): δ=1.35-1.55 (m, 2H), 1.78-1.95 (m, 2H), 2.34-2.43 (m, 2H), 2.45-2.58 (m, 4H), 2.60-2.70 (m, 2H), 2.70-3.76 (m, 2H), 3.80-3.95 (m, 4H), 4.00-4.18 (m, 2H), 5.41 (brs, 1H), 5.67 (brs, 1H), 5.91 (brs, 1H), 6.62 (s, 1H), 7.10 (d, 2H, J=8.0 Hz), 7.27 (d, 2H, J=8.0 Hz), 7.40-7.55 (m, 3H), 8.38-8.50 (m, 2H), 9.40 (brs, 1H). MS (ES): 546.0 (M$^+$+1).

Activity of Compounds

The biological activity of the compounds of the present invention is illustrated by performing a radioligand binding assay. Selected compounds disclosed herein show a selectivity for the A$_{2b}$ adenosine receptor over the A$_1$, A$_{2a}$, and A$_3$ receptors of 2-57 fold and nanomolar potency in binding assays. The preparation of the binding assay is described below.

Specifically, the following selectivities for the A$_{2B}$ receptor relative to the A$_1$, A$_{2A}$, and A$_3$ receptor were observed:

17.7: 26×, 17.7.MsOH: 24×, 26.5: 20×, 26.42: 57×, 26.135: 19×, 26.135.MsOH: 17×, 26.237: 57×, 26.237.MsOH: 33×, 26.71: A$_1$/A$_{2B}$ dual antagonist with 82×.

Specifically, the following K$_i$ for the A$_{2B}$ receptor was observed:

17.7: 5 nM.

Materials and Methods

Materials. [$^3$H]-DPCPX [cyclopentyl-1,3-dipropylxanthine] (120 Ci/mmol) was purchased from New England Nuclear (Boston, Mass.). The adenosine deaminase and complete protease inhibitor cocktail tablets were purchased from Boehringer Mannheim Corp. (Indianapolis, Ind.). Cell culture reagents were from Life Technologies (Grass Island, N.Y.) except for serum that was from Hyclone (Logan, Utah).

Cell line. HEK293 stably expressing the human A$_{2B}$ receptor were used for radioligand binding assays. Cells were grown in DMEM Glutamax containing 10% FBS, 0.2 mg/ml G418 at 37° C. in 5% CO$_2$/95% atmosphere.

Membrane Preparation. Cells were washed with cold PBS buffer twice, scraped off the plates, and centrifuged at 1000×g for 5 minutes. Cells were homogenized with ice-cold buffer of 5 mM Tris, pH 7.4, 5 mM EDTA, 5 mM EGTA, protease inhibitor cocktail tablets and incubated for 10 min on ice. The homogenate was centrifuged at 32,000×g for 30 min. The membranes were resuspended in buffer of 50 mM Tris, pH 7.4, 0.6 mM EDTA, 5 mM MgCl$_2$, stored at −80° C. until use. Protein concentration was determined by the methods of Bradford.

Radioligand binding assay. Membranes were homogenized in buffer containing 10 mM HEPES-KOH, pH 7.4 containing 1.0 mM EDTA; 2 U/ml adenosine deaminase; and 0.1 mM Benzamidine and incubated for 30 min at room temperature. Dissociation constants of radioligand (K$_d$ values) and maximum binding sites (B$_{max}$) were determined in saturation binding experiments. Saturation binding assays were carried out in a reaction mixture containing 50 μl of membrane suspension, 25 μl of 4% DMSO, 25 μl of increasing amounts of radioligand, [$^3$H]-DPCPX (final concentration 1-200 nM). Competition binding assays were performed in a reaction mixture containing 50 μl of membrane suspension (~5 μg/well), 25 μl of [$^3$H]-DPCPX (final concentration is ~22 nM), and 25 µl compounds. Nonspecific binding was measured in the presence of 100 µM NECA. Compounds were dissolved in DMSO and then diluted with 4% DMSO; the final maximum DMSO concentrations were 1%. Incubations were carried out in triplicate for 1 hr at 23.5° C. Reactions were terminated by rapid filtration over GF/C filters using a cell harvester. The filters were washed ten times with 0.4 ml of ice-cold buffer containing 10 mM HEPES-KOH, pH 7.4. The filters were dried, covered with scintillation fluid and counted with a TopCount.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the structure:

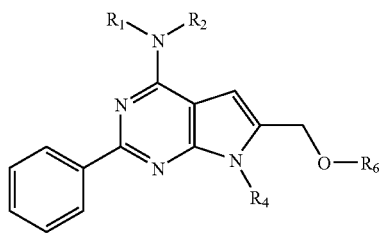

wherein,
$R_1$, $R_2$ and N together form a substituted azetidine or piperazine ring;
$R_4$ is H; and
$R_6$ is a substituted or unsubstituted heteroaryl ring or a substituted phenyl;
wherein the substituent on the phenyl ring is —OCH$_3$, —CH$_3$, —C(=O)OCH$_3$, —NH$_2$, or —NHC(=O)CH$_3$;
or a pharmaceutically acceptable salt thereof.

2. A compound having the structure:

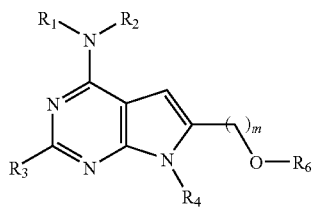

wherein,
$R_1$ is —(CH$_2$)2NHC(=O)CH$_3$;
$R_2$ is hydrogen or methyl;
$R_3$ is substituted or unsubstituted phenyl;
$R_4$ is hydrogen or methyl;
$R_6$ is substituted or unsubstituted cyclopentyl; and
m is 0, 1, 2 or 3;
or a pharmaceutically acceptable salt thereof.

3. A compound having the structure:

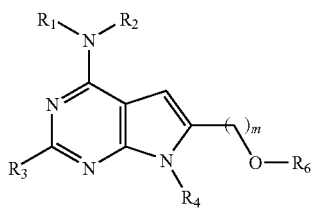

wherein,
$R_1$ is a substituted or unsubstituted alkyl, wherein the substituent is hydroxyl, carboxyl, —C(=O) NR$_a$R$_b$, —NR$_a$R$_b$, —NR$_a$C(=O) NR$_a$R$_b$, —NR$_a$C(=O)OR$_a$, —OC(=O)NR$_a$R$_b$, or —NHC(=O)R$_a$;
$R_2$ is hydrogen or a substituted or unsubstituted alkyl, wherein the substituent is hydroxyl, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$, or
$R_1$, $R_2$ and N together form a substituted piperazine ring, substituted azetidine ring, or a pyrrolidine ring substituted with —(CH$_2$)$_2$OH or —CH$_2$C(=O)OH;
$R_3$ is a substituted or unsubstituted phenyl or a 5-6 membered heteroaryl ring, wherein the substituent is halogen, hydroxyl, cyano, (C$_1$-C$_{15}$) alkyl, (C$_1$-C$_{15}$) alkoxy, or —NR$_a$R$_b$;
$R_4$ is hydrogen or substituted or unsubstituted (C$_1$-C$_{15}$) alkyl;
$R_6$ is a substituted or unsubstituted 4-8 membered heterocyclic ring;
$R_a$ and $R_b$ are each independently hydrogen or alkyl; and
m is 0, 1, 2 or 3;
or a pharmaceutically acceptable salt thereof.

4. A compound having the structure:

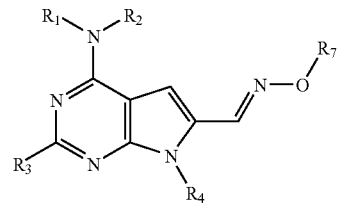

wherein,
$R_1$ is a substituted or unsubstituted alkyl, wherein the substituent is hydroxyl, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$;
$R_2$ is hydrogen or a substituted or unsubstituted alkyl, wherein the substituent is hydroxyl, carboxyl, —C(=O)NR$_a$R$_b$, —NR$_a$R$_b$, —NR$_a$C(=O)NR$_a$R$_b$, —NR$_a$C(=O)OR$_a$, —OC(=O)NR$_a$R$_b$, or —NHC(=O)R$_a$, or
$R_1$, $R_2$ and N together form a substituted piperazine ring, substituted azetidine ring, or a pyrrolidine ring substituted with —(CH$_2$)$_2$OH or —CH$_2$C(=O)OH;
$R_3$ is a substituted or unsubstituted phenyl or a 5-6 membered heteroaryl ring, wherein the substituent is halogen, hydroxyl, cyano, (C$_1$-C$_{15}$) alkyl, (C$_1$-C$_{15}$) alkoxy, or NR$_a$R$_b$;
$R_4$ is hydrogen or substituted or unsubstituted (C$_1$C$_{15}$) alkyl;

$R_a$ and $R_b$ are each independently hydrogen or alkyl; and
$R_7$ is hydrogen, or a substituted or unsubstituted ($C_1$-$C_{30}$) alkyl, ($C_1$-$C_{30}$)alkylaryl;

or a pharmaceutically acceptable salt thereof.

5. A compound having the structure:

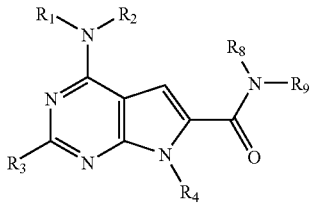

wherein, $R_1$ is a substituted or unsubstituted alkyl, wherein the substituent is hydroxyl, carboxyl, —C(=O) $NR_aR_b$, —$NR_aR_b$, —$NR_aC$(=O)$NR_aR_b$, —$NR_aC$(=O) $OR_a$, —OC(=O)$NR_aR_b$, or —NHC(=O)$R_a$;

$R_2$ is hydrogen or a substituted or unsubstituted alkyl, wherein the substituent is hydroxyl, carboxyl, —C(=O) $NR_aR_b$, —$NR_aR_b$, —$NR_aC$(=O)$NR_aR_b$, —$NR_aC$(=O)$OR_a$, —OC(=O)$NR_aR_b$, or —NHC(=O)$R_a$, or $R_1$, $R_2$ and N together form a substituted piperazine ring, substituted azetidine ring, or a pyrrolidine ring substituted with —(CH$_2$)$_2$OH or —CH$_2$C(=O)OH;

$R_3$ is a substituted or unsubstituted phenyl or a 5-6 membered heteroaryl ring, wherein the substituent is halogen, hydroxyl, cyano, ($C_1$-$C_{15}$) alkyl, ($C_1$-$C_{15}$) alkoxy, or $NR_aR_b$;

$R_4$ is hydrogen or substituted or unsubstituted ($C_1C_{15}$) alkyl;

$R_a$ and $R_b$ are each independently hydrogen or alkyl; and $R_8$ and $R_9$ are each independently hydrogen, or a substituted or unsubstituted ($C_1$-$C_{30}$)alkyl, ($C_1$-$C_{30}$) alkylaryl, ($C_1$-$C_3$) alkylamino, ($C_1$-$C_3$) alkoxy, or a substituted or unsubstituted, saturated or unsaturated, monocyclic or bicyclic, carbocyclic or heterocyclic ring;

or a pharmaceutically acceptable salt thereof.

6. A compound having the structure:

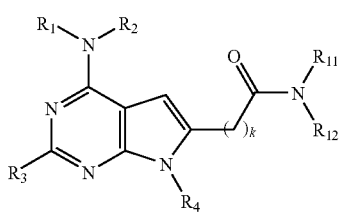

wherein, $R_1$ is a substituted or unsubstituted alkyl, wherein the substituent is hydroxyl, carboxyl, —C(=O)$NR_aR_b$, —$NR_aR_b$, —$NR_aC$(=O)$NR_aR_b$, —$NR_aC$(=O) $OR_a$, —OC(=O)$NR_aR_b$, or —NHC(=O)$R_a$;

$R_2$ is hydrogen or a substituted or unsubstituted alkyl, wherein the substituent is hydroxyl, carboxyl, —C(=O) $NR_aR_b$, —$NR_aR_b$, —$NR_aC$(=O)$NR_aR_b$, —$NR_aC$ (=O)$OR_a$, —OC(=O)$NR_aR_b$, or —NHC(=O)$R_a$, or $R_1$, $R_2$ and N together form a substituted piperazine ring, substituted azetidine ring, or a pyrrolidine ring substituted with —(CH$_2$)2OH or —CH$_2$C(=O)OH;

$R_3$ is a substituted or unsubstituted phenyl or a 5-6 membered heteroaryl ring, wherein the substituent is halogen, hydroxyl, cyano, ($C_1$-$C_{15}$) alkyl, ($C_1$-$C_{15}$) alkoxy, or —$NR_aR_b$;

$R_4$ is hydrogen or substituted or unsubstituted ($C_1$-$C_{15}$) alkyl;

$R_{11}NR_{12}$ together form a substituted or unsubstituted 4-8 membered heterocyclic ring;

$R_a$ and $R_b$ are each independently hydrogen or alkyl; and k is 0, 1, 2 or 3;

or a pharmaceutically acceptable salt thereof.

7. The compound of claim 3, wherein the compound is selected from the group consisting of:

N-(2-{6-[1-(Benzenesulfonyl)piperidin-4-yloxymethyl]-2-phenyl-7H-pyrrolo[2,3-d]pyrimidin-4-ylamino}ethyl)acetamide;

N-{2-[6-(1-Phenethylpiperidin-4-yloxymethyl)-2-phenyl-7H-pyrrolo[2,3-d]pyrimidin-4-ylamino] ethyl}acetamide;

N-[2-{6-[1-(3-Phenylpropyl)piperidin-4-yloxymethyl]-2-phenyl-7H-pyrrolo[2,3-d]pyrimidin-4-ylamino}ethyl] acetamide;

N-(2-{6-[1-(4-Bromobenzyl)piperidin-4-yloxymethyl]-2-phenyl-7H-pyrrolo[2,3-d]pyrimidin-4-ylamino}ethyl) acetamide;

N-[2-(6-{1-[2-(2-Chlorophenyl)ethyl]piperidin-4-yloxymethyl{-2-phenyl-7H-pyrrolo[2,3-d]pyrimidin-4-ylamino) ethyl]acetamide;

N-[2-(6-{1-[2-(3-Chlorophenyl)ethyl]piperidin-4-yloxymethyl}-2-phenyl-7H-pyrrolo[2,3-d]pyrimidin-4-ylamino) ethyl]acetamide;

N-(2-{6-[1-(3-Chlorobenzyl)piperidin-4-yloxymethyl]-2-phenyl-7H-pyrrolo[2,3-d]pyrimidin-4-ylamino}ethyl) acetamide;

N-[2-(6-{1-[2-(4-Chlorophenyl)ethyl]piperidin-4-yloxymethyl}-2 -phenyl-7H-pyrrolo[2,3-d]pyrimidin-4-ylamino) ethyl]acetamide;

N-[2-(6-{1-[2-(2-Methoxyphenyl)ethyl]piperidin-4-yloxymethyl)-2-phenyl-7H-pyrrolo[2,3-d]pyrimidin-4-ylamino)ethyl]acetamide;

N-[2-(6-{1-[2-(3-Methoxyphenyl)ethyl]piperidin-4-yloxymethyl}-2-phenyl-7H-pyrrolo[2,3-d]pyrimidin-4-ylamino) ethyl]acetamide;

N-[2-(6-{1-[2-(4-Methoxyphenyl)ethyl]piperidin-4-yloxymethyl}-2-phenyl-7H-pyrrolo[2,3-d]pyrimidin-4-ylamino) ethyl]acetamide;

N-[2-(6-{1-[2-(4-Fluorophenyl)ethyl]piperidin-4-yloxymethyl}-2-phenyl-7H-pyrrolo[2,3-d]pyrimidin-4-ylamino) ethyl]acetamide;

N-[2-(6-{1-[2-(2-Chloro-4-fluorophenyl)ethyl]piperidin-4-yloxymethyl}-2-phenyl-7H-pyrrolo[2,3-d]pyrimidin-4-ylamino) ethyl]acetamide;

N-[2-(6-{1-[2-(2-Chloro-6-fluorophenyl)ethyl]piperidin-4-yloxyrnethyl}-2-phenyl-7H-pyrrolo[2,3-d]pyrimidin-4-ylamino) ethyl]acetamide;

N-[2-(6-{1-[2-(2-Trifluoromethylphenyl)ethyl]piperidin-4-yloxymethyl}-2-phenyl-7H-pyrrolo[2,3-d]pyrimidin-4-ylamino) ethyl]acetamide; and N-[2-(6-{1-[2-(2-Bromophenyl)ethyl]piperidin-4-yloxymethyl}-2-phenyl-7H-pyrrolo[2,3-d]pyrimidin-4-ylamino) ethyl]acetamide;

or a pharmaceutically acceptable salt thereof.

8. The compound of claim 5, wherein the compound is selected from the group consisting of:

4-(2-Acetylaminoethylamino)-2-phenyl-7H-pyrrolo[2,3-d]pyrimidine-6-carboxylic acid (3-phenoxyphenyl)-amide;

4-(2-Acetylaminoethylamino)-2-phenyl-7H-pyrrolo[2,3-d]pyrimidine-6-carboxylic acid (1-benzylpiperidin-4-yl)-amide;

4-(2-Acetylaminoethylamino)-2-phenyl-7H-pyrrolo[2,3-d]pyrimidine-6-carboxylic acid (1-benzylpyrrolidin-3-yl)-amide;

4-(2-Acetylaminoethylamino)-2-phenyl-7H-pyrrolo[2,3-d]pyrimidine-6-carboxylic acid 4-[1,2,3]thiadiazol-4-yl-benzylamide;

4-(2-Acetylaminoethylamino)-2-phenyl-7H-pyrrolo[2,3-d]pyrimidine-6-carboxylic acid benzylamide;

4-(2-Acetylaminoethylainino)-2-phenyl-7H-pyrrolo[2,3-d]pyrimidine-6-carboxylic acid (2-hydroxy-1-hydroxymethylethyl)-amide;

4-(2-Acetylaminoethylamino)-2-phenyl-7H-pyrrolo[2,3-d]pyrimidine-6-carboxylic acid (1-hydroxycyclohexylmethyl)-amide; and 4-(2-Acetylaminoethylamino)-2-phenyl-7H-pyrrolo[2,3-d]pyrimidine-6-carboxylic acid [2-(4-phenoxyphenyl)-ethyl]-amide;

or a pharmaceutically acceptable salt thereof.

9. The compound of claim 6, wherein the compound is selected from the group consisting of:

N-(2-{2-Phenyl-6-[4-(3-phenylallyl)-piperazine-1-carbonyl]-7H-pyrrolo[2,3-d]pyrimidin-4-ylamino}-ethyl)-acetamide;

N-{2-[6-(4-Hydroxy-4-isopropylpiperidine-1-carbonyl)-2-phenyl-7H-pyrrolo[2,3-d]pyrimidin-4-ylaxnino]-ethyl}-acetamide;

N-(2-{2-Phenyl-6-[4-(3-phenylpropyl)-piperazine-1-carbonyl]-7H-pyrrolo[2,3-d]pyrimidin-4-ylainino}-ethyl)-acetamide;

N-{2-[6-(4-Phenethylpiperazine-1-carbonyl)-2-phenyl-7H-pyrrolo[2,3-d]pyrimidin-4-ylainino]-ethyl}-acetamide;

2-{2-Phenyl-6-[4-(3-phenylpropyl)-piperazine-1-carbonyl]-7H-pyrrolo[2,3-d]pyrimidin-4-ylamino}-acetamide;

N-[2-(6-{4-[2-(4-Chlorophenoxy)-ethyl]-piperazine-1-carbonyl}-2-phenyl-7H-pyrrolo[2,3-d]pyrimidin-4-ylamino)-ethyl]-acetamide;

N-{2-[6-(4-Cyano-4-phenylpiperidine-1-carbonyl)-2-phenyl-7H-pyrrolo(2,3-d]pyrimidin-4-ylamino]-ethyl}-acetamide;

N-(2-{2-Phenyl-6-[4-(3-phenylprop-2-ynyl)-piperazine-1-carbonyl]-7H-pyrrolo[2,3-d]pyrimidin-4-ylamino}-ethyl)-acetamide;

N-(2-{6-[cis-3,5-Dimethyl-4-(3-phenylpropyl)-piperazine-1-carbonyl]-2-phenyl-7H-pyrrolo[2,3-d]pyrimidin-4-ylaxnino}-ethyl)-acetamide;

N-{2-[6-(4,4-Diphenylpiperidine-1-carbonyl)-2-phenyl-7H-pyrrolo[2,3-d]pyrimidin-4-ylamino]-ethyl}-acetamide;

N-{2-[6-(3,3-Diphenylpiperidine-1-carbonyl)-2-phenyl-7H-pyrrolo[2,3-d]pyrimidin-4-ylamino]-ethyl}-acetamide;

N-{2-[6-(4-Methoxy-4-phenylpiperidine-1-carbonyl)-2-phenyl-7H-pyrrolo[2,3-d]pyrimidin-4-ylamino]-ethyl}-acetamide;

N-(2-{6-[trans-2,5-Dimethyl-4-(3-phenylpropyl)-piperazine-1-carbonyl]-2-phenyl-7H-pyrrolo[2,3-d]pyrimidin-4-ylamino}-ethyl)-acetamide;

N-{2-[6-(trans-2,5-Dimethylpiperazine-1-carbonyl)-2-phenyl-7H-pyrrolo[2,3-d]pyrirnidin-4-ylainino]-ethyl}-acetamide;

N-{2-[6-(4-Benzyl-cis-3,5-dimethylpiperazine-1-carbonyl)-2-phenyl-7H-pyrrolo[2,3-d]pyrimidin-4-ylamino]-ethyl}-acetamide;

N-{2-[6-(cis-3,5-Dimethyl-4-phenethylpiperazine-1-carbonyl)-2-phenyl-7H-pyrrolo[2,3-d]pyrimidin-4-ylamino]-ethyl }-acetamide;

N-{2-[6-(3-Methyl-3-phenylpiperidine-1-carbonyl)-2-phenyl-7H-pyrrolo[2,3-d]-pyrimidin-4-ylamino]-ethyl}-acetamide;

N-(2-{2-Phenyl-6-[4-(5-trifluoromethylpyridin-2-yl)-piperazine-1-carbonyi]-7H-pyrrolo[2,3-d]pyrirnidin-4-ylamino}-ethyl)-acetamide;

N-(2-{6[4-(2'-Chlorobiphenyl-2-yl)-4-methoxypiperidine-1-carbonyl]-2-phenyl-7H-pyrrolo[2,3-d]pyrimidin-4-ylamino}-ethyl)-acetamide;

N-(2-{6-[4-(2-Chlorophenyl)-4-methoxypiperidine-1-carbonyl]-2-phenyl-7H-pyrrolo[2,3-d]pyrimidin-4-ylamino}-ethyl)-acetamide;

N-(2-{6-[4-(2-Chlorophenyl)-4-hydroxypiperidine-1-carbonyl]-2-phenyl-7H-pyrrolo[2,3 -d]pyrimidin-4-ylamino}-ethyl)-acetamide;

N-(2-{6-[4-(2'-Chlorobiphenyl-2-yl)-4-hydroxypiperidine-1-carbonyl]-2-phenyl-7H-pyrrolo[2,3-d]pyrimidin-4-ylamino}-ethyl)-acetamide;

N-(2-{6-[4-(4-Fluorophenyl)-4-methoxypiperidine-1-carbonyl]-2-phenyl-7H-pyrrolo[2,3-d]pyrimidin-4-ylamino}-ethyl)-acetamide;

N-(2-{2-Phenyl-6-[4-(4-phenylbutyl)-piperazine-1-carbonyl]-7H-pyrrolo[2,3-d]pyrimidin-4-ylamino}-ethyl)-acetamide;

N-(2-{2-Phenyl-6-[4-(3-phenylpropyl)-piperidine-1-carbonyl]-7H-pyrrolo[2,3-d]pyrimidin-4-ylamino}-ethyl)-acetamide;

N-{2-[2-Phenyl-6-(4-pyrrolidin-1-yl-piperidine-1-carbonyl)-7H-pyrrolo[2,3-d]pyrimidin-4-ylamino]-ethyl}-acetamide;

N-(2-{6-[4-(3-Cyclohexylpropyl)-piperazine-1-carbonyl]-2-phenyl-7H-pyrrolo[2,3-d]pyrimidin-4-ylamino}-ethyl)-acetamide;

N-(2-{6-[4-(4-Methylpentyl)-piperazine-1-carbonyl]-2-phenyl-7H-pyrrolo[2,3-d]pyrimidin-4-ylainino}-ethyl)-acetamide;

N-{2-[6-([1,4']Bipiperidinyl-1'-carbonyl)-2-phenyl-7H-pyrrolo[2,3-d]pyrimidin-4-ylamino]-ethyl}-acetamide;

N-{2-[6-(4-Cyclopentylpiperazine-1-carbonyl)-2-phenyl-7H-pyrrolo[2,3-d]pyrimidin-4-ylamino]-ethyl}-acetamide;

N-{2-[6-(4-Aminopiperidine-1-carbonyl)-2-phenyl-7H-pyrrolo[2,3-d]pyrimidin-4-ylamino]-ethyl}-acetamide;

N-{2-[6-(4-Acetyl-4-phenylpiperidine-1-carbonyl)-2-phenyl-7H-pyrrolo[2,3-d]pyrimidin-4-ylamino]-ethyl}-acetamide;

N-(2-{6-[4-(2-Cyclohexylethyl)-piperazine-1-carbonyl]-2-phenyl-7H-pyrrolo[2,3-d]pyrimidin-4-ylamino}-ethyl)-acetamide;

N-{2-[2-Phenyl-6-(4-phenylethynyl-3,6-dihydro-2H-pyridine-1-carbonyl)-7H-pyrrolo[2,3-d]pyrimidin-4-ylamino]-ethyl }-acetamide;

N-{2-[6-(4-tert-Butylpiperidine-1-carbonyl)-2-phenyl-7H-pyrrolo[2,3-d]pyrimidin-4-ylainino]-ethyl}-acetamide;

N-{2-[6-(4-Phenethylpiperidine-1-carbonyl)-2-phenyl-7H-pyrrolo[2,3-d]pyrimidin-4-ylantino]-ethyl}-acetamide;

N-[2-(6-{4-[3-(2-Cyanophenyl)-prop-2-ynyl]-piperazine-1-carbonyl}-2-phenyl-7H-pyrrolo[2,3-d]pyrimidin-4-ylamino)-ethyl]-acetamide;

N-[2-(6-{4-[3-(3-Cyanophenyl)-prop-2-ynyl]-piperazine-1-carbonyl}-2-phenyl-7H-pyrrolo[2,3-d]pyrimidin-4-ylamino)-ethyl]-acetamide;
N-[2-(6-{4-[3-(4-Cyanophenyl)-prop-2-ynyl]-piperazine-1-carbonyl -2-phenyl-7H-pyrrolo[2,3-d]pyrimidin-4-ylamino)-ethyl]-acetamide;
1-[4-(2-Acetylaminoethylamino)-2-phenyl-7H-pyrrolo[2,3-d]pyrimidine-6-carbonyl]-4-phenylpiperidine-4-carboxylic acid methyl ester;
N-(2-{6-[4-(1-Hydroxyethyl)-4-phenylpiperidine-1-carbonyl]-2-phenyl-7H-pyrrolo[2,3-d]pyrimidin-4-ylamino}-ethyl)-acetamide;
N-[2-(6-{4-[3-(4-Cyanophenyl)-propyl]-piperazine-1-carbonyl}-2-phenyl-7H-pyrrolo[2,3-d]pyrimidin-4-ylamino)- ethyl]-acetamide;
1-[4-(2-Acetylaminoethylainino)-2-phenyl-7H-pyrrolo[2,3-d]pyrimidine-6 carbony]-4-phenylpiperidine-4-carboxylic acid ethyl ester;
1-[4-(2-Acetylaminoethylamino)-2-phenyl-7H-pyrrolo[2,3-d]pyrimidine-6-carbonyl]-4-phenylpiperidine-4-carboxylic acid amide;
1-[4-(2-Acetylaminoethylamino)-2-phenyl-7H-pyrrolo[2,3-d]pyrimidine-6-carbonyl]-4-phenylpiperidine-4-carboxylic acid methylamide;
1-[4-(2-Acetylaininoethylamino)-2-phenyl-7H-pyrrolo[2,3-d]pyrimidine-6-carbonyl]-4-phenylpiperidine-4-carboxylic acid dimethylamide;
1-[4-(2-Acetylaminoethylamino)-2-phenyl-7H-pyrrolo[2,3-d]pyrimidine-6-carbonyl]-4-phenylpiperidine-4-carboxylic acid benzylamide;
1-[4-(2-Acetylaminoethylamino)-2-phenyl-7H-pyrrolo[2,3-d]pyrimidine-6-carbonyl]-4-phenylpiperidine-4-carboxylic acid ethylamide;
1-[4-(2-Acetylaminoethylamino)-2-phenyl-7H-pyrrolo[2,3-d]pyrimidine-6-carbonyl]-4-phenylpiperidine-4-carboxylic acid diethylamide;
N-(2-{6-[4-(Azetidine-1-carbonyl)-4-phenylpiperidine-1-carbonyl]-2-phenyl-7H-pyrrolo[2,3-d]pyrimidin-4-ylamino}-ethyl)-acetamide;
N-(2-{2-Phenyl-6-[4-phenyl-4-(pyrrolidine-1-carbonyl)-piperidine-1-carbonyl]-7H-pyrrolo[2,3-d]pyrimidin-4-ylamino}-ethyl)-acetamide;
N-(2-{2-Phenyl-6-[4-phenyl-4-(piperidine-1-carbonyl)-piperidine-1-carbonyl]-7H-pyrrolo[2,3-d]pyrimidin-4-ylamino}-ethyl)-acetamide;
N-(2-{6-[4-(Morpholine-4-carbonyl)-4-phenylpiperidine-1-carbonyl]-2-phenyl-7H-pyrrolo[2,3-d]pyrimidin-4-ylamino}-ethyl)-acetamide;
1-[4-(2-Acetylaminoethylamino)-2-phenyl-7H-pyrrolo[2,3-d]pyrimidine-6-carbonyl]-4-phenylpiperidine-4-carboxylic acid tert-butylamide;
N-{2-[6-(4-Isopropyl-4-phenylpiperidine-1-carbonyl)-2-phenyl-7H-pyrrolo[2,3-d]pyrimidin-4-ylamino]-ethyl}-acetamide;
N-(2-{2-Phenyl-6-[4-(3-thiophen-2-yl-prop-2-ynyl)-piperazine-1-carbonyl]-7H-pyrrolo[2,3-d]pyrimidin-4-ylamino}-ethyl)-acetamide;
1-[4-(2-Acetylaminoethylamino)-2-phenyl-7H-pyrrolo[2,3-d]pyrimidine-6-carbonyl]-4-phenylpiperidine-4-carboxylic acid cyclobutylmethyl ester;
N-(2-{6-[4-(4-Chlorophenyl)-4-methoxypiperidine-1-carbonyl]-2-phenyl-7H-pyrrolo[2,3-d]pyrimidin-4-ylamino}-ethyl)-acetamide;
N-(2-{6-[4-(4-Chlorophenyl)-piperazine-1-carbonyl]-2-phenyl-7H-pyrrolo[2,3-d]pyrimidin-4-ylamino}-ethyl)-acetamide;
N-(2-{6-[4-Methoxy-4-(3-trifluoromethyiphenyl)-piperidine-1-carbonyl]-2-phenyl-7H-pyrrolo[2,3-d]pyrimidin-4-ylamino 1-ethyl)-acetamide;
N-{2-[6-(4-Isopropyl-4-methoxypiperidine-1-carbonyl)-2-phenyl-7H-pyrrolo[2,3-d]pyrimidin-4-ylamino]-ethyl}-acetamide;
N-{2-[6-(4-Acetylamino-4-phenylpiperidine-1-carbonyl)-2-phenyl-7H-pyrrolo[2,3-d]pyrimidin-4-ylamino]-ethyl-acetamide;
1-[4-(2-Acetylaininoethylamino)-2-phenyl-7H-pyrrolo[2,3-d]pyrimidine-6-carbonyl]-4-phenylpiperidine-4-carboxylic acid isopropyl ester;
1-[4-(2-Acetylaininoethylainino)-2-phenyl-7H-pyrrolo[2,3-d]pyrimidine-6-carbonyl]-4-ethylaxninopiperidine-4-carboxylic acid amide;
N-(2-{6-[4-Methoxy-4-(3-methoxyphenyl)-piperidine-1-carbonyl]-2-phenyl-7H-pyrrolo[2,3-d]pyrimidin-4-ylaxnino}-ethyl)-acetamide;
1-[4-(2-Acetylaminoethylamino)-2-phenyl-7H-pyrrolo[2,3-d]pyrimidine-6-carbonyl]-4-pyrrolidin-1-ylpiperidine-4-carboxylic acid amide;
N-(2-{6-[4-(2-Methoxyphenyl)-3,6-dihydro-2H-pyridine-1-carbonyl]-2-phenyl-7H-pyrrolo[2,3-d]pyrimidin-4-ylamino}-ethyl)-acetamide;
N-{2-[6-(4-Amino-4-phenylpiperidine-1-carbonyl)-2-phenyl-7H-pyrrolo[2,3-d]pyrimidin-4-ylaxnino]-ethyl}-acetamide;
N-{2-[6-(4-Formyl-4-phenylpiperidine-1-carbonyl)-2-phenyl-7H-pyrrolo[2,3-d]pyrimidin-4-ylamino]-ethyl}-acetamide;
N-{2-[6-(4-Benzyl-4-methoxypiperidine-1-carbonyl)-2-phenyl-7H-pyrrolo[2,3-d]pyrimidin-4-ylamino]-ethyl}-acetamide;
N-{2-[6-(4-Methoxy-4-o-tolylpiperidine-1-carbonyl)-2-phenyl-7H-pyrrolo[2,3-d]pyrimidin-4-ylamino]-ethyl}-acetamide;
N-{2-[6-(4-Methoxyxnethyl-4-phenylpiperidine-1-carbonyl)-2-phenyl-7H-pyrrolo[2,3-d]pyrimidin-4-ylamino]-ethyl)-acetamide;
N-[2-(6-{4-[3-(2-Chlorophenyl)-propyl]-piperazine-1-carbonyl}-2-phenyl-7H-pyrrolo[2,3-d]pyrimidin-4-ylamino)-ethyl]-acetamide;
N-[2-(6-{4-[3-(3-Chlorophenyl)-propyl]-piperazine-1-carbonyl}-2-phenyl-7H-pyrrolo[2,3-d]pyrimidin-4-ylamino)-ethyl]-acetamide;
N-[2-(6-{4-[3-(4-Chlorophenyl)-propyl]-piperazine-1-carbonyl}-2-phenyl-7H-pyrrolo[2,3-d]pyrimidin-4-ylamino)-ethyl]-acetamide;
N-[2-(6-{4-[3-(2-Methoxyphenyl)-propyl]-piperazine-1-carbonyl}-2-phenyl-7H-pyrrolo[2,3-d]pyrimidin-4-ylamino)-ethyl]-acetamide;
N-[2-(6-{4-[3-(3-Methoxyphenyl)-propyl]-piperazine-1-carbonyl}-2-phenyl-7H-pyrrolo[2,3-d]pyrimidin-4-ylamino)-ethyl]-acetamide;
N-[2-(6-{4-[3-(4-Methoxyphenyl)-propyl]-piperazine-1-carbonyl}-2-phenyl-7H-pyrrolo[2,3-d]pyrimidin-4-ylamino)-ethyl]-acetamide;
N-[2-(6-{4-[3-(4-Chlorophenyl)-propionyl]-piperazine-1-carbonyl -2-phenyl-7H-pyrrolo[2,3-d]pyrimidin-4-ylamino)-ethyl]-acetamide;
N-[2-(6-{4-[3-(3-Chlorophenyl)-propionyl]-piperazine-1-carbonyl}-2-phenyl-7H-pyrrolo[2,3-d]pyrimidin-4-ylamino)-ethyl]-acetamide;
N-[2-(6-{4-[3-(2-Chlorophenyl)-propionyl]-piperazine-1-carbonyl}-2-phenyl-7H-pyrrolo[2,3-d]pyrimidin-4-ylamino)-ethyl]-acetamide;

N-[2-(6-{4-[5-(4-Chlorophenyl)-2H-pyrazol-3-yl]-piperidine-1-carbonyl}-2-phenyl-7H-pyrrolo[2,3-d]pyrimidin-4-ylamino)-ethyl]-acetamide;
2-{4-[4-(2-Acetylaminoethylamino)-2-phenyl-7H-pyrrolo[2,3-d]pyrimidine-6-carbonyl]-piperazin-1-yl}-N-methyl-N-phenyl acetamide;
4-[4-(2-Acetylaminoethylamino)-2-phenyl-7H-pyrrolo[2,3-d]pyrimidine-6-carbonyl]-piperazine-1-carboxylic acid benzyl ester;
N-{2-[6-(4-Oxo-1-phenyl-1,3,8-triazaspiro[4.5]decane-8-carbonyl)-2-phenyl-7H-pyrrolo[2,3-d]pyrimidin-4-ylainino]-ethyl}-acetamide;
N-(2-{6-[4-(Methylphenethylamino)-piperidine-1-carbonyl]-2-phenyl-7H-pyrrolo[2,3-d]pyrimidin-4-ylamino}-ethyl)-acetamide;
N-{2-[6-(4-Phenethylaminopiperidine-1-carbonyl)-2-phenyl-7H-pyrrolo[2,3-d]pyrimidin-4-ylarnino]-ethyl}-acetamide;
N-[2-(6-{4-[2-(4-Chlorophenyl)-ethylamino]-piperidine-1-carbonyl}-2-phenyl-7H-pyrrolo[2,3-d]pyrimidin-4-ylamino)-ethyl]-acetamide;
N-[2-(6-{4-[2-(3H-Imidazol-4-yl)-ethylainino]-piperidine-1-carbonyl}-2-phenyl-7H-pyrrolo[2,3-d]pyrimidin-4-ylamino)-ethyl]-acetamide;
N-(2-{2-Phenyl-6-[4-(2-pyridin-4-ylethylamino)-piperidine-1-carbonyl]-7H-pyrrolo[2,3-d]pyrimidin4ylamiriol-ethyl)-acetamide;
N-(2-{2-Phenyl-6-114-(2-pyridin-2-ylethylamino)-piperidine-1-carbonyl]-7H-pyrrolo[2,3-d]pyrimidin-4-ylamino}-ethyl)-acetamide;
N-{2-(6-(4-Benzylaminopiperidine-1-carbonyl)-2-phenyl-7H-pyrrolo[2,3-d]pyrimidin-4-ylamino]-ethyl}-acetamide;
N-(2-{6-[4-(Benzylmethylamino)-piperidine-1-carbonyl]-2-phenyl-7H-pyrrolo[2,3-d]pyrimidin-4-ylamino}-ethyl)-acetamide;
N-[2-(2-Phenyl-6-{4-[(pyridin-4-ylmethyl)-amino]-piperidine-1-carbonyl}-7H-pyrrolo[2,3-d]pyrimidin-4-ylamino)-ethyl]-acetamide;
N-(2-{2-Phenyl-6-[4-(2-pyridin-3-ylethylamino)-piperidine-1-carbonyl]-7H-pyrrolo[2,3-d]pyrimidin-4-ylamino}-ethyl)-acetamide;
N-{2-[2-Phenyl-6-((S)-2-phenylaminomethylpyrrolidine-1-carbonyl)-7H-pyrrolo (2,3-d]pyrimidin-4-ylamino]-ethyl}-acetamide;
N-[2-(2-Phenyl-6-{4-[3-(4-trifluoromethyiphenyl)-propyl]-piperazine-1-carbonyl}-7H-pyrrolo[2,3-d]pyrimidin-4-ylamino)- ethyl]-acetamide;
N-[2-(6-{4-(3-(4-Fluorophenyl)-propyl]-piperazine-1-carbonyl}-2-phenyl-7H-pyrrolo[2,3-d]pyrimidin-4-ylamino)-ethyl]-acetamide;
N-(2-{6-[4-(3-Benzo[1,3]dioxol-5-yl-propyl)-piperazine-1-carbonyl]-2-phenyl-7H-pyrrolo(2,3-d]pyrimidin-4-ylamino}-ethyl)-acetamide;
N-(2-{2-Phenyl-6-[4-(3-p-tolylpropyl)-piperazine-1-carbonyl]-7H-pyrrolo[2,3-d]pyrimidin-4-ylamino}-ethyl)-acetamide;
N-[2-(6-{4-[3-(4-Bromophenyl)-propyl]-piperazine-1-carbonyl}-2-phenyl-7H-pyrrolo[2,3-d]pyrimidin-4-ylamino)-ethyl]-acetamide;
N-[2-(6-{4-[3-(3,4-Dichlorophenyl)-propyl]-piperazine-1-carbonyl}-2-phenyl-7H-pyrrolo[2,3-d]pyrimidin-4-ylamino)-ethyl]-acetamide;
N-[2-(6-{4-[3-(2,4-Dichlorophenyl)-propyl]-piperazine-1-carbonyl}-2-phenyl-7H-pyrrolo[2,3-d]pyrimidin-4-ylamino)-ethyl]-acetamide;
N-{2-[6-(4-Benzyl-[1,4]diazepane-1-carbonyl)-2-phenyl-7H-pyrrolo[2,3-d]pyrimidin-4-ylamino]-ethyl}-acetamide;
N-{2-[6-(4-Phenethyl-[1,4]diazepane-1-carbonyl)-2-phenyl-7H-pyrrolo[2,3-d]pyrimidin-4-ylamino]-ethyl}-acetamide;
N-(2-{2-Phenyl-6-[4-(3-phenylpropyl)-[1,4]diazepane-1-carbonyl]-7H-pyrrolo[2,3-d]pyrimidin-4-ylamino}-ethyl)-acetamide;
N-(2-{6-[4-(4-Acetylaminophenyl)-piperazine-1-carbonyl]-2-phenyl-7H-pyrrolo[2,3-d]pyrimidin-4-ylamino}-ethyl)-acetamide;
N-(2-{6-[4-(2-Cyanophenyl)-piperazine-1-carbonyl]-2-phenyl-7H-pyrrolo[2,3-d]pyrimidin-4-ylainino}-ethyl)-acetamide;
N-[2-(6-{4-[4-(Acetylmethylamino)-phenyl]-piperazine-1-carbonyl}-2-phenyl-7H-pyrrolo[2,3-d]pyrimidin-4-ylamino)-ethyl]-acetamide;
N-(2-{6-[4-(2,6-Dimethyiphenyl)-piperazine-1-carbonyl]-2-phenyl-7H-pyrrolo[2,3-d]pyrimidin-4-ylamino}-ethyl)-acetamide;
N-(2-{6-[4-(2-Chlorophenyl)-piperazine-1-carbonyl]-2-phenyl-7H-pyrrolo[2,3-d]pyrimidin-4-ylamino}-ethyl)-acetamide;
N-(2-{6-[4-(2,4-Dimethoxyphenyl)-piperazine-1-carbonyl]-2-phenyl-7H-pyrrolo[2,3-d]pyrimidin-4-ylamino}-ethyl)-acetamide;
N-(2-{6-[4-(5-Chloro-2-methoxyphenyl)-piperazine-1-carbonyl]-2-phenyl-7H-pyrrolo[2,3-d]pyrimidin-4-ylamino}-ethyl)-acetamide;
N-(2-{6-[4-(4-Chlorophenoxymethyl)-piperidine-1-carbonyl]-2-phenyl-7H-pyrrolo[2,3-d]pyrimidin-4-ylainino}-ethyl)-acetamide;
N-{2-[6-(5-Benzyl-2,5-diazabicyclo[2.2.1]heptane-2-carbonyl)-2-phenyl-7H-pyrrolo[2,3-d]pyrimidin-4-ylamino]-ethyl}-acetamide;
N-{2-[6-(4-Phenoxyrnethylpiperidine-1-carbonyl)-2-phenyl-7H-pyrrolo[2,3 -d]pyrimidin-4-ylamino]-ethyl}-acetamide;
N-(2-{6-[4-(4-Cyanophenoxymethyl)-piperidine-1-carbonyl]-2-phenyl-7H-pyrrolo[2,3-d]pyrimidin-4-ylamino}-ethyl)-acetamide;
N-(2-{6-[4-(3-Cyanophenoxymethyl)-piperidine-1-carbonyl]-2-phenyl-7H-pyrrolo[2,3-d]pyrimidin-4-ylainino}-ethyl)-acetamide;
N-(2-{6-[4-(2—Nitrophenyl)-piperazine-1-carbonyl]-2-phenyl-7H-pyrrolo[2,3-d]pyrimidin-4-ylamino}-ethyl)-acetamide;
2-{4-[4-(2-Acetylaminoethylamino)-2-phenyl-7H-pyrrolo[2,3-d]pyrimidine-6-carbonyl]-piperazin-1-yl}-benzoic acid methyl ester;
N-{2-[2-Phenyl-6-(4-o-tolylpiperazine-1-carbonyl)-7H-pyrrolo[2,3-d]pyrimidin-4-ylamino]-ethyl}-acetamide;
N-(2-{6-[4-(3,4-Dichlorophenoxymethyl)-piperidine-1-carbonyl]-2-phenyl-7H-pyrrolo[2,3-d]pyrimidin-4-ylamino}-ethyl)-acetamide;
N-(2-{6-[4-(2-Cyanophenoxymethyl)-piperidine-1-carbonyl]-2-phenyl-7H-pyrrolo[2,3-d]pyrimidin-4-ylamino}-ethyl)-acetamide;
N-(2-{6-[4-(2-Chlorophenyl)-4-cyanopiperidine-1-carbonyl]-2 -phenyl-7H-pyrrolo[2,3-d]pyrimidin-4-ylamino}-ethyl)-acetamide; 2-{4-[4-(2-Acetylaminoethylamino)-2-phenyl-7H-pyrrolo[2,3-d]pyrimidine-6-carbonyl]-piperazin-1-yl}-benzamide;

N-(2-{6-[4-Cyano-4-(2-methoxyphenyl)-piperidine-1-carbonyl]-2-phenyl-7H-pyrrolo[2,3-d]pyrimidin-4-ylamino}-ethyl)-acetarnide;

N-(2-{6-[4-(3-Chlorophenyl)-4-cyanopiperidine-1-carbonyl]-2-phenyl-7H-pyrrolo[2,3-d]pyrimidin-4-ylamino}-ethyl)-acetamide;

N-(2-{6-[4-Cyano-4-(3-methoxyphenyl)-piperidine-1-carbonyl]-2-phenyl-7H-pyrrolo[2,3-d]pyrimidin-4-ylamino}-ethyl)-acetamide;

N-(2-{6-[4-Cyano-4-(4-methoxyphenyl)-piperidine-1-carbonyl]-2-phenyl-7H-pyrrolo[2,3-d]pyrimidin-4-ylamino}-ethyl)-acetamide; and N-(2-{6-[3-(4-Benzylpiperazin-1-yl)-3-oxopropyl]-2-phenyl-7H-pyrrolo[2,3-d]pyrimidin-4-ylamino}-ethyl)-acetamide;

or a pharmaceutically acceptable salt thereof.

10. The compound of claim 6, wherein the compound is:

N-(2-{6-[4-(4-Chlorophenyl)-piperazine-1-carbonyl]-2-phenyl-7H-pyrrolo[2,3-d]pyrimidin-4-ylamino}-ethyl)-acetamide;

or a pharmaceutically acceptable salt thereof.

* * * * *

UNITED STATES PATENT AND TRADEMARK OFFICE
CERTIFICATE OF CORRECTION

PATENT NO. : 7,645,754 B2
APPLICATION NO. : 10/536119
DATED : January 12, 2010
INVENTOR(S) : Castelhano et al.

It is certified that error appears in the above-identified patent and that said Letters Patent is hereby corrected as shown below:

Claim 1, column 271, line 60, the definition for $R_1$ in Claim 1 recites the term "–(CH$_2$)2NHC(=O)CH$_3$," which should be replaced with -- –(CH$_2$)$_2$NHC(=O)CH$_3$ --;

Claim 3, column 272, line 32, "4-8membered," should be replaced with -- 4-8 membered --;

Claim 5, column 273, line 34, "($C_1C_{15}$)," should be replaced with -- ($C_1$-$C_{15}$) --;

Claim 5, column 273, line 39, "($C_1$-$C_3$)alkylamino, ($C_1$-$C_3$)alkoxy," should be replaced with -- ($C_1$-$C_{30}$)alkylamino, ($C_1$-$C_{30}$)alkoxy --; and Claim 6, column 273, line 67, "–(CH$_2$)2OH," should be replaced with -- –(CH$_2$)$_2$OH --.

Signed and Sealed this

Eighteenth Day of May, 2010

David J. Kappos
*Director of the United States Patent and Trademark Office*